(12) United States Patent
Nash et al.

(10) Patent No.: US 8,808,694 B2
(45) Date of Patent: Aug. 19, 2014

(54) THERAPEUTIC PEPTIDOMIMETIC MACROCYCLES

(75) Inventors: Huw M. Nash, Concord, MA (US); David Allen Annis, Cambridge, MA (US); Rosana Kapeller-Libermann, Chestnut Hill, MA (US); Tomi K. Sawyer, Southborough, MA (US); Noriyuki Kawahata, Somerville, MA (US); Jiawen Han, Newton, MA (US)

(73) Assignee: Aileron Therapeutics, Inc., Cambridge, MA (US)

( * ) Notice: Subject to any disclaimer, the term of this patent is extended or adjusted under 35 U.S.C. 154(b) by 0 days.

(21) Appl. No.: 13/352,223

(22) Filed: Jan. 17, 2012

(65) Prior Publication Data

US 2012/0149648 A1    Jun. 14, 2012

Related U.S. Application Data

(63) Continuation of application No. 12/378,047, filed on Feb. 9, 2009, now abandoned.

(60) Provisional application No. 61/027,326, filed on Feb. 8, 2008, provisional application No. 61/120,380, filed on Dec. 5, 2008.

(51) Int. Cl.
| | | |
|---|---|---|
| *A61K 39/395* | (2006.01) | |
| *C12N 15/00* | (2006.01) | |
| *A61K 38/12* | (2006.01) | |
| *A61K 38/17* | (2006.01) | |

(52) U.S. Cl.
CPC ............. *A61K 38/12* (2013.01); *A61K 38/1761* (2013.01)
USPC ..................................... 424/130.1; 435/69.1

(58) Field of Classification Search
None
See application file for complete search history.

(56) References Cited

U.S. PATENT DOCUMENTS

| | | | |
|---|---|---|---|
| 5,364,851 A | 11/1994 | Joran | |
| 5,446,128 A | 8/1995 | Kahn | |
| 5,622,852 A | 4/1997 | Korsmeyer | |
| 5,663,316 A | 9/1997 | Xudong | |
| 5,672,584 A | 9/1997 | Borchardt et al. | |
| 5,708,136 A | 1/1998 | Burrell et al. | |
| 5,750,767 A | 5/1998 | Carpino et al. | |
| 5,811,515 A | 9/1998 | Grubbs et al. | |
| 5,824,483 A | 10/1998 | Houston, Jr. et al. | |
| 5,834,209 A | 11/1998 | Korsmeyer | |
| 5,856,445 A | 1/1999 | Korsmeyer | |
| 5,874,529 A | 2/1999 | Gilon et al. | |
| 5,922,863 A | 7/1999 | Grubbs et al. | |
| 5,955,593 A | 9/1999 | Korsmeyer | |
| 5,965,703 A | 10/1999 | Horne et al. | |
| 5,998,583 A | 12/1999 | Korsmeyer | |
| 6,030,997 A | 2/2000 | Eilat et al. | |
| 6,043,339 A | 3/2000 | Lin et al. | |
| 6,046,289 A | 4/2000 | Komazawa et al. | |
| 6,153,391 A | 11/2000 | Picksley et al. | |
| 6,271,198 B1 | 8/2001 | Braisted et al. | |
| 6,326,354 B1 | 12/2001 | Gross et al. | |
| 6,495,674 B1 | 12/2002 | Lemke et al. | |
| 6,569,993 B1 | 5/2003 | Sledeski et al. | |
| 6,613,874 B1 | 9/2003 | Mazur et al. | |
| 6,703,382 B2 | 3/2004 | Wang et al. | |
| 6,713,280 B1 | 3/2004 | Huang et al. | |
| 6,936,586 B1 | 8/2005 | Larsen et al. | |
| 7,064,193 B1 | 6/2006 | Cory et al. | |
| 7,083,983 B2 | 8/2006 | Lane et al. | |
| 7,084,244 B2 | 8/2006 | Gilon et al. | |
| 7,192,713 B1 | 3/2007 | Verdine et al. | |
| 7,202,332 B2 | 4/2007 | Arora et al. | |
| 7,247,700 B2 | 7/2007 | Korsemeyer | |
| 7,538,190 B2 | 5/2009 | Robinson et al. | |
| 7,705,118 B2 | 4/2010 | Arora et al. | |
| 7,723,469 B2 | 5/2010 | Walensky et al. | |
| 7,745,573 B2 | 6/2010 | Robinson et al. | |
| 7,786,072 B2 | 8/2010 | Verdine et al. | |
| 8,124,726 B2 | 2/2012 | Robinson et al. | |
| 8,324,428 B2 | 12/2012 | Verdine | |
| 8,399,405 B2 | 3/2013 | Nash et al. | |
| 2004/0115135 A1 | 6/2004 | Quay | |
| 2004/0171809 A1 | 9/2004 | Korsmeyer et al. | |
| 2004/0230380 A1* | 11/2004 | Chirino et al. | 702/19 |
| 2004/0235746 A1 | 11/2004 | Hawiger et al. | |
| 2005/0250680 A1* | 11/2005 | Walensky et al. | 514/9 |
| 2006/0008848 A1 | 1/2006 | Verdine et al. | |
| 2006/0014675 A1 | 1/2006 | Arora et al. | |
| 2007/0161690 A1 | 7/2007 | Castro et al. | |
| 2008/0262200 A1* | 10/2008 | Nash | 530/331 |
| 2009/0047711 A1 | 2/2009 | Nash | |
| 2009/0088553 A1 | 4/2009 | Nash | |

(Continued)

FOREIGN PATENT DOCUMENTS

| | | |
|---|---|---|
| JP | 2002-524391 | 8/2002 |
| WO | WO 00/06187 A2 | 2/2000 |

(Continued)

OTHER PUBLICATIONS

U.S. Appl. No. 13/366,113, filed Feb. 3, 2012, Nash et al.
U.S. Appl. No. 13/370,057, filed Feb. 9, 2012, Nash et al.
Annis, et al. A General Technique to Rank Protein—Ligand Binding Affinities and Determine Allosteric versus Direct Binding Site Competition in Compound Mixtures. J. Am. Chem. Soc. 2004;126(47):15495-15503.
Annis, et al. ALIS: An Affinity Selection-Mass Spectrometry System for the Discovery and Characterization of Protein-Ligand Interactions. In: Wanner, K. and Höfner, G. eds. Mass Spectrometry in Medicinal Chemistry. Wiley-VCH; 2007:121-156.
Deiters, et al. Adding amino acids with novel reactivity to the genetic code of *Saccharomyces cerevisiae*. J. Am. Chem. Soc. Oct. 1, 2003;125(39):11782-11783.
Greenaway, J., et al. ABT-510 induces tumor cell apoptosis and inhibits ovarian tumor growth in an orthotopic, syngeneic model of epithelial ovarian cancer. Mol. Cancer Ther. Jan. 8, 2009:64-74.

(Continued)

*Primary Examiner* — Lei Yao
(74) *Attorney, Agent, or Firm* — Wilson Sonsini Goodrich & Rosati, P.C.

(57) ABSTRACT

The present invention provides biologically active peptidomimetic macrocycles for the treatment of cell proliferative disorders such as cancer and immunoproliferative disease.

16 Claims, 56 Drawing Sheets

(56) References Cited

U.S. PATENT DOCUMENTS

| | | |
|---|---|---|
| 2009/0149630 A1 | 6/2009 | Walensky et al. |
| 2009/0176964 A1 | 7/2009 | Walensky et al. |
| 2009/0275519 A1 | 11/2009 | Nash et al. |
| 2010/0184628 A1 | 7/2010 | Nash |
| 2010/0184645 A1 | 7/2010 | Verdine et al. |
| 2010/0216688 A1 | 8/2010 | Nash et al. |
| 2010/0234563 A1 | 9/2010 | Arora et al. |
| 2010/0298201 A1 | 11/2010 | Nash et al. |
| 2011/0028753 A1 | 2/2011 | Verdine et al. |
| 2011/0223149 A1 | 9/2011 | Nash et al. |
| 2011/0263815 A1 | 10/2011 | Nash |
| 2012/0172311 A1 | 7/2012 | Nash et al. |
| 2012/0190818 A1 | 7/2012 | Nash |
| 2013/0005943 A1 | 1/2013 | Arora et al. |
| 2013/0023646 A1 | 1/2013 | Nash et al. |
| 2013/0211046 A1 | 8/2013 | Verdine et al. |

FOREIGN PATENT DOCUMENTS

| | | |
|---|---|---|
| WO | WO 00/06187 A3 | 5/2000 |
| WO | WO 02/064790 A2 | 8/2002 |
| WO | WO 02/064790 A3 | 5/2003 |
| WO | WO 03/106491 A2 | 12/2003 |
| WO | WO 2004/058804 A1 | 7/2004 |
| WO | WO 03/106491 A3 | 12/2004 |
| WO | WO 2005/040202 A2 | 5/2005 |
| WO | WO 2005/044839 A2 | 5/2005 |
| WO | WO 2005/040202 A3 | 6/2005 |
| WO | WO 2005/044839 A3 | 7/2005 |
| WO | WO 2005/090388 A1 | 9/2005 |
| WO | WO 2005/118634 A2 | 12/2005 |
| WO | WO 2005/118634 A3 | 5/2006 |
| WO | WO 2006/103666 A2 | 10/2006 |
| WO | WO 2006/103666 A3 | 3/2007 |
| WO | WO 2008/104000 A2 | 8/2008 |
| WO | WO 2008/104000 A3 | 11/2008 |
| WO | WO 2009/042237 A2 | 4/2009 |
| WO | WO 2009/042237 A3 | 12/2009 |

OTHER PUBLICATIONS

Grubbs, et al. Ring Closing Metathesis and Related Processes in organic Synthesis. Acc. Chem. Res. 1995;28(11):446-452.

Hunt, S. The Non-Protein Amino Acids. In: Barrett G.C., ed. Chemistry and Biochemistry of the Amino Acids. New York; Chapman and Hall; 1985.

Lelekakis, M., et al. A novel orthotopic model of breast cancer metastasis to bone. Clin. Exp. Metastasis.Mar. 1999;17(2):163-70.

Mannhold, R., Kubinyi, H., Folkers, G., series eds. Molecular Drug Properties: Measurement and Prediction (Methods and Principles in Medicinal Chemistry). Wiley-VCH; 2007.

Mosberg, et al. Dithioeter-containing cyclic peptides. J. Am. Chem. Soc. 1985;107(10):2986-2987.

Mustapa, et al. Synthesis of a Cyclic Peptide Containing Norlanthionine: Effect of the Thioether Bridge on Peptide Conformation. J. Org. Chem. 2003;68(21):8193-8198.

Rasmussen, et al. Ruthenium-catalyzed cycloaddition of aryl azides and alkynes. Org. Lett. Dec. 20, 2007;9(26):5337-5339.

Rostovtsev, et al. A stepwise huisgen cycloaddition process: copper (i)-catalyzed regioselective "ligation" of azides and terminal alkynes. Angew. Chem. Int. Ed. Engl. Jul. 15, 2002;41(14):2596-2599.

Szewczuk, et al. Synthesis and biological activity of new conformationally restricted analogues of pepstatin. Int. J. Pept. Protein Res. Sep.-Oct. 1992;40(3-4):233-42.

Walensky, et al. A stapled BID BH3 helix directly binds and activates BAX. Mol. Cell. Oct. 20, 2006;24(2):199-210.

U.S. Appl. No. 13/250,344, filed Sep. 30, 2011, Arora et al.

U.S. Appl. No. 13/252,751, filed Oct. 4, 2011, Walensky et al.

Andrews et al. Fomiing Stable Helical Peptide Using Natural and Artificial Amino Acids. Tetrahedron. 1999;55:11711-11743.

Baell, J.B. Prospects for Targeting the Bcl-2 Family of Proteins to Develop Novel cytotoxic drugs. Biochem Pharmacol. Sep. 2002;64(5-6):851-63.

Belokon, et al. Improved procedures for the synthesis of (s)-2-[N-(N'-benzylprolyl)amino]benzophenone (BPB) and Ni(II) complexes of Schiff's bases derived from BPB and amino acids. Tetrahedron Asymm. Dec. 11, 1998;9(23):4249-4252.

Bernal, et al. Reactivation of the p53 tumor suppressor pathway by a stapled p53 peptide. J Am Chem Soc. Mar. 7, 2007;129(9):2456-7.

Blackwell, et al. Highly Efficient Synthesis of Covalently Cross-Linked Peptide Helices by Ring-Closing Metathesis. Angewandte Chemie International Edition. 1998; 37(23):3281-3284.

Blackwell, et al. Ring-closing metathesis of olefinic peptides: design, synthesis, and structural characterization of macrocyclic helical peptides. J Org Chem. Aug. 10, 2001;66(16):5291-302.

Boguslavsky, et al. Effect of peptide conformation on membrane permeability. J Pept Res. Jun. 2003;61(6):287-97.

Brunel, F.M. and Dawson, P.E. Synthesis of constrained helical peptides by thioether ligation: application to analogs of gp41. Chem. Commun. (Camb.) May 28, 2005;(20):2552-4.

Chittenden, et al. A conserved domain in Bak, distinct from BH1 and BH2, mediates cell death and protein binding functions. EMBO J. 1995;14(22):5589-96.

European search report and search opinion dated May 6, 2011 for Application No. 10195495.6.

European search report and search opinion dated May 9, 2011 for Application No. 10195490.7.

European search report dated Nov. 7, 2008 for Application No. 8016651.5.

European search report dated Aug. 22, 2008 for Application No. 4811198.3.

Galande, et al. An effective method of on-resin disulfide bond formation in peptides. J. Comb. Chem. Mar.-Apr. 2005;7(2):174-177.

Goodson, L.H. et al., Potential Growth Antagonists. I. Hydantoins and Disubstituted Glycines. Journal of Organic Chemistry. 1960;25:1920-1924.

International search report dated Oct. 22, 2009 for PCT Application No. US2009/00837.

International search report dated May 18, 2005 for PCT Application No. US2004/38403.

Jackson et al. General approach to the synthesis of short alpha-helical peptides. JACS. 1991;113:9391-9392.

Kwon, et al. Quantitative comparison of the relative cell permeability of cyclic and linear peptides. Chem Biol. Jun. 2007;14(6):671-7.

Lee, et al. A novel BH3 ligand that selectively targets Mcl-1 reveals that apoptosis can proceed without Mcl-1 degradation. J Cell Biol. Jan. 28, 2008;180(2):341-355.

Mai et al. A proapoptotic peptide for the treatment of solid tumors Cancer Res. Nov. 1, 2001;61(21):7709-12.

McNamara et al. Peptides constrained by an aliphatic linkage between two C(alpha) sites: design, synthesis, and unexpected conformational properties of an i,(i+4)-linked peptide. J Org Chem. Jun. 29, 2001;66(13):4585-95.

Mustapa, et al. Synthesis of a cyclic peptide containing norlanthionine: effect of the thioether bridge on peptide conformation. J Org Chem. Oct. 17, 2003;68(21):8193-8.

Non-Final Office Action dated Dec. 5, 2008 from U.S. Appl. No. 10/981,873.

Office action dated Feb. 17, 2011 for U.S. Appl. No. 12/796,212.

Office action dated Apr. 18, 2011 for U.S. Appl. No. 12/182,673.

Office action dated Aug. 9, 2010 for U.S. Appl. No. 12/182,673.

Office action dated Oct. 18, 2011 for U.S. Appl. No. 12/796,212.

Office action dated Dec. 29, 2011 for U.S. Appl. No. 12/233,555.

Or et al. Cysteine alkylation in unprotected peptides: synthesis of a carbavasopressin analogue by intramolecular cystein alkylation. J. Org. Chem. Apr. 1991;56(9):3146-3149.

Punna, et al. Head-to-tail peptide cyclodimerization by copper-catalyzed azide-alkyne cycloaddition. Angew. Chem. Int. Ed. Engl. Apr. 8, 2005;44(15):2215-20.

Ruffolo and Shore. BCL-2 Selectively Interacts with the BID-Induced Open Conformer of BAK, Inhibiting BAK Auto-Oligomerization. J. Biol. Chern. 2003;278(27):25039-25045.

Sanchez-Garcia, et al. Tumorigenic activity of the BCR-ABL oncogenes is mediated by BCL2. Proc Natl Acad Sci U S A. Jun. 6, 1995;92(12):5287-91.

(56) References Cited

OTHER PUBLICATIONS

Schafmeister, et al. An All-Hydrocarbon Cross-Linking System for Enhancing the Helicity and Metabolic Stability of Peptides. J. Am. Chem. Soc. 2000;122(24):5891-5892.
Schmiedeberg et al. Reversible backbone protection enables combinatorial solid-phase ring-closing metathesis reaction (RCM) in peptides. Org Lett. Jan. 10, 2002;4(1):59-62.
Seebach, et al. Self-Regeneration of Stereocenters (SRS)—Applications, Limitations, and Abandonment of a Synthetic Principle. Angew. Chem. Int. Ed. Engl. 1996;35:2708-2748.
Tahir, et al. Influence of Bcl-2 family members on the cellular response of small-cell lung cancer cell lines to ABT-737. Cancer Res. Feb. 1, 2007;67(3):1176-83.
Thallinger, et al. Mcl-1 is a novel therapeutic target for human sarcoma: synergistic inhibition of human sarcoma xenotransplants by a combination of mcl-1 antisense oligonucleotides with low-dose cyclophosphamide. Clin. Cancer Res. Jun. 15, 2004;10(12 Pt 1):4185-91.
Titus, et al. Human K/natural killer cells targeted with hetero-cross-linked antibodies specifically lyse tumor cells in vitro and prevent tumor growth in vivo. J Immunol. Nov. 1, 1987;139(9):3153-8.
Tornoe, et al. Peptidotriazoles on solid phase: [1,2,3]-triazoles by regiospecific copper(i)-catalyzed 1,3-dipolar cycloadditions of terminal alkynes to azides. J. Org. Chem. May 3, 2002;67(9):3057-64.
Twombly, R. Cancer Surpasses Heart Disease as Leading Cause of Death for All but the Very Elderly. Journal of the National Cancer Institute. Mar. 2, 2005;97(5):330-331.
Tyndall et al. Macrocycles mimic the extended peptide conformation recognized by aspartic, serine, cysteine and metallo proteases. Curr Med Chem. Jul. 2001;8(8):893-907.
Viallet, et al. Tallimustine is inactive in patients with previously treated small cell lung cancer. A phase II trial of the National Cancer Institute of Canada Clinical Trials Group. Lung Cancer. Nov. 1996;15(3):367-73.
Walensky, et al. Activation of Apoptosis in Vivo by a Hydrocarbon-Stapled BH3 Helix. Science. Sep. 3, 2004;305(5689):1466-1470.
Wang et al. Cell permeable Bcl-2 binding peptides: a chemical approach to apoptosis induction in tumor cells. Cancer Res. Mar. 15, 2000;60(6):1498-502.
Wang et al. Enhanced metabolic stability and protein-binding properties of artificial alpha helices derived from a hydrogen-bond surrogate: application to Bcl-xL. Angew Chem Int Ed Engl. Oct. 14, 2005;44(40):6525-9.
Wang, et al. BID: a novel BH3 domain-only death agonist. Genes Dev. Nov. 15, 1996;10(22):2859-69.
Wei, et al. tBID, a membrane-targeted death ligand, oligomerizes BAK to release cytochrome c. Genes Dev. Aug. 15, 2000;14(16):2060-71.
Williams, R.M. and IM, M.N. Asymmetric synthesis of monosubstituted and .alpha.,.alpha.-disubstituted .alpha.-amino acids via diastereoselective glycine enolate alkylations. J. Am. Chem. Soc. 1991;113(24):9276-9286.
Yang, et al. Synthesis and helical structure of lactam bridged BH3 peptides derived from pro-apoptotic Bcl-2 family proteins. Bioorg. Med. Chem. Lett. Mar. 22, 2004;14(6):1403-6.
Zamzami et al. The thiol crosslinking agent diamide overcomes the apoptosis-inhibitory effect of Bcl-2 by enforcing mitochondrial permeability transition. Oncogene. Feb. 26, 1998;16(8):1055-63.
Zhang, et al. Ruthenium-catalyzed cycloaddition of alkynes and organic azides. J. Am. Chem. Soc. Nov. 23, 2005;127(46):15998-9.
U.S. Appl. No. 14/068,844, filed Oct. 31, 2013, Verdine et al.
U.S. Appl. No. 14/070,354, filed Nov. 1, 2013, Walensky et al.
U.S. Appl. No. 14/070,367, filed Nov. 1, 2013, Nash.
U.S. Appl. No. 14/156,350, filed Jan. 15, 2014, Nash et al.
Office action dated Feb. 6, 2014 for U.S. Appl. No. 13/680,905.
Office action dated Sep. 23, 2013 for U.S. Appl. No. 13/680,905.
U.S. Appl. No. 13/494,846, filed Jun. 12, 2012, Nash et al.
U.S. Appl. No. 13/680,905, filed Nov. 19, 2012, Verdine et al.

Austin et al., "A Template for Stabilization of a Peptide α-Helix: Synthesis and Evaluation of Conformational Effects by Circular Dichroism and NMR," J. Am. Chem. Soc. 119:6461-6472 (1997).
Bakhshi, et al. Cloning the chromosomal breakpoint of t(14;18) human lymphomas: clustering around JH on chromosome 14 and near a transcriptional unit on 18. Cell. Jul. 1985;41(3):899-906.
Banerji et al., "Synthesis of Cyclic β-Turn Mimics from L-Pro-Phe/Phe-L-Pro Derived Di- and Tripeptides via Ring Closing Metathesis: The Role of Chirality of the Phe Residue During Cyclization," Tetrahedron Lett. 43:6473-6477 (2002).
Bang, et al. Total chemical synthesis of crambin. J Am Chem Soc. Feb. 11, 2004;126(5):1377-83.
Berendsen, H.J. A glimpse of the Holy Grail? Science. Oct. 23, 1998;282(5389):642-3.
Bossy-Wetzel, et al. Assays for cytochrome c release from mitochondria during apoptosis. Methods Enzymol. 2000;322:235-42.
Bossy-Wetzel, et al. Detection of apoptosis by annexin V labeling. Methods Enzymol. 2000;322:15-8.
Bracken, et al. Synthesis and nuclear magnetic resonance structure determination of an alpha-helical, bicyclic, lactam-bridged hexapeptide. J. Am. Chem. Soc. 1994;116:6431-6432.
Bradley, et al. Limits of cooperativity in a structurally modular protein: response of the Notch ankyrin domain to analogous alanine substitutions in each repeat. J Mol Biol. Nov. 22, 2002;324(2):373-86.
Cabezas & Satterthwait, "The Hydrogen Bond Mimic Approach: Solid-phase Synthesis of a Peptide Stabilized as an α-Helix with a Hydrazone Link," J. Am. Chem. Soc. 121:3862-3875 (1999).
Chakrabartty et al., "Helix Capping Propensities in Peptides Parallel Those in Proteins," Proc. Nat'l Acad. Sci. USA 90:11332-11336 (1993).
Chapman et al., "A Highly Stable Short α-Helix Constrained by a Main-chain Hydrogen-bond Surrogate," J. Am. Chem. Soc. 126:12252-12253 (2004).
Chapman, et al. Optimized synthesis of hydrogen-bond surrogate helices: surprising effects of microwave heating on the activity of Grubbs catalysts. Org Left. Dec. 7, 2006;8(25):5825-8.
Chin & Schepartz, "Design and Evolution of a Miniature Bcl-2 Binding Protein," Angew. Chem. Int. Ed. 40(20):3806-3809 (2001).
Chin et al., "Circular Dichroism Spectra of Short, Fixed-nucleus Alanine Helices," Proc. Nat'l Acad. Sci. USA 99(24):15416-15421 (2002).
Chittenden, et al. A conserved domain in Bak, distinct from BH1 and BH2, mediates cell death and protein binding functions. EMBO J. Nov. 15, 1995;14(22):5589-96.
Cleary, et al. Nucleotide sequence of a t(14;18) chromosomal breakpoint in follicular lymphoma and demonstration of a breakpoint-cluster region near a transcriptionally active locus on chromosome 18. Proc Natl Acad Sci U S A. Nov. 1985; 82(21):7439-43.
Danial, et al. Cell death: critical control points. Cell. 2004; 116:204-219.
Degterev et al., "Identification of Small-molecule Inhibitors of Interaction between the BH3 Domain and Bcl-xL," Nature Cell Biol. 3:173-182 (2001).
Designing Custom Peptide. from SIGMA Genosys, pp. 1-2. Accessed Dec. 16, 2004.
Dimartino, et al. Solid-phase synthesis of hydrogen-bond surrogate-derived alpha-helices. Org Lett. Jun. 9, 2005;7(12):2389-92.
European office action dated Aug. 20, 2012 for EP Application No. 09730445.5.
Felix et al., "Synthesis, Biological Activity and Conformational Analysis of Cyclic GRF Analogs," Int. J. Pep. Protein Res. 32:441-454 (1988).
Fischer, et al. Apoptosis-based therapies and drug targets. Cell Death and Differentiation. 2005; 12:942-961.
Formaggio, et al. Inversion of 3(10)-helix screw sense in a (D-alpha Me)Leu homo-tetrapeptide induced by a guest D-(alpha Me)Val residue. J Pept Sci. Nov.-Dec. 1995;1(6):396-402.
Fulda, et al. Extrinsic versus intrinsic apoptosis pathways in anticancer chemotherapy. Oncogene. Aug. 7, 2006;25(34):4798-811.

(56) References Cited

OTHER PUBLICATIONS

Furstner, et al. Alkyne metathesis: development of a novel molybdenum-based catalyst system and its application to the total synthesis of epothilone A and C. Chemistry. Dec. 17, 2001;7(24):5299-317.
Furstner, et al. Mo[N(t-Bu)(Ar)]3 Complexes as catalyst precursors: In situ activation and application to metathesis reactions of alkynes and diynes. J Am chem Soc. 1999; 121:9453-54.
Gallivan, et al. A neutral, water-soluble olefin metathesis catalyst based on an N-heterocyclic carbene ligand. Tetrahedron Letters. 2005; 46:2577-80.
Galluzzi, et al. Guidelines for the use and interpretation of assays for monitoring cell death in higher eukaryotes. Cell Death Differ. Aug. 2009;16(8):1093-107. Epub Apr. 17, 2009.
Ghadiri & Choi, "Secondary Structure Nucleation in Peptides. Transition Metal Ion Stabilized α-Helices," J. Am. Chem. Soc. 112:1630-1632 (1990).
Gras-Masse, et al. Influence of helical organization on immunogenicity and antigenicity of synthetic peptides. Mol Immunol. Jul. 1988;25(7):673-8.
Hiroshige, et al. Palladium-mediated macrocyclisations on solid support and its applica-tions to combinatorial synthesis. J. Am. Chem. Soc. 1995; 117:11590-11591.
Hoveyda et al., "Ru Complexes Bearing Bidentate Carbenes: From Innocent Curiosity to Uniquely Effective Catalysts for Olefin Metathesis," Org. Biomolec. Chem. 2:8-23 (2004).
International search report dated Nov. 30, 2009 for PCT Application No. US2009/02225.
Karle, et al. Structural charateristics of alpha-helical peptide molecules containing Aib residues. Biochemistry. Jul. 24, 1990;29(29):6747-56.
Karle. Flexibility in peptide molecules and restraints imposed by hydrogen bonds, the Aib residue, and core inserts. Biopolymers. 1996;40(1):157-80.
Kelso et al., "A Cyclic Metallopeptide Induces α Helicity in Short Peptide Fragments of Thermolysin," Angew. Chem. Int. Ed. 42(4):421-424 (2003).
Kelso et al., "α-Turn Mimetics: Short Peptide α-Helices Composed of Cyclic Metallopentapeptide Modules," J. Am. Chem. Soc. 126:4828-4842 (2004).
Kemp et al., "Studies of N-Terminal Templates for α-Helix Formation. Synthesis and Conformational Analysis of (2S,5S,8S,11S)-1-Acetyl-1,4-diaza-3-keto-5-carboxy-10-thiatricyclo[2.8.1.04,8]-tridecane (Ac-Hell-OH)," J. Org. Chem. 56:6672-6682 (1991).
Kent. Advanced Biology. Oxford University Press. 2000.
Kilby et al., "Potent Suppression of HIV-1 Replication in Humans by T-20, a Peptide Inhibitor of gp41-Mediated Virus Entry," Nat. Med. 4(11):1302-1307 (1998).
Kritzer et al., "Helical β-Peptide Inhibitors of the p53-hDM2 Interaction," J. Am. Chem. Soc. 126:9468-9469 (2004).
Kutzki et al., "Development of a Potent Bcl-xL Antagonist Based on α-Helix Mimicry," J. Am. Chem. Soc. 124:11838-11839 (2002).
Leduc, et al. Helix-stabilized cyclic peptides as selective inhibitors of steroid receptor-coactivator interactions. Proc Natl Acad Sci U S A. Sep. 30, 2003;100(20):11273-8.
Liskamp, et al. Conformationally restricted amino acids and dipeptides, (non)peptidomimetics and secondary structure mimetics. Recl Travl Chim Pays-Bas. 1994; 113:1-19.
Litowski & Hodges, "Designing Heterodimeric Two-stranded α-Helical Coiled-coils: Effects of Hydrophobicity and α-Helical Propensity on Protein Folding, Stability, and Specificity," J. Biol. Chem. 277(40):37272-37279 (2002).
Luo, et al. Mechanism of helix induction by trifluoroethanol: a framework for extrapolating the helix-forming properties of peptides from trifluoroethanol/water mixtures back to water. Biochemistry. Jul. 8, 1997;36(27):8413-21.
Lyu & Wemmer, "Capping Interactions in Isolated α Helices: Position-dependent Substitution Effects and Structure of a Serine-capped Peptide Helix," Biochemistry 32:421-425 (1993).
Lyu et al, "α-Helix Stabilization by Natural and Unnatural Amino Acids with Alkyl Side Chains," Proc. Nat'l Acad. Sci. USA 88:5317-5320 (1991).
McGahon, et al. The end of the (cell) line: methods for the study of apoptosis in vitro. Methods Cell Biol. 1995;46:153-85.
Muchmore, et al. X-ray and NMR structure of human Bcl-xL, an inhibitor of programmed cell death. Nature. May 23, 1996;381(6580):335-41.
Nelson & Kallenbach, "Persistence of the α-Helix Stop Signal in the S-Peptide in Trifluoroethanol Solutions," Biochemistry 28:5256-5261 (1989).
Ngo, et al. Computational complexity, protein structure predictioni, and the levinthal paradox. In the Protein Folding Problem and Tertiary Structure Prediction. K. Merc Jr, et al. Eds. 1994; 491-495.
O'Neil & DeGrado, "A Thermodynamic Scale for the Helix-forming Tendencies of the Commonly Occurring Amino Acids," Science 250:646-651(1990).
Office action dated Jan. 26, 2009 for U.S. Appl. No. 11/148,976.
Office action dated Jan. 30, 2008 for U.S. Appl. No. 10/981,873.
Office action dated Feb. 9, 2012 for U.S. Appl. No. 12/420,816.
Office action dated Mar. 22, 2013 for U.S. Appl. No. 12/233,555.
Office action dated Jul. 15, 2013 for U.S. Appl. No. 13/570,146.
Office action dated Aug. 22, 2011 for U.S. Appl. No. 12/378,047.
Office action dated Nov. 5, 2002 for U.S. Appl. No. 09/574,086.
Office action dated Nov. 25, 2009 for U.S. Appl. No. 11/148,976.
Ösapay & Taylor, "Multicyclic Polypeptide Model Compounds. 2. Synthesis and Conformational Properties of a Highly α-Helical Uncosapeptide Constrained by Three Side-chain to Side-chain Lactam Bridges," J. Am. Chem. Soc. 114:6966-6973 (1992).
Phelan, et al. A General Method for Constraining Short Peptides to an α-Helical Conformation. J. Am. Chem. Soc. 1997;119:455-460.
Punna, et al. Head-to-tail peptide cyclodimerization by copper-catalyzed azide-alkyne cycloaddition. Angew Chem Int Ed Engl. Apr. 8, 2005;44(15):2215-20.
Roberts, et al. Efficient synthesis of thioether-based cyclic peptide libraries. Tetrahedon Letters. 1998; 39: 8357-8360.
Roberts, et al. Examination of methodology for the synthesis of cyclic thioether peptide libraries derived from linear tripeptides. J Pept Sci. Dec. 2007;13(12):811-21.
Ruan et al., "Metal Ion Enhanced Helicity in Synthetic Peptides Containing Unnatural, Metal-ligating Residues," J. Am. Chem. Soc. 112:9403-9404 (1990).
Rudinger, J. Characteristics of the amino acids as components of a peptide hormone sequence. In Peptide Hormones. J. A. Parsons, ed. University Park Press. Jun. 1976; pp. 1-7.
Sattler et al. Structure of Bcl-xL-Back peptide complex: recognition between regulators of apoptosis. Science. 1997;275:983-986.
Schinzel, et al. The phosphate recognition site of *Escherichia coli* maltodextrin phosphorylase. FEBS Lett. Jul. 29, 1991;286(1-2):125-8.
Scorrano, et al. A distinct pathway remodels mitochondrial cristae and mobilizes cytochrome c during apoptosis. Dev Cell. Jan. 2002;2(1):55-67.
Shepherd et al., "Single Turn Peptide Alpha Helices with Exceptional Stability in Water," J. Am. Chem. Soc. 127:2974-2983 (2005).
Sia et al., "Short Constrained Peptides that Inhibit HIV-1 Entry," Proc. Nat'l Acad. Sci. USA 99(23):14664-14669 (2002).
Spierings, et al. Connected to death: the (unexpurgated) mitochondrial pathway of apoptosis. Science. 2005; 310:66-67.
Spouge, et al. Strong conformational propensities enhance t cell antigenicity. J Immunol. Jan. 1, 1987;138(1):204-12.
Stewart, et al. Cell-penetrating peptides as delivery vehicles for biology and medicine. Org Biomol Chem. Jul. 7, 2008;6(13):2242-55. doi: 10.1039/b719950c. Epub Apr. 15, 2008.
Suzuki, et al. Structure of Bax: coregulation of dimer formation and intracellular localization. Cell. Nov. 10, 2000;103(4):645-54.
Tanaka, M. Design and synthesis of non-proteinogenic amino acids and secondary structures of their peptides. Yakugaku Zasshi. Oct. 2006;126(10):931-44.
Taylor. The synthesis and study of side-chain lactam-bridged peptides. Biopolymers. 2002;66(1):49-75.

(56) References Cited

OTHER PUBLICATIONS

Trnka & Grubbs, "The Development of L2X2Ru=CHR Olefin Metathesis Catalysts: An Organometallic Success Story," Acc. Chem. Res. 34:18-29 (2001).

Tugyi, et al. The effect of cyclization on the enzymatic degradation of herpes simplex virus glycoprotein D derived epitope peptide. J Pept Sci. Oct. 2005;11(10):642-9.

Vaickus, et al. Immune markers in hematologic malignancies. Crit Rev Oncol Hematol. Dec. 1991;11(4):267-97.

Voet, et al. Biochemistry, Second Edition. John Wiley & Sons, Inc. 1995; pp. 235-241.

Wang, et al. Evaluation of biologically relevant short alpha-helices stabilized by a main-chain hydrogen-bond surrogate. J Am Chem Soc. Jul. 19, 2006;128(28):9248-56.

Wang, et al. Nucleation and stability of hydrogen-bond surrogate-based alpha-helices. Org Biomol Chem. Nov. 21, 2006;4(22):4074-81.

Wild et al., "Peptides Corresponding to a Predictive α-Helical Domain of Human Immunodeficiency Virus Type 1 gp4l are Potent Inhibitors of Virus Infection," Proc. Nat'l Acad. Sci. USA 91:9770-9774 (1994).

Yang, et al. Calculation of protein conformation from circular dichroism. Methods Enzymol. 1986;130:208-69.

Zhang, et al. 310 Helix versus alpha-helix: a molecular dynamics study of conformational preferences of Aib and Alanine. J. American Cancer Society. Dec. 1994;116(26):11915-11921.

Office action dated Jun. 26, 2012 for U.S. Appl. No. 12/378,047.

Office action dated Jun. 28, 2012 for U.S. Appl. No. 12/233,555.

\* cited by examiner

| PK Parameters | 10 mg/Kg IV SP-1 | 10 mg/Kg IV SP-4 |
|---|---|---|
| T ½ (hr) | 3.3 | 2.96 |
| Cmax (ng/ml) | 125644 | 29655 |
| AUC all (hr*ng/ml) | 190195 | 90791 |
| Vss (ml/Kg) | 110 | 299 |
| Cl (ml/hr/Kg) | 53.4 | 110 |

Figure 24

```
                           SEQUENCE LISTING

<160> NUMBER OF SEQ ID NOS: 120

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 1

Ile Trp Ile Ala Gln Glu Leu Arg Xaa Ile Gly Asp Xaa Phe Asn Ala
1               5                   10                  15

Tyr Tyr Ala Arg Arg
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine

<400> SEQUENCE: 2

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 3
<211> LENGTH: 25
<212> TYPE: PRT
<213> ORGANISM: Homo sapiens

<400> SEQUENCE: 3

Gln Glu Asp Ile Ile Arg Asn Ile Ala Arg His Leu Ala Gln Val Gly
```

```
                1               5                   10                  15
Asp Ser Met Asp Arg Ser Ile Pro Pro
            20                  25

<210> SEQ ID NO 4
<211> LENGTH: 25
<212> TYPE: PRT
<213> ORGANISM: Homo sapiens

<400> SEQUENCE: 4

Asp Asn Arg Pro Glu Ile Trp Ile Ala Gln Glu Leu Arg Arg Ile Gly
1               5                   10                  15

Asp Glu Phe Asn Ala Tyr Tyr Ala Arg
            20                  25

<210> SEQ ID NO 5
<211> LENGTH: 25
<212> TYPE: PRT
<213> ORGANISM: Homo sapiens

<400> SEQUENCE: 5

Asn Leu Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 6
<211> LENGTH: 25
<212> TYPE: PRT
<213> ORGANISM: Homo sapiens

<400> SEQUENCE: 6

Glu Glu Gln Trp Ala Arg Glu Ile Gly Ala Gln Leu Arg Arg Met Ala
1               5                   10                  15

Asp Asp Leu Asn Ala Gln Tyr Glu Arg
            20                  25

<210> SEQ ID NO 7
<211> LENGTH: 24
<212> TYPE: PRT
<213> ORGANISM: Homo sapiens

<400> SEQUENCE: 7

Arg Ser Ser Ala Ala Gln Leu Thr Ala Ala Arg Leu Lys Ala Leu Gly
1               5                   10                  15

Asp Glu Leu His Gln Arg Thr Met
            20

<210> SEQ ID NO 8
<211> LENGTH: 22
<212> TYPE: PRT
<213> ORGANISM: Homo sapiens

<400> SEQUENCE: 8

Ala Glu Leu Pro Pro Glu Phe Ala Ala Gln Leu Arg Lys Ile Gly Asp
1               5                   10                  15

Lys Val Tyr Cys Thr Trp
            20

<210> SEQ ID NO 9
<211> LENGTH: 25
<212> TYPE: PRT
```

<213> ORGANISM: Homo sapiens

<400> SEQUENCE: 9

Val Pro Ala Asp Leu Lys Asp Glu Cys Ala Gln Leu Arg Arg Ile Gly
1               5                   10                  15

Asp Lys Val Asn Leu Arg Gln Lys Leu
            20                  25

<210> SEQ ID NO 10
<211> LENGTH: 24
<212> TYPE: PRT
<213> ORGANISM: Homo sapiens

<400> SEQUENCE: 10

Gln His Arg Ala Glu Val Gln Ile Ala Arg Lys Leu Gln Cys Ile Ala
1               5                   10                  15

Asp Gln Phe His Arg Leu His Thr
            20

<210> SEQ ID NO 11
<211> LENGTH: 22
<212> TYPE: PRT
<213> ORGANISM: Homo sapiens

<400> SEQUENCE: 11

Ser Ser Ala Ala Gln Leu Thr Ala Ala Arg Leu Lys Ala Leu Gly Asp
1               5                   10                  15

Glu Leu His Gln Arg Thr
            20

<210> SEQ ID NO 12
<211> LENGTH: 25
<212> TYPE: PRT
<213> ORGANISM: Homo sapiens

<400> SEQUENCE: 12

Cys Met Glu Gly Ser Asp Ala Leu Ala Leu Arg Leu Ala Cys Ile Gly
1               5                   10                  15

Asp Glu Met Asp Val Ser Leu Arg Ala
            20                  25

<210> SEQ ID NO 13
<211> LENGTH: 24
<212> TYPE: PRT
<213> ORGANISM: Homo sapiens

<400> SEQUENCE: 13

Asp Ile Glu Arg Arg Lys Glu Val Glu Ser Ile Leu Lys Lys Asn Ser
1               5                   10                  15

Asp Trp Ile Trp Asp Trp Ser Ser
            20

<210> SEQ ID NO 14
<211> LENGTH: 22
<212> TYPE: PRT
<213> ORGANISM: Homo sapiens

<400> SEQUENCE: 14

Gly Arg Leu Ala Glu Val Cys Ala Val Leu Leu Arg Leu Gly Asp Glu
1               5                   10                  15

Leu Glu Met Ile Arg Pro
            20

```
<210> SEQ ID NO 15
<211> LENGTH: 25
<212> TYPE: PRT
<213> ORGANISM: Homo sapiens

<400> SEQUENCE: 15

Pro Gln Asp Ala Ser Thr Lys Lys Ser Glu Cys Leu Lys Arg Ile Gly
1               5                   10                  15

Asp Glu Leu Asp Ser Asn Met Glu Leu
            20                  25

<210> SEQ ID NO 16
<211> LENGTH: 22
<212> TYPE: PRT
<213> ORGANISM: Homo sapiens

<400> SEQUENCE: 16

Pro Ser Ser Thr Met Gly Gln Val Gly Arg Gln Leu Ala Ile Ile Gly
1               5                   10                  15

Asp Asp Ile Asn Arg Arg
            20

<210> SEQ ID NO 17
<211> LENGTH: 14
<212> TYPE: PRT
<213> ORGANISM: Homo sapiens

<400> SEQUENCE: 17

Lys Gln Ala Leu Arg Glu Ala Gly Asp Glu Phe Glu Leu Arg
1               5                   10

<210> SEQ ID NO 18
<211> LENGTH: 22
<212> TYPE: PRT
<213> ORGANISM: Homo sapiens

<400> SEQUENCE: 18

Leu Ser Pro Pro Val Val His Leu Ala Leu Ala Leu Arg Gln Ala Gly
1               5                   10                  15

Asp Asp Phe Ser Arg Arg
            20

<210> SEQ ID NO 19
<211> LENGTH: 23
<212> TYPE: PRT
<213> ORGANISM: Homo sapiens

<400> SEQUENCE: 19

Glu Val Ile Pro Met Ala Ala Val Lys Gln Ala Leu Arg Glu Ala Gly
1               5                   10                  15

Asp Glu Phe Glu Leu Arg Tyr
            20

<210> SEQ ID NO 20
<211> LENGTH: 20
<212> TYPE: PRT
<213> ORGANISM: Homo sapiens

<400> SEQUENCE: 20

Pro Ala Asp Pro Leu His Gln Ala Met Arg Ala Ala Gly Asp Glu Phe
1               5                   10                  15
```

Glu Thr Arg Phe
            20

<210> SEQ ID NO 21
<211> LENGTH: 23
<212> TYPE: PRT
<213> ORGANISM: Homo sapiens

<400> SEQUENCE: 21

Ala Thr Ser Arg Lys Leu Glu Thr Leu Arg Arg Val Gly Asp Gly Val
1               5                   10                  15

Gln Arg Asn His Glu Thr Ala
            20

<210> SEQ ID NO 22
<211> LENGTH: 19
<212> TYPE: PRT
<213> ORGANISM: Homo sapiens

<400> SEQUENCE: 22

Leu Ala Glu Val Cys Thr Val Leu Leu Arg Leu Gly Asp Glu Leu Glu
1               5                   10                  15

Gln Ile Arg

<210> SEQ ID NO 23
<211> LENGTH: 19
<212> TYPE: PRT
<213> ORGANISM: Homo sapiens

<400> SEQUENCE: 23

Met Thr Val Gly Glu Leu Ser Arg Ala Leu Gly His Glu Asn Gly Ser
1               5                   10                  15

Leu Asp Pro

<210> SEQ ID NO 24
<211> LENGTH: 22
<212> TYPE: PRT
<213> ORGANISM: Homo sapiens

<400> SEQUENCE: 24

Val Val Glu Gly Glu Lys Glu Val Glu Ala Leu Lys Lys Ser Ala Asp
1               5                   10                  15

Trp Val Ser Asp Trp Ser
            20

<210> SEQ ID NO 25
<211> LENGTH: 20
<212> TYPE: PRT
<213> ORGANISM: Homo sapiens

<400> SEQUENCE: 25

Ser Met Ala Arg Asp Pro Gln Arg Tyr Leu Val Ile Gln Gly Asp Asp
1               5                   10                  15

Arg Met Lys Leu
            20

<210> SEQ ID NO 26
<211> LENGTH: 25
<212> TYPE: PRT
<213> ORGANISM: Homo sapiens
<220> FEATURE:
<221> NAME/KEY: MOD_RES
<222> LOCATION: (14)..(14)

-continued

```
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 26

Gln Glu Asp Ile Ile Arg Asn Ile Ala Arg His Leu Ala Xaa Val Gly
1               5                   10                  15

Asp Xaa Met Asp Arg Ser Ile Pro Pro
            20                  25

<210> SEQ ID NO 27
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 27

Asp Asn Arg Pro Glu Ile Trp Ile Ala Gln Glu Leu Arg Xaa Ile Gly
1               5                   10                  15

Asp Xaa Phe Asn Ala Tyr Tyr Ala Arg
            20                  25

<210> SEQ ID NO 28
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 28

Asn Leu Trp Ala Ala Gln Arg Tyr Gly Arg Glu Leu Arg Xaa Met Ser
1               5                   10                  15

Asp Xaa Phe Val Asp Ser Phe Lys Lys
            20                  25

<210> SEQ ID NO 29
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
```

```
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 29

Glu Glu Gln Trp Ala Arg Glu Ile Gly Ala Gln Leu Arg Xaa Met Ala
1               5                   10                  15

Asp Xaa Leu Asn Ala Gln Tyr Glu Arg
            20                  25

<210> SEQ ID NO 30
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 30

Arg Ser Ser Ala Ala Gln Leu Thr Ala Ala Arg Leu Lys Xaa Leu Gly
1               5                   10                  15

Asp Xaa Leu His Gln Arg Thr Met
            20

<210> SEQ ID NO 31
<211> LENGTH: 22
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: misc_feature
<222> LOCATION: (13)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any amino acid available for cross linking

<400> SEQUENCE: 31

Ala Glu Leu Pro Pro Glu Phe Ala Ala Gln Leu Arg Xaa Ile Gly Asp
1               5                   10                  15

Xaa Val Tyr Cys Thr Trp
            20

<210> SEQ ID NO 32
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
```

```
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 32

Val Pro Ala Asp Leu Lys Asp Glu Cys Ala Gln Leu Arg Xaa Ile Gly
1               5                   10                  15

Asp Xaa Val Asn Leu Arg Gln Lys Leu
            20                  25

<210> SEQ ID NO 33
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 33

Gln His Arg Ala Glu Val Gln Ile Ala Arg Lys Leu Gln Xaa Ile Ala
1               5                   10                  15

Asp Xaa Phe His Arg Leu His Thr
            20

<210> SEQ ID NO 34
<211> LENGTH: 22
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: misc_feature
<222> LOCATION: (13)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any amino acid available for cross linking

<400> SEQUENCE: 34

Ser Ser Ala Ala Gln Leu Thr Ala Ala Arg Leu Lys Xaa Leu Gly Asp
1               5                   10                  15

Xaa Leu His Gln Arg Thr
            20

<210> SEQ ID NO 35
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
```

```
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 35

Cys Met Glu Gly Ser Asp Ala Leu Ala Leu Arg Leu Ala Xaa Ile Gly
1               5                   10                  15

Asp Xaa Met Asp Val Ser Leu Arg Ala
            20                  25

<210> SEQ ID NO 36
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 36

Asp Ile Glu Arg Arg Lys Glu Val Glu Ser Ile Leu Lys Xaa Asn Ser
1               5                   10                  15

Asp Xaa Ile Trp Asp Trp Ser Ser
            20

<210> SEQ ID NO 37
<211> LENGTH: 22
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking

<400> SEQUENCE: 37

Gly Arg Leu Ala Glu Val Cys Ala Val Leu Leu Xaa Leu Gly Asp Xaa
1               5                   10                  15

Leu Glu Met Ile Arg Pro
            20

<210> SEQ ID NO 38
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
```

<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 38

Pro Gln Asp Ala Ser Thr Lys Lys Ser Glu Cys Leu Lys Xaa Ile Gly
1               5                   10                  15

Asp Xaa Leu Asp Ser Asn Met Glu Leu
            20                  25

<210> SEQ ID NO 39
<211> LENGTH: 22
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 39

Pro Ser Ser Thr Met Gly Gln Val Gly Arg Gln Leu Ala Xaa Ile Gly
1               5                   10                  15

Asp Xaa Ile Asn Arg Arg
            20

<210> SEQ ID NO 40
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Any amino acid available for cross linking
<220> FEATURE:
<221> NAME/KEY: misc_feature
<222> LOCATION: (6)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any amino acid available for cross linking

<400> SEQUENCE: 40

Lys Gln Ala Leu Arg Xaa Ala Gly Asp Xaa Phe Glu Leu Arg
1               5                   10

<210> SEQ ID NO 41
<211> LENGTH: 22
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)

<223> OTHER INFORMATION: Any amino acid available for cross linking

<400> SEQUENCE: 41

Leu Ser Pro Pro Val Val His Leu Ala Leu Ala Leu Arg Xaa Ala Gly
1               5                   10                  15

Asp Xaa Phe Ser Arg Arg
            20

<210> SEQ ID NO 42
<211> LENGTH: 23
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 42

Glu Val Ile Pro Met Ala Ala Val Lys Gln Ala Leu Arg Xaa Ala Gly
1               5                   10                  15

Asp Xaa Phe Glu Leu Arg Tyr
            20

<210> SEQ ID NO 43
<211> LENGTH: 20
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Any amino acid available for cross linking
<220> FEATURE:
<221> NAME/KEY: misc_feature
<222> LOCATION: (11)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross linking

<400> SEQUENCE: 43

Pro Ala Asp Pro Leu His Gln Ala Met Arg Xaa Ala Gly Asp Xaa Phe
1               5                   10                  15

Glu Thr Arg Phe
            20

<210> SEQ ID NO 44
<211> LENGTH: 23
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Any amino acid available for cross linking
<220> FEATURE:
<221> NAME/KEY: misc_feature
<222> LOCATION: (11)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross linking -continued

<400> SEQUENCE: 44

Ala Thr Ser Arg Lys Leu Glu Thr Leu Arg Xaa Val Gly Asp Xaa Val
1               5                   10                  15

Gln Arg Asn His Glu Thr Ala
            20

<210> SEQ ID NO 45
<211> LENGTH: 19
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Any amino acid available for cross linking
<220> FEATURE:
<221> NAME/KEY: misc_feature
<222> LOCATION: (10)..(14)
<223> OTHER INFORMATION: Crosslink between residues
<220> FEATURE:
<221> NAME/KEY: MOD_RES
<222> LOCATION: (14)..(14)
<223> OTHER INFORMATION: Any amino acid available for cross linking

<400> SEQUENCE: 45

Leu Ala Glu Val Cys Thr Val Leu Leu Xaa Leu Gly Asp Xaa Leu Glu
1               5                   10                  15

Gln Ile Arg

<210> SEQ ID NO 46
<211> LENGTH: 19
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking

<400> SEQUENCE: 46

Met Thr Val Gly Glu Leu Ser Arg Ala Leu Gly Xaa Glu Asn Gly Xaa
1               5                   10                  15

Leu Asp Pro

<210> SEQ ID NO 47
<211> LENGTH: 22
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: misc_feature
<222> LOCATION: (13)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any amino acid available for cross linking

<400> SEQUENCE: 47

```
Val Val Glu Gly Glu Lys Glu Val Glu Ala Leu Lys Xaa Ser Ala Asp
1               5                   10                  15

Xaa Val Ser Asp Trp Ser
            20

<210> SEQ ID NO 48
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking

<400> SEQUENCE: 48

Ser Met Ala Arg Asp Pro Gln Arg Tyr Leu Val Xaa Gln Gly Asp Xaa
1               5                   10                  15

Arg Met Lys Leu
            20

<210> SEQ ID NO 49
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 49

Gln Glu Asp Ile Ile Arg Asn Ile Xaa Arg His Leu Xaa Gln Val Gly
1               5                   10                  15

Asp Ser Met Asp Arg Ser Ile Pro Pro
            20                  25

<210> SEQ ID NO 50
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 50

Asp Asn Arg Pro Glu Ile Trp Ile Xaa Gln Glu Leu Xaa Arg Ile Gly
```

```
                1               5                   10                  15
Asp Glu Phe Asn Ala Tyr Tyr Ala Arg
                20                  25

<210> SEQ ID NO 51
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 51

Asn Leu Trp Ala Ala Gln Arg Tyr Xaa Arg Glu Leu Xaa Arg Met Ser
1               5                   10                  15

Asp Glu Phe Val Asp Ser Phe Lys Lys
                20                  25

<210> SEQ ID NO 52
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 52

Glu Glu Gln Trp Ala Arg Glu Ile Xaa Ala Gln Leu Xaa Arg Met Ala
1               5                   10                  15

Asp Asp Leu Asn Ala Gln Tyr Glu Arg
                20                  25

<210> SEQ ID NO 53
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 53

Arg Ser Ser Ala Ala Gln Leu Thr Xaa Ala Arg Leu Xaa Ala Leu Gly
1               5                   10                  15
```

```
Asp Glu Leu His Gln Arg Thr Met
            20

<210> SEQ ID NO 54
<211> LENGTH: 22
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Any amino acid available for cross linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross linking

<400> SEQUENCE: 54

Ala Glu Leu Pro Pro Glu Phe Xaa Ala Gln Leu Xaa Lys Ile Gly Asp
1               5                   10                  15

Lys Val Tyr Cys Thr Trp
            20

<210> SEQ ID NO 55
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 55

Val Pro Ala Asp Leu Lys Asp Glu Xaa Ala Gln Leu Xaa Arg Ile Gly
1               5                   10                  15

Asp Lys Val Asn Leu Arg Gln Lys Leu
            20                  25

<210> SEQ ID NO 56
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 56

Gln His Arg Ala Glu Val Gln Ile Xaa Arg Lys Leu Xaa Cys Ile Ala
1               5                   10                  15
```

-continued

Asp Gln Phe His Arg Leu His Thr
            20

<210> SEQ ID NO 57
<211> LENGTH: 22
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Any amino acid available for cross linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross linking

<400> SEQUENCE: 57

Ser Ser Ala Ala Gln Leu Thr Xaa Ala Arg Leu Xaa Ala Leu Gly Asp
1               5                   10                  15

Glu Leu His Gln Arg Thr
            20

<210> SEQ ID NO 58
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 58

Cys Met Glu Gly Ser Asp Ala Leu Xaa Leu Arg Leu Xaa Cys Ile Gly
1               5                   10                  15

Asp Glu Met Asp Val Ser Leu Arg Ala
            20                  25

<210> SEQ ID NO 59
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 59

Asp Ile Glu Arg Arg Lys Glu Val Xaa Ser Ile Leu Xaa Lys Asn Ser
1               5                   10                  15

Asp Trp Ile Trp Asp Trp Ser Ser

<210> SEQ ID NO 60
<211> LENGTH: 22
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Any amino acid available for cross linking
<220> FEATURE:
<221> NAME/KEY: misc_feature
<222> LOCATION: (7)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid available for cross linking

<400> SEQUENCE: 60

Gly Arg Leu Ala Glu Val Xaa Ala Val Leu Xaa Arg Leu Gly Asp Glu
1               5                   10                  15

Leu Glu Met Ile Arg Pro
            20

<210> SEQ ID NO 61
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 61

Pro Gln Asp Ala Ser Thr Lys Lys Xaa Glu Cys Leu Xaa Arg Ile Gly
1               5                   10                  15

Asp Glu Leu Asp Ser Asn Met Glu Leu
            20                  25

<210> SEQ ID NO 62
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 62

Pro Ser Ser Thr Met Gly Gln Val Xaa Arg Gln Leu Xaa Ile Ile Gly
1               5                   10                  15

Asp Asp Ile Asn Arg Arg
            20

```
<210> SEQ ID NO 63
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any amino acid available for cross linking
<220> FEATURE:
<221> NAME/KEY: misc_feature
<222> LOCATION: (1)..(5)
<223> OTHER INFORMATION: Crosslink between residues
<220> FEATURE:
<221> NAME/KEY: MOD_RES
<222> LOCATION: (5)..(5)
<223> OTHER INFORMATION: Any amino acid available for cross linking

<400> SEQUENCE: 63

Xaa Gln Ala Leu Xaa Glu Ala Gly Asp Glu Phe Glu Leu Arg
1               5                   10

<210> SEQ ID NO 64
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 64

Leu Ser Pro Pro Val Val His Leu Xaa Leu Ala Leu Xaa Gln Ala Gly
1               5                   10                  15

Asp Asp Phe Ser Arg Arg
            20

<210> SEQ ID NO 65
<211> LENGTH: 23
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 65

Glu Val Ile Pro Met Ala Ala Val Xaa Gln Ala Leu Xaa Glu Ala Gly
1               5                   10                  15

Asp Glu Phe Glu Leu Arg Tyr
            20

<210> SEQ ID NO 66
<211> LENGTH: 20
```

```
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Any amino acid available for cross linking
<220> FEATURE:
<221> NAME/KEY: misc_feature
<222> LOCATION: (6)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any amino acid available for cross linking

<400> SEQUENCE: 66

Pro Ala Asp Pro Leu Xaa Gln Ala Met Xaa Ala Ala Gly Asp Glu Phe
1               5                   10                  15

Glu Thr Arg Phe
            20

<210> SEQ ID NO 67
<211> LENGTH: 23
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Any amino acid available for cross linking
<220> FEATURE:
<221> NAME/KEY: misc_feature
<222> LOCATION: (6)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any amino acid available for cross linking

<400> SEQUENCE: 67

Ala Thr Ser Arg Lys Xaa Glu Thr Leu Xaa Arg Val Gly Asp Gly Val
1               5                   10                  15

Gln Arg Asn His Glu Thr Ala
            20

<210> SEQ ID NO 68
<211> LENGTH: 19
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Any amino acid available for cross linking
<220> FEATURE:
<221> NAME/KEY: misc_feature
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Any amino acid available for cross linking

<400> SEQUENCE: 68

Leu Ala Glu Val Xaa Thr Val Leu Xaa Arg Leu Gly Asp Glu Leu Glu
1               5                   10                  15

Gln Ile Arg

<210> SEQ ID NO 69
<211> LENGTH: 19
<212> TYPE: PRT
<213> ORGANISM: Homo sapiens
```

```
<220> FEATURE:
<221> NAME/KEY: MOD_RES
<222> LOCATION: (7)..(7)
<223> OTHER INFORMATION: Any amino acid available for cross linking
<220> FEATURE:
<221> NAME/KEY: misc_feature
<222> LOCATION: (7)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid available for cross linking

<400> SEQUENCE: 69

Met Thr Val Gly Glu Leu Xaa Arg Ala Leu Xaa His Glu Asn Gly Ser
1               5                   10                  15

Leu Asp Pro

<210> SEQ ID NO 70
<211> LENGTH: 22
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Any amino acid available for cross linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross linking

<400> SEQUENCE: 70

Val Val Glu Gly Glu Lys Glu Xaa Glu Ala Leu Xaa Lys Ser Ala Asp
1               5                   10                  15

Trp Val Ser Asp Trp Ser
            20

<210> SEQ ID NO 71
<211> LENGTH: 20
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Any amino acid available for cross linking
<220> FEATURE:
<221> NAME/KEY: misc_feature
<222> LOCATION: (7)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid available for cross linking

<400> SEQUENCE: 71

Ser Met Ala Arg Asp Pro Xaa Arg Tyr Leu Xaa Ile Gln Gly Asp Asp
1               5                   10                  15

Arg Met Lys Leu
            20

<210> SEQ ID NO 72
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine

<400> SEQUENCE: 72

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 73
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 73

Ile Trp Ile Ala Gln Glu Leu Arg Xaa Ile Gly Asp Xaa Phe Asn Ala
1               5                   10                  15

Tyr Tyr Ala Arg Arg
            20

<210> SEQ ID NO 74
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 74

Arg Trp Ile Ala Gln Ala Leu Arg Xaa Ile Gly Asp Xaa Phe Asn Ala
```

```
1               5                  10                 15

Phe Tyr Ala Arg Arg
            20

<210> SEQ ID NO 75
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 75

Arg Trp Ile Ala Gln Ala Leu Arg Xaa Ile Gly Asn Xaa Phe Asn Ala
1               5                  10                 15

Tyr Tyr Ala Arg Arg
            20

<210> SEQ ID NO 76
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 76

Ile Trp Ile Ala Gln Ala Leu Arg Xaa Ile Gly Asn Xaa Phe Asn Ala
1               5                  10                 15

Tyr Tyr Ala Arg Arg
            20

<210> SEQ ID NO 77
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
```

```
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 77

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 78
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 78

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 79
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
```

```
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 79

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 80
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 80

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
```

```
<220> FEATURE:
<223> OTHER INFORMATION: C-term amidated

<400> SEQUENCE: 81

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 82

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 83
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 83
```

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 84

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 85
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 85

Asp Ile Ile Arg Asn Ile Ala Arg His Leu Ala Xaa Val Gly Asp Xaa
1               5                   10                  15

Xaa Asp Arg Ser Ile
            20

```
<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 86

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 87
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 87

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 88
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 88

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 89
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 89

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 90
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 90

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 91
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 91

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 92
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
```

```
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 92

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 93

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 94
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
```

-continued

```
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 94

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 95

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
```

```
<222> LOCATION: (17)..(17)
<223> OTHER INFORMATION: Norleucine
<220> FEATURE:
<223> OTHER INFORMATION: C-term amidated

<400> SEQUENCE: 96

Asp Ile Ile Arg Asn Ile Ala Arg His Leu Ala Xaa Val Glu Asp Xaa
1               5                   10                  15

Xaa Asp Arg Ser Ile
            20

<210> SEQ ID NO 97
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (17)..(17)
<223> OTHER INFORMATION: Norleucine
<220> FEATURE:
<223> OTHER INFORMATION: C-term amidated

<400> SEQUENCE: 97

Asp Ile Ile Arg Asn Ile Ala Arg His Leu Ala Gln Val Gly Asp Ser
1               5                   10                  15

Xaa Asp Arg Ser Ile
            20

<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 98

Ile Trp Ile Ala Gln Glu Leu Arg Xaa Ile Gly Asp Xaa Phe Asn Ala
1               5                   10                  15

Tyr Tyr Ala Arg Arg
            20

<210> SEQ ID NO 99
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 99

Ile Trp Ile Ala Gln Glu Leu Arg Xaa Ile Glu Asp Xaa Phe Asn Ala
1               5                   10                  15

Tyr Tyr Ala Arg Arg
            20

<210> SEQ ID NO 100
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 100

Ile Trp Ile Ala Gln Glu Leu Arg Arg Ile Gly Asp Glu Phe Asn Ala
1               5                   10                  15

Tyr Tyr Ala Arg Arg
            20

<210> SEQ ID NO 101
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Propionyl-Arg
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (11)..(11)
<223> OTHER INFORMATION: 2-aminoisobutyric acid
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: MOD_RES
<222> LOCATION: (14)..(14)
<223> OTHER INFORMATION: Norleucine
<220> FEATURE:
```

<223> OTHER INFORMATION: C-term amidated

<400> SEQUENCE: 101

Arg Asn Ile Ala Arg His Leu Ala Xaa Val Xaa Asp Xaa Xaa Asp Arg
1               5                   10                  15

Ser Ile

<210> SEQ ID NO 102
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Propionyl-Arg
<220> FEATURE:
<221> NAME/KEY: MOD_RES
<222> LOCATION: (8)..(8)
<223> OTHER INFORMATION: 2-aminoisobutyric acid
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (11)..(11)
<223> OTHER INFORMATION: 2-aminoisobutyric acid
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: MOD_RES
<222> LOCATION: (14)..(14)
<223> OTHER INFORMATION: Norleucine
<220> FEATURE:
<223> OTHER INFORMATION: C-term amidated

<400> SEQUENCE: 102

Arg Asn Ile Ala Arg His Leu Xaa Xaa Val Xaa Asp Xaa Xaa Asp Arg
1               5                   10                  15

Ser Ile

<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Propionyl-Arg
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (11)..(11)
<223> OTHER INFORMATION: 2-aminoisobutyric acid

```
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 103

Arg Asn Ile Ala Arg His Leu Ala Xaa Val Xaa Asp Xaa Phe Ala Arg
1               5                   10                  15

Ser Ile

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Propionyl-Arg
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (15)..(15)
<223> OTHER INFORMATION: 2-aminoisobutyric acid
<220> FEATURE:
<223> OTHER INFORMATION: C-term amidated

<400> SEQUENCE: 104

Arg Asn Ile Ala Arg His Leu Ala Xaa Val Gly Asp Xaa Xaa Xaa Arg
1               5                   10                  15

Ser Ile

<210> SEQ ID NO 105
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
```

<223> OTHER INFORMATION: C-term amidated

<400> SEQUENCE: 105

Ile Trp Ile Ala Gln Ala Leu Arg Xaa Ile Gly Asp Xaa Phe Asn Ala
1               5                   10                  15

Tyr Tyr Ala Arg Arg
            20

<210> SEQ ID NO 106
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (12)..(12)
<223> OTHER INFORMATION: Norleucine
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 106

Arg Trp Ile Ala Gln Ala Leu Arg Xaa Ile Gly Xaa Xaa Phe Asn Ala
1               5                   10                  15

Tyr Tyr Ala Arg Arg
            20

<210> SEQ ID NO 107
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Propionyl-Arg
<220> FEATURE:
<221> NAME/KEY: MOD_RES
<222> LOCATION: (3)..(3)
<223> OTHER INFORMATION: Cyclohexylglycine
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (11)..(11)
<223> OTHER INFORMATION: 2-aminoisobutyric acid
<220> FEATURE:
<221> NAME/KEY: MOD_RES
<222> LOCATION: (13)..(13)
<223> OTHER INFORMATION: Any amino acid available for cross linking

```
<220> FEATURE:
<223> OTHER INFORMATION: C-term amidated

<400> SEQUENCE: 107

Arg Asn Xaa Ala Arg His Leu Ala Xaa Val Xaa Asp Xaa Phe Asn Ala
1               5                   10                  15

Tyr Tyr Ala Arg Arg
            20

<210> SEQ ID NO 108
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: MOD_RES
<222> LOCATION: (16)..(16)
<223> OTHER INFORMATION: 2-aminoisobutyric acid
<220> FEATURE:
<223> OTHER INFORMATION: C-term amidated

<400> SEQUENCE: 108

Ile Trp Ile Ala Gln Ala Leu Arg Xaa Ile Gly Asp Xaa Phe Asn Xaa
1               5                   10                  15

Tyr Tyr Ala Arg Arg
            20

<210> SEQ ID NO 109
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
```

<223> OTHER INFORMATION: C-term amidated

<400> SEQUENCE: 109

Arg Trp Ile Ala Gln Ala Leu Arg Xaa Ile Gly Asp Xaa Phe Asn Ala
1               5                   10                  15

Phe Tyr Ala Arg Arg
            20

<210> SEQ ID NO 110
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 110

Arg Trp Ile Ala Gln Ala Leu Arg Xaa Ile Gly Ala Xaa Phe Asn Ala
1               5                   10                  15

Tyr Tyr Ala Arg Arg
            20

<210> SEQ ID NO 111
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (6)..(6)
<223> OTHER INFORMATION: 2-aminoisobutyric acid
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: MOD_RES
<222> LOCATION: (16)..(16)
<223> OTHER INFORMATION: 2-aminoisobutyric acid
<220> FEATURE:
<223> OTHER INFORMATION: C-term amidated

<400> SEQUENCE: 111

Ile Trp Ile Ala Gln Xaa Leu Arg Xaa Ile Gly Asp Xaa Phe Asn Xaa

```
1               5                   10                  15

Tyr Tyr Ala Arg Arg
            20

<210> SEQ ID NO 112
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 112

Ile Trp Ile Ala Gln Gln Leu Arg Xaa Ile Gly Asp Xaa Phe Asn Ala
1               5                   10                  15

Tyr Tyr Ala Arg Arg
            20

<210> SEQ ID NO 113
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 113

Arg Trp Ile Ala Gln Gln Leu Arg Xaa Ile Gly Asp Xaa Phe Asn Ala
1               5                   10                  15

Tyr Tyr Ala Arg Arg
            20
```

```
<210> SEQ ID NO 114
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 114

Ile Trp Ile Ala Gln Ala Leu Arg Xaa Ile Gly Asp Xaa Phe Asn Ala
1               5                   10                  15

Arg Arg Ala

<210> SEQ ID NO 115
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 115

Ile Trp Ile Ala Gln Ala Leu Arg Xaa Ile Gly Asp Xaa Phe Asn Ala
1               5                   10                  15

Tyr Lys Ala

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
```

```
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 116

Ile Trp Ile Ala Gln Ala Leu Arg Xaa Ile Gly Asp Xaa Phe Asn Ala
1               5                   10                  15

Tyr Lys

<210> SEQ ID NO 117
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 117

Arg Trp Ile Ala Gln Ala Leu Arg Xaa Ile Gly Asn Xaa Phe Asn Ala
1               5                   10                  15

Tyr Tyr Ala Arg Arg
            20

<210> SEQ ID NO 118
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated
```

-continued

```
<400> SEQUENCE: 118

Ile Trp Ile Ala Gln Ala Ala Arg Xaa Asp Ile Gly Xaa Ala Asn Ala
1               5                   10                  15

Tyr Tyr Ala Arg Arg
            20

<210> SEQ ID NO 119
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 119

Ile Trp Ile Ala Gln Ala Leu Arg Xaa Ile Gly Asn Xaa Phe Asn Ala
1               5                   10                  15

Tyr Tyr Ala Arg Arg
            20

<210> SEQ ID NO 120
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 120

Ile Trp Ile Ala Gln Ala Leu Arg Arg Ile Gly Asp Glu Phe Asn Ala
1               5                   10                  15

Tyr Tyr Ala Arg Arg
            20
```

THERAPEUTIC PEPTIDOMIMETIC MACROCYCLES

CROSS-REFERENCE

This application is a Continuation Application which claims the benefit of U.S. application Ser. No. 12/378,047, filed 9 Feb. 2009; which claims the benefit of U.S. Provisional Application No. 61/027,326 filed 8 Feb. 2008 and U.S. Provisional Application No. 61/120,380 filed 5 Dec. 2008, each of which applications is incorporated herein in its entirety by reference.

SEQUENCE LISTING

The instant application contains a Sequence Listing which has been submitted in ASCII format via EFS-Web and is hereby incorporated by reference in its entirety. Said ASCII copy, created on Feb. 16, 2012, is named 35224301.txt and is 65,421 bytes in size.

BACKGROUND OF THE INVENTION

Uncontrolled cell proliferation is implicated in a wide number of disorders ranging from cancer to immunoproliferative diseases. For example, in the U.S. alone, cancer surpasses heart disease as the leading cause of death for the largest fraction of the population (Journal of the National Cancer Institute, Vol. 97, No. 5, Mar. 2, 2005, p. 330) and contributes to more than 500,000 deaths annually. Despite decades of intense research efforts in this area, the treatment of cell proliferative disorders remains a challenge.

Therapeutic methods for cancer such as surgery or chemotherapy are still limited in terms of efficacy, side effect profile and cost. In particular, the efficacy and applicability of the available therapeutic options varies greatly by the specific type of tumor and disease. Thus, there remains a need for compositions and methods of treating cell proliferative disorders and other diseases.

SUMMARY OF THE INVENTION

The present invention addresses this and other needs. The invention provides compositions and methods of treatment based on the surprising finding that certain peptidomimetic macrocycles exhibit unexpected specificity, efficacy and potency when used for treatment of cell proliferative disorders.

In one aspect, the present invention provides a method of treating cancer in a human patient in need thereof comprising administering to the patient a peptidomimetic macrocycle, wherein the cancer is selected from the group consisting of small cell lung carcinoma, melanoma, ovarian cancer, prostate cancer, renal cancer, breast cancer, pancreatic cancer, and Ph+ acute lymphocytic leukemia (Ph+ ALL). In one embodiment, the peptidomimetic macrocycle comprises an α-helix. In another embodiment, the peptidomimetic macrocycle comprises a BH3 domain. The peptidomimetic macrocycle can be, for example, a BIM polypeptide. In some cases, an amino acid sequence of the BIM polypeptide is more than about 60% identical to an amino acid sequence IWIAQELR*IGD*FNAYYARR (SEQ ID NO: 1) wherein * is a tethered amino acid. Alternatively, the amino acid sequence of the BIM polypeptide is more than about 80% identical to an amino acid sequence IWIAQELR*IGD*FNAYYARR (SEQ ID NO: 1) wherein * is a tethered amino acid. Furthermore, an amino acid sequence of said BIM polypeptide may be more than about 95% identical to an amino acid sequence IWIAQELR*IGD*FNAYYARR (SEQ ID NO: 1) wherein * is a tethered amino acid. In some embodiments, the cancer is at least 2-fold less sensitive to treatment using a corresponding cross-linked BID polypeptide as measured in an in vitro cell viability assay. In other embodiments, the cancer is at least 5-fold less sensitive to treatment using a corresponding cross-linked BID polypeptide as measured in an in vitro cell viability assay. In yet other embodiments, the cancer is at least 8-fold less sensitive to treatment using a corresponding cross-linked BID polypeptide as measured in an in vitro cell viability assay.

In selected embodiments, the cancer is breast cancer, for example an invasive breast carcinoma such as an invasive ductal carcinoma. Alternatively, the cancer is prostate cancer. In other embodiments, the cancer is ovarian cancer. In still other embodiments, the cancer is pancreatic cancer. In further embodiments, the cancer is renal cancer. Alternatively, the cancer is Ph+ acute lymphocytic leukemia (Ph+ ALL).

The invention also provides a method of treating cancer in a human patient in need thereof comprising administering to the patient a peptidomimetic macrocycle, wherein the cancer is colon cancer. In one embodiment, the peptidomimetic macrocycle comprises an α-helix. In another embodiment, the peptidomimetic macrocycle comprises a BH3 domain. The peptidomimetic macrocycle can be, for example, a BID polypeptide. In some cases, an amino acid sequence of the BID polypeptide is more than about 60% identical to a sequence DIIRNIARHLA*VGD*NleDRSI (SEQ ID NO: 2) and wherein * is a tethered amino acid and Nle is norleucine. Alternatively, an amino acid sequence of the BID polypeptide is more than about 80% identical to a sequence DIIRNIARHLA*VGD*NleDRSI (SEQ ID NO: 2) wherein * is a tethered amino acid and Nle is norleucine. Furthermore, an amino acid sequence of said BID polypeptide may be more than about 95% identical to a sequence DIIRNIARHLA*VGD*NleDRSISEQ ID NO: 2) wherein * is a tethered amino acid and Nle is norleucine. In some embodiments, the cancer is at least 2-fold less sensitive to treatment using a corresponding cross-linked BIM polypeptide as measured in an in vitro cell viability assay. In other embodiments, the cancer is at least 5-fold less sensitive to treatment using a corresponding cross-linked BIM polypeptide as measured in an in vitro cell viability assay. In yet other embodiments, the cancer is at least 8-fold less sensitive to treatment using a corresponding cross-linked BIM polypeptide as measured in an in vitro cell viability assay.

Also provided is a method of treating cancer in a human patient in need thereof comprising administering to the patient a peptidomimetic macrocycle wherein said peptidomimetic macrocycle shows an $EC_{50}$ lower than about 5 μM when tested in an in vitro cell viability assay against a cell line derived from said cancer. In some embodiments, the $EC_{50}$ may be lower than about 4 μM. In other embodiments, the $EC_{50}$ may be lower than about 3 μM. In yet other embodiments, the $EC_{50}$ may be lower than about 2 μM. In yet other embodiments, the $EC_{50}$ may be lower than about 1 μM. In some embodiments, the in vitro assay is performed in the presence of serum. For example, the assay may be performed in 10% human serum. In some aspects, the cancer is selected from the group consisting of ovarian cancer, skin cancer, prostate cancer, renal cancer, breast cancer, pancreatic cancer, small-cell lung cancer, colon cancer, multiple myeloma, Burkitt's lymphoma, acute lymphocytic leukemia (ALL) of T cell lineage or B cell lineage or mixed lineage, chronic lymphocytic leukemia (CLL), cutaneous T cell lymphoma (CTCL), acute myelocytic leukemia (AML), chronic myelocytic leukemia, and follicular lymphoma.

In one aspect, the present invention provides a method of treating cancer in a human patient in need thereof comprising administering to the patient a peptidomimetic macrocycle, wherein the cancer is selected from the group consisting of ovarian cancer, prostate cancer, renal cancer, breast cancer, pancreatic cancer, and Ph+ acute lymphocytic leukemia. In one embodiment, the peptidomimetic macrocycle comprises an α-helix. In another embodiment, the peptidomimetic macrocycle comprises a BH3 domain. The peptidomimetic macrocycle can be, for example, a BIM polypeptide. In some cases, an amino acid sequence of the BIM polypeptide is more than about 60% identical to an amino acid sequence IWIAQELR*IGD*FNAYYARR (SEQ ID NO: 1) wherein * is a tethered amino acid. Alternatively, the amino acid sequence of the BIM polypeptide is more than about 80% identical to an amino acid sequence IWIAQELR*IGD*FNAYYARR (SEQ ID NO: 1) wherein * is a tethered amino acid. Furthermore, an amino acid sequence of said BIM polypeptide may be more than about 95% identical to an amino acid sequence IWIAQELR*IGD*FNAYYARR (SEQ ID NO: 1) wherein * is a tethered amino acid.

In some embodiments, the cancer is selected from the group consisting of colon cancer, small-cell lung cancer, liver cancer, ovarian cancer, skin cancer, prostate cancer, renal cancer, breast cancer, pancreatic cancer, glioma, multiple myeloma, Burkitt's lymphoma, acute lymphocytic leukemia (ALL) of T cell lineage or B cell lineage or mixed lineage, chronic lymphocytic leukemia (CLL), cutaneous T cell lymphoma (CTCL), acute myelocytic leukemia (AML), chronic myelocytic leukemia and follicular lymphoma. In one embodiment, the peptidomimetic macrocycle comprises an α-helix. In another embodiment, the peptidomimetic macrocycle comprises a BH3 domain. The peptidomimetic macrocycle can be, for example, a BID polypeptide. In some cases, an amino acid sequence of the BID polypeptide is more than about 60% identical to a sequence DIIRNIARHLA*VGD*NleDRSI (SEQ ID NO: 2) and wherein * is a tethered amino acid and Nle is norleucine. Alternatively, an amino acid sequence of the BID polypeptide is more than about 80% identical to a sequence DIIRNIARHLA*VGD*NleDRSI (SEQ ID NO: 2) wherein * is a tethered amino acid and Nle is norleucine. Furthermore, an amino acid sequence of said BID polypeptide may be more than about 95% identical to a sequence DIIRNIARHLA*VGD*NleDRSI (SEQ ID NO: 2) wherein * is a tethered amino acid and Nle is norleucine.

The present invention additionally provides a method of treating a disorder in a human patient in need thereof comprising administering to the patient a peptidomimetic macrocycle, comprising a) preparing a peptidomimetic macrocycle by introducing a cross-link between two amino acid residues of a polypeptide; b) testing the peptidomimetic macrocycle for the presence or absence of an immunogenic response; and c) administering the peptidomimetic macrocycle to a patient if said immunogenic response does not cause a substantial side-effect. The non-immunogenicity may be evidenced as minimal antibody response in an in vivo assay in rodents such as mice, in non-human primates, or in humans. When administered to a human patient, a compound which is nonimmunogenic may induce no substantial or minimal side-effects related to its immunogenicity in the patient. The disorder may be, for example, cancer, a metabolic disease, cardiovascular disease, inflammatory disease or a degenerative disease. In one embodiment, the peptidomimetic macrocycle comprises an α-helix. In another embodiment, the peptidomimetic macrocycle comprises a BH3 domain. The peptidomimetic macrocycle can be, for example, a BID polypeptide. In some cases, an amino acid sequence of the BID polypeptide is more than about 60% identical to a sequence DIIRNIARHLA*VGD*NleDRSI (SEQ ID NO: 2) and wherein * is a tethered amino acid and Nle is norleucine. Alternatively, an amino acid sequence of the BID polypeptide is more than about 80% identical to a sequence DIIRNIARHLA*VGD*NleDRSI (SEQ ID NO: 2) wherein * is a tethered amino acid and Nle is norleucine. Furthermore, an amino acid sequence of said BID polypeptide may be more than about 95% identical to a sequence DIIRNIARHLA*VGD*NleDRSI (SEQ ID NO: 2) wherein * is a tethered amino acid and Nle is norleucine. The peptidomimetic macrocycle may also be, for example, a BIM polypeptide. In some cases, an amino acid sequence of the BIM polypeptide is more than about 60% identical to an amino acid sequence IWIAQELR*IGD*FNAYYARR (SEQ ID NO: 1) wherein * is a tethered amino acid. Alternatively, the amino acid sequence of the BIM polypeptide is more than about 80% identical to an amino acid sequence IWIAQELR*IGD*FNAYYARR (SEQ ID NO: 1) wherein * is a tethered amino acid. Furthermore, an amino acid sequence of said BIM polypeptide may be more than about 95% identical to an amino acid sequence IWIAQELR*IGD*FNAYYARR (SEQ ID NO: 1) wherein * is a tethered amino acid.

In another aspect, the invention provides a method of treating an immunoproliferative disorder in a human patient in need thereof comprising administering to the patient a peptidomimetic macrocycle. The peptidomimetic macrocycle may reduce activated hPBL proliferation by more than about 5%, 10%, 20%, 30%, 40%, or 50% in an in vitro BrdU incorporation assay. The immunoproliferative disease may be, for example, a lymphoproliferative disorder, or an autoimmune disease, for example, systemic lupus erythematosus. The peptidomimetic macrocycle can be, for example, a BID polypeptide. In some cases, an amino acid sequence of the BID polypeptide is more than about 60% identical to a sequence DIIRNIARHLA*VGD*NleDRSI (SEQ ID NO: 2) and wherein * is a tethered amino acid and Nle is norleucine. Alternatively, an amino acid sequence of the BID polypeptide is more than about 80% identical to a sequence DIIRNIARHLA*VGD*NleDRSI (SEQ ID NO: 2) wherein * is a tethered amino acid and Nle is norleucine. Furthermore, an amino acid sequence of said BID polypeptide may be more than about 95% identical to a sequence DIIRNIARHLA*VGD*NleDRSI (SEQ ID NO: 2) wherein * is a tethered amino acid and Nle is norleucine. The peptidomimetic macrocycle may also be, for example, a BIM polypeptide. In some cases, an amino acid sequence of the BIM polypeptide is more than about 60% identical to an amino acid sequence IWIAQELR*IGD*FNAYYARR (SEQ ID NO: 1) wherein * is a tethered amino acid. Alternatively, the amino acid sequence of the BIM polypeptide is more than about 80% identical to an amino acid sequence IWIAQELR*IGD*FNAYYARR (SEQ ID NO: 1) wherein * is a tethered amino acid. Furthermore, an amino acid sequence of said BIM polypeptide may be more than about 95% identical to an amino acid sequence IWIAQELR*IGD*FNAYYARR (SEQ ID NO: 1) wherein * is a tethered amino acid.

For any of the peptidomimetic macrocyles disclosed above, an α-carbon atom in said peptidomimetic macrocycle may be additionally substituted with independent substituents of formula R—, wherein R— is alkyl, alkenyl, alkynyl, arylalkyl, cycloalkylalkyl, heteroalkyl, or heterocycloalkyl, unsubstituted or substituted with halo-. In some embodiments, an α-carbon atom to which the crosslinker is attached is additionally substituted with a substituent of formula R—. In other embodiments, an α-carbon atom to which the crosslinker is not attached is additionally substituted with a substituent of formula R—. Alternatively, two α-carbon atoms in a peptidomimetic macrocycle are additionally substituted with independent substituents of formula R—. In some embodiments, two α-carbon atoms to which the crosslinker is attached are additionally substituted with independent substituents of formula R—. In other embodiments, two α-carbon atoms to which the crosslinker is not attached are additionally substituted with independent substituents of formula R—. R— may be, for example, alkyl such as methyl, ethyl, propyl or isopropyl. The crosslinker may connect two α-carbon atoms. In some embodiments, R— and any portion of the crosslinker taken together form a cyclic structure. In other embodiments, the crosslinker is formed of consecutive carbon-carbon bonds. In still other embodiments, the crosslinker contains about 6, 7, 8, 9, 10, 11, 12 or 13 consecutive bonds. In yet other embodiments, the crosslinker comprises at least about 5, 6, 7, 8, or 9 carbon atoms.

Also provided is a method of treating cancer in a human patient in need thereof comprising administering to the patient a peptidomimetic macrocycle wherein said peptidomimetic macrocycle interacts with Mcl-1. In some embodiments, the peptidomimetic macrocycle antagonizes the interaction between Mcl-1 and pro-apoptotic proteins such as Bid, Bim, Bax or Bak. In other embodiments, the peptidomimetic macrocycles of the invention are used to treat cancer in a human patient wherein the cancer is resistant to ABT-737 or an analog thereof, or is resistant to a compound that possesses an affinity greater than 1, 2, 5 or 10 µM for Mcl-1.

The invention further provides a method of treating ABT-737 resistant small cell lung cancer in a human patient in need thereof comprising administering to the patient a peptidomimetic macrocycle, wherein the peptidomimetic macrocycle comprises a BH3 domain. The invention also provides a method of treating prostate cancer in a human patient in need thereof comprising administering to the patient a peptidomimetic macrocycle, wherein the peptidomimetic macrocycle comprises a BH3 domain.

In any of the methods of treatment indicated herein, the peptidomimetic macrocycle is administered in conjunction with a standard method of care. The standard method of care may, for example, be chemotherapy. Alternatively, the standard method of care may be radiation therapy. In a further embodiment, the standard method of care is surgery.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 24 shows the pharmacokinetic properties of SP-1 and SP-4 exhibit in rats.

DETAILED DESCRIPTION OF THE INVENTION

Figure 1:
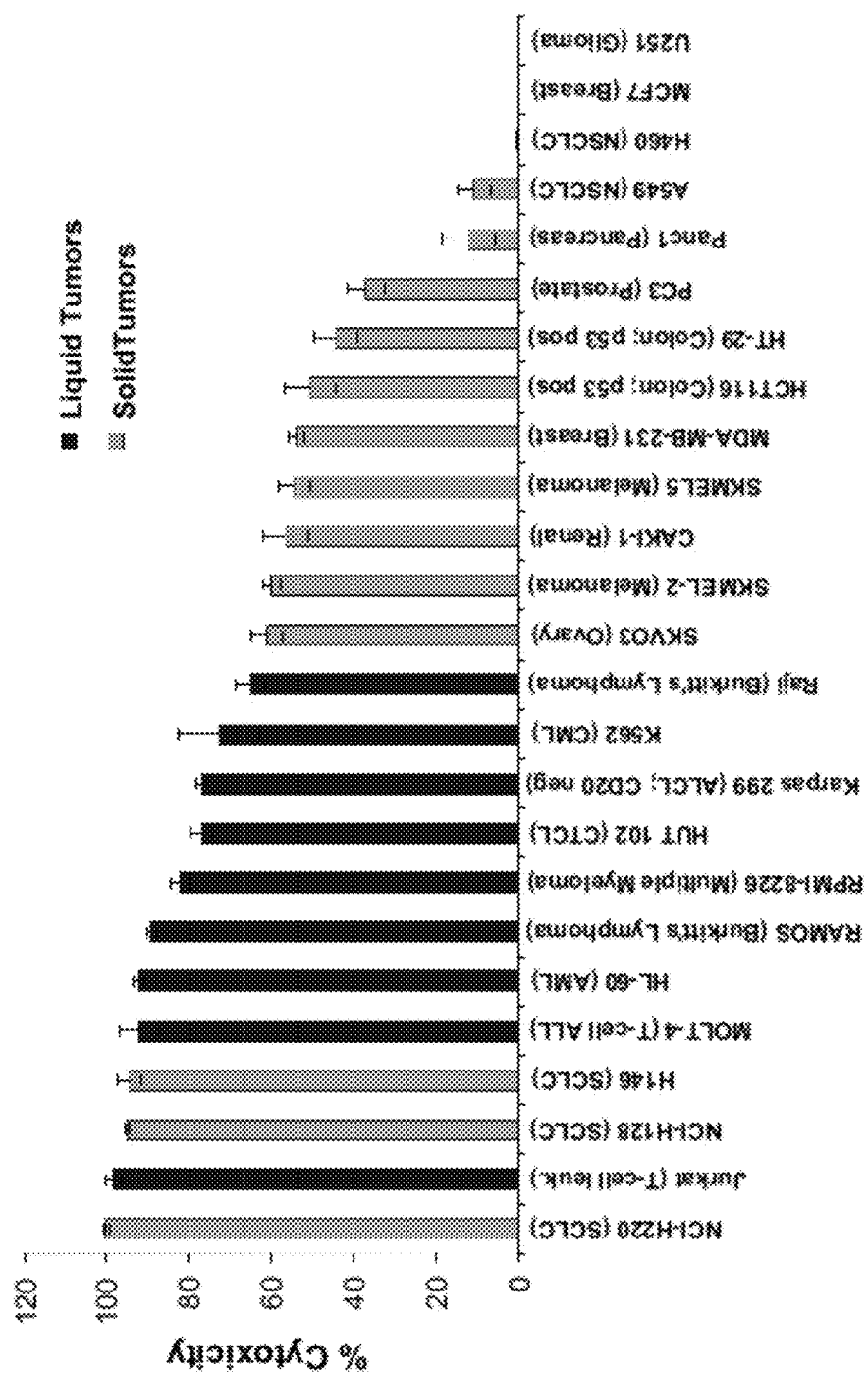
FIG. 1 shows the sensitivity of 24 different tumor cell lines to treatment with 20 µM SP-1.

As used herein, the terms "treating" and "to treat", mean to alleviate symptoms, eliminate the causation either on a temporary or permanent basis, or to prevent or slow the appearance of symptoms. The term "treatment" includes alleviation, elimination of causation (temporary or permanent) of, or prevention of symptoms and disorders associated with any condition. The treatment may be a pre-treatment as well as a treatment at the onset of symptoms.

The term "standard method of care" refers to any therapeutic or diagnostic method, compound, or practice which is part of the standard of care for a particular indication. The "standard of care" may be established by any authority such as a health care provider or a national or regional institute for any diagnostic or treatment process that a clinician should follow for a certain type of patient, illness, or clinical circumstance. Exemplary standard of care methods for various type of cancers are provided for instance by the National Cancer Institute.

As used herein, the term "cell proliferative disorder" encompasses cancer, hyperproliferative disorders, neoplastic disorders, immunoproliferative disorders and other disorders. A "cell proliferative disorder" relates to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A metastatic tumor can arise from a multitude of primary tumor types, including but not limited to those of breast, lung, liver, colon and ovarian origin. "Pathologic hyperproliferative" cells occur in disease states characterized by malignant tumor growth and immunoproliferative diseases. Examples of non-pathologic hyperproliferative cells include proliferation of cells associated with wound repair. Examples of cellular proliferative and/or differentiative disorders include cancer, e.g., carcinoma, sarcoma, or metastatic disorders.

The term "derived from" in the context of the relationship between a cell line and a related cancer signifies that the cell line may be established from any cancer in a specific broad category of cancers.

As used herein, the term "macrocycle" refers to a molecule having a chemical structure including a ring or cycle formed by at least 9 covalently bonded atoms.

As used herein, the term "peptidomimetic macrocycle", "crosslinked polypeptide" or "stapled peptide" refers to a compound comprising a plurality of amino acid residues joined by a plurality of peptide bonds and at least one macrocycle-forming linker which forms a macrocycle between a first naturally-occurring or non-naturally-occurring amino acid residue (or analog) and a second naturally-occurring or non-naturally-occurring amino acid residue (or analog) within the same molecule. Peptidomimetic macrocycles include embodiments where the macrocycle-forming linker connects the α carbon of the first amino acid residue (or analog) to the α carbon of the second amino acid residue (or analog). The peptidomimetic macrocycles optionally include one or more non-peptide bonds between one or more amino acid residues and/or amino acid analog residues, and optionally include one or more non-naturally-occurring amino acid residues or amino acid analog residues in addition to any which form the macrocycle.

As used herein, the term "stability" refers to the maintenance of a defined secondary structure in solution by a peptidomimetic macrocycle of the invention as measured by circular dichroism, NMR or another biophysical measure, or resistance to proteolytic degradation in vitro or in vivo. Non-limiting examples of secondary structures contemplated in this invention are α-helices, β-turns, and β-pleated sheets.

As used herein, the term "helical stability" refers to the maintenance of α helical structure by a peptidomimetic macrocycle of the invention as measured by circular dichroism or NMR. For example, in some embodiments, the peptidomimetic macrocycles of the invention exhibit at least a 1.25, 1.5, 1.75 or 2-fold increase in α-helicity as determined by circular dichroism compared to a corresponding uncrosslinked polypeptide.

The term "α-amino acid" or simply "amino acid" refers to a molecule containing both an amino group and a carboxyl group bound to a carbon which is designated the α-carbon. Suitable amino acids include, without limitation, both the D- and L-isomers of the naturally-occurring amino acids, as well as non-naturally occurring amino acids prepared by organic synthesis or other metabolic routes. Unless the context specifically indicates otherwise, the term amino acid, as used herein, is intended to include amino acid analogs.

The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The term "amino acid analog" or "non-natural amino acid" refers to a molecule which is structurally similar to an amino acid and which can be substituted for an amino acid in the formation of a peptidomimetic macrocycle Amino acid analogs include, without limitation, compounds which are structurally identical to an amino acid, as defined herein, except for the inclusion of one or more additional methylene groups between the amino and carboxyl group (e.g., α-amino β-carboxy acids), or for the substitution of the amino or carboxy group by a similarly reactive group (e.g., substitution of the primary amine with a secondary or tertiary amine, or substitution or the carboxy group with an ester).

A "non-essential" amino acid residue is a residue that can be altered from the wild-type sequence of a polypeptide (e.g., a BH3 domain or the p53 MDM2 binding domain) without abolishing or substantially altering its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a BH3 polypeptide, for example, is preferably replaced with another amino acid residue from the same side chain family. Other examples of acceptable substitutions are substitutions based on isosteric considerations (e.g. norleucine for methionine) or other properties (e.g. 2-thienylalanine for phenylalanine).

The term "member" as used herein in conjunction with macrocycles or macrocycle-forming linkers refers to the atoms that form or can form the macrocycle, and excludes substituent or side chain atoms. By analogy, cyclodecane, 1,2-difluoro-decane and 1,3-dimethyl cyclodecane are all considered ten-membered macrocycles as the hydrogen or fluoro substituents or methyl side chains do not participate in forming the macrocycle.

The symbol " ⫽ " when used as part of a molecular structure refers to a single bond or a trans or cis double bond.

The term "amino acid side chain" refers to a moiety attached to the α-carbon in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an α,α di-substituted amino acid).

The term "α,α di-substituted amino" acid refers to a molecule or moiety containing both an amino group and a carboxyl group bound to a carbon (the α-carbon) that is attached to two natural or non-natural amino acid side chains.

The term "polypeptide" encompasses two or more naturally or non-naturally-occurring amino acids joined by a covalent bond (e.g., an amide bond). Polypeptides as described herein include full length proteins (e.g., fully processed proteins) as well as shorter amino acid sequences (e.g., fragments of naturally-occurring proteins or synthetic polypeptide fragments).

The term "macrocyclization reagent" or "macrocycle-forming reagent" as used herein refers to any reagent which may be used to prepare a peptidomimetic macrocycle of the invention by mediating the reaction between two reactive groups. Reactive groups may be, for example, an azide and alkyne, in which case macrocyclization reagents include, without limitation, Cu reagents such as reagents which provide a reactive Cu(I) species, such as CuBr, CuI or CuOTf, as well as Cu(II) salts such as $Cu(CO_2CH_3)_2$, $CuSO_4$, and $CuCl_2$ that can be converted in situ to an active Cu(I) reagent by the addition of a reducing agent such as ascorbic acid or sodium ascorbate. Macrocyclization reagents may additionally include, for example, Ru reagents known in the art such as Cp*RuCl(PPh$_3$)$_2$, [Cp*RuCl]$_4$ or other Ru reagents which may provide a reactive Ru(II) species. In other cases, the reactive groups are terminal olefins. In such embodiments, the macrocyclization reagents or macrocycle-forming reagents are metathesis catalysts including, but not limited to, stabilized, late transition metal carbene complex catalysts such as Group VIII transition metal carbene catalysts. For example, such catalysts are Ru and Os metal centers having a +2 oxidation state, an electron count of 16 and pentacoordinated. Additional catalysts are disclosed in Grubbs et al., "Ring Closing Metathesis and Related Processes in Organic Synthesis" Acc. Chem. Res. 1995, 28, 446-452, and U.S. Pat. No. 5,811,515. In yet other cases, the reactive groups are thiol groups. In such embodiments, the macrocyclization reagent is, for example, a linker functionalized with two thiol-reactive groups such as halogen groups.

The term "halo" or "halogen" refers to fluorine, chlorine, bromine or iodine or a radical thereof.

The term "alkyl" refers to a hydrocarbon chain that is a straight chain or branched chain, containing the indicated number of carbon atoms. For example, $C_1$-$C_{10}$ indicates that the group has from 1 to 10 (inclusive) carbon atoms in it. In the absence of any numerical designation, "alkyl" is a chain (straight or branched) having 1 to 20 (inclusive) carbon atoms in it.

The term "alkylene" refers to a divalent alkyl (i.e., —R—).

The term "alkenyl" refers to a hydrocarbon chain that is a straight chain or branched chain having one or more carbon-carbon double bonds. The alkenyl moiety contains the indicated number of carbon atoms. For example, $C_2$-$C_{10}$ indicates that the group has from 2 to 10 (inclusive) carbon atoms in it. The term "lower alkenyl" refers to a $C_2$-$C_6$ alkenyl chain. In the absence of any numerical designation, "alkenyl" is a chain (straight or branched) having 2 to 20 (inclusive) carbon atoms in it.

The term "alkynyl" refers to a hydrocarbon chain that is a straight chain or branched chain having one or more carbon-carbon triple bonds. The alkynyl moiety contains the indicated number of carbon atoms. For example, $C_2$-$C_{10}$ indicates that the group has from 2 to 10 (inclusive) carbon atoms in it. The term "lower alkynyl" refers to a $C_2$-$C_6$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

"Arylalkyl" refers to an aryl group, as defined above, wherein one of the aryl group's hydrogen atoms has been replaced with a $C_1$-$C_5$ alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl.

"Arylamido" refers to an aryl group, as defined above, wherein one of the aryl group's hydrogen atoms has been replaced with one or more —C(O)NH$_2$ groups. Representative examples of an arylamido group include 2-C(O)NH2-phenyl, 3-C(O)NH$_2$-phenyl, 4-C(O)NH$_2$-phenyl, 2-C(O)NH$_2$-pyridyl, 3-C(O)NH$_2$-pyridyl, and 4-C(O)NH$_2$-pyridyl, "Alkylheterocycle" refers to a $C_1$-$C_5$ alkyl group, as defined above, wherein one of the $C_1$-$C_5$ alkyl group's hydrogen atoms has been replaced with a heterocycle. Representative examples of an alkylheterocycle group include, but are not limited to, —CH$_2$CH$_2$-morpholine, —CH$_2$CH$_2$-piperidine, —CH$_2$CH$_2$CH$_2$-morpholine, and —CH$_2$CH$_2$CH$_2$-imidazole.

"Alkylamido" refers to a $C_1$-$C_5$ alkyl group, as defined above, wherein one of the $C_1$-$C_5$ alkyl group's hydrogen atoms has been replaced with a —C(O)NH$_2$ group. Representative examples of an alkylamido group include, but are not limited to, —CH$_2$—C(O)NH$_2$, —CH$_2$CH$_2$—C(O)NH$_2$, —CH$_2$CH$_2$CH$_2$C(O)NH$_2$, —CH$_2$CH$_2$CH$_2$CH$_2$C(O)NH$_2$, —CH$_2$CH$_2$CH$_2$CH$_2$CH$_2$C(O)NH$_2$, —CH$_2$CH(C(O)NH$_2$)CH$_3$, —CH$_2$CH(C(O)NH$_2$)CH$_2$CH$_3$, —CH(C(O)NH$_2$)CH$_2$CH$_3$, —C(CH$_3$)$_2$CH$_2$C(O)NH$_2$, —CH$_2$—CH$_2$—NH—C(O)—CH$_3$, —CH$_2$—CH$_2$—NH—C(O)—CH$_3$—CH3, and —CH$_2$—CH$_2$—NH—C(O)—CH=CH$_2$.

"Alkanol" refers to a $C_1$-$C_5$ alkyl group, as defined above, wherein one of the $C_1$-$C_5$ alkyl group's hydrogen atoms has been replaced with a hydroxyl group. Representative examples of an alkanol group include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH(OH)CH$_3$, —CH$_2$CH(OH)CH$_2$CH$_3$, —CH(OH)CH$_3$ and —C(CH$_3$)$_2$CH$_2$OH.

"Alkylcarboxy" refers to a $C_1$-$C_5$ alkyl group, as defined above, wherein one of the $C_1$-$C_5$ alkyl group's hydrogen atoms has been replaced with a —COOH group. Representative examples of an alkylcarboxy group include, but are not limited to, —CH$_2$COOH, —CH$_2$CH$_2$COOH, —CH$_2$CH$_2$CH$_2$COOH, —CH$_2$CH$_2$CH$_2$CH$_2$COOH, —CH$_2$CH(COOH)CH$_3$, —CH$_2$CH$_2$CH$_2$CH$_2$CH$_2$COOH, —CH$_2$CH(COOH)CH$_2$CH$_3$, —CH(COOH)CH$_2$CH$_3$ and —C(CH$_3$)$_2$CH$_2$COOH.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Some cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2, 3, or 4 atoms of each ring are substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2 or 3 atoms of each ring are substituted by a substituent. Examples of heterocyclyl groups include piperazinyl, pyrrolidinyl, dioxanyl, morpholinyl, tetrahydrofuranyl, and the like.

The term "substituent" refers to a group replacing a second atom or group such as a hydrogen atom on any molecule, compound or moiety. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

In some embodiments, the compounds of this invention contain one or more asymmetric centers and thus occur as racemates and racemic mixtures, single enantiomers, individual diastereomers and diastereomeric mixtures. All such isomeric forms of these compounds are included in the present invention unless expressly provided otherwise. In some embodiments, the compounds of this invention are also represented in multiple tautomeric forms, in such instances, the invention includes all tautomeric forms of the compounds described herein (e.g., if alkylation of a ring system results in alkylation at multiple sites, the invention includes all such reaction products). All such isomeric forms of such compounds are included in the present invention unless expressly provided otherwise. All crystal forms of the compounds described herein are included in the present invention unless expressly provided otherwise.

As used herein, the terms "increase" and "decrease" mean, respectively, to cause a statistically significantly (i.e., $p<0.1$) increase or decrease of at least 5%.

As used herein, the recitation of a numerical range for a variable is intended to convey that the invention may be practiced with the variable equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, or any other real values >0 and <2 if the variable is inherently continuous.

As used herein, unless specifically indicated otherwise, the word "or" is used in the inclusive sense of "and/or" and not the exclusive sense of "either/or."

The term "on average" represents the mean value derived from performing at least three independent replicates for each data point.

The term "biological activity" encompasses structural and functional properties of a macrocycle of the invention. Biological activity is, for example, structural stability, alpha-helicity, affinity for a target, resistance to proteolytic degradation, cell penetrability, intracellular stability, in vivo stability, or any combination thereof.

The details of one or more particular embodiments of the invention are set forth in the accompanying drawings and the description below. Other features, objects, and advantages of the invention will be apparent from the description and drawings, and from the claims.

Design of the Peptidomimetic Macrocycles of the Invention

Any protein or polypeptide with a known primary amino acid sequence which contains a helical structure believed to impart biological activity is the subject of the present invention. For example, the sequence of the polypeptide can be analyzed and amino acid analogs containing groups reactive with macrocyclization reagents can be substituted at the appropriate positions. The appropriate positions are determined by ascertaining which molecular surface(s) of the secondary structure is (are) required for biological activity and, therefore, across which other surface(s) the macrocycle forming linkers of the invention can form a macrocycle without sterically blocking the surface(s) required for biological activity. Such determinations are made using methods such as X-ray crystallography of complexes between the secondary structure and a natural binding partner to visualize residues (and surfaces) critical for activity; by sequential mutagenesis of residues in the secondary structure to functionally identify residues (and surfaces) critical for activity; or by other methods. By such determinations, the appropriate amino acids are substituted with the amino acids analogs and macrocycle-forming linkers of the invention. For example, for an α-helical secondary structure, one surface of the helix (e.g., a molecular surface extending longitudinally along the axis of the helix and radially 45-135° about the axis of the helix) may be required to make contact with another biomolecule in vivo or in vitro for biological activity. In such a case, a macrocycle-forming linker is designed to link two α-carbons of the helix while extending longitudinally along the surface of the helix in the portion of that surface not directly required for activity.

In some embodiments of the invention, the peptide sequence is derived from the BCL-2 family of proteins. The BCL-2 family is defined by the presence of up to four conserved BCL-2 homology (BH) domains designated BH1, BH2, BH3, and BH4, all of which include α-helical segments (Chittenden et al. (1995), *EMBO* 14:5589; Wang et al. (1996), *Genes Dev.* 10:2859). Anti-apoptotic proteins, such as BCL-2 and BCL-$X_L$, display sequence conservation in all BH domains. Pro-apoptotic proteins are divided into "multidomain" family members (e.g., BAK, BAX), which possess homology in the BH1, BH2, and BH3 domains, and "BH3-domain only" family members (e.g., BID, BAD, BIM, BIK, NOXA, PUMA), that contain sequence homology exclusively in the BH3 amphipathic α-helical segment. BCL-2 family members have the capacity to form homo- and heterodimers, suggesting that competitive binding and the ratio between pro- and anti-apoptotic protein levels dictates susceptibility to death stimuli. Anti-apoptotic proteins function to protect cells from pro-apoptotic excess, i.e., excessive programmed cell death. Additional "security" measures include regulating transcription of pro-apoptotic proteins and maintaining them as inactive conformers, requiring either proteolytic activation, dephosphorylation, or ligand-induced conformational change to activate pro-death functions. In certain cell types, death signals received at the plasma membrane trigger apoptosis via a mitochondrial pathway. The mitochondria can serve as a gatekeeper of cell death by sequestering cytochrome c, a critical component of a cytosolic complex which activates caspase 9, leading to fatal downstream proteolytic events. Multidomain proteins such as BCL-2/BCL-$X_L$ and BAK/BAX play dueling roles of guardian and executioner at the mitochondrial membrane, with their activities further regulated by upstream BH3-only members of the BCL-2 family. For example, BID is a member of the BH3-domain only family of pro-apoptotic proteins, and transmits death signals received at the plasma membrane to effector pro-apoptotic proteins at the mitochondrial membrane. BID has the capability of interacting with both pro- and anti-apoptotic proteins, and upon activation by caspase 8, triggers cytochrome c release and mitochondrial apoptosis. Deletion and mutagenesis studies determined that the amphipathic α-helical BH3 segment of pro-apoptotic family members may function as a death domain and thus may represent a critical structural motif for interacting with multidomain apoptotic proteins. Structural studies have shown that the BH3 helix can interact with anti-apoptotic proteins by inserting into a hydrophobic groove formed by the interface of BH1, 2 and 3 domains. Activated BID can be bound and sequestered by anti-apoptotic proteins (e.g., BCL-2 and BCL-$X_L$) and can trigger activation of the pro-apoptotic proteins BAX and BAK, leading to cytochrome c release and a mitochondrial apoptosis program. BAD is also a BH3-domain only pro-apoptotic family member whose expression triggers the activation of BAX/BAK. In contrast to BID, however, BAD displays preferential binding to anti-apoptotic family members, BCL-2 and BCL-X$_L$. Whereas the BAD BH3 domain exhibits high affinity binding to BCL-2, BAD BH3 peptide is unable to activate cytochrome c release from mitochondria in vitro, suggesting that BAD is not a direct activator of BAX/BAK. Mitochondria that over-express BCL-2 are resistant to BID-induced cytochrome c release, but co-treatment with BAD can restore BID sensitivity. Induction of mitochondrial apoptosis by BAD appears to result from either: (1) displacement of BAX/BAK activators, such as BID and BID-like proteins, from the BCL-2/BCL-XL binding pocket, or (2) selective occupation of the BCL-2/BCL-XL binding pocket by BAD to prevent sequestration of BID-like proteins by anti-apoptotic proteins. Thus, two classes of BH3-domain only proteins have emerged, BID-like proteins that directly activate mitochondrial apoptosis, and BAD-like proteins, that have the capacity to sensitize mitochondria to BID-like pro-apoptotics by occupying the binding pockets of multidomain anti-apoptotic proteins. Various α-helical domains of BCL-2 family member proteins amenable to the methodology disclosed herein have been disclosed (Walensky et al. (2004), Science 305:1466; and Walensky et al., U.S. Patent Publication No. 2005/0250680, the entire disclosures of which are incorporated herein by reference).

A non-limiting exemplary list of suitable peptide sequences for use in the present invention is given below:

TABLE 1

| Name | Sequence (bold = critical residues) | SEQ ID NO: | Cross-linked Sequence (X = x-link residue) | SEQ ID NO: |
|---|---|---|---|---|
| BH3 peptides | | | | |
| BID-BH3 | QEDIIRNIARHLAQVGDSMDRSIPP | 3 | QEDIIRNIARHLAXVGDXMDRSIPP | 26 |
| BIM-BH3 | DNRPEIWIAQELRRIGDEFNAYYAR | 4 | DNRPEIWIAQELRXIGDXFNAYYAR | 27 |
| BAD-BH3 | NLWAAQRYGRELRRMSDEFVDSFKK | 5 | NLWAAQRYGRELRXMSDXFVDSFKK | 28 |
| PUMA-BH3 | EEQWAREIGAQLRRMADDLNAQYER | 6 | EEQWAREIGAQLRXMADXLNAQYER | 29 |
| Hrk-BH3 | RSSAAQLTAARLKALGDELHQRTM | 7 | RSSAAQLTAARLKXLGDXLHQRTM | 30 |
| NOXAA-BH3 | AELPPEFAAQLRKIGDKVYCTW | 8 | AELPPEFAAQLRXIGDXVYCTW | 31 |
| NOXAB-BH3 | VPADLKDECAQLRRIGDKVNLRQKL | 9 | VPADLKDECAQLRXIGDXVNLRQKL | 32 |
| BMF-BH3 | QHRAEVQIARKLQCIADQFHRLHT | 10 | QHRAEVQIARKLQXIADXFHRLHT | 33 |
| BLK-BH3 | SSAAQLTAARLKALGDELHQRT | 11 | SSAAQLTAARLKXLGDXLHQRT | 34 |
| BIK-BH3 | CMEGSDALALRLACIGDEMDVSLRA | 12 | CMEGSDALALRLAXIGDXMDVSLRA | 35 |
| Bnip3 | DIERRKEVESILKKNSDWIWDWSS | 13 | DIERRKEVESILKXNSDXIWDWSS | 36 |
| BOK-BH3 | GRLAEVCAVLLRLGDELEMIRP | 14 | GRLAEVCAVLLXLGDXLEMIRP | 37 |
| BAX-BH3 | PQDASTKKSECLKRIGDELDSNMEL | 15 | PQDASTKKSECLKXIGDXLDSNMEL | 38 |
| BAK-BH3 | PSSTMGQVGRQLAIIGDDINRR | 16 | PSSTMGQVGRQLAXIGDXINRR | 39 |
| BCL2L1-BH3 | KQALREAGDEFELR | 17 | KQALRXAGDXFELR | 40 |
| BCL2-BH3 | LSPPVVHLALALRQAGDDFSRR | 18 | LSPPVVHLALALRXAGDXFSRR | 41 |
| BCL-XL-BH3 | EVIPMAAVKQALREAGDEFELRY | 19 | EVIPMAAVKQALRXAGDXFELRY | 42 |
| BCL-W-BH3 | PADPLHQAMRAAGDEFETRF | 20 | PADPLHQAMRXAGDXFETRF | 43 |
| MCL1-BH3 | ATSRKLETLRRVGDGVQRNHETA | 21 | ATSRKLETLRXVGDXVQRNHETA | 44 |
| MTD-BH3 | LAEVCTVLLRLGDELEQIR | 22 | LAEVCTVLLXLGDXLEQIR | 45 |
| MAP-1-BH3 | MTVGELSRALGHENGSLDP | 23 | MTVGELSRALGXENGXLDP | 46 |
| NIX-BH3 | VVEGEKEVEALKKSADWVSDWS | 24 | VVEGEKEVEALKXSADXVSDWS | 47 |
| 4ICD(ERBB4)-BH3 | SMARDPQRYLVIQGDDRMKL | 25 | SMARDPQRYLVXQGDXRMKL | 48 |

Table 1 lists human sequences which target the BH3 binding site and are implicated in cancers, autoimmune disorders, metabolic diseases and other human disease conditions.

TABLE 2

| Name | Sequence (bold = critical residues) | SEQ ID NO: | Cross-linked Sequence (X = x-link residue) | SEQ ID NO: |
|---|---|---|---|---|
| BH3 peptides | | | | |
| BID-BH3 | QEDIIRNIARHLAQVGDSMDRSIPP | 3 | QEDIIRNIXRHLXQVGDSMDRSIPP | 49 |
| BIM-BH3 | DNRPEIWIAQELRRIGDEFNAYYAR | 4 | DNRPEIWIXQELXRIGDEFNAYYAR | 50 |
| BAD-BH3 | NLWAAQRYGRELRRMSDEFVDSFKK | 5 | NLWAAQRYXRELXRMSDEFVDSFKK | 51 |
| PUMA-BH3 | EEQWAREIGAQLRRMADDLNAQYER | 6 | EEQWAREIXAQLXRMADDLNAQYER | 52 |
| Hrk-BH3 | RSSAAQLTAARLKALGDELHQRTM | 7 | RSSAAQLTXARLXALGDELHQRTM | 53 |
| NOXAA-BH3 | AELPPEFAAQLRKIGDKVYCTW | 8 | AELPPEFXAQLXKIGDKVYCTW | 54 |
| NOXAB-BH3 | VPADLKDECAQLRRIGDKVNLRQKL | 9 | VPADLKDEXAQLXRIGDKVNLRQKL | 55 |
| BMF-BH3 | QHRAEVQIARKLQCIADQFHRLHT | 10 | QHRAEVQIXRKLXCIADQFHRLHT | 56 |
| BLK-BH3 | SSAAQLTAARLKALGDELHQRT | 11 | SSAAQLTXARLXALGDELHQRT | 57 |
| BIK-BH3 | CMEGSDALALRLACIGDEMDVSLRA | 12 | CMEGSDALXLRLXCIGDEMDVSLRA | 58 |
| Bnip3 | DIERRKEVESILKKNSDWIWDWSS | 13 | DIERRKEVXSILXKNSDWIWDWSS | 59 |
| BOK-BH3 | GRLAEVCAVLLRLGDELEMIRP | 14 | GRLAEVXAVLXRLGDELEMIRP | 60 |
| BAX-BH3 | PQDASTKKSECLKRIGDELDSNMEL | 15 | PQDASTKKXECLXRIGDELDSNMEL | 61 |
| BAK-BH3 | PSSTMGQVGRQLAIIGDDINRR | 16 | PSSTMGQVXRQLXIIGDDINRR | 62 |
| BCL2L1-BH3 | KQALREAGDEFELR | 17 | XQALXEAGDEFELR | 63 |
| BCL2-BH3 | LSPPVVHLALALRQAGDDFSRR | 18 | LSPPVVHLXLALXQAGDDFSRR | 64 |
| BCL-XL-BH3 | EVIPMAAVKQALREAGDEFELRY | 19 | EVIPMAAVXQALXEAGDEFELRY | 65 |
| BCL-W-BH3 | PADPLHQAMRAAGDEFETRF | 20 | PADPLXQAMXAAGDEFETRF | 66 |
| MCL1-BH3 | ATSRKLETLRRVGDGVQRNHETA | 21 | ATSRKXETLXRVGDGVQRNHETA | 67 |
| MTD-BH3 | LAEVCTVLLRLGDELEQIR | 22 | LAEVXTVLXRLGDELEQIR | 68 |
| MAP-1-BH3 | MTVGELSRALGHENGSLDP | 23 | MTVGELXRALXHENGSLDP | 69 |
| NIX-BH3 | VVEGEKEVEALKKSADWVSDWS | 24 | VVEGEKEXEALXKSADWVSDWS | 70 |
| 4ICD(ERBB4)-BH3 | SMARDPQRYLVIQGDDRMKL | 25 | SMARDPXRYLXIQGDDRMKL | 71 |

Table 2 lists human sequences which target the BH3 binding site and are implicated in cancers, autoimmune disorders, metabolic diseases and other human disease conditions.

Peptidomimetic Macrocycles of the Invention

In some embodiments of the method, a polypeptide of the invention contains one crosslink. In other embodiments of the method, said polypeptide contains two cross-links. In some embodiments of the method, one crosslink connects two α-carbon atoms. In other embodiments of the method, one α-carbon atom to which one crosslink is attached is substituted with a substituent of formula R—. In another embodiment of the method, two α-carbon atoms to which one crosslink is attached are substituted with independent substituents of formula R—. In one embodiment of the methods of the invention, R— is alkyl. For example, R— is methyl. Alternatively, R— and any portion of one crosslink taken together can form a cyclic structure. In another embodiment of the method, one crosslink is formed of consecutive carbon-carbon bonds. For example, one crosslink may comprise at least 8, 9, 10, 11, or 12 consecutive bonds. In other embodiments, one crosslink may comprise at least 7, 8, 9, 10, or 11 carbon atoms.

In another embodiment of the method, the crosslinked polypeptide comprises an α-helical domain of a BCL-2 family member. For example, the crosslinked polypeptide comprises a BH3 domain. In other embodiments, the crosslinked polypeptide comprises at least 60%, 70%, 80%, 85%, 90% or 95% of any of the sequences in Tables 1, 2, 3 and 4. In some embodiments of the method, the crosslinked polypeptide penetrates cell membranes by an energy-dependent process and binds to an intracellular target.

In some embodiments, said helical polypeptide contains one crosslink. In other embodiments, said helical polypeptide contains two cross-links.

In some embodiments, one crosslink connects two α-carbon atoms. In other embodiments, one α-carbon atom to which one crosslink is attached is substituted with a substituent of formula R—. In another embodiment, two α-carbon atoms to which one crosslink is attached are substituted with independent substituents of formula R—. In one embodiment of the invention, R— is alkyl. For example, R— is methyl. Alternatively, R— and any portion of one crosslink taken together can form a cyclic structure. In another embodiment, one crosslink is formed of consecutive carbon-carbon bonds. For example, one crosslink may comprise at least 8, 9, 10, 11, or 12 consecutive bonds. In other embodiments, one crosslink may comprise at least 7, 8, 9, 10, or 11 carbon atoms.

In another embodiment, the crosslinked polypeptide comprises an α-helical domain of a BCL-2 family member. For example, the crosslinked polypeptide comprises a BH3 domain. In other embodiments, the crosslinked polypeptide comprises at least 60%, 70%, 80%, 85%, 90% or 95% of any of the sequences in Tables 1, 2, 3 and 4. In some embodiments, the crosslinked polypeptide penetrates cell membranes by an energy-dependent process and binds to an intracellular target.

In some embodiments, the peptidomimetic macrocycles of the invention have the Formula (I):

Formula (I)

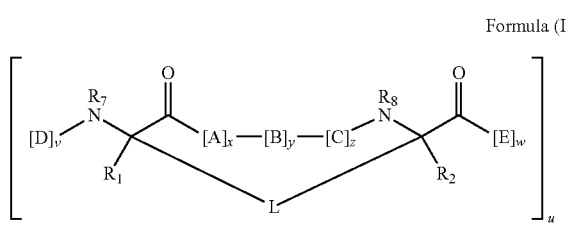

wherein:

each A, C, D, and E is independently a natural or non-natural amino acid;

B is a natural or non-natural amino acid, amino acid analog,

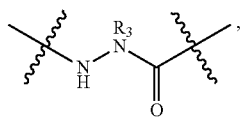

[—NH-$L_3$-CO—], [—NH-$L_3$-$SO_2$—], or [—NH-$L_3$-];

$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

L is a macrocycle-forming linker of the formula -$L_1$-$L_2$-;

$L_1$ and $L_2$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each $R_4$ is alkylene, alkenylene, alkynylene, heteroalkylene, cycloalkylene, heterocycloalkylene, arylene, or heteroarylene;

each K is O, S, SO, $SO_2$, CO, $CO_2$, or $CONR_3$;

each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;

$R_8$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;

each of v and w is independently an integer from 1-1000;

each of x, y, and z is independently an integer from 0-10; u is an integer from 1-10; and n is an integer from 1-5.

In one example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl.

In some embodiments of the invention, x+y+z is at least 3. In other embodiments of the invention, x+y+z is 1, 2, 3, 4, 5, 6, 7, 8, 9 or 10. Each occurrence of A, B, C, D or E in a macrocycle or macrocycle precursor of the invention is independently selected. For example, a sequence represented by the formula [A]$_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.

In some embodiments, the peptidomimetic macrocycle of the invention comprises a secondary structure which is an α-helix and $R_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

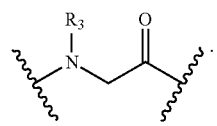

In other embodiments, the length of the macrocycle-forming linker L as measured from a first Cα to a second Cα is selected to stabilize a desired secondary peptide structure, such as an α-helix formed by residues of the peptidomimetic macrocycle including, but not necessarily limited to, those between the first Cα to a second Cα.

In one embodiment, the peptidomimetic macrocycle of Formula (I) is:

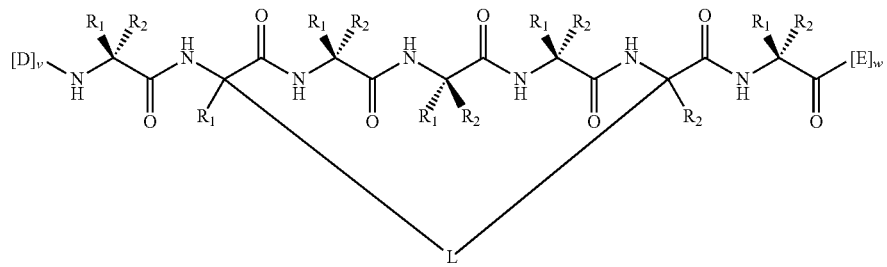

wherein each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-.

In related embodiments, the peptidomimetic macrocycle of Formula (I) is:

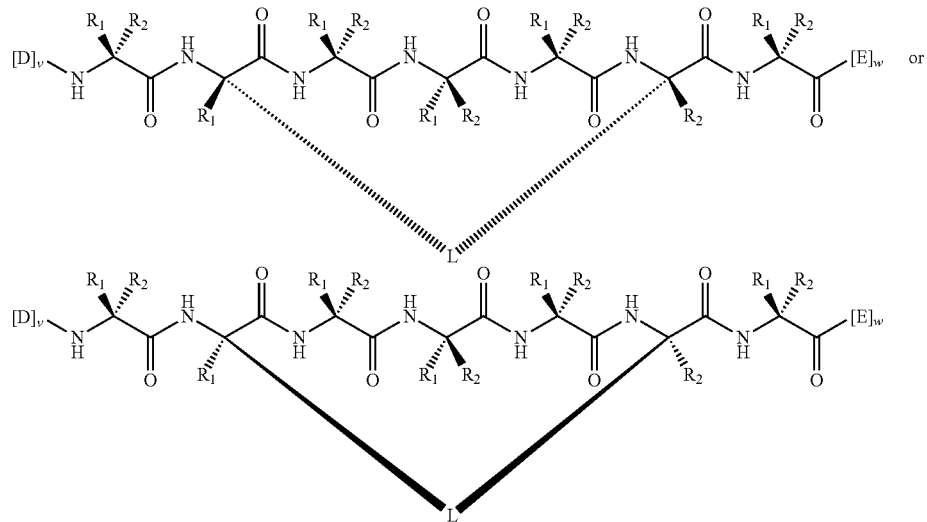

In other embodiments, the peptidomimetic macrocycle of Formula (I) is a compound of any of the formulas shown below:

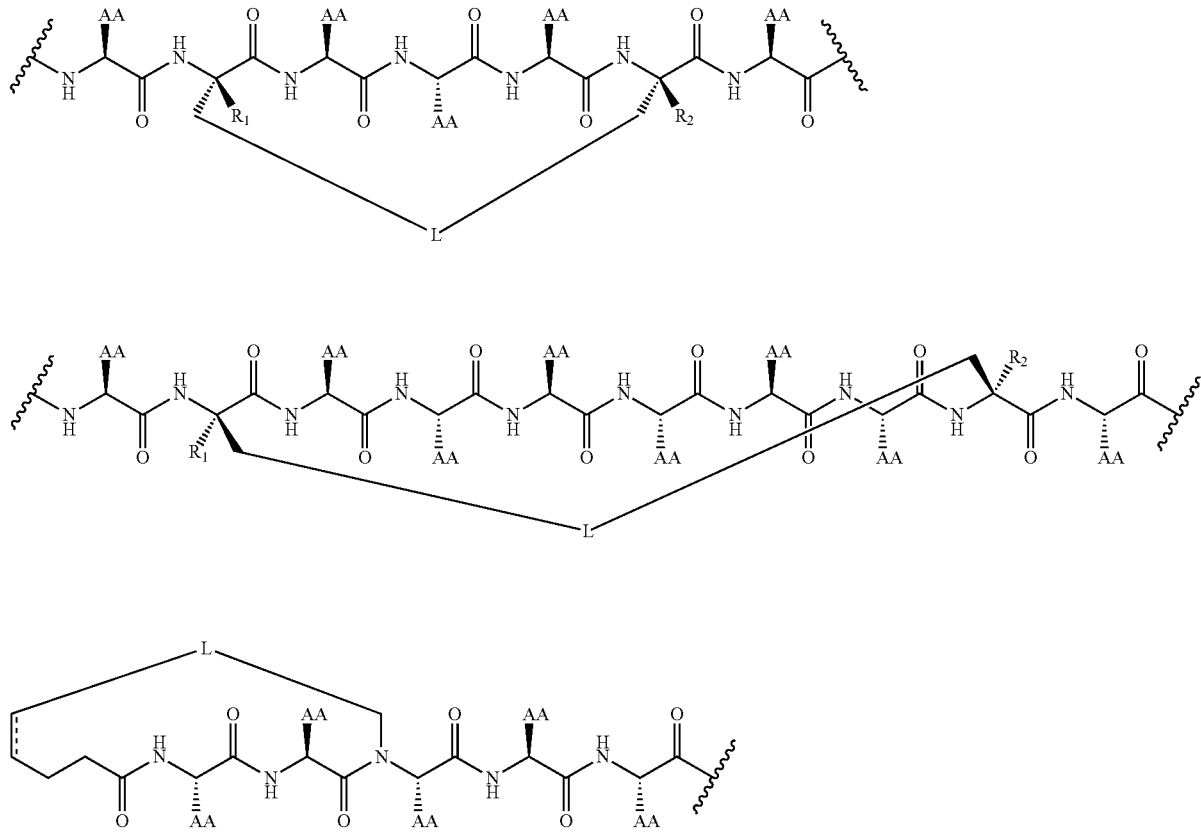

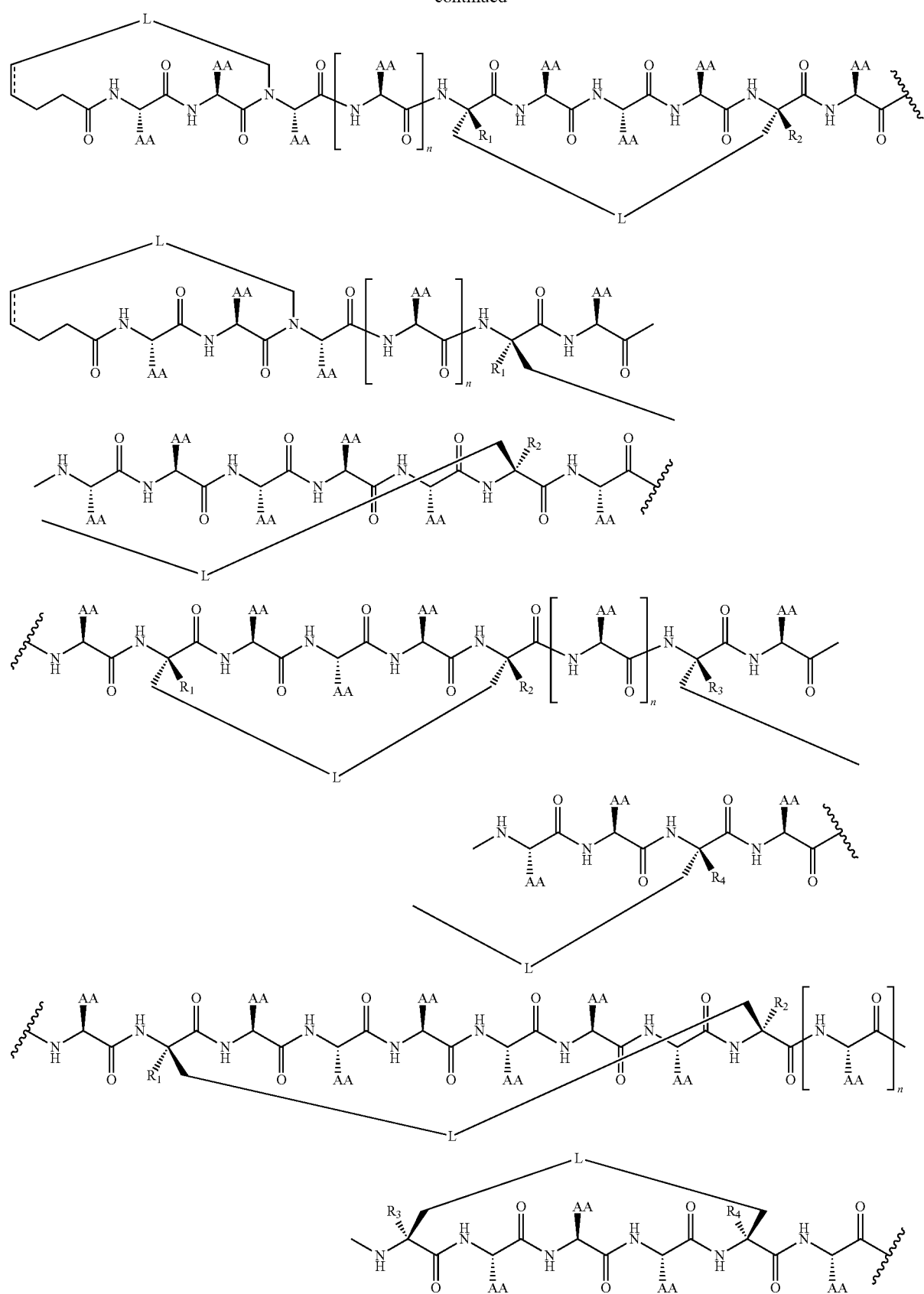

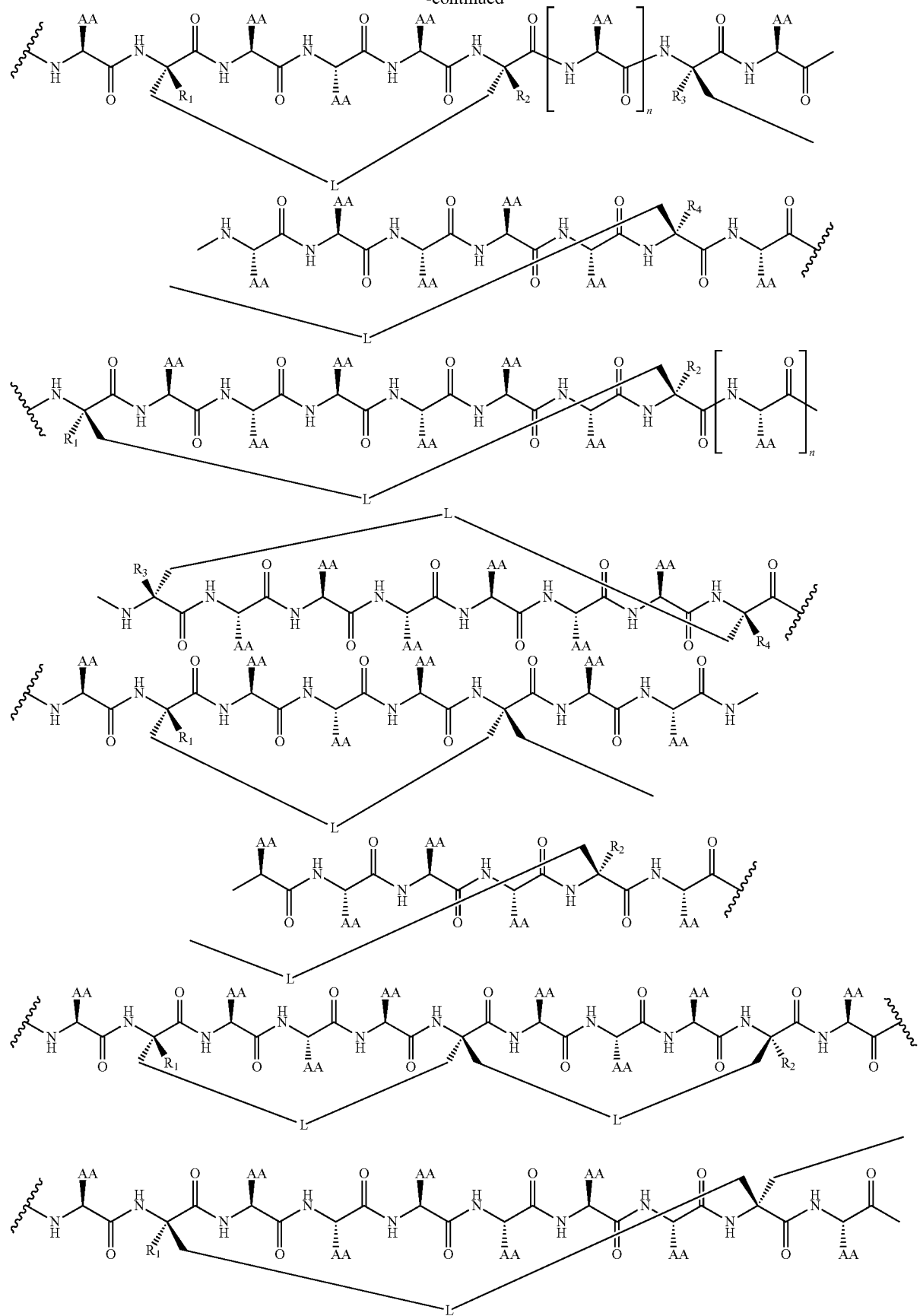

-continued

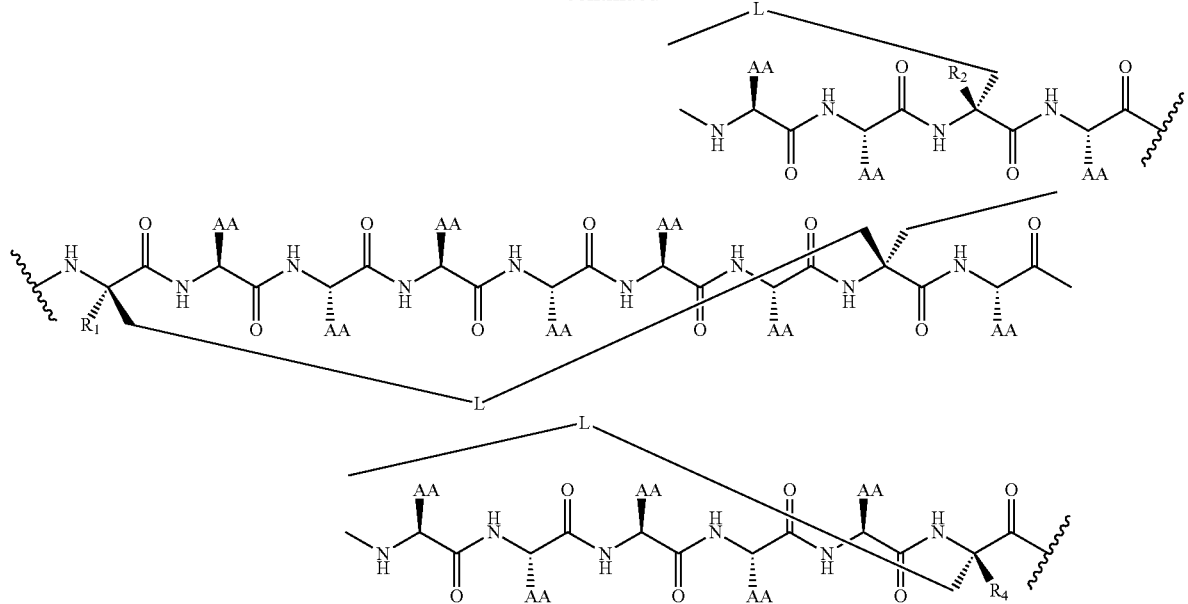

wherein "AA" represents any natural or non-natural amino acid side chain and "⌇" is $[D]_v$, $[E]_w$ as defined above, and n is an integer between 0 and 20, 50, 100, 200, 300, 400 or 500. In some embodiments, n is 0. In other embodiments, n is less than 50.

Exemplary embodiments of the macrocycle-forming linker L are shown below.

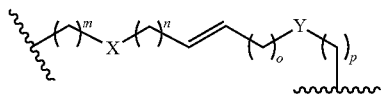

where X, Y = —CH$_2$—, O, S, or NH
m, n, o, p = 0-10

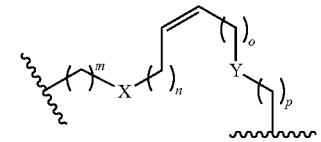

where X, Y = —CH$_2$—, O, S, or NH
m, n, o, p = 0-10

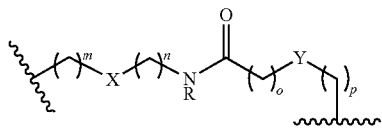

where X, Y = —CH$_2$—, O, S, or NH
m, n, o, p = 0-10
R = H, alkyl, other substituent

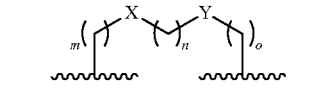

where X, Y = —CH$_2$—, O, S, or NH
m, n, o, p = 0-10

In some embodiments, the peptidomimetic macrocycles of the invention have the Formula (II):

Formula (II)

$$\left[ [D]_v \overset{R_7}{\underset{R_1}{N}} \overset{O}{\underset{}{\|}} [A]_x - [B]_y - [C]_z \overset{R_8}{\underset{R_2}{N}} \overset{O}{\underset{}{\|}} [E]_w \right]_u$$

$$\underset{L}{\diagdown\diagup}$$

wherein:
each A, C, D, and E is independently a natural or non-natural amino acid;
B is a natural or non-natural amino acid, amino acid analog,

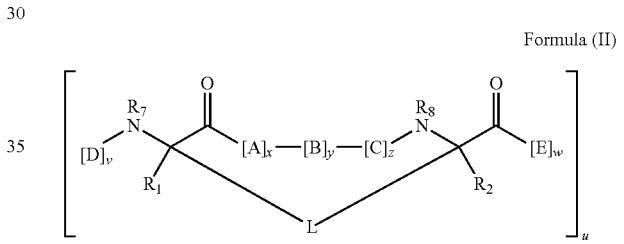

[—NH-L$_3$-CO—], [—NH-L$_3$-SO$_2$—], or [—NH-L$_3$-];
R$_1$ and R$_2$ are independently —H, alkyl, alkenyl, alkynyl, arylalkyl, cycloalkyl, cycloalkylalkyl, heteroalkyl, or heterocycloalkyl, unsubstituted or substituted with halo-;
R$_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with R$_5$;
L is a macrocycle-forming linker of the formula $$\underset{N=N}{\overset{L_1 \diagup \diagdown L_2}{\diagdown\diagup}}\overset{}{\underset{NH}{}};$$

L$_1$, L$_2$ and L$_3$ are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;

each R$_4$ is alkylene, alkenylene, alkynylene, heteroalkylene, cycloalkylene, heterocycloalkylene, arylene, or heteroarylene;

each K is O, S, SO, SO$_2$, CO, CO$_2$, or CONR$_3$;

each R$_5$ is independently halogen, alkyl, —OR$_6$, —N(R$_6$)$_2$, —SR$_6$, —SOR$_E$, —SO$_2$R$_6$, —CO$_2$R$_6$, a fluorescent moiety, a radioisotope or a therapeutic agent;

each R$_6$ is independently —H, alkyl, alkenyl, alkynyl, arylalkyl, cycloalkylalkyl, heterocycloalkyl, a fluorescent moiety, a radioisotope or a therapeutic agent;

R$_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with a D residue;

R$_8$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with an E residue;

each of v and w is independently an integer from 1-1000;

each of x, y, and z is independently an integer from 0-10; u is an integer from 1-10; and n is an integer from 1-5.

In one example, at least one of R$_1$ and R$_2$ is alkyl, unsubstituted or substituted with halo-. In another example, both R$_1$ and R$_2$ are independently alkyl, unsubstituted or substituted with halo-. In some embodiments, at least one of R$_1$ and R$_2$ is methyl. In other embodiments, R$_1$ and R$_2$ are methyl.

In some embodiments of the invention, x+y+z is at least 3. In other embodiments of the invention, x+y+z is 1, 2, 3, 4, 5, 6, 7, 8, 9 or 10. Each occurrence of A, B, C, D or E in a macrocycle or macrocycle precursor of the invention is independently selected. For example, a sequence represented by the formula [A]$_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.

In some embodiments, the peptidomimetic macrocycle of the invention comprises a secondary structure which is an α-helix and R$_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

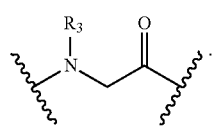

In other embodiments, the length of the macrocycle-forming linker L as measured from a first Cα to a second Cα is selected to stabilize a desired secondary peptide structure, such as an α-helix formed by residues of the peptidomimetic macrocycle including, but not necessarily limited to, those between the first Cα to a second Cα.

Exemplary embodiments of the macrocycle-forming linker L are shown below.

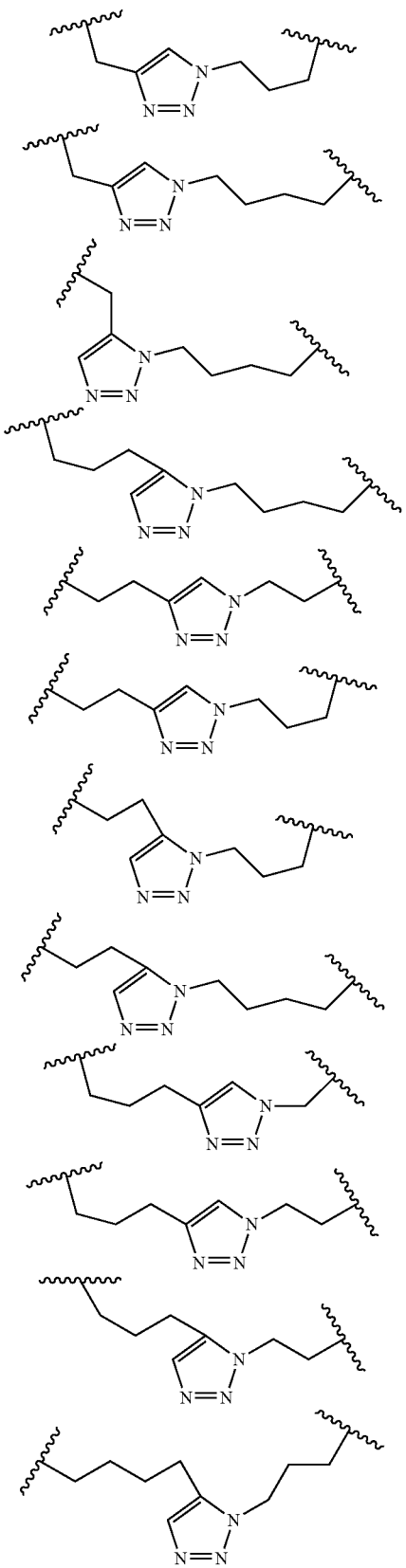

31
-continued
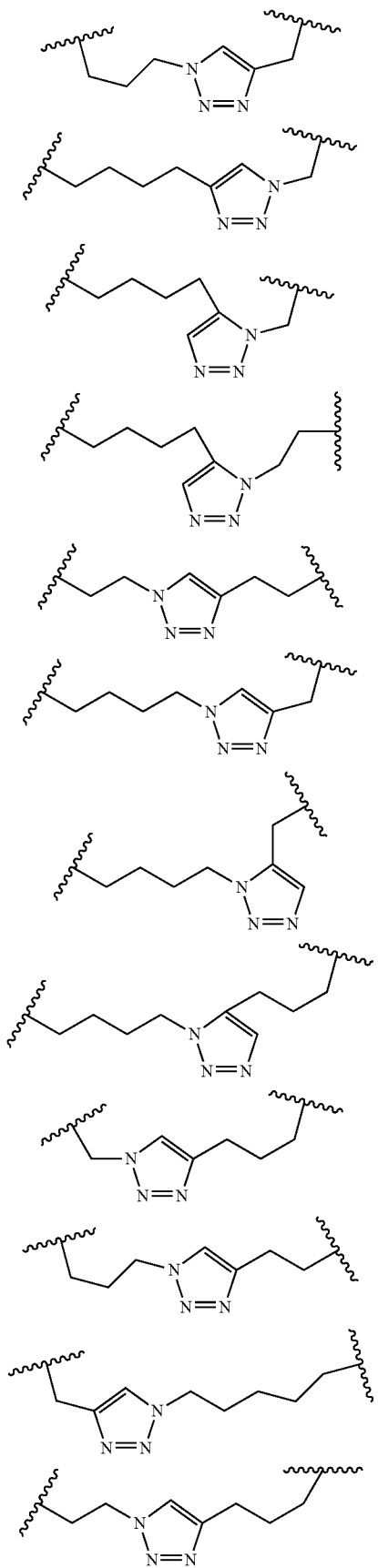
32
-continued
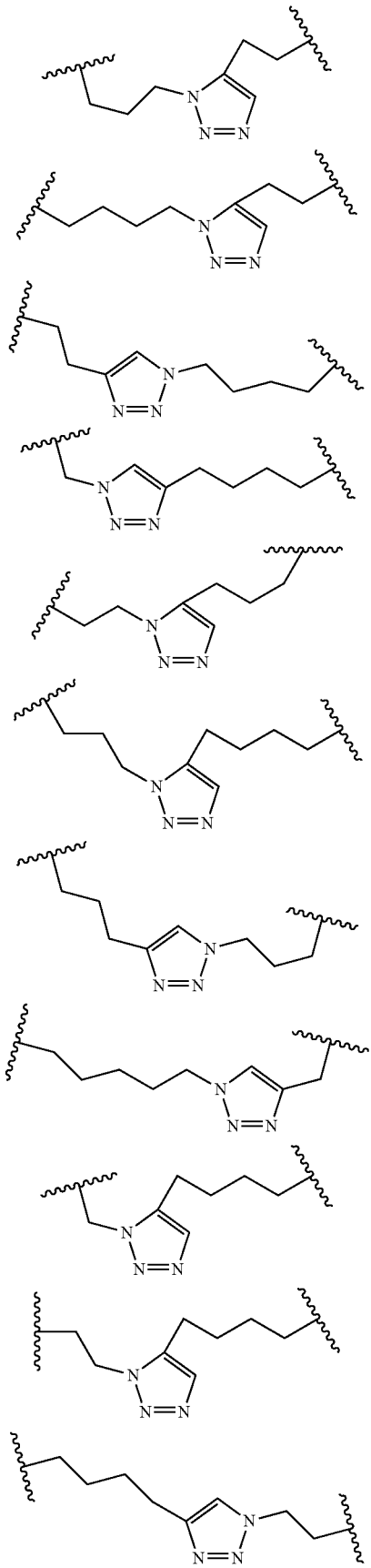

33
-continued
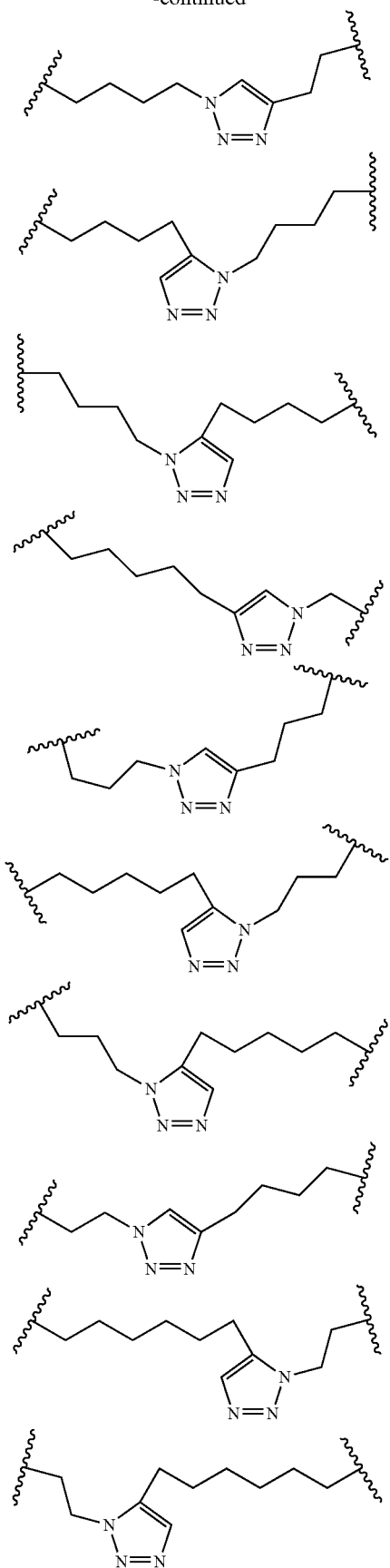
34
-continued
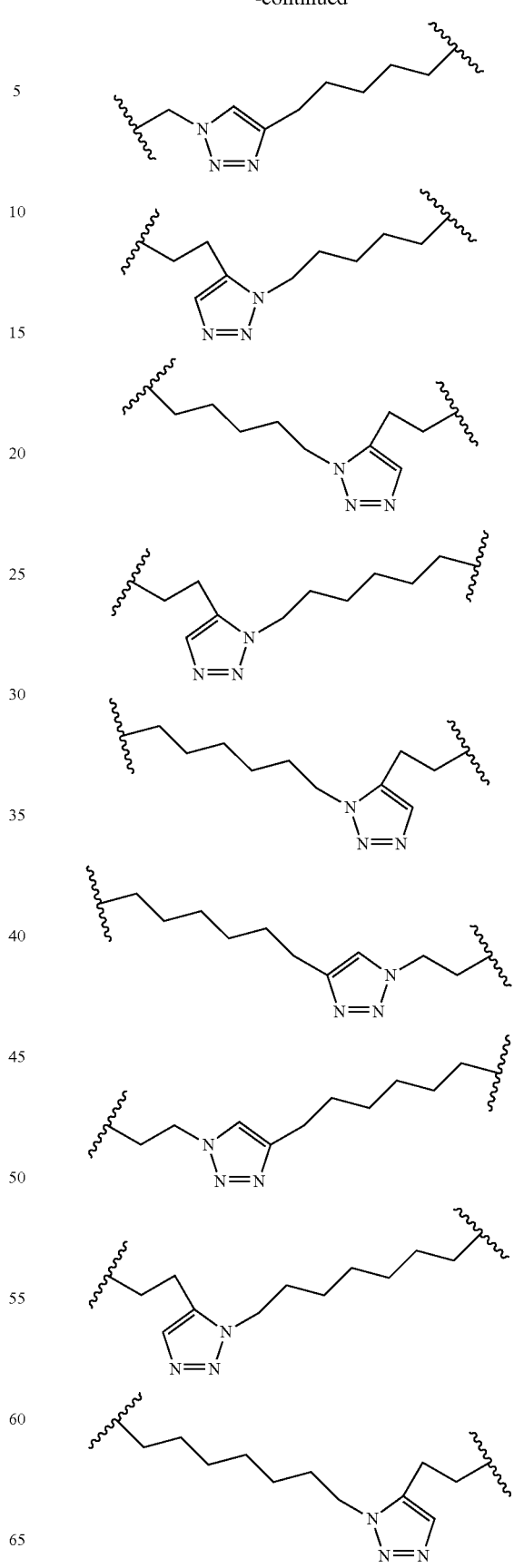

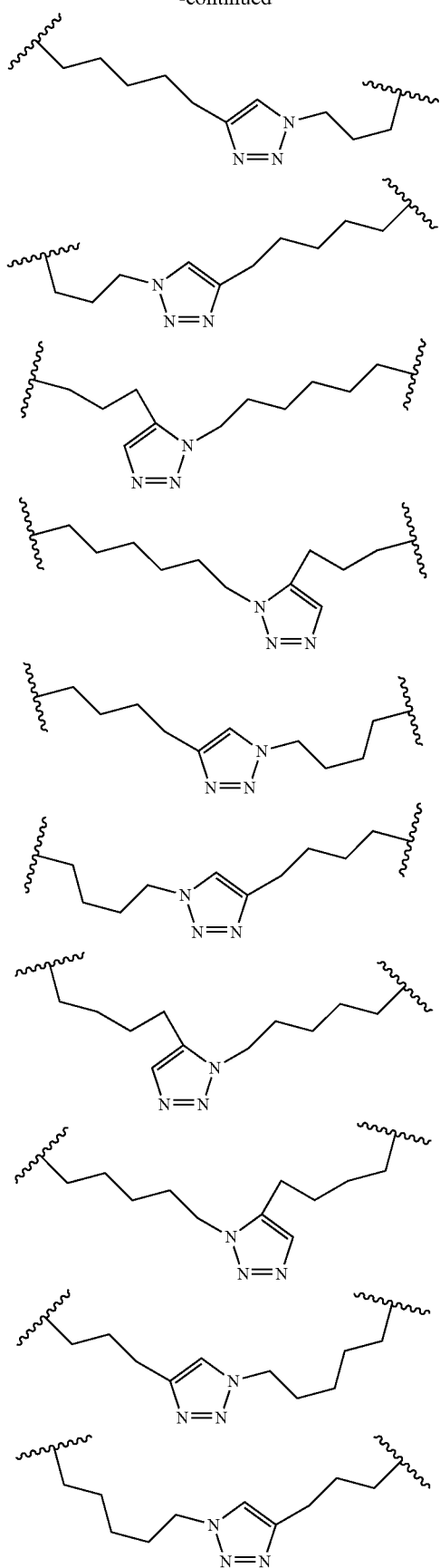
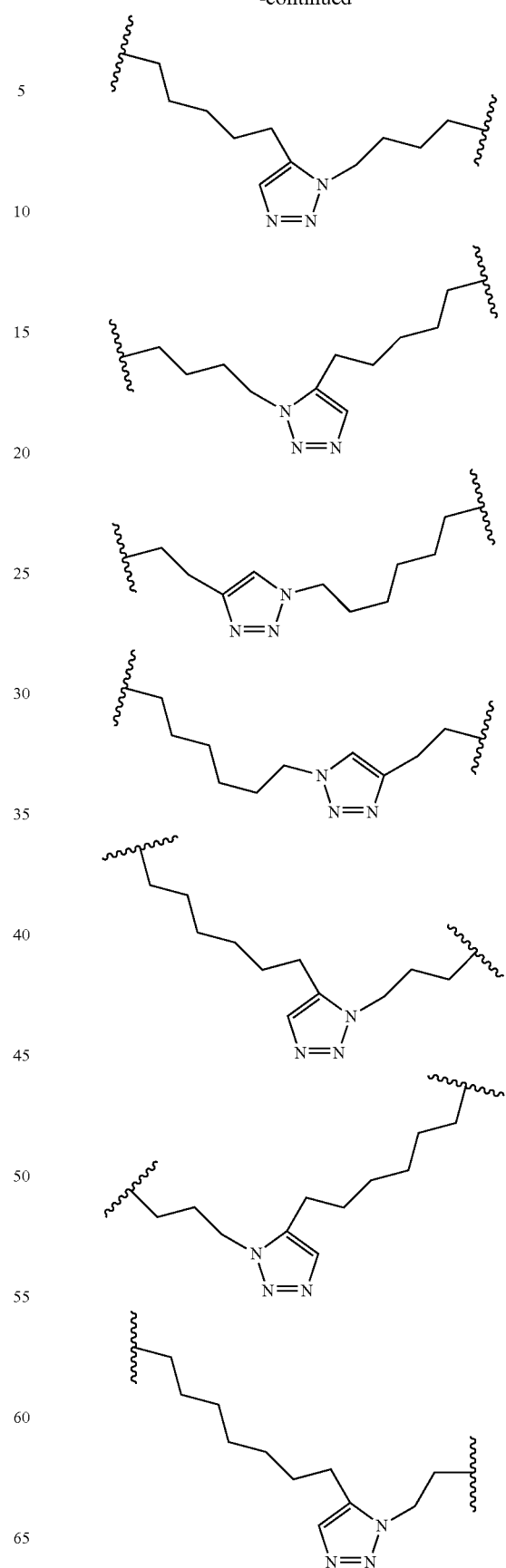

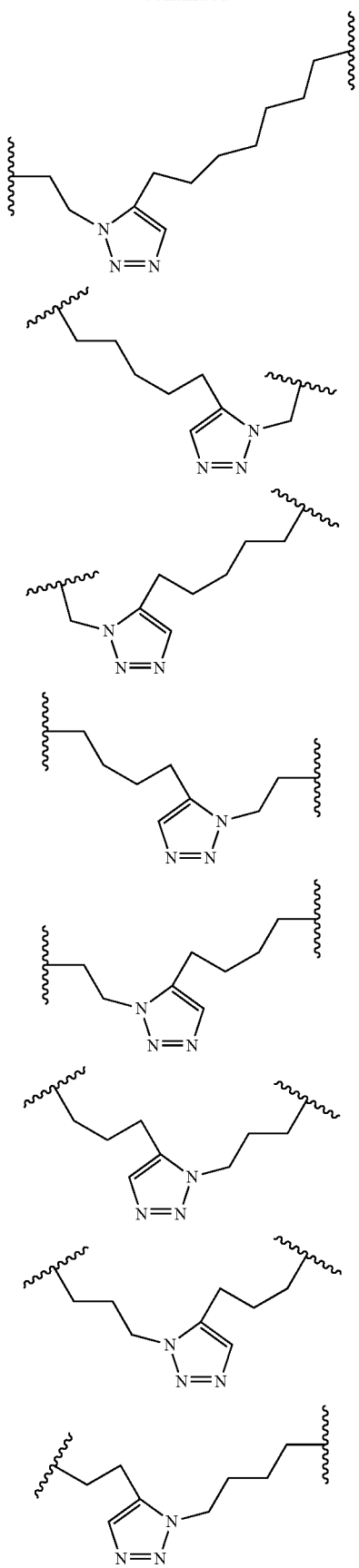

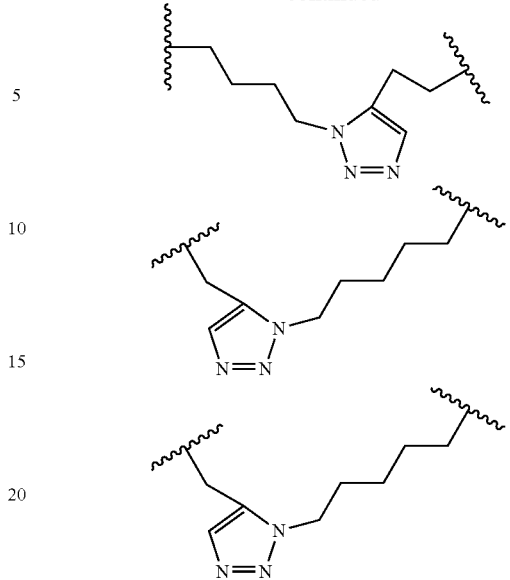

In other embodiments, the invention provides peptidomimetic macrocycles of Formula (III):

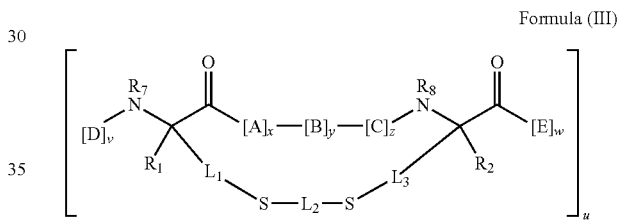

Formula (III)

wherein:

each A, C, D, and E is independently a natural or non-natural amino acid;

B is a natural or non-natural amino acid, amino acid analog,

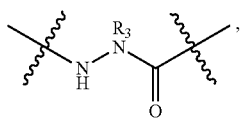

[—NH-L$_4$-CO—], [—NH-L$_4$-SO$_2$—], or [—NH-L$_4$-];

R$_1$ and R$_2$ are independently —H, alkyl, alkenyl, alkynyl, arylalkyl, cycloalkyl, cycloalkylalkyl, heteroalkyl, or heterocycloalkyl, unsubstituted or substituted with halo-;

R$_3$ is hydrogen, alkyl, alkenyl, alkynyl, arylalkyl, heteroalkyl, cycloalkyl, heterocycloalkyl, cycloalkylalkyl, cycloaryl, or heterocycloaryl, unsubstituted or substituted with R$_5$;

L$_1$, L$_2$, L$_3$ and L$_4$ are independently alkylene, alkenylene, alkynylene, heteroalkylene, cycloalkylene, heterocycloalkylene, cycloarylene, heterocycloarylene or [—R$_4$—K—R$_4$—]$_n$, each being unsubstituted or substituted with R$_5$;

K is O, S, SO, SO$_2$, CO, CO$_2$, or CONR$_3$;

each R$_4$ is alkylene, alkenylene, alkynylene, heteroalkylene, cycloalkylene, heterocycloalkylene, arylene, or heteroarylene;

each $R_5$ is independently halogen, alkyl, —$OR_6$, —$N(R_6)_2$, —$SR_6$, —$SOR_E$, —$SO_2R_6$, —$CO_2R_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, unsubstituted or substituted with $R_5$, or part of a cyclic structure with a D residue;

$R_8$ is —H, alkyl, alkenyl, alkynyl, arylalkyl, cycloalkyl, heteroalkyl, cycloalkylalkyl, heterocycloalkyl, cycloaryl, or heterocycloaryl, unsubstituted or substituted with $R_5$, or part of a cyclic structure with an E residue; each of v and w is independently an integer from 1-1000;

each of x, y, and z is independently an integer from 0-10; u is an integer from 1-10; and n is an integer from 1-5.

In one example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl.

In some embodiments of the invention, x+y+z is at least 3. In other embodiments of the invention, x+y+z is 3, 4, 5, 6, 7, 8, 9 or 10. Each occurrence of A, B, C, D or E in a macrocycle or macrocycle precursor of the invention is independently selected. For example, a sequence represented by the formula $[A]_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.

In some embodiments, the peptidomimetic macrocycle of the invention comprises a secondary structure which is an α-helix and $R_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

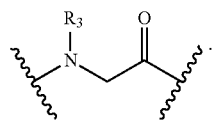

In other embodiments, the length of the macrocycle-forming linker [-$L_1$-S-$L_2$-S-$L_3$-] as measured from a first Cα to a second Cα is selected to stabilize a desired secondary peptide structure, such as an α-helix formed by residues of the peptidomimetic macrocycle including, but not necessarily limited to, those between the first Cα to a second Cα.

Macrocycles or macrocycle precursors are synthesized, for example, by solution phase or solid-phase methods, and can contain both naturally-occurring and non-naturally-occurring amino acids. See, for example, Hunt, "The Non-Protein Amino Acids" in *Chemistry and Biochemistry of the Amino Acids*, edited by G. C. Barrett, Chapman and Hall, 1985. In some embodiments, the thiol moieties are the side chains of the amino acid residues L-cysteine, D-cysteine, α-methyl-L cysteine, α-methyl-D-cysteine, L-homocysteine, D-homocysteine, α-methyl-L-homocysteine or α-methyl-D-homocysteine. A bis-alkylating reagent is of the general formula X-$L_2$-Y wherein $L_2$ is a linker moiety and X and Y are leaving groups that are displaced by —SH moieties to form bonds with $L_2$. In some embodiments, X and Y are halogens such as I, Br, or Cl.

In other embodiments, D and/or E in the compound of Formula I, II or III are further modified in order to facilitate cellular uptake. In some embodiments, lipidating or PEGylating a peptidomimetic macrocycle facilitates cellular uptake, increases bioavailability, increases blood circulation, alters pharmacokinetics, decreases immunogenicity and/or decreases the needed frequency of administration.

In other embodiments, at least one of [D] and [E] in the compound of Formula I, II or III represents a moiety comprising an additional macrocycle-forming linker such that the peptidomimetic macrocycle comprises at least two macrocycle-forming linkers. In a specific embodiment, a peptidomimetic macrocycle comprises two macrocycle-forming linkers.

In the peptidomimetic macrocycles of the invention, any of the macrocycle-forming linkers described herein may be used in any combination with any of the sequences shown in Tables 1-4 and also with any of the R— substituents indicated herein.

In some embodiments, the peptidomimetic macrocycle comprises at least one α-helix motif. For example, A, B and/or C in the compound of Formula I, II or III include one or more α-helices. As a general matter, α-helices include between 3 and 4 amino acid residues per turn. In some embodiments, the α-helix of the peptidomimetic macrocycle includes 1 to 5 turns and, therefore, 3 to 20 amino acid residues. In specific embodiments, the α-helix includes 1 turn, 2 turns, 3 turns, 4 turns, or 5 turns. In some embodiments, the macrocycle-forming linker stabilizes an α-helix motif included within the peptidomimetic macrocycle. Thus, in some embodiments, the length of the macrocycle-forming linker L from a first Cα to a second Cα is selected to increase the stability of an α-helix. In some embodiments, the macrocycle-forming linker spans from 1 turn to 5 turns of the α-helix. In some embodiments, the macrocycle-forming linker spans approximately 1 turn, 2 turns, 3 turns, 4 turns, or 5 turns of the α-helix. In some embodiments, the length of the macrocycle-forming linker is approximately 5 Å to 9 Å per turn of the α-helix, or approximately 6 Å to 8 Å per turn of the α-helix. Where the macrocycle-forming linker spans approximately 1 turn of an α-helix, the length is equal to approximately 5 carbon-carbon bonds to 13 carbon-carbon bonds, approximately 7 carbon-carbon bonds to 11 carbon-carbon bonds, or approximately 9 carbon-carbon bonds. Where the macrocycle-forming linker spans approximately 2 turns of an α-helix, the length is equal to approximately 8 carbon-carbon bonds to 16 carbon-carbon bonds, approximately 10 carbon-carbon bonds to 14 carbon-carbon bonds, or approximately 12 carbon-carbon bonds. Where the macrocycle-forming linker spans approximately 3 turns of an α-helix, the length is equal to approximately 14 carbon-carbon bonds to 22 carbon-carbon bonds, approximately 16 carbon-carbon bonds to 20 carbon-carbon bonds, or approximately 18 carbon-carbon bonds. Where the macrocycle-forming linker spans approximately 4 turns of an α-helix, the length is equal to approximately 20 carbon-carbon bonds to 28 carbon-carbon bonds, approximately 22 carbon-carbon bonds to 26 carbon-carbon bonds, or approximately 24 carbon-carbon bonds. Where the macrocycle-forming linker spans approximately 5 turns of an α-helix, the length is equal to approximately 26 carbon-carbon bonds to 34 carbon-carbon bonds, approximately 28 carbon-carbon bonds to 32 carbon-carbon bonds, or approximately 30 carbon-carbon bonds. Where the macrocycle-forming linker spans approximately 1 turn of an α-helix, the linkage contains approximately 4 atoms to 12 atoms, approximately 6 atoms to 10 atoms, or approximately 8 atoms. Where the macrocycle-forming linker spans approximately 2 turns of the α-helix, the linkage contains approximately 7 atoms to 15 atoms, approximately 9 atoms to 13 atoms, or approximately 11 atoms. Where the macrocycle-forming linker spans approximately 3 turns of the α-helix, the linkage contains approximately 13 atoms to 21 atoms, approximately 15 atoms to 19 atoms, or approximately 17 atoms. Where the macrocycle-forming linker spans approximately 4 turns of the α-helix, the linkage contains approximately 19 atoms to 27 atoms, approximately 21 atoms to 25 atoms, or approximately 23 atoms. Where the macrocycle-forming linker spans approximately 5 turns of the α-helix, the linkage contains approximately 25 atoms to 33 atoms, approximately 27 atoms to 31 atoms, or approximately 29 atoms. Where the macrocycle-forming linker spans approximately 1 turn of the α-helix, the resulting macrocycle forms a ring containing approximately 17 members to 25 members, approximately 19 members to 23 members, or approximately 21 members. Where the macrocycle-forming linker spans approximately 2 turns of the α-helix, the resulting macrocycle forms a ring containing approximately 29 members to 37 members, approximately 31 members to 35 members, or approximately 33 members. Where the macrocycle-forming linker spans approximately 3 turns of the α-helix, the resulting macrocycle forms a ring containing approximately 44 members to 52 members, approximately 46 members to 50 members, or approximately 48 members. Where the macrocycle-forming linker spans approximately 4 turns of the α-helix, the resulting macrocycle forms a ring containing approximately 59 members to 67 members, approximately 61 members to 65 members, or approximately 63 members. Where the macrocycle-forming linker spans approximately 5 turns of the α-helix, the resulting macrocycle forms a ring containing approximately 74 members to 82 members, approximately 76 members to 80 members, or approximately 78 members.

In other embodiments, the invention provides peptidomimetic macrocycles of Formula (IV) or (IVa):

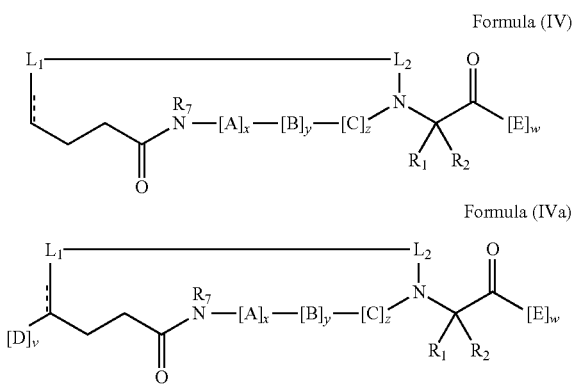

wherein:

each A, C, D, and E is independently a natural or non-natural amino acid;

B is a natural or non-natural amino acid, amino acid analog,

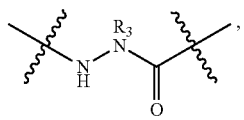

[—NH-$L_3$-CO—], [—NH-$L_3$-$SO_2$—], or [—NH-$L_3$-];

$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-, or part of a cyclic structure with an E residue;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

L is a macrocycle-forming linker of the formula -$L_1$-$L_2$-;

$L_1$ and $L_2$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each $R_4$ is alkylene, alkenylene, alkynylene, heteroalkylene, cycloalkylene, heterocycloalkylene, arylene, or heteroarylene;

each K is O, S, SO, $SO_2$, CO, $CO_2$, or $CONR_3$;

each $R_5$ is independently halogen, alkyl, —$OR_6$, —$N(R_6)_2$, —$SR_6$, —$SOR_E$, —$SO_2R_6$, —$CO_2R_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$;

v is an integer from 1-1000;

w is an integer from 1-1000;

x is an integer from 0-10;

y is an integer from 0-10;

z is an integer from 0-10; and n is an integer from 1-5.

In one example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl.

In some embodiments of the invention, x+y+z is at least 3. In other embodiments of the invention, x+y+z is 1, 2, 3, 4, 5, 6, 7, 8, 9 or 10. Each occurrence of A, B, C, D or E in a macrocycle or macrocycle precursor of the invention is independently selected. For example, a sequence represented by the formula [A]$_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.

In some embodiments, the peptidomimetic macrocycle of the invention comprises a secondary structure which is an α-helix and $R_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

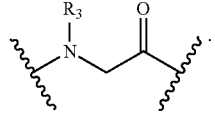

In other embodiments, the length of the macrocycle-forming linker L as measured from a first Cα to a second Cα is selected to stabilize a desired secondary peptide structure, such as an α-helix formed by residues of the peptidomimetic macrocycle including, but not necessarily limited to, those between the first Cα to a second Cα.

Exemplary embodiments of the macrocycle-forming linker L are shown below.

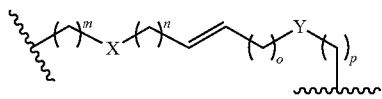

where X, Y = —CH$_2$—, O, S, or NH
m, n, o, p = 0-10

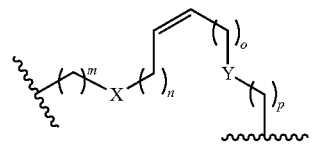

where X, Y = —CH$_2$—, O, S, or NH
m, n, o, p = 0-10

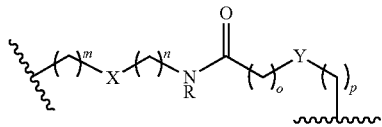

where X, Y = —CH$_2$—, O, S, or NH
m, n, o, p = 0-10
R = H, alkyl, other substituent

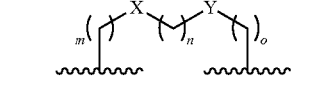

where X, Y = —CH$_2$—, O, S, or NH
m, n, o, p = 0-10

Preparation of Peptidomimetic Macrocycles

Peptidomimetic macrocycles of the invention may be prepared by any of a variety of methods known in the art. For example, any of the residues indicated by "X" in Tables 1, 2, 3 or 4 may be substituted with a residue capable of forming a crosslinker with a second residue in the same molecule or a precursor of such a residue.

Various methods to effect formation of peptidomimetic macrocycles are known in the art. For example, the preparation of peptidomimetic macrocycles of Formula I is described in Schafineister et al., J. Am. Chem. Soc. 122:5891-5892 (2000); Schafineister & Verdin, J. Am. Chem. Soc. 122:5891 (2005); Walensky et al., Science 305:1466-1470 (2004); and U.S. Pat. No. 7,192,713. The α,α-disubstituted amino acids and amino acid precursors disclosed in the cited references may be employed in synthesis of the peptidomimetic macrocycle precursor polypeptides. Following incorporation of such amino acids into precursor polypeptides, the terminal olefins are reacted with a metathesis catalyst, leading to the formation of the peptidomimetic macrocycle.

In other embodiments, the peptidomimetic macrocyles of the invention are of Formula IV or IVa. Methods for the preparation of such macrocycles are described, for example, in U.S. Pat. No. 7,202,332.

In some embodiments, the synthesis of these peptidomimetic macrocycles involves a multi-step process that features the synthesis of a peptidomimetic precursor containing an azide moiety and an alkyne moiety; followed by contacting the peptidomimetic precursor with a macrocyclization reagent to generate a triazole-linked peptidomimetic macrocycle. Macrocycles or macrocycle precursors are synthesized, for example, by solution phase or solid-phase methods, and can contain both naturally-occurring and non-naturally-occurring amino acids. See, for example, Hunt, "The Non-Protein Amino Acids" in Chemistry and Biochemistry of the Amino Acids, edited by G. C. Barrett, Chapman and Hall, 1985.

In some embodiments, an azide is linked to the α-carbon of a residue and an alkyne is attached to the α-carbon of another residue. In some embodiments, the azide moieties are azido-analogs of amino acids L-lysine, D-lysine, alpha-methyl-L-lysine, alpha-methyl-D-lysine, L-ornithine, D-ornithine, alpha-methyl-L-ornithine or alpha-methyl-D-ornithine. In another embodiment, the alkyne moiety is L-propargylglycine. In yet other embodiments, the alkyne moiety is an amino acid selected from the group consisting of L-propargylglycine, D-propargylglycine, (S)-2-amino-2-methyl-4-pentynoic acid, (R)-2-amino-2-methyl-4-pentynoic acid, (S)-2-amino-2-methyl-5-hexynoic acid, (R)-2-amino-2-methyl-5-hexynoic acid, (S)-2-amino-2-methyl-6-heptynoic acid, (R)-2-amino-2-methyl-6-heptynoic acid, (S)-2-amino-2-methyl-7-octynoic acid, (R)-2-amino-2-methyl-7-octynoic acid, (S)-2-amino-2-methyl-8-nonynoic acid and (R)-2-amino-2-methyl-8-nonynoic acid.

In some embodiments, the invention provides a method for synthesizing a peptidomimetic macrocycle, the method comprising the steps of contacting a peptidomimetic precursor of Formula V or Formula VI:

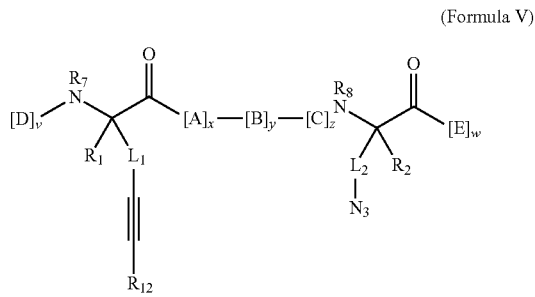

(Formula V)

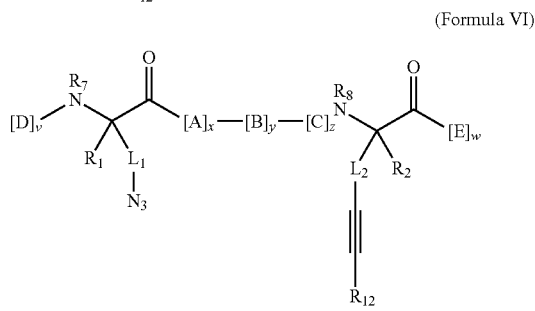

(Formula VI)

with a macrocyclization reagent;
wherein v, w, x, y, z, A, B, C, D, E, $R_1$, $R_2$, $R_7$, $R_8$, $L_1$ and $L_2$ are as defined for Formula (II); $R_{12}$ is —H when the macrocyclization reagent is a Cu reagent and $R_{12}$ is —H or alkyl when the macrocyclization reagent is a Ru reagent; and further wherein said contacting step results in a covalent linkage being formed between the alkyne and azide moiety in Formula III or Formula IV. For example, $R_{12}$ may be methyl when the macrocyclization reagent is a Ru reagent.

In the peptidomimetic macrocycles of the invention, at least one of $R_1$ and $R_2$ is alkyl, alkenyl, alkynyl, arylalkyl, cycloalkyl, cycloalkylalkyl, heteroalkyl, or heterocycloalkyl, unsubstituted or substituted with halo-. In some embodiments, both $R_1$ and $R_2$ are independently alkyl, alkenyl, alkynyl, arylalkyl, cycloalkyl, cycloalkylalkyl, heteroalkyl, or heterocycloalkyl, unsubstituted or substituted with halo-. In some embodiments, at least one of A, B, C, D or E is an α,α-disubstituted amino acid. In one example, B is an α,α-disubstituted amino acid. For instance, at least one of A, B, C, D or E is 2-aminoisobutyric acid.

For example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl. The macrocyclization reagent may be a Cu reagent or a Ru reagent.

In some embodiments, the peptidomimetic precursor is purified prior to the contacting step. In other embodiments, the peptidomimetic macrocycle is purified after the contacting step. In still other embodiments, the peptidomimetic macrocycle is refolded after the contacting step. The method may be performed in solution, or, alternatively, the method may be performed on a solid support.

Also envisioned herein is performing the method of the invention in the presence of a target macromolecule that binds to the peptidomimetic precursor or peptidomimetic macrocycle under conditions that favor said binding. In some embodiments, the method is performed in the presence of a target macromolecule that binds preferentially to the peptidomimetic precursor or peptidomimetic macrocycle under conditions that favor said binding. The method may also be applied to synthesize a library of peptidomimetic macrocycles.

In some embodiments, the alkyne moiety of the peptidomimetic precursor of Formula V or Formula VI is a sidechain of an amino acid selected from the group consisting of L-propargylglycine, D-propargylglycine, (S)-2-amino-2-methyl-4-pentynoic acid, (R)-2-amino-2-methyl-4-pentynoic acid, (S)-2-amino-2-methyl-5-hexynoic acid, (R)-2-amino-2-methyl-5-hexynoic acid, (S)-2-amino-2-methyl-6-heptynoic acid, (R)-2-amino-2-methyl-6-heptynoic acid, (S)-2-amino-2-methyl-7-octynoic acid, (R)-2-amino-2-methyl-7-octynoic acid, (S)-2-amino-2-methyl-8-nonynoic acid, and (R)-2-amino-2-methyl-8-nonynoic acid. In other embodiments, the azide moiety of the peptidomimetic precursor of Formula V or Formula VI is a sidechain of an amino acid selected from the group consisting of ε-azido-L-lysine, ε-azido-D-lysine, □ε-azido-α-methyl-L-lysine, ε-azido-α-methyl-D-lysine, δ-azido-α-methyl-L-ornithine, and δ-azido-α-methyl-D-ornithine.

In some embodiments, x+y+z is 3, and A, B and C are independently natural or non-natural amino acids. In other embodiments, x+y+z is 6, and A, B and C are independently natural or non-natural amino acids.

In some embodiments of peptidomimetic macrocycles of the invention, $[D]_v$ and/or $[E]_w$ comprise additional peptidomimetic macrocycles or macrocyclic structures. For example, $[D]_v$ may have the formula:

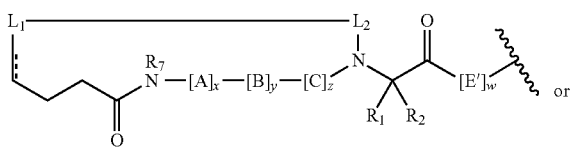 or

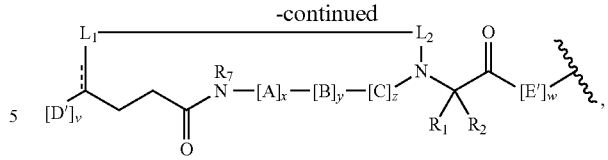

wherein each A, C, D', and E' is independently a natural or non-natural amino acid;

B is a natural or non-natural amino acid, amino acid analog,

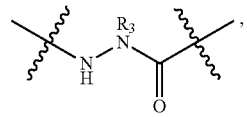

[—NH-$L_3$-CO—], [—NH-$L_3$-SO$_2$—], or [—NH-$L_3$-];

$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-, or part of a cyclic structure with an E residue;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

$L_1$ and $L_2$ are independently alkylene, alkenylene, alkynylene, heteroalkylene, cycloalkylene, heterocycloalkylene, cycloarylene, heterocycloarylene, or [—$R_4$—K—$R_4$—]$_1$, each being optionally substituted with $R_5$;

each $R_4$ is alkylene, alkenylene, alkynylene, heteroalkylene, cycloalkylene, heterocycloalkylene, arylene, or heteroarylene;

each K is O, S, SO, SO$_2$, CO, CO$_2$, or CONR$_3$;

each $R_5$ is independently halogen, alkyl, —OR$_6$, —N(R$_6$)$_2$, —SR$_6$, —SOR$_E$, —SO$_2$R$_6$, —CO$_2$R$_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$;

v is an integer from 1-1000;
w is an integer from 1-1000; and
x is an integer from 0-10.

In another embodiment, $[E]_w$ has the formula:

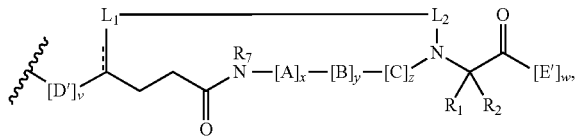

wherein the substituents are as defined in the preceding paragraph.

In some embodiments, the contacting step is performed in a solvent selected from the group consisting of protic solvent, aqueous solvent, organic solvent, and mixtures thereof. For example, the solvent may be chosen from the group consisting of H$_2$O, THF, THF/H$_2$O, tBuOH/H$_2$O, DMF, DIPEA, CH$_3$CN or CH$_2$Cl$_2$, ClCH$_2$CH$_2$Cl or a mixture thereof. The solvent may be a solvent which favors helix formation.

Alternative but equivalent protecting groups, leaving groups or reagents are substituted, and certain of the synthetic steps are performed in alternative sequences or orders to produce the desired compounds. Synthetic chemistry transformations and protecting group methodologies (protection and deprotection) useful in synthesizing the compounds described herein include, for example, those such as described in Larock, *Comprehensive Organic Transformations*, VCH Publishers (1989); Greene and Wuts, *Protective Groups in Organic Synthesis*, 2d. Ed., John Wiley and Sons (1991); Fieser and Fieser, *Fieser and Fieser's Reagents for Organic Synthesis*, John Wiley and Sons (1994); and Paquette, ed., *Encyclopedia of Reagents for Organic Synthesis*, John Wiley and Sons (1995), and subsequent editions thereof.

The peptidomimetic macrocycles of the invention are made, for example, by chemical synthesis methods, such as described in Fields et al., Chapter 3 in *Synthetic Peptides: A User's Guide*, ed. Grant, W. H. Freeman & Co., New York, N.Y., 1992, p. 77. Hence, for example, peptides are synthesized using the automated Merrifield techniques of solid phase synthesis with the amine protected by either tBoc or Fmoc chemistry using side chain protected amino acids on, for example, an automated peptide synthesizer (e.g., Applied Biosystems (Foster City, Calif.), Model 430A, 431, or 433).

One manner of producing the peptidomimetic precursors and peptidomimetic macrocycles described herein uses solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Side chain functional groups are protected as necessary with base stable, acid labile groups.

Longer peptidomimetic precursors are produced, for example, by conjoining individual synthetic peptides using native chemical ligation. Alternatively, the longer synthetic peptides are biosynthesized by well known recombinant DNA and protein expression techniques. Such techniques are provided in well-known standard manuals with detailed protocols. To construct a gene encoding a peptidomimetic precursor of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptidomimetic precursors are made, for example, in a high-throughput, combinatorial fashion using, for example, a high-throughput polychannel combinatorial synthesizer (e.g., Thuramed TETRAS multichannel peptide synthesizer from CreoSalus, Louisville, Ky. or Model Apex 396 multichannel peptide synthesizer from AAPPTEC, Inc., Louisville, Ky.).

The following synthetic schemes are provided solely to illustrate the present invention and are not intended to limit the scope of the invention, as described herein. To simplify the drawings, the illustrative schemes depict azido amino acid analogs ε-azido-α-methyl-L-lysine and ε-azido-α, -methyl-D-lysine, and alkyne amino acid analogs L-propargylglycine, (S)-2-amino-2-methyl-4-pentynoic acid, and (S)-2-amino-2-methyl-6-heptynoic acid. Thus, in the following synthetic schemes, each $R_1$, $R_2$, $R_7$ and $R_8$ is —H; each $L_1$ is —$(CH_2)_4$—; and each $L_2$ is —$(CH_2)$—. However, as noted throughout the detailed description above, many other amino acid analogs can be employed in which $R_1$, $R_2$, $R_7$, $R_8$, $L_1$ and $L_2$ can be independently selected from the various structures disclosed herein.

Synthetic Scheme 1:

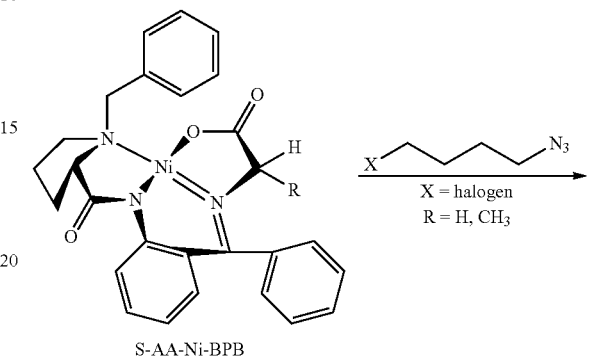

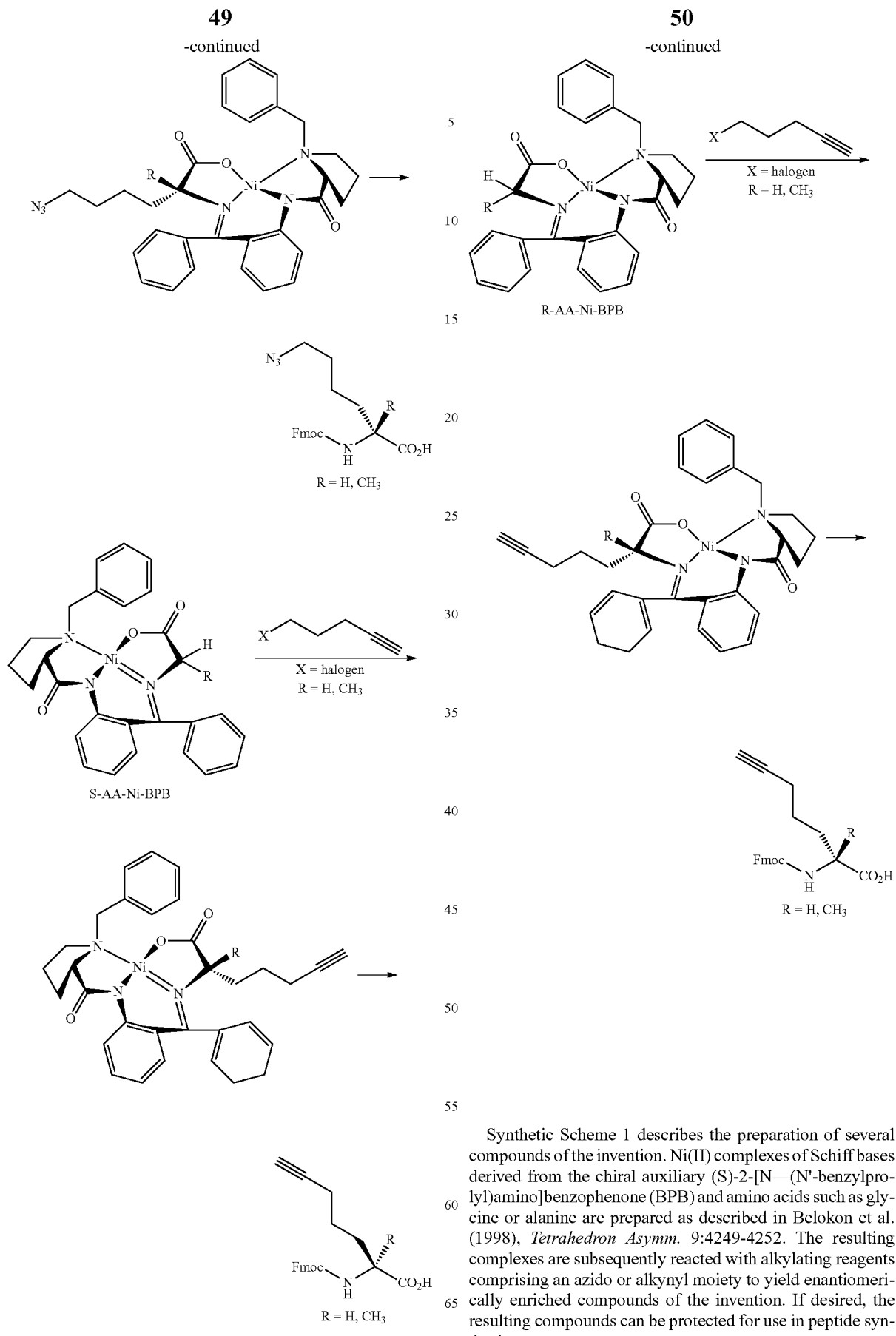

Synthetic Scheme 1 describes the preparation of several compounds of the invention. Ni(II) complexes of Schiff bases derived from the chiral auxiliary (S)-2-[N—(N'-benzylprolyl)amino]benzophenone (BPB) and amino acids such as glycine or alanine are prepared as described in Belokon et al. (1998), *Tetrahedron Asymm.* 9:4249-4252. The resulting complexes are subsequently reacted with alkylating reagents comprising an azido or alkynyl moiety to yield enantiomerically enriched compounds of the invention. If desired, the resulting compounds can be protected for use in peptide synthesis.

Synthetic Scheme 2:
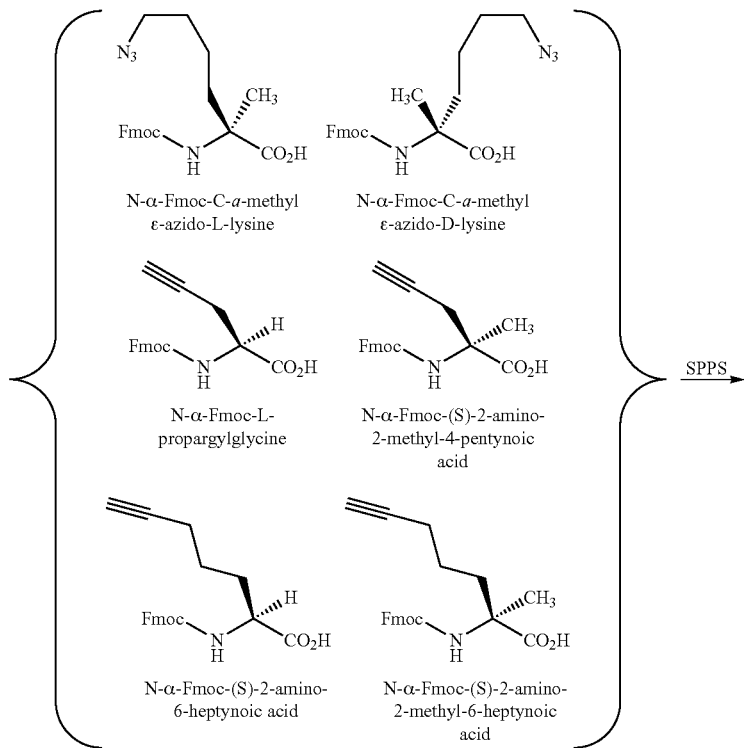
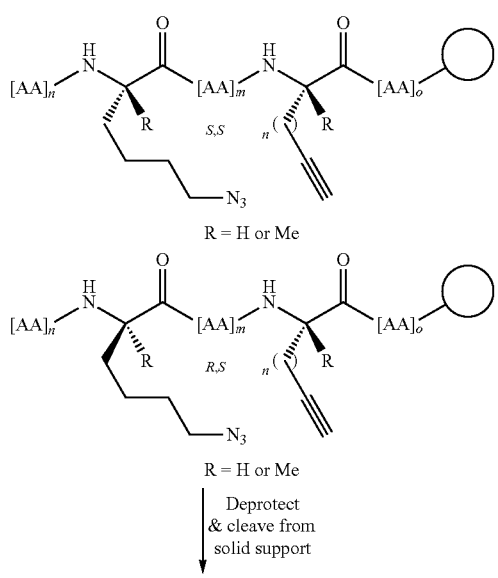
R = H or Me
Deprotect & cleave from solid support

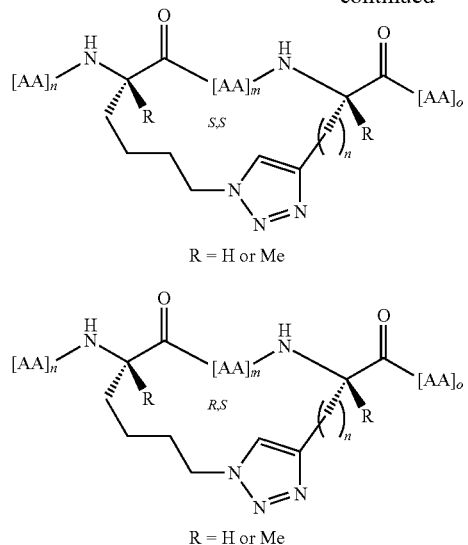

In the general method for the synthesis of peptidomimetic macrocycles shown in Synthetic Scheme 2, the peptidomimetic precursor contains an azide moiety and an alkyne moiety and is synthesized by solution-phase or solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is then deprotected and cleaved from the solid-phase resin by standard conditions (e.g., strong acid such as 95% TFA). The peptidomimetic precursor is reacted as a crude mixture or is purified prior to reaction with a macrocyclization reagent such as a Cu(I) in organic or aqueous solutions (Rostovtsev et al. (2002), Angew. Chem. Int. Ed. 41:2596-2599; Tornoe et al. (2002), J. Org. Chem. 67:3057-3064; Deiters et al. (2003), J. Am. Chem. Soc. 125:11782-11783; Punna et al. (2005), Angew. Chem. Int. Ed. 44:2215-2220). In one embodiment, the triazole forming reaction is performed under conditions that favor α-helix formation. In one embodiment, the macrocyclization step is performed in a solvent chosen from the group consisting of $H_2O$, THF, $CH_3CN$, DMF, DIPEA, tBuOH or a mixture thereof. In another embodiment, the macrocyclization step is performed in DMF. In some embodiments, the macrocyclization step is performed in a buffered aqueous or partially aqueous solvent.

Synthetic Scheme 3:

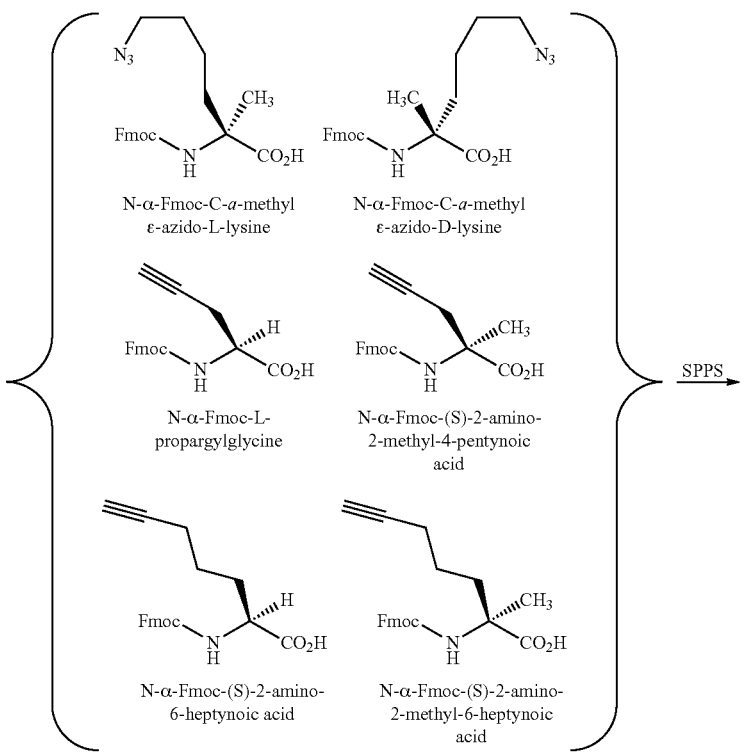

-continued

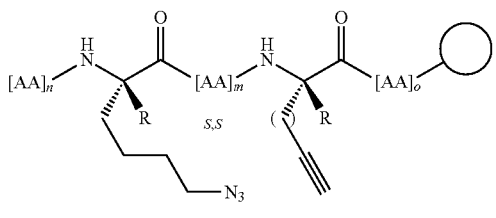
R = H or Me

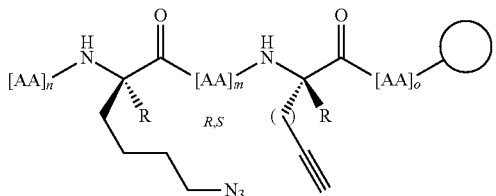
R = H or Me

↓ Cu (I)

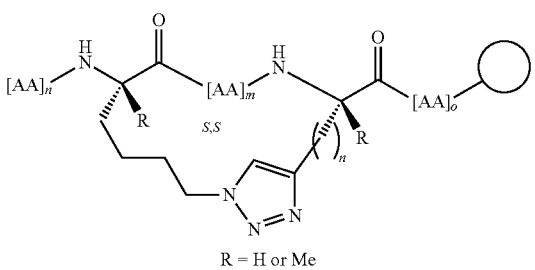
R = H or Me

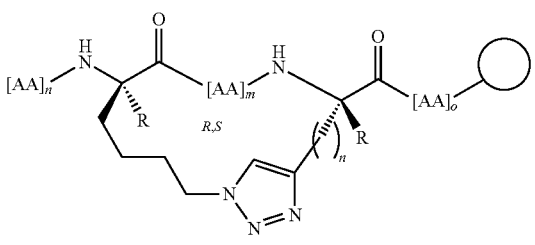
R = H or Me

← Deprotect & cleave from solid support

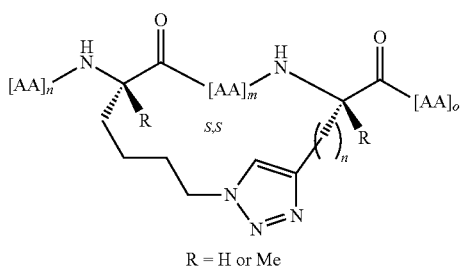
R = H or Me

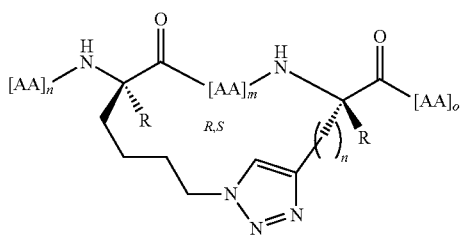
R = H or Me

In the general method for the synthesis of peptidomimetic macrocycles shown in Synthetic Scheme 3, the peptidomimetic precursor contains an azide moiety and an alkyne moiety and is synthesized by solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is reacted with a macrocyclization reagent such as a Cu(I) reagent on the resin as a crude mixture (Rostovtsev et al. (2002), *Angew. Chem. Int. Ed.* 41:2596-2599; Tornoe et al. (2002), *J. Org. Chem.* 67:3057-3064; Deiters et al. (2003), *J. Am. Chem. Soc.* 125:11782-11783; Punna et al. (2005), *Angew. Chem. Int. Ed.* 44:2215-2220). The resultant triazole-containing peptidomimetic macrocycle is then deprotected and cleaved from the solid-phase resin by standard conditions (e.g., strong acid such as 95% TFA). In some embodiments, the macrocyclization step is performed in a solvent chosen from the group consisting of $CH_2Cl_2$, $ClCH_2CH_2Cl$, DMF, THF, NMP, DIPEA, 2,6-lutidine, pyridine, DMSO, $H_2O$ or a mixture thereof. In some embodiments, the macrocyclization step is performed in a buffered aqueous or partially aqueous solvent.

Synthetic Scheme 4:
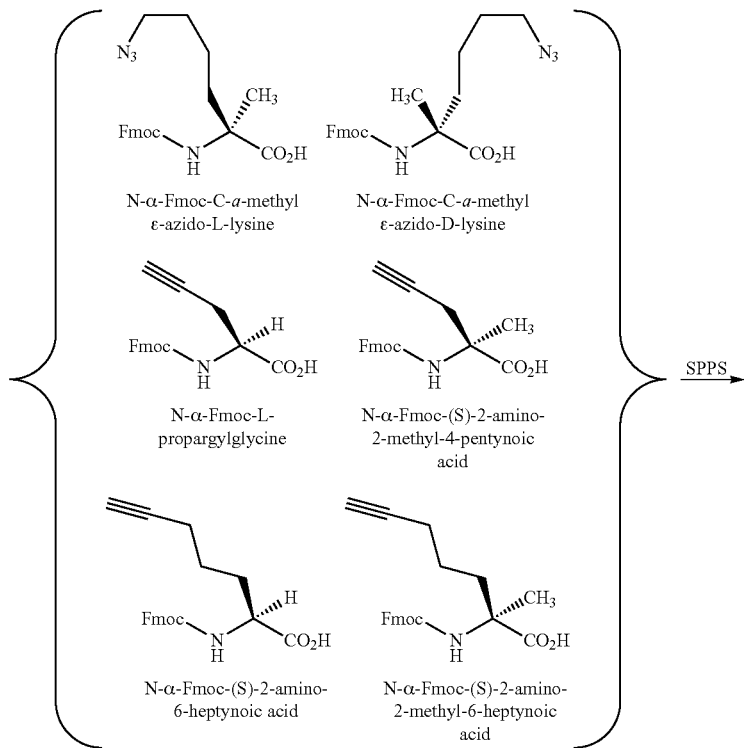
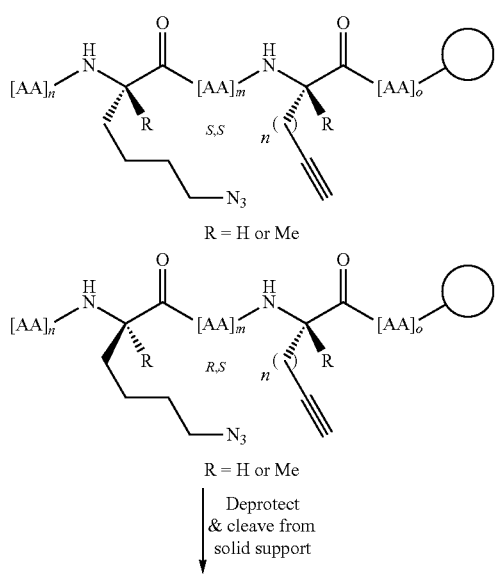

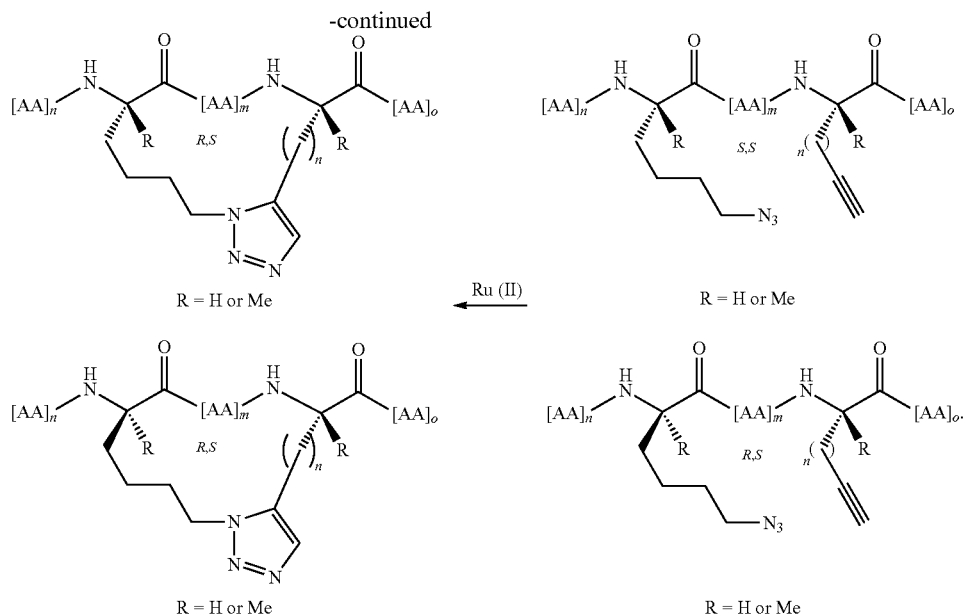

R = H or Me

Ru (II)

R = H or Me

R = H or Me

R = H or Me

In the general method for the synthesis of peptidomimetic macrocycles shown in Synthetic Scheme 4, the peptidomimetic precursor contains an azide moiety and an alkyne moiety and is synthesized by solution-phase or solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is then deprotected and cleaved from the solid-phase resin by standard conditions (e.g., strong acid such as 95% TFA). The peptidomimetic precursor is reacted as a crude mixture or is purified prior to reaction with a macrocyclization reagent such as a Ru(II) reagents, for example Cp*RuCl(PPh$_3$)$_2$ or [Cp*RuCl]$_4$ (Rasmussen et al. (2007), *Org. Lett.* 9:5337-5339; Zhang et al. (2005), *J. Am. Chem. Soc.* 127:15998-15999). In some embodiments, the macrocyclization step is performed in a solvent chosen from the group consisting of DMF, CH$_3$CN and THF.

Synthetic Scheme 5:

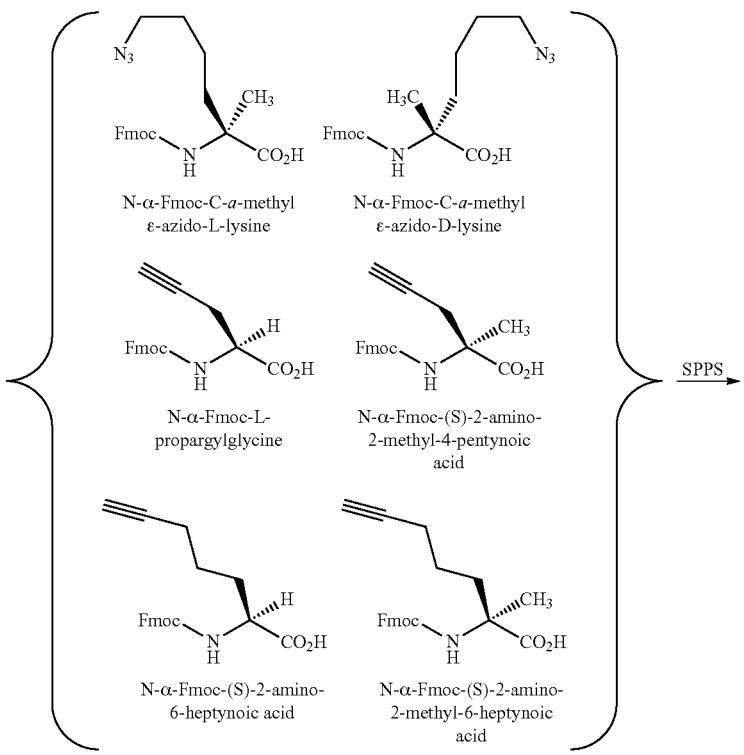

SPPS

-continued

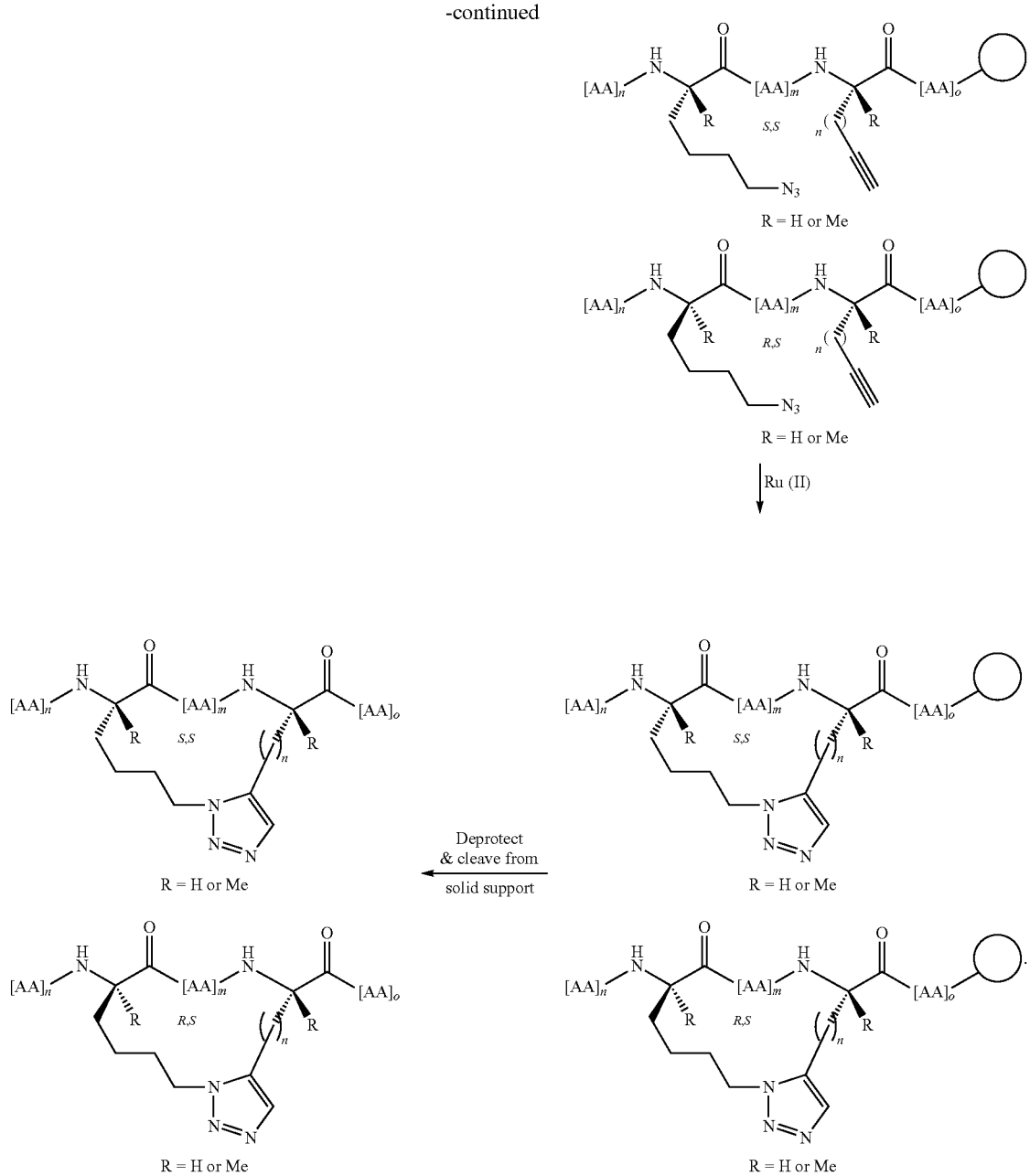

In the general method for the synthesis of peptidomimetic macrocycles shown in Synthetic Scheme 5, the peptidomimetic precursor contains an azide moiety and an alkyne moiety and is synthesized by solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is reacted with a macrocyclization reagent such as a Ru(II) reagent on the resin as a crude mixture. For example, the reagent can be Cp*RuCl(PPh$_3$)$_2$ or [Cp*RuCl]$_4$ (Rasmussen et al. (2007), Org. Lett. 9:5337-5339; Zhang et al. (2005), J. Am. Chem. Soc. 127:15998-15999). In some embodiments, the macrocyclization step is performed in a solvent chosen from the group consisting of CH$_2$Cl$_2$, ClCH$_2$CH$_2$Cl, CH$_3$CN, DMF, and THF.

Several exemplary peptidomimetic macrocycles are shown in Table 5 (SEQ ID NOS 77-88, respectively, in order of appearance). "Nle" represents norleucine and replaces a methionine residue. It is envisioned that similar linkers are used to synthesize peptidomimetic macrocycles based on the polypeptide sequences disclosed in Table 1 through Table 4.

TABLE 5
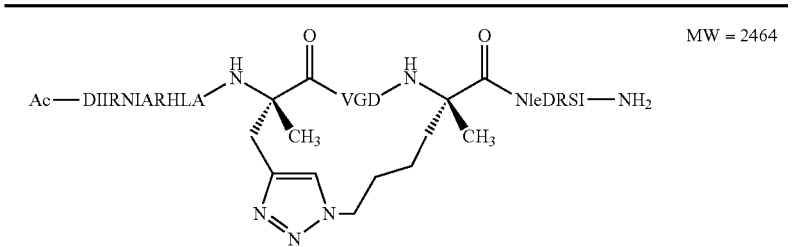
MW = 2464
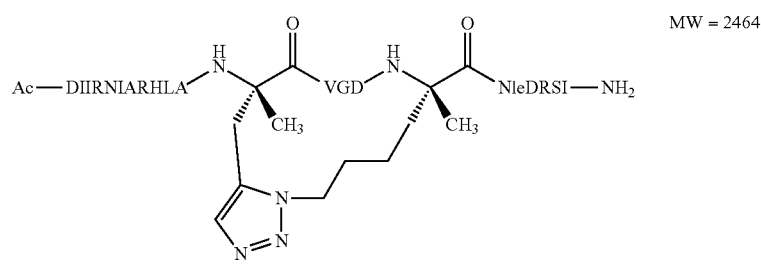
MW = 2464
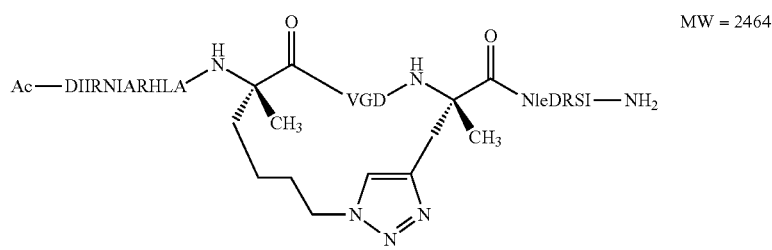
MW = 2464
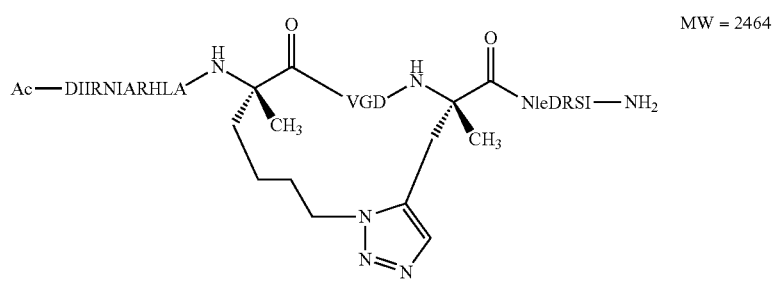
MW = 2464
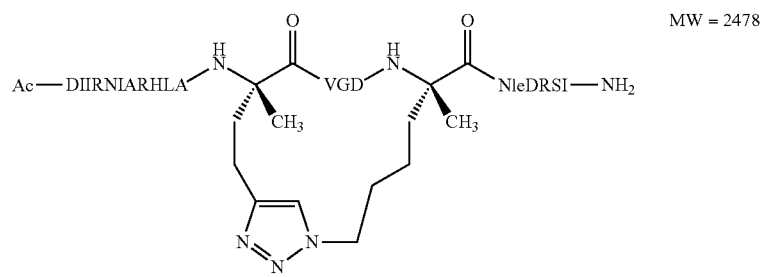
MW = 2478

TABLE 5-continued
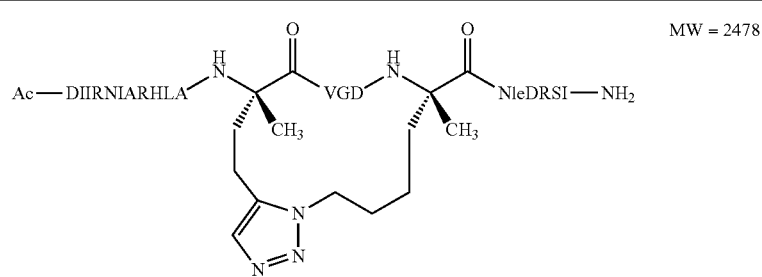
MW = 2478
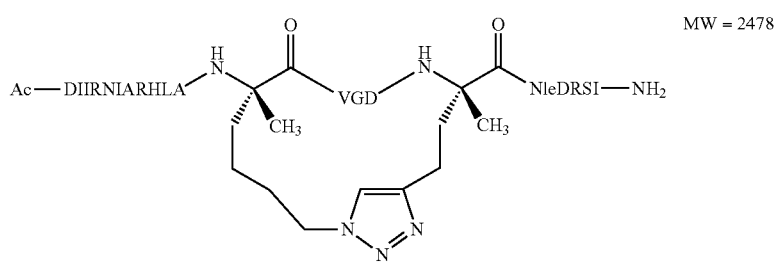
MW = 2478
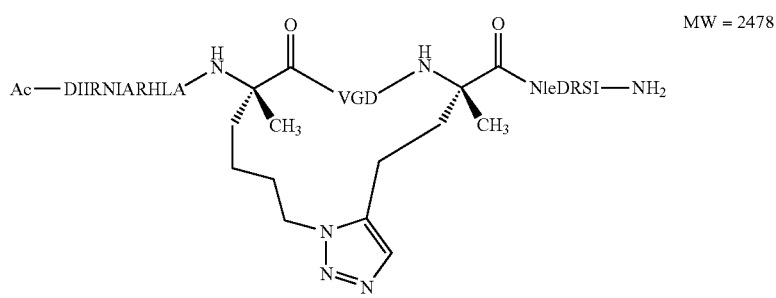
MW = 2478
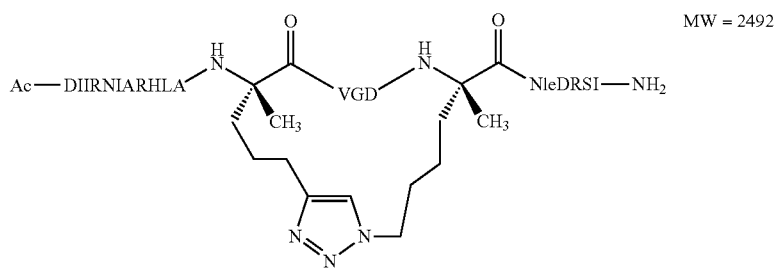
MW = 2492

TABLE 5-continued

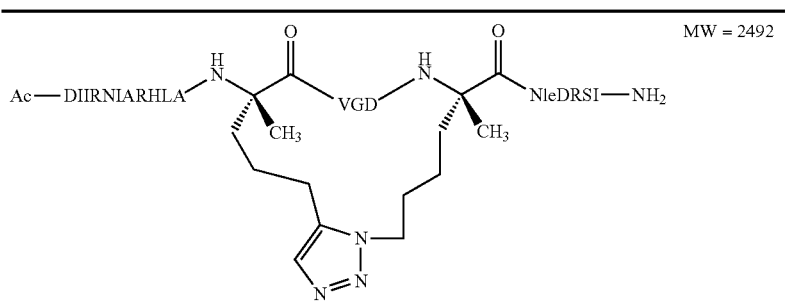

MW = 2492

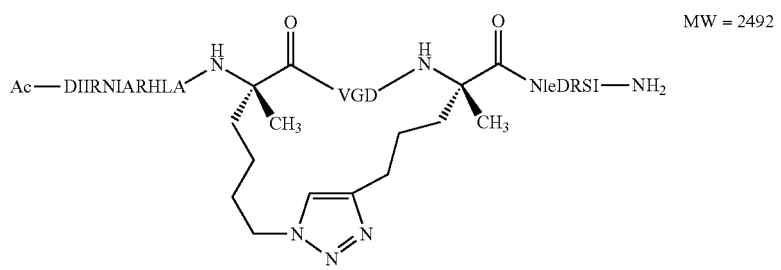

MW = 2492

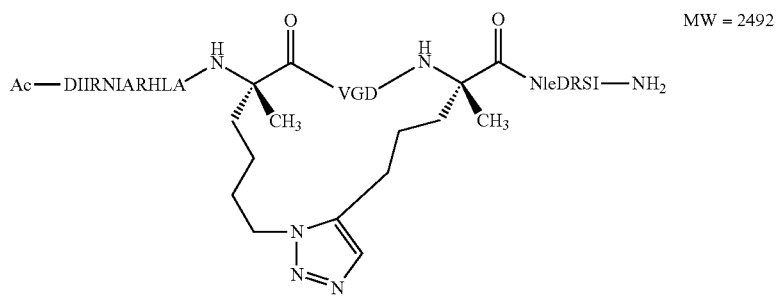

MW = 2492

Table 5 shows exemplary peptidommimetic macrocycles of the invention. "Nle" represents norleucine.

The present invention contemplates the use of non-naturally-occurring amino acids and amino acid analogs in the synthesis of the peptidomimetic macrocycles described herein. Any amino acid or amino acid analog amenable to the synthetic methods employed for the synthesis of stable triazole containing peptidomimetic macrocycles can be used in the present invention. For example, L-propargylglycine is contemplated as a useful amino acid in the present invention. However, other alkyne-containing amino acids that contain a different amino acid side chain are also useful in the invention. For example, L-propargylglycine contains one methylene unit between the α-carbon of the amino acid and the alkyne of the amino acid side chain. The invention also contemplates the use of amino acids with multiple methylene units between the α-carbon and the alkyne. Also, the azido-analogs of amino acids L-lysine, D-lysine, alpha-methyl-L-lysine, and alpha-methyl-D-lysine are contemplated as useful amino acids in the present invention. However, other terminal azide amino acids that contain a different amino acid side chain are also useful in the invention. For example, the azido-analog of L-lysine contains four methylene units between the α-carbon of the amino acid and the terminal azide of the amino acid side chain. The invention also contemplates the use of amino acids with fewer than or greater than four methylene units between the α-carbon and the terminal azide. Table 6 shows some amino acids useful in the preparation of peptidomimetic macrocycles of the invention.

TABLE 6

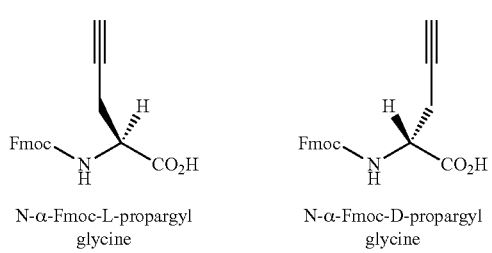

N-α-Fmoc-L-propargyl glycine

N-α-Fmoc-D-propargyl glycine

TABLE 6-continued

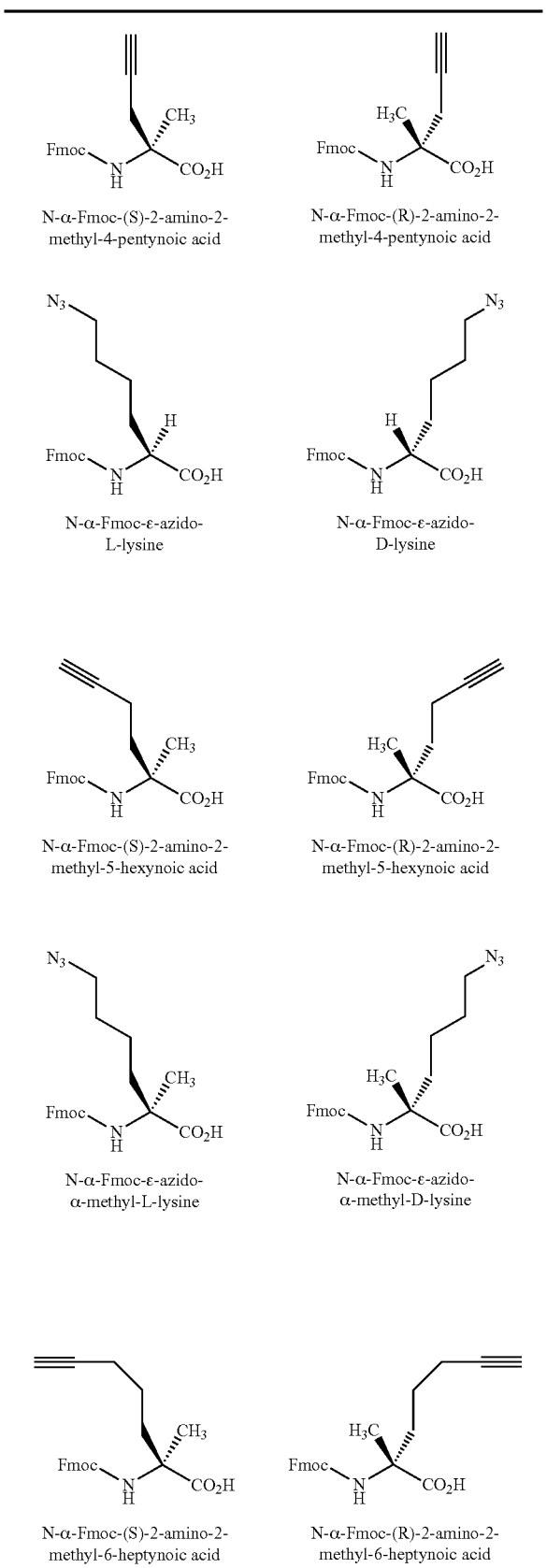

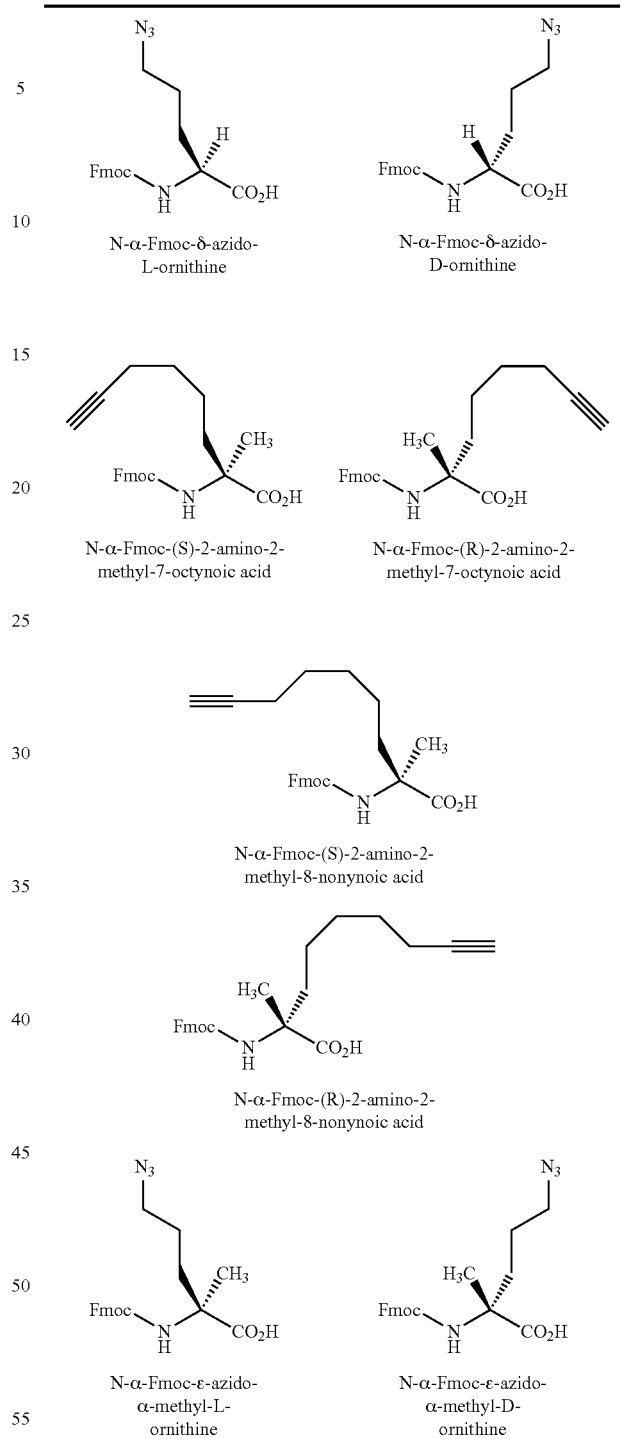

Table 6 shows exemplary amino acids useful in the preparation of peptidomimetic macrocycles of the invention.

In some embodiments the amino acids and amino acid analogs are of the D-configuration. In other embodiments they are of the L-configuration. In some embodiments, some of the amino acids and amino acid analogs contained in the peptidomimetic are of the D-configuration while some of the amino acids and amino acid analogs are of the L-configuration. In some embodiments the amino acid analogs are α,α-disubstituted, such as α-methyl-L-propargylglycine, α-methyl-D-propargylglycine, ε-azido-alpha-methyl-L-lysine, and ε-azido-alpha-methyl-D-lysine. In some embodiments the amino acid analogs are N-alkylated, e.g., N-methyl-L-propargylglycine, N-methyl-D-propargylglycine, N-methyl-ε-azido-L-lysine, and N-methyl-ε-azido-D-lysine.

In some embodiments, the —NH moiety of the amino acid is protected using a protecting group, including without limitation -Fmoc and -Boc. In other embodiments, the amino acid is not protected prior to synthesis of the peptidomimetic macro cycle.

In other embodiments, peptidomimetic macrocycles of Formula III are synthesized. The following synthetic schemes describe the preparation of such compounds. To simplify the drawings, the illustrative schemes depict amino acid analogs derived from L- or D-cysteine, in which $L_1$ and $L_3$ are both —$(CH_2)$—. However, as noted throughout the detailed description above, many other amino acid analogs can be employed in which $L_1$ and $L_3$ can be independently selected from the various structures disclosed herein. The symbols "$[AA]_m$", "$[AA]_n$", "$[AA]_o$" represent a sequence of amide bond-linked moieties such as natural or unnatural amino acids. As described previously, each occurrence of "AA" is independent of any other occurrence of "AA", and a formula such as "$[AA]_m$" encompasses, for example, sequences of non-identical amino acids as well as sequences of identical amino acids.

Synthetic Scheme 6:

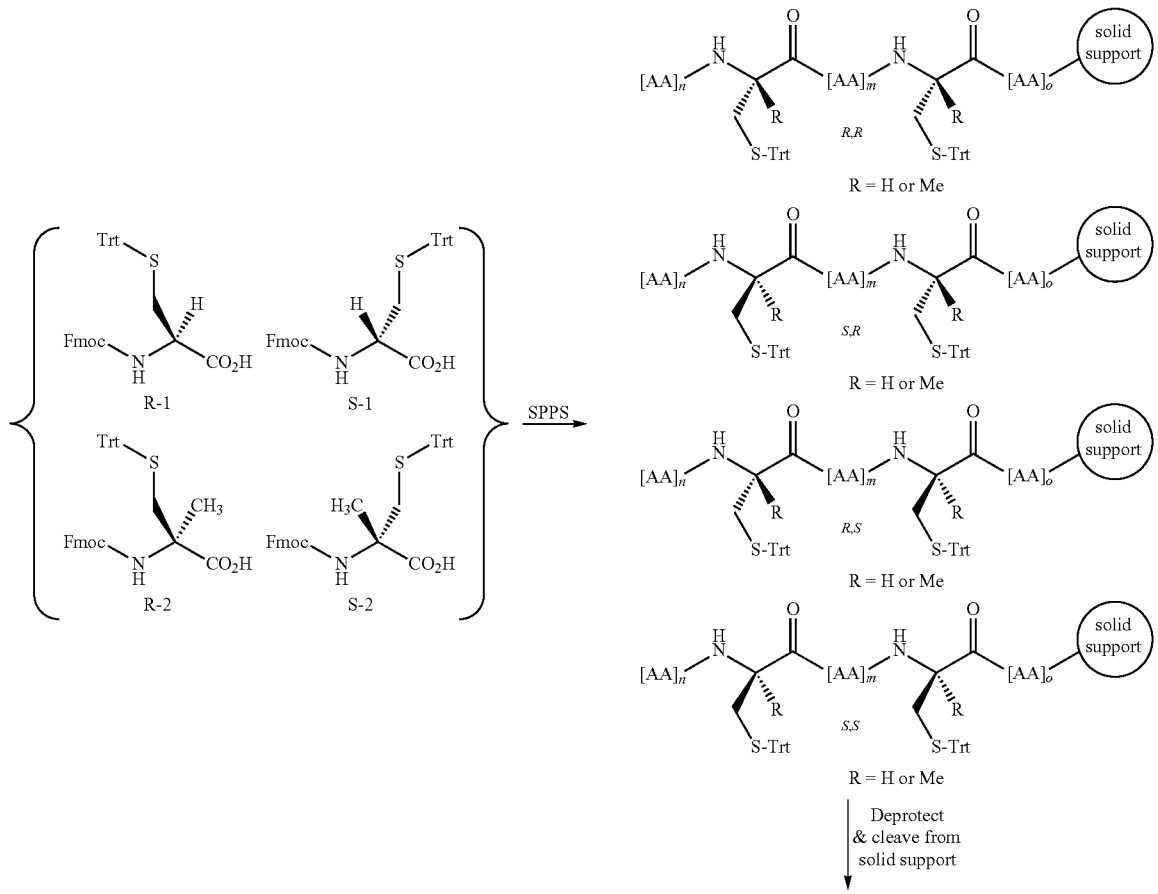

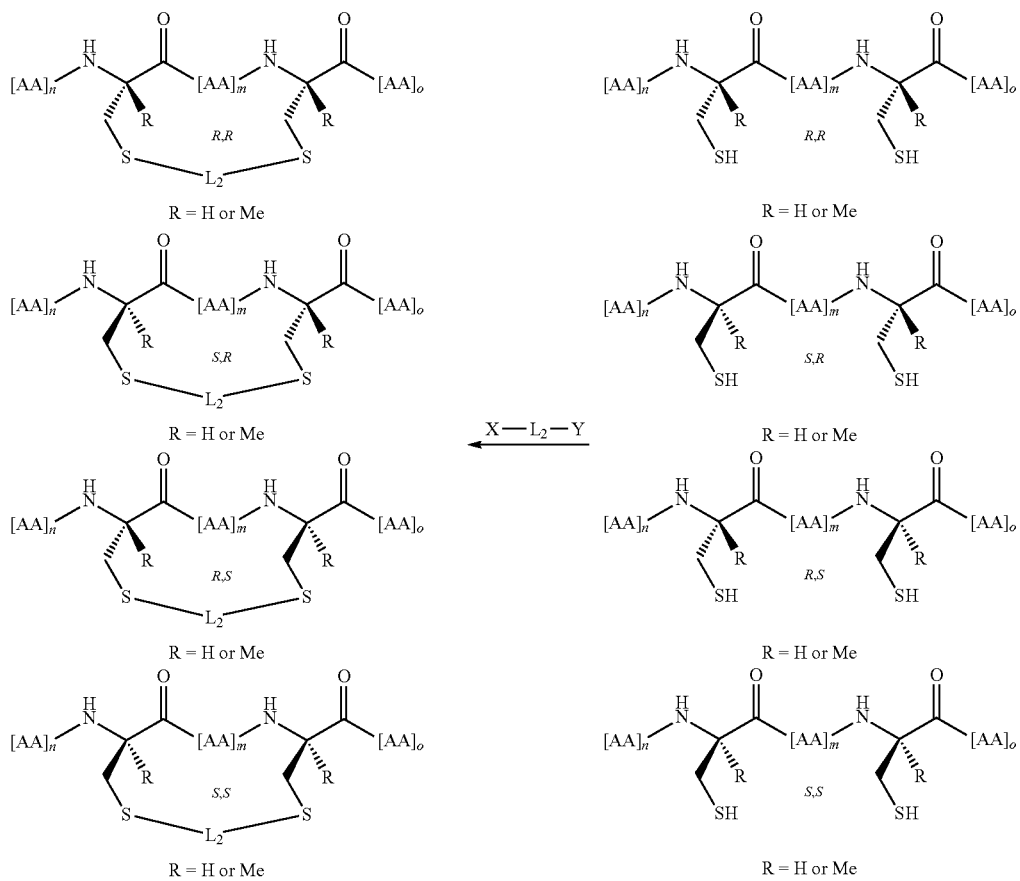

In Scheme 6, the peptidomimetic precursor contains two —SH moieties and is synthesized by solid-phase peptide synthesis (SPPS) using commercially available N-α-Fmoc amino acids such as N-α-Fmoc-S-trityl-L-cysteine or N-α-Fmoc-S-trityl-D-cysteine. Alpha-methylated versions of D-cysteine or L-cysteine are generated by known methods (Seebach et al. (1996), *Angew. Chem. Int. Ed. Engl.* 35:2708-2748, and references therein) and then converted to the appropriately protected N-α-Fmoc-S-trityl monomers by known methods (*"Bioorganic Chemistry: Peptides and Proteins"*, Oxford University Press, New York: 1998, the entire contents of which are incorporated herein by reference). The precursor peptidomimetic is then deprotected and cleaved from the solid-phase resin by standard conditions (e.g., strong acid such as 95% TFA). The precursor peptidomimetic is reacted as a crude mixture or is purified prior to reaction with X-L$_2$-Y in organic or aqueous solutions. In some embodiments the alkylation reaction is performed under dilute conditions (i.e. 0.15 mmol/L) to favor macrocyclization and to avoid polymerization. In some embodiments, the alkylation reaction is performed in organic solutions such as liquid NH$_3$ (Mosberg et al. (1985), J. Am. Chem. Soc. 107:2986-2987; Szewczuk et al. (1992), Int. J. Peptide Protein Res. 40:233-242), NH$_3$/MeOH, or NH$_3$/DMF (Or et al. (1991), J. Org. Chem. 56:3146-3149). In other embodiments, the alkylation is performed in an aqueous solution such as 6M guanidinium HCL, pH 8 (Brunel et al. (2005), Chem. Commun. (20):2552-2554). In other embodiments, the solvent used for the alkylation reaction is DMF or dichloroethane.

Synthetic Scheme 7:
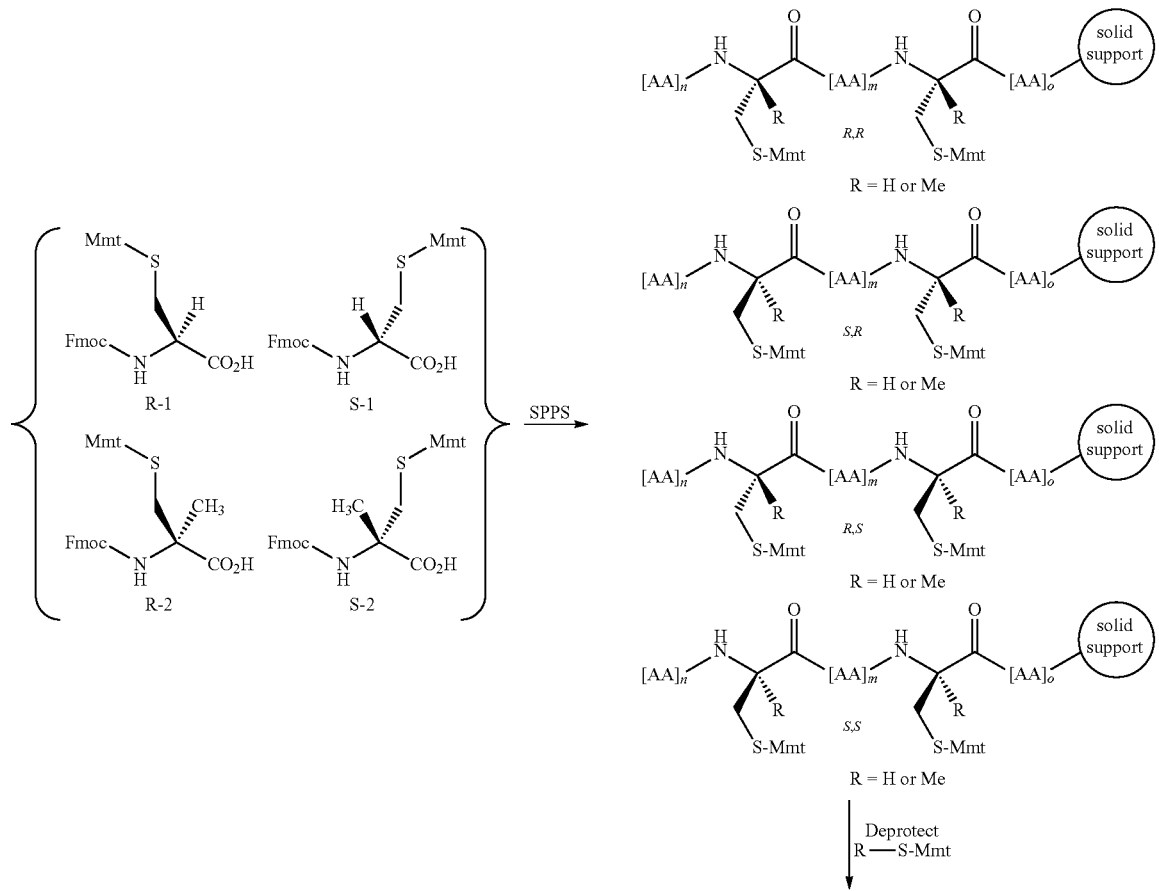

-continued

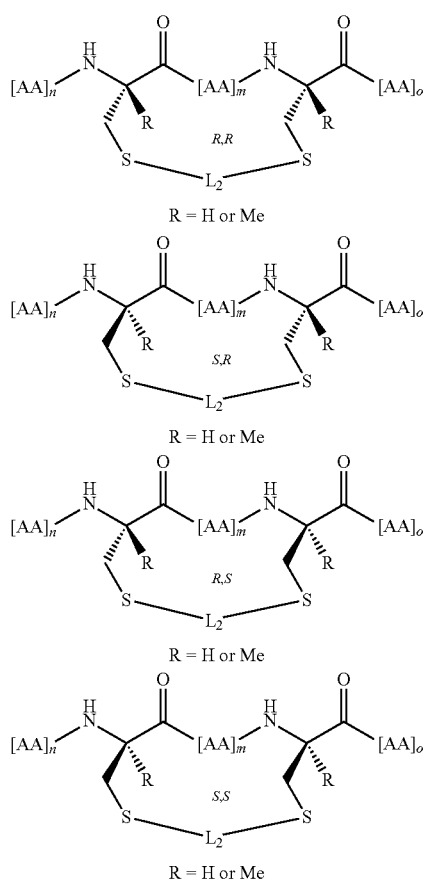

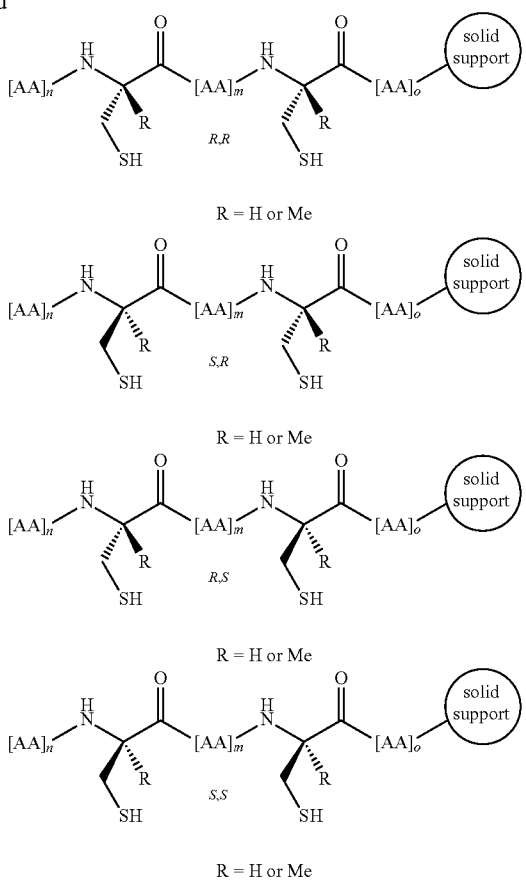

In Scheme 7, the precursor peptidomimetic contains two or more —SH moieties, of which two are specially protected to allow their selective deprotection and subsequent alkylation for macrocycle formation. The precursor peptidomimetic is synthesized by solid-phase peptide synthesis (SPPS) using commercially available N-α-Fmoc amino acids such as N-α-Fmoc-S-p-methoxytrityl-L-cysteine or N-α-Fmoc-S-p-methoxytrityl-D-cysteine. Alpha-methylated versions of D-cysteine or L-cysteine are generated by known methods (Seebach et al. (1996), *Angew. Chem. Int. Ed. Engl.* 35:2708-2748, and references therein) and then converted to the appropriately protected N-α-Fmoc-S-p-methoxytrityl monomers by known methods (*Bioorganic Chemistry: Peptides and Proteins*, Oxford University Press, New York: 1998, the entire contents of which are incorporated herein by reference). The Mmt protecting groups of the peptidomimetic precursor are then selectively cleaved by standard conditions (e.g., mild acid such as 1% TFA in DCM). The precursor peptidomimetic is then reacted on the resin with X-$L_2$-Y in an organic solution. For example, the reaction takes place in the presence of a hindered base such as diisopropylethylamine. In some embodiments, the alkylation reaction is performed in organic solutions such as liquid $NH_3$ (Mosberg et al. (1985), *J. Am. Chem. Soc.* 107:2986-2987; Szewczuk et al. (1992), *Int. J. Peptide Protein Res.* 40:233-242), $NH_3$/MeOH or $NH_3$/DMF (Or et al. (1991), *J. Org. Chem.* 56:3146-3149). In other embodiments, the alkylation reaction is performed in DMF or dichloroethane. The peptidomimetic macrocycle is then deprotected and cleaved from the solid-phase resin by standard conditions (e.g., strong acid such as 95% TFA).

Synthetic Scheme 8:

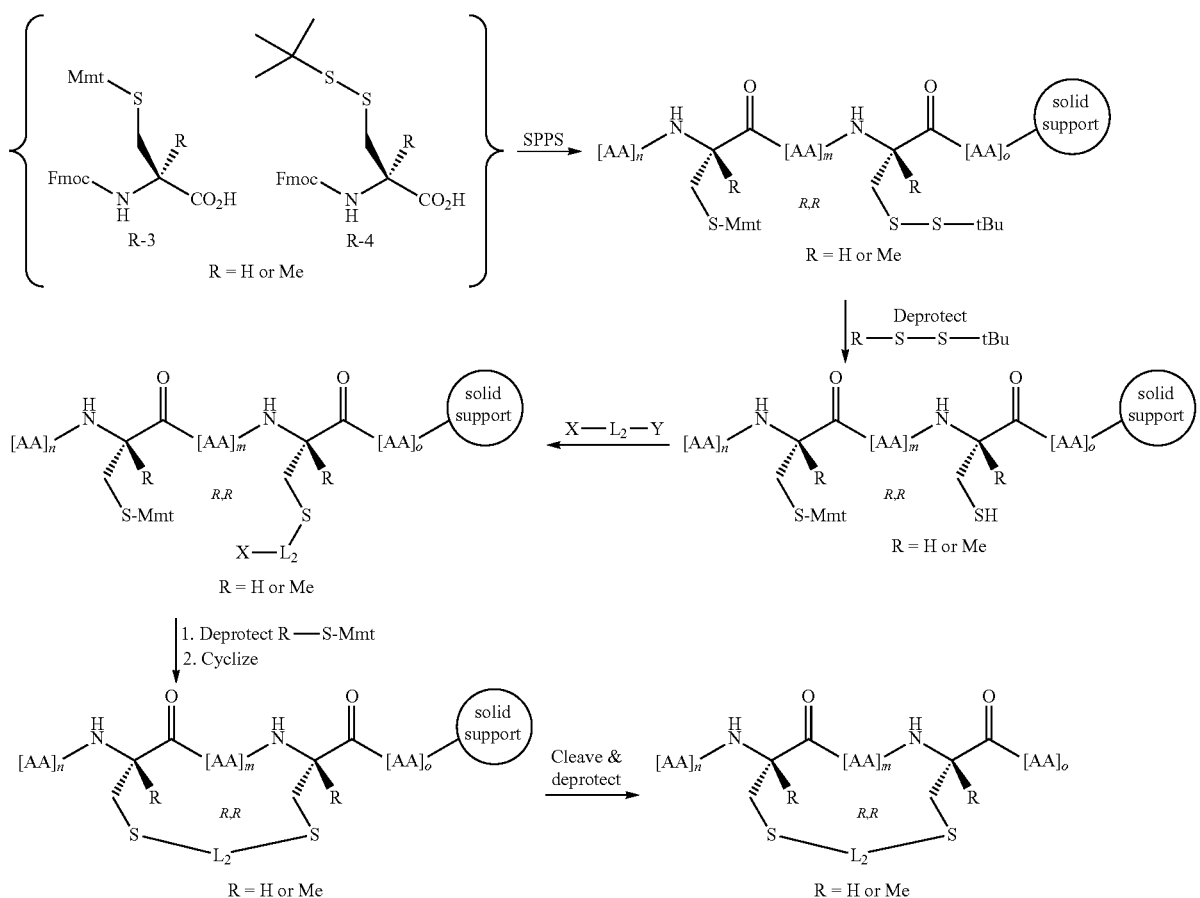

In Scheme 8, the peptidomimetic precursor contains two or more —SH moieties, of which two are specially protected to allow their selective deprotection and subsequent alkylation for macrocycle formation. The peptidomimetic precursor is synthesized by solid-phase peptide synthesis (SPPS) using commercially available N-α-Fmoc amino acids such as N-α-Fmoc-S-p-methoxytrityl-L-cysteine, N-α-Fmoc-S-p-methoxytrityl-D-cysteine, N-α-Fmoc-S—S-t-butyl-L-cysteine, and N-α-Fmoc-S—S-t-butyl-D-cysteine. Alpha-methylated versions of D-cysteine or L-cysteine are generated by known methods (Seebach et al. (1996), *Angew. Chem. Int. Ed. Engl.* 35:2708-2748, and references therein) and then converted to the appropriately protected N-α-Fmoc-S-p-methoxytrityl or N-α-Fmoc-S—S-t-butyl monomers by known methods (*Bioorganic Chemistry: Peptides and Proteins*, Oxford University Press, New York: 1998, the entire contents of which are incorporated herein by reference). The S—S-tButyl protecting group of the peptidomimetic precursor is selectively cleaved by known conditions (e.g., 20% 2-mercaptoethanol in DMF, reference: Galande et al. (2005), *J. Comb. Chem.* 7:174-177). The precursor peptidomimetic is then reacted on the resin with a molar excess of X-L$_2$-Y in an organic solution. For example, the reaction takes place in the presence of a hindered base such as diisopropylethylamine. The Mmt protecting group of the peptidomimetic precursor is then selectively cleaved by standard conditions (e.g., mild acid such as 1% TFA in DCM). The peptidomimetic precursor is then cyclized on the resin by treatment with a hindered base in organic solutions. In some embodiments, the alkylation reaction is performed in organic solutions such as NH$_3$/MeOH or NH$_3$/DMF (Or et al. (1991), *J. Org. Chem.* 56:3146-3149). The peptidomimetic macrocycle is then deprotected and cleaved from the solid-phase resin by standard conditions (e.g., strong acid such as 95% TFA).

Synthetic Scheme 9:

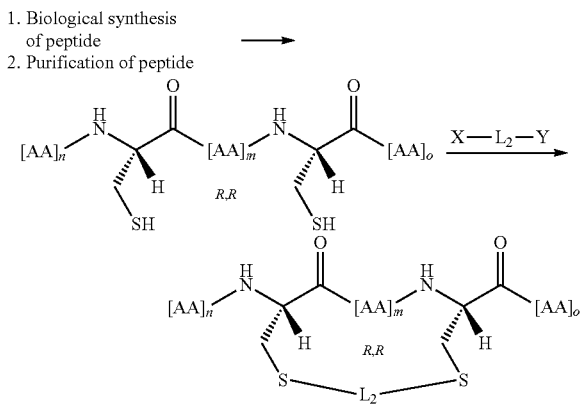

In Scheme 9, the peptidomimetic precursor contains two L-cysteine moieties. The peptidomimetic precursor is synthesized by known biological expression systems in living cells or by known in vitro, cell-free, expression methods. The precursor peptidomimetic is reacted as a crude mixture or is purified prior to reaction with X-L2-Y in organic or aqueous solutions. In some embodiments the alkylation reaction is performed under dilute conditions (i.e. 0.15 mmol/L) to favor macrocyclization and to avoid polymerization. In some embodiments, the alkylation reaction is performed in organic solutions such as liquid $NH_3$ (Mosberg et al. (1985), J. Am. Chem. Soc. 107:2986-2987; Szewczuk et al. (1992), Int. J. Peptide Protein Res. 40:233-242), $NH_3$/MeOH, or $NH_3$/DMF (Or et al. (1991), J. Org. Chem. 56:3146-3149). In other embodiments, the alkylation is performed in an aqueous solution such as 6M guanidinium HCL, pH 8 (Brunel et al. (2005), Chem. Commun. (20):2552-2554). In other embodiments, the alkylation is performed in DMF or dichloroethane. In another embodiment, the alkylation is performed in nondenaturing aqueous solutions, and in yet another embodiment the alkylation is performed under conditions that favor α-helical structure formation. In yet another embodiment, the alkylation is performed under conditions that favor the binding of the precursor peptidomimetic to another protein, so as to induce the formation of the bound α-helical conformation during the alkylation.

Various embodiments for X and Y are envisioned which are suitable for reacting with thiol groups. In general, each X or Y is independently be selected from the general category shown in Table 5. For example, X and Y are halides such as —Cl, —Br or —I. Any of the macrocycle-forming linkers described herein may be used in any combination with any of the sequences shown in Tables 1-4 and also with any of the R— substituents indicated herein.

TABLE 7

Examples of Reactive Groups Capable of Reacting with Thiol Groups and Resulting Linkages

| (1) | X or Y | (2) | Resulting Covalent Linkage |
|---|---|---|---|
| (3) | acrylamide | (4) | Thioether |
| (5) | halide (e.g. alkyl or aryl halide) | (6) | Thioether |
| (7) | sulfonate | (8) | Thioether |
| (9) | aziridine | (10) | Thioether |
| (11) | epoxide | (12) | Thioether |
| (13) | haloacetamide | (14) | Thioether |
| (15) | maleimide | (16) | Thioether |
| (17) | sulfonate ester | (18) | Thioether |

Table 8 shows exemplary macrocycles of the invention (SEQ ID NOS 89-94, respectively, in order of appearance). "$N_L$" represents norleucine and replaces a methionine residue. It is envisioned that similar linkers are used to synthesize peptidomimetic macrocycles based on the polypeptide sequences disclosed in Table 1 through Table 4.

TABLE 8

Examples of Peptidomimetic Macrocycles of the Invention

Ac—DIIRNIARHLA-[structure with VGD bridge, CH3 groups, and S-(CH2)4-S linker]-$N_L$DRSI—$NH_2$    MW = 2477

Ac—DIIRNIARHLA-[structure with VGD bridge, CH3 groups, and S-(CH2)3-S linker]-$N_L$DRSI—$NH_2$    MW = 2463

Ac—DIIRNIARHLA-[structure with VGD bridge, CH3 groups, and S-CH2-xylyl-CH2-S linker]-$N_L$DRSI—$NH_2$    MW = 2525

Ac—DIIRNIARHLA-[structure with VGD bridge, CH3 groups, and S-CH2-cyclohexyl-CH2-S linker]-$N_L$DRSI—$NH_2$    MW = 2531

TABLE 8-continued

Examples of Peptidomimetic Macrocycles of the Invention

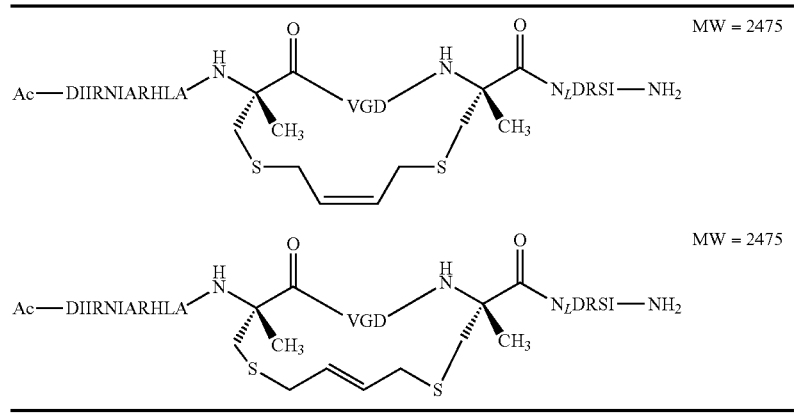

For the examples shown in this table, "N$_L$" represents norleucine.

The present invention contemplates the use of both naturally-occurring and non-naturally-occurring amino acids and amino acid analogs in the synthesis of the peptidomimetic macrocycles of Formula (III). Any amino acid or amino acid analog amenable to the synthetic methods employed for the synthesis of stable bis-sulfhydryl containing peptidomimetic macrocycles can be used in the present invention. For example, cysteine is contemplated as a useful amino acid in the present invention. However, sulfur containing amino acids other than cysteine that contain a different amino acid side chain are also useful. For example, cysteine contains one methylene unit between the α-carbon of the amino acid and the terminal —SH of the amino acid side chain. The invention also contemplates the use of amino acids with multiple methylene units between the α-carbon and the terminal —SH. Non-limiting examples include α-methyl-L-homocysteine and α-methyl-D-homocysteine. In some embodiments the amino acids and amino acid analogs are of the D-configuration. In other embodiments they are of the L-configuration. In some embodiments, some of the amino acids and amino acid analogs contained in the peptidomimetic are of the D-configuration while some of the amino acids and amino acid analogs are of the L-configuration. In some embodiments the amino acid analogs are α,α-disubstituted, such as α-methyl-L-cysteine and α-methyl-D-cysteine.

The invention includes macrocycles in which macrocycle-forming linkers are used to link two or more —SH moieties in the peptidomimetic precursors to form the peptidomimetic macrocycles of the invention. As described above, the macrocycle-forming linkers impart conformational rigidity, increased metabolic stability and/or increased cell penetrability. Furthermore, in some embodiments, the macrocycle-forming linkages stabilize the α-helical secondary structure of the peptidomimetic macrocyles. The macrocycle-forming linkers are of the formula X-L$_2$-Y, wherein both X and Y are the same or different moieties, as defined above. Both X and Y have the chemical characteristics that allow one macrocycle-forming linker -L$_2$- to bis alkylate the bis-sulfhydryl containing peptidomimetic precursor. As defined above, the linker -L$_2$- includes alkylene, alkenylene, alkynylene, heteroalkylene, cycloalkylene, heterocycloalkylene, cycloarylene, or heterocycloarylene, or —R$_4$—K—R$_4$—, all of which can be optionally substituted with an R$_5$ group, as defined above. Furthermore, one to three carbon atoms within the macrocycle-forming linkers -L$_2$-, other than the carbons attached to the —SH of the sulfhydryl containing amino acid, are optionally substituted with a heteroatom such as N, S or O.

The L$_2$ component of the macrocycle-forming linker X-L$_2$-Y may be varied in length depending on, among other things, the distance between the positions of the two amino acid analogs used to form the peptidomimetic macrocycle. Furthermore, as the lengths of L$_1$ and/or L$_3$ components of the macrocycle-forming linker are varied, the length of L$_2$ can also be varied in order to create a linker of appropriate overall length for forming a stable peptidomimetic macrocycle. For example, if the amino acid analogs used are varied by adding an additional methylene unit to each of L$_1$ and L$_3$, the length of L$_2$ are decreased in length by the equivalent of approximately two methylene units to compensate for the increased lengths of L$_1$ and L$_3$.

In some embodiments, L$_2$ is an alkylene group of the formula —(CH$_2$)$_n$—, where n is an integer between about 1 and about 15. For example, n is 1, 2, 3, 4, 5, 6, 7, 8, 9 or 10. In other embodiments, L$_2$ is an alkenylene group. In still other embodiments, L$_2$ is an aryl group.

Table 9 shows additional embodiments of X-L$_2$-Y groups.

TABLE 9

Exemplary X—L$_2$—Y groups of the invention.

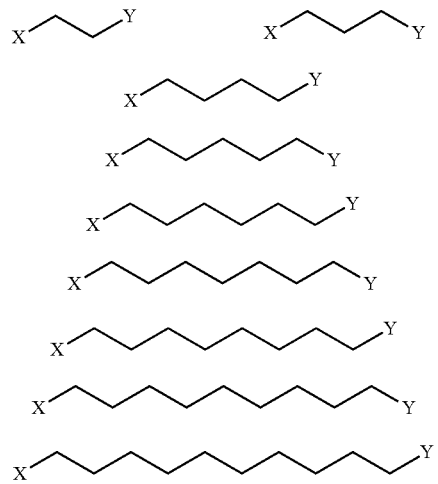

TABLE 9-continued

Exemplary X—L$_2$—Y groups of the invention.

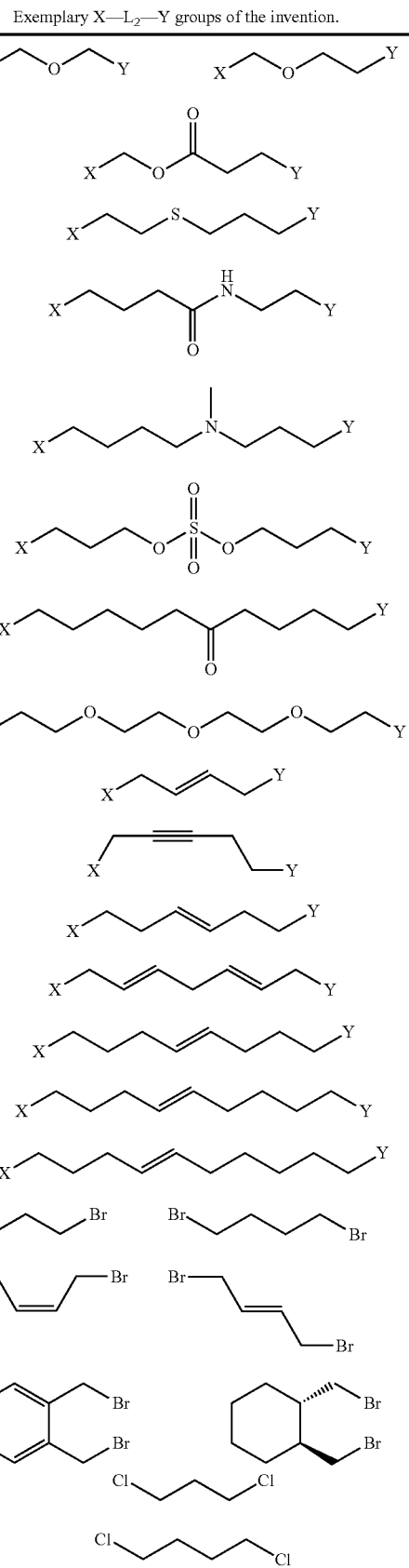

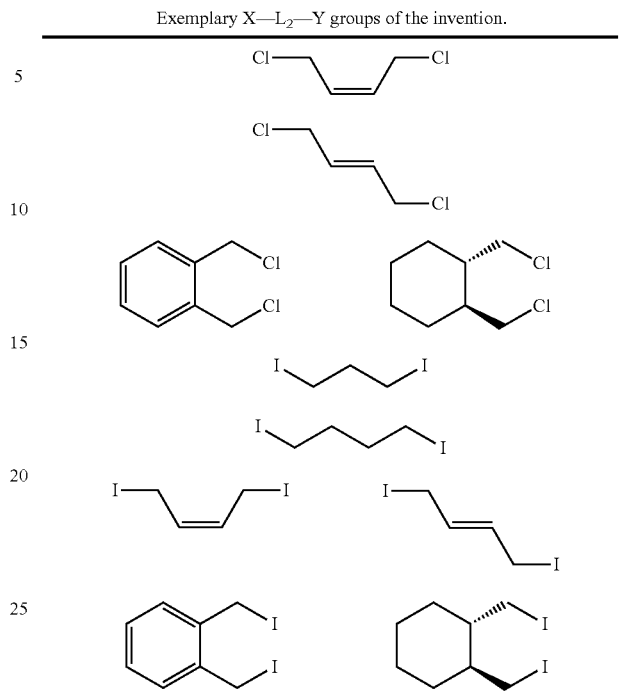

Each X and Y in this table, is, for example, independently Cl—, Br—, or I—.

Additional methods of forming peptidomimetic macrocycles which are envisioned as suitable to perform the present invention include those disclosed by Mustapa, M. Firouz Mohd et al., J. Org. Chem (2003), 68, pp. 8193-8198; Yang, Bin et al. Bioorg Med. Chem. Lett. (2004), 14, pp. 1403-1406; U.S. Pat. No. 5,364,851; U.S. Pat. No. 5,446,128; U.S. Pat. No. 5,824,483; U.S. Pat. No. 6,713,280; and U.S. Pat. No. 7,202,332. In such embodiments, aminoacid precursors are used containing an additional substituent R— at the alpha position. Such aminoacids are incorporated into the macrocycle precursor at the desired positions, which may be at the positions where the crosslinker is substituted or, alternatively, elsewhere in the sequence of the macrocycle precursor. Cyclization of the precursor is then effected according to the indicated method.

Assays

The properties of the peptidomimetic macrocycles of the invention are assayed, for example, by using the methods described below.

Assay to Determine α-Helicity.

In solution, the secondary structure of polypeptides with α-helical domains will reach a dynamic equilibrium between random coil structures and α-helical structures, often expressed as a "percent helicity". Thus, for example, unmodified pro-apoptotic BH3 domains are predominantly random coils in solution, with α-helical content usually under 25%. Peptidomimetic macrocycles with optimized linkers, on the other hand, possess, for example, an alpha-helicity that is at least two-fold greater than that of a corresponding uncrosslinked polypeptide. In some embodiments, macrocycles of the invention will possess an alpha-helicity of greater than 50%. To assay the helicity of peptidomimetic macrocyles of the invention, such as BH3 domain-based macrocycles, the compounds are dissolved in an aqueous solution (e.g. 50 mM potassium phosphate solution at pH 7, or distilled H$_2$O, to concentrations of 25-50 μM). Circular dichroism (CD) spectra are obtained on a spectropolarimeter (e.g., Jasco J-710) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity (e.g. [Φ]222obs) by the reported value for a model helical decapeptide (Yang et al. (1986), *Methods Enzymol.* 130:208)).

Assay to Determine Melting Temperature (Tm).

A peptidomimetic macrocycle of the invention comprising a secondary structure such as an α-helix exhibits, for example, a higher melting temperature than a corresponding uncrosslinked polypeptide. Typically peptidomimetic macrocycles of the invention exhibit Tm of >60° C. representing a highly stable structure in aqueous solutions. To assay the effect of macrocycle formation on meltine temperature, peptidomimetic macrocycles or unmodified peptides are dissolved in distilled $H_2O$ (e.g. at a final concentration of 50 μM) and the Tm is determined by measuring the change in ellipticity over a temperature range (e.g. 4 to 95° C.) on a spectropolarimeter (e.g., Jasco J-710) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

Protease Resistance Assay.

The amide bond of the peptide backbone is susceptible to hydrolysis by proteases, thereby rendering peptidic compounds vulnerable to rapid degradation in vivo. Peptide helix formation, however, typically buries the amide backbone and therefore may shield it from proteolytic cleavage. The peptidomimetic macrocycles of the present invention may be subjected to in vitro trypsin proteolysis to assess for any change in degradation rate compared to a corresponding uncrosslinked polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln [S] versus time (k=−1× slope).

Ex Vivo Stability Assay.

Peptidomimetic macrocycles with optimized linkers possess, for example, an ex vivo half-life that is at least two-fold greater than that of a corresponding uncrosslinked polypeptide, and possess an ex vivo half-life of 12 hours or more. For ex vivo serum stability studies, a variety of assays may be used. For example, a peptidomimetic macrocycle and/or a corresponding uncrosslinked polypeptide (2 mcg) are each incubated with fresh mouse, rat and/or human serum (e.g. 1-2 mL) at 37° C. for 0, 1, 2, 4, 8, and 24 hours. Samples of differing macrocycle concentration may be prepared by serial dilution with serum. To determine the level of intact compound, the following procedure may be used: The samples are extracted by transferring 100 μl of sera to 2 ml centrifuge tubes followed by the addition of 10 μL of 50% formic acid and 500 μL acetonitrile and centrifugation at 14,000 RPM for 10 min at 4±2° C. The supernatants are then transferred to fresh 2 ml tubes and evaporated on Turbovap under $N_2$<10 psi, 37° C. The samples are reconstituted in 100 μL of 50:50 acetonitrile:water and submitted to LC-MS/MS analysis. Equivalent or similar procedures for testing ex vivo stability are known and may be used to determine stability of macrocycles in serum.

In Vitro Binding Assays.

To assess the binding and affinity of peptidomimetic macrocycles and peptidomimetic precursors to acceptor proteins, a fluorescence polarization assay (FPA) issued, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

For example, fluoresceinated peptidomimetic macrocycles (25 nM) are incubated with the acceptor protein (25-1000 nM) in binding buffer (140 mM NaCl, 50 mM Tris-HCL, pH 7.4) for 30 minutes at room temperature. Binding activity is measured, for example, by fluorescence polarization on a luminescence spectrophotometer (e.g. Perkin-Elmer LS50B). Kd values may be determined by nonlinear regression analysis using, for example, Graphpad Prism software (GraphPad Software, Inc., San Diego, Calif.). A peptidomimetic macrocycle of the invention shows, in some instances, similar or lower Kd than a corresponding uncrosslinked polypeptide.

Acceptor proteins for BH3-peptides such as BCL-2, BCL-$X_L$, BAX or MCL1 may, for example, be used in this assay. Additional methods to perform such assays are described in the Example section below.

In Vitro Displacement Assays to Characterize Antagonists of Peptide-Protein Interactions.

To assess the binding and affinity of compounds that antagonize the interaction between a peptide (e.g. a BH3 peptide or a p53 peptide) and an acceptor protein, a fluorescence polarization assay (FPA) utilizing a fluoresceinated peptidomimetic macrocycle derived from a peptidomimetic precursor sequence is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution). A compound that antagonizes the interaction between the fluoresceinated peptidomimetic macrocycle and an acceptor protein will be detected in a competitive binding FPA experiment.

For example, putative antagonist compounds (1 nM to 1 mM) and a fluoresceinated peptidomimetic macrocycle (25 nM) are incubated with the acceptor protein (50 nM) in binding buffer (140 mM NaCl, 50 mM Tris-HCL, pH 7.4) for 30 minutes at room temperature. Antagonist binding activity is measured, for example, by fluorescence polarization on a luminescence spectrophotometer (e.g. Perkin-Elmer LS50B). Kd values may be determined by nonlinear regression analysis using, for example, Graphpad Prism software (GraphPad Software, Inc., San Diego, Calif.).

Any class of molecule, such as small organic molecules, peptides, oligonucleotides or proteins can be examined as putative antagonists in this assay. Acceptor proteins for BH3-peptides such as BCL2, BCL-XL, BAX or MCL1 can be used in this assay. Additional methods to perform such assays are described in the Example section below.

Binding Assays in Cell Lysates or Intact Cells.

It is possible to measure binding of peptides or peptidomimetic macrocycles to their natural acceptors in cell lysates or intact cells by immunoprecipitation and pull-down experiments. For example, intact cells are incubated with fluoresceinated (FITC-labeled) or biotinylated compounds for 4 hrs in the absence of serum, followed by serum replacement and further incubation that ranges from 4-18 hrs. Alternatively, cells can be incubated for the duration of the experiment in Opti-MEM (Invitrogen). Cells are then pelleted and incubated in lysis buffer (50 mM Tris [pH 7.6], 150 mM NaCl, 1% CHAPS and protease inhibitor cocktail) for 10 minutes at 4° C. 1% NP-40 or Triton X-100 may be used instead of CHAPS. Extracts are centrifuged at 14,000 rpm for 15 minutes and supernatants collected and incubated with 10 µl goat anti-FITC antibody or streptavidin-coated beads for 2 hrs, rotating at 4° C. followed by further 2 hrs incubation at 4° C. with protein A/G Sepharose (50 µl of 50% bead slurry).). No secondary step is necessary if using streptavidin beads to pull down biotinylated compounds. Alternatively FITC-labeled or biotinylated compounds are incubated with cell lysates, prepared as described above, for 2 hrs, rotating at 4° C. followed by incubation with 10 µl goat anti-FITC antibody or streptavidin-coated beads for 2 hrs, rotating at 4° C. followed by further 2 hrs incubation at 4° C. with protein A/G Sepharose (50 µl of 50% bead slurry), no secondary step is necessary if using streptavidin beads to pull down biotinylated compounds. After quick centrifugation, the pellets may be washed in lysis buffer containing increasing salt concentration (e.g., 150, 300, 500 mM of NaCl). The beads may be then re-equilibrated at 150 mM NaCl before addition of SDS-containing sample buffer and boiling. The beads and cell lysates may be electrophoresed using 4%-12% gradient Bis-Tris gels followed by transfer into Immobilon-P membranes. After blocking, blots may be incubated with an antibody that detects FITC or biotin, respectively and also with one or more antibodies that detect proteins that bind to the peptidomimetic macrocycle, including BCL2, MCL1, BCL-XL, A1, BAX, and BAK. The lysate blots are also probed with anti-Hsc-70 for loading control. Alternatively, after electrophoresis the gel may be silver stained to detect proteins that come down specifically with FITC-labeled or biotinylated compounds.

Cellular Penetrability Assays.

A peptidomimetic macrocycle is, for example, more cell permeable compared to a corresponding uncrosslinked polypeptide. In some embodiments, the peptidomimetic macrocycles are more cell permeable than a corresponding uncrosslinked polypeptides. Peptidomimetic macrocycles with optimized linkers possess, for example, cell penetrability that is at least two-fold greater than a corresponding uncrosslinked polypeptide, and often 20% or more of the applied peptidomimetic macrocycle will be observed to have penetrated the cell after 4 hours. To measure the cell penetrability of peptidomimetic macrocycles and corresponding uncrosslinked polypeptides, intact cells are incubated with fluoresceinated peptidomimetic macrocycles or corresponding uncrosslinked polypeptides (10 µM) for 4 hrs in serum free media at 37° C., washed twice with media and incubated with trypsin (0.25%) for 10 min at 37° C. The cells are washed again and resuspended in PBS. Cellular fluorescence is analyzed, for example, by using either a FACSCalibur flow cytometer or Cellomics' KineticScan® HCS Reader. Additional methods of quantitating cellular penetration may be used. A particular method is described in more details in the Examples provided.

Cellular Efficacy Assays.

The efficacy of certain peptidomimetic macrocycles is determined, for example, in cell-based killing assays using a variety of tumorigenic and non-tumorigenic cell lines and primary cells derived from human or mouse cell populations. Cell viability is monitored, for example, over 24-96 hrs of incubation with peptidomimetic macrocycles (0.5 to 50 µM) to identify those that kill at $EC_{50}<10$ µM. In this context, $EC_{50}$ refers to the half maximal effective concentration, which is the concentration of peptidomimetic macrocycle at which 50% the population is viable. Several standard assays that measure cell viability are commercially available and are optionally used to assess the efficacy of the peptidomimetic macrocycles. In addition, assays that measure Annexin V and caspase activation are optionally used to assess whether the peptidomimetic macrocycles kill cells by activating the apoptotic machinery. For example, the Cell Titer-glo assay is used which determines cell viability as a function of intracellular ATP concentration.

In Vivo Stability Assay.

To investigate the in vivo stability of the peptidomimetic macrocycles, the compounds are, for example, administered to mice and/or rats by IV, IP, SC, PO or inhalation routes at concentrations ranging from 0.1 to 50 mg/kg and blood specimens withdrawn at 0', 5', 15', 30', 1 hr, 4 hrs, 8 hrs, 12 hrs, 24 hrs and 48 hrs post-injection. Levels of intact compound in 25 µL of fresh serum are then measured by LC-MS/MS as described herein.

In Vivo Efficacy in Animal Models.

To determine the anti-oncogenic activity of peptidomimetic macrocycles of the invention in vivo, the compounds are, for example, given alone (IP, IV, SC, PO, by inhalation or nasal routes) or in combination with sub-optimal doses of relevant chemotherapy (e.g., cyclophosphamide, doxorubicin, etoposide). In one example, $5\times10^6$ SEMK2 cells (established from the bone marrow of a patient with acute lymphoblastic leukemia) that stably express luciferase are injected by tail vein in NOD-SCID, SCID-beige or NOD.IL2rg KO mice 3 hrs after they have been subjected to total body irradiation. Non-radiated mice may also be used for these studies. If left untreated, this form of leukemia is fatal in 3 weeks in this model. The leukemia is readily monitored, for example, by injecting the mice with D-luciferin (60 mg/kg) and imaging the anesthetized animals (e.g., Xenogen In Vivo Imaging System, Caliper Life Sciences, Hopkinton, Mass.). Total body bioluminescence is quantified by integration of photonic flux (photons/sec) by Living Image Software (Caliper Life Sciences, Hopkinton, Mass.). Peptidomimetic macrocycles alone or in combination with sub-optimal doses of relevant chemotherapeutics agents are, for example, administered to leukemic mice (8-10 days after injection/day 1 of experiment, in bioluminescence range of 14-16) by tail vein or IP routes at doses ranging from 0.1 mg/kg to 50 mg/kg for 7 to 21 days. Optionally, the mice are imaged throughout the experiment every other day and survival monitored daily for the duration of the experiment. Expired mice are optionally subjected to necropsy at the end of the experiment. Another animal model is implantation into NOD-SCID mice of DoHH2, a cell line derived from human follicular lymphoma, that stably expresses luciferase. These in vivo tests optionally generate preliminary pharmacokinetic, pharmacodynamic and toxicology data.

Clinical Trials.

To determine the suitability of the peptidomimetic macrocycles of the invention for treatment of humans, clinical trials are performed. For example, patients diagnosed with cancer and in need of treatment are selected and separated in treatment and one or more control groups, wherein the treatment group is administered a peptidomimetic macrocycle of the invention, while the control groups receive a placebo, a known anti-cancer drug, or the standard of care. The treatment safety and efficacy of the peptidomimetic macrocycles of the invention can thus be evaluated by performing comparisons of the patient groups with respect to factors such as survival and quality-of-life. In this example, the patient group treated with a peptidomimetic macrocycle show improved long-term survival compared to a patient control group treated with a placebo or the standard of care.

Pharmaceutical Compositions and Routes of Administration

Methods of administration include but are not limited to intradermal, intramuscular, intraperitoneal, intravenous, subcutaneous, intranasal, epidural, oral, sublingual, intracerebral, intravaginal, transdermal, rectal, by inhalation, or topical by application to ears, nose, eyes, or skin.

The peptidomimetic macrocycles of the invention also include pharmaceutically acceptable derivatives or prodrugs thereof. A "pharmaceutically acceptable derivative" means any pharmaceutically acceptable salt, ester, salt of an ester, pro-drug or other derivative of a compound of this invention which, upon administration to a recipient, is capable of providing (directly or indirectly) a compound of this invention. For example, pharmaceutically acceptable derivatives may increase the bioavailability of the compounds of the invention when administered to a mammal (e.g., by increasing absorption into the blood of an orally administered compound) or which increases delivery of the active compound to a biological compartment (e.g., the brain or lymphatic system) relative to the parent species. Some pharmaceutically acceptable derivatives include a chemical group which increases aqueous solubility or active transport across the gastrointestinal mucosa.

In some embodiments, the peptidomimetic macrocycles of the invention are modified by covalently or non-covalently joining appropriate functional groups to enhance selective biological properties. Such modifications include those which increase biological penetration into a given biological compartment (e.g., blood, lymphatic system, central nervous system), increase oral availability, increase solubility to allow administration by injection, alter metabolism, and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts.

For preparing pharmaceutical compositions from the compounds of the present invention, pharmaceutically acceptable carriers include either solid or liquid carriers. Solid form preparations include powders, tablets, pills, capsules, cachets, suppositories, and dispersible granules. A solid carrier can be one or more substances, which also acts as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa.

In powders, the carrier is a finely divided solid, which is in a mixture with the finely divided active component. In tablets, the active component is mixed with the carrier having the necessary binding properties in suitable proportions and compacted in the shape and size desired.

Suitable solid excipients are carbohydrate or protein fillers include, but are not limited to sugars, including dextrose, lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents are added, such as the cross-linked polyvinyl pyrrolidone, agar, alginic acid, or a salt thereof, such as sodium alginate.

Liquid form preparations include solutions, suspensions, and emulsions, for example, water or water/propylene glycol solutions. For parenteral injection, liquid preparations can be formulated in solution in aqueous polyethylene glycol solution. The term "parenteral" as used herein refers modes of administration including intravenous, intraarterial, intramuscular, intraperitoneal, intrasternal, and subcutaneous.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

When the compositions of this invention comprise a combination of a peptidomimetic macrocycle and one or more additional therapeutic or prophylactic agents, both the compound and the additional agent should be present at dosage levels of between about 1 to 100%, and more preferably between about 5 to 95% of the dosage normally administered in a monotherapy regimen. In some embodiments, the additional agents are administered separately, as part of a multiple dose regimen, from the compounds of this invention. Alternatively, those agents are part of a single dosage form, mixed together with the compounds of this invention in a single composition.

Methods of Use

In one aspect, the present invention provides novel peptidomimetic macrocycles that are useful in competitive binding assays to identify agents which bind to the natural ligand(s) of the proteins or peptides upon which the peptidomimetic macrocycles are modeled. For example, in the BH3/BCL-$X_L$ anti-apoptotic system labeled peptidomimetic macrocycles based on BH3 can be used in a BCL-$X_L$ binding assay along with small molecules that competitively bind to BCL-$X_L$. Competitive binding studies allow for rapid in vitro evaluation and determination of drug candidates specific for the BH3/BCL-$X_L$ system. The invention further provides for the generation of antibodies against the peptidomimetic macrocycles. In some embodiments, these antibodies specifically bind both the peptidomimetic macrocycle and the BH3 peptidomimetic precursors upon which the peptidomimetic macrocycles are derived. Such antibodies, for example, disrupt the BH3/BCL-XL systems, respectively.

In other aspects, the present invention provides for both prophylactic and therapeutic methods of treating a subject at risk of (or susceptible to) a disorder or having a disorder associated with aberrant (e.g., insufficient or excessive)

BCL-2 family member expression or activity (e.g., extrinsic or intrinsic apoptotic pathway abnormalities). It is believed that some BCL-2 type disorders are caused, at least in part, by an abnormal level of one or more BCL-2 family members (e.g., over or under expression), or by the presence of one or more BCL-2 family members exhibiting abnormal activity. As such, the reduction in the level and/or activity of the BCL-2 family member or the enhancement of the level and/or activity of the BCL-2 family member, is used, for example, to ameliorate or reduce the adverse symptoms of the disorder.

In one embodiment, the compounds of the invention are used to treat disorders associated with expression or overexpression of Mcl-1. Mcl-1 has been shown to be expressed in many tissues and neoplastic cell lines and is thought to participate in the development of malignancies (Thallinger et al. (2004) Clin. Cancer Res. 10:4185-4191). The peptidomimetic macrocycles of the invention may be used for the treatment of such malignancies.

In one embodiment, the disorder being treated (e.g. cancer) is differentially responsive to the peptidomimetic macrocycles of the invention. In some embodiments, the cancer is treated with a BIM peptidomimetic macrocycle and is at least 2-fold less sensitive to treatment using a BID polypeptide (such as a BID peptidomimetic macrocycle or uncrosslinked polypeptide) as measured in an in vitro cell viability assay. In other embodiments, the cancer is at least 5-fold less sensitive to treatment using a BID polypeptide as measured in an in vitro cell viability assay. In yet other embodiments, the cancer is at least 8-fold less sensitive to treatment using a BID polypeptide as measured in an in vitro cell viability assay. In other embodiments, the cancer is treated with a BID peptidomimetic macrocycle and is at least 2-fold less sensitive to treatment using a BIM polypeptide (such as a BIM peptidomimetic macrocycle or uncrosslinked polypeptide) as measured in an in vitro cell viability assay. In other embodiments, the cancer is at least 5-fold less sensitive to treatment using a BIM polypeptide as measured in an in vitro cell viability assay. In yet other embodiments, the cancer is at least 8-fold less sensitive to treatment using a BIM polypeptide as measured in an in vitro cell viability assay.

In another embodiment, a method of treating a human patient is provided comprising performing an assay to evaluate the levels of a BCL-family protein and administering to the patient a peptidomimetic macrocycle if an aberrant or irregular level of expression of the BCL-family protein is detected. BCL-family proteins include, for example, BCL-2, BCL-XL, MCL-1, Bfl1/A1, BOO/DIVA, NRH/NR13, BAX, BAD, BAK, BOK, BIK, PUMA, BIM, BMF, BLK, BNIP3, HRK, NIX, SPIKE, and Noxa. In one embodiment, a method of treating a human patient is provided comprising performing an assay to evaluate the levels of BCL-2 in the patient and administering to the patient a peptidomimetic macrocycle if an aberrant or irregular level of expression of BCL-2 is detected. In another embodiment, a method of treating a human patient is provided comprising performing an assay to evaluate the levels of BCL-XL in the patient and administering to the patient a peptidomimetic macrocycle if an aberrant or irregular level of expression of BCL-XL is detected. In another embodiment, a method of treating a human patient is provided comprising performing an assay to evaluate the levels of MCL-1 in the patient and administering to the patient a peptidomimetic macrocycle if an aberrant or irregular level of expression of MCL-1 is detected. In another embodiment, a method of treating a human patient is provided comprising performing an assay to evaluate the levels of BAX in the patient and administering to the patient a peptidomimetic macrocycle if an aberrant or irregular level of expression of BAX is detected. In another embodiment, a method of treating a human patient is provided comprising performing an assay to evaluate the levels of BAD in the patient and administering to the patient a peptidomimetic macrocycle if an aberrant or irregular level of expression of BAD is detected. In another embodiment, a method of treating a human patient is provided comprising performing an assay to evaluate the levels of BAK in the patient and administering to the patient a peptidomimetic macrocycle if an aberrant or irregular level of expression of BAK is detected. In another embodiment, a method of treating a human patient is provided comprising performing an assay to evaluate the levels of PUMA in the patient and administering to the patient a peptidomimetic macrocycle if an aberrant or irregular level of expression of PUMA is detected. In another embodiment, a method of treating a human patient is provided comprising performing an assay to evaluate the levels of Noxa in the patient and administering to the patient a peptidomimetic macrocycle if an aberrant or irregular level of expression of Noxa is detected. In another embodiment, a method of treating a human patient is provided comprising performing an assay to evaluate the levels of Noxa in the patient and administering to the patient a peptidomimetic macrocycle if an aberrant or irregular level of expression of Noxa is detected. In another embodiment, a method of treating a human patient is provided comprising performing an assay to evaluate the levels of Bfl1/A1 in the patient and administering to the patient a peptidomimetic macrocycle if an aberrant or irregular level of expression of Bfl1/A1 is detected. In another embodiment, a method of treating a human patient is provided comprising performing an assay to evaluate the levels of BOO/DIVA in the patient and administering to the patient a peptidomimetic macrocycle if an aberrant or irregular level of expression of BOO/DIVA is detected. In another embodiment, a method of treating a human patient is provided comprising performing an assay to evaluate the levels of NRH/NR13 in the patient and administering to the patient a peptidomimetic macrocycle if an aberrant or irregular level of expression of NRH/NR13 is detected. In another embodiment, a method of treating a human patient is provided comprising performing an assay to evaluate the levels of BOK in the patient and administering to the patient a peptidomimetic macrocycle if an aberrant or irregular level of expression of BOK is detected. In another embodiment, a method of treating a human patient is provided comprising performing an assay to evaluate the levels of BIK in the patient and administering to the patient a peptidomimetic macrocycle if an aberrant or irregular level of expression of BIK is detected. In another embodiment, a method of treating a human patient is provided comprising performing an assay to evaluate the levels of BMF in the patient and administering to the patient a peptidomimetic macrocycle if an aberrant or irregular level of expression of BMF is detected. In another embodiment, a method of treating a human patient is provided comprising performing an assay to evaluate the levels of BLK in the patient and administering to the patient a peptidomimetic macrocycle if an aberrant or irregular level of expression of BLK is detected. In another embodiment, a method of treating a human patient is provided comprising performing an assay to evaluate the levels of BNIP3 in the patient and administering to the patient a peptidomimetic macrocycle if an aberrant or irregular level of expression of BNIP3 is detected. In another embodiment, a method of treating a human patient is provided comprising performing an assay to evaluate the levels of HRK in the patient and administering to the patient a peptidomimetic macrocycle if an aberrant or irregular level of expression of HRK is detected. In another embodiment, a method of treating a human patient is provided comprising performing an assay to evaluate the levels of Nix in the patient and administering to the patient a peptidomimetic macrocycle if an aberrant or irregular level of expression of Nix is detected. In another embodiment, a method of treating a human patient is provided comprising performing an assay to evaluate the levels of SPIKE in the patient and administering to the patient a peptidomimetic macrocycle if an aberrant or irregular level of expression of SPIKE is detected.

As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

In some embodiments, the peptidomimetics macrocycles of the invention is used to treat, prevent, and/or diagnose cancers and neoplastic conditions. As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A metastatic tumor can arise from a multitude of primary tumor types, including but not limited to those of breast, lung, liver, colon and ovarian origin. "Pathologic hyperproliferative" cells occur in disease states characterized by malignant tumor growth. Examples of non-pathologic hyperproliferative cells include proliferation of cells associated with wound repair. Examples of cellular proliferative and/or differentiative disorders include cancer, e.g., carcinoma, sarcoma, or metastatic disorders. In some embodiments, the peptidomimetics macrocycles are novel therapeutic agents for controlling breast cancer, ovarian cancer, colon cancer, lung cancer, metastasis of such cancers and the like.

Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991), *Crit Rev. Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

Breast Cancer

In one aspect, the invention provides methods of treating breast cancer by administering the peptidomimetic macrocycles of the invention. Breast cancer includes invasive breast carcinomas, such as invasive ductal carcinoma, invasive lobular carcinoma, tubular carcinoma, invasive cribriform carcinoma, medullary carcinoma, mucinous carcinoma and other tumours with abundant mucin, cystadenocarcinoma, columnar cell mucinous carcinoma, signet ring cell carcinoma, neuroendocrine tumours (including solid neuroendocrine carcinoma, atypical carcinoid tumour, small cell/oat cell carcinoma, or large cell neuroendocrine carcioma), invasive papillary carcinoma, invasive micropapillary carcinoma, apocrine carcinoma, metaplastic carcinomas, pure epithelial metaplastic carciomas, mixed epithelial/mesenchymal metaplastic carcinomas, lipid-rich carcinoma, secretory carcinoma, oncocytic carcinoma, adenoid cystic carcinoma, acinic cell carcinoma, glycogen-rich clear cell carcinoma, sebaceous carcinoma, inflammatory carcinoma or bilateral breast carcinoma; mesenchymal tumors such as haemangioma, angiomatosis, haemangiopericytoma, pseudoangiomatous stromal hyperplasia, myofibroblastoma, fibromatosis (aggressive), inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma, or leiomysarcoma; myoepithelial lesions such as myoepitheliosis, adenomyoepithelial adenosis, adenomyoepithelioma, or malignant myoepithelioma; fibroepithelial tumours such as fibroadenoma, phyllodes tumour, low grade periductal stromal sarcoma, or mammary hamartoma; and tumours of the nipple such as nipple adenoma, syringomatous adenoma, or Paget's disease of the nipple.

Treatment of breast cancer may be effected in conjunction with any additional therapy, such as a therapy that is part of the standard of care. A surgical technique such as lumpectomy or mastectomy may be performed prior to, during, or following treatment with the peptidomimetic macrocycles of the invention. Alternatively, radiation therapy may be used for the treatment of breast cancer in conjunction with the peptidomimetic macrocycles of the invention. In other cases, the peptidomimetic macrocycles of the invention are administered in combination with a second therapeutic agent. Such an agent may be a chemotherapeutic agent such as an individual drug or combination of drugs and therapies. For example, the chemotherapeutic agent can be an adjuvant chemotherapeutic treatment such as CMF (cyclophosphamide, methotrexate, and 5-fluorouracil); FAC or CAF (5-fluorouracil, doxorubicin, cyclophosphamide); AC or CA (doxorubicin and cyclophosphamide); AC-Taxol (AC followed by paclitaxel); TAC (docetaxel, doxorubicin, and cyclophosphamide); FEC (5-fluorouracil, epirubicin and cyclophosphamide); FECD (FEC followed by docetaxel); TC (docetaxel and cyclophosphamide). In addition to chemotherapy, trastuzumab may also be added to the regimen depending on the tumor characteristics (i.e. HER2/neu status) and risk of relapse. Hormonal therapy may also be appropriate before, during or following chemotherapeutic treatment. For example, tamoxifen may be administered or a compound in the category of aromatase inhibitors including, but not limited to aminogluthetimide, anastrozole, exemestane, formestane, letrozole, or vorozole. In other embodiments, an antiangiogenic agent may be used in combination therapy for the treatment of breast cancer. The antiangiogenic agent may be an anti-VEGF agent including, but not limited to bevacizumab.

Ovarian Cancer

In another aspect, the peptidomimetic macrocycles of the invention may be used to treat ovarian cancer. Ovarian cancers include ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

The peptidomimetic macrocycles of the invention may be administered in conjunction with a second therapy such as a therapy that is part of the standard of care. Surgery, immunotherapy, chemotherapy, hormone therapy, radiation therapy, or a combination thereof are some possible treatments available for ovarian cancer. Some possible surgical procedures include debulking, and a unilateral or bilateral oophorectomy and/or a unilateral or bilateral salpigectomy.

Anti-cancer drugs that may be used include cyclophosphamide, etoposide, altretamine, and ifosfamide. Hormone therapy with the drug tamoxifen may be used to shrink ovarian tumors. Radiation therapy may be external beam radiation therapy and/or brachytherapy.

Prostate Cancer

In another aspect, the peptidomimetic macrocycles of the invention may be used to treat prostate cancer. Prostate cancers include adenocarcinomas and metastasized adenocarcinomas. The peptidomimetic macrocycles of the invention may be administered in conjunction with a second therapy such as a therapy that is part of the standard of care. Treatment for prostate cancer may involve surgery, radiation therapy, High Intensity Focused Ultrasound (HIFU), chemotherapy, cryosurgery, hormonal therapy, or any combination thereof. Surgery may involve prostatectomy, radical perineal prostatectomy, laparoscopic radical prostatectomy, transurethral resection of the prostate or orchiectomy. Radiation therapy may include external beam radiation therapy and/or brachytherapy. Hormonal therapy may include orchiectomy; administration of antiandrogens such as flutamide, bicalutamide, nilutamide, or cyproterone acetate; medications which inhibit the production of adrenal androgens such as DHEA, such as ketoconazole and aminoglutethimide; and GnRH antagonists or agonists such as Abarelix (Plenaxis®), Cetrorelix (Cetrotide®), Ganirelix (Antagon®), leuprolide, goserelin, triptorelin, or buserelin. Treatment with an anti-androgen agent, which blocks androgen activity in the body, is another available therapy. Such agents include flutamide, bicalutamide, and nilutamide. This therapy is typically combined with LHRH analog administration or an orchiectomy, which is termed a combined androgen blockade (CAB). Chemotherapy includes, but is not limited to, administration of docetaxel, for example with a corticosteroid such as prednisone. Anti-cancer drugs such as doxorubicin, estramustine, etoposide, mitoxantrone, vinblastine, paclitaxel, carboplatin may also be administered to slow the growth of prostate cancer, reduce symptoms and improve the quality of life. Additional compounds such as bisphosphonate drugs may also be administered.

Renal Cancer

In another aspect, the peptidomimetic macrocycles of the invention may be used to treat renal cancer. Renal cancers include, but are not limited to, renal cell carcinomas, metastases from extra-renal primary neoplasms, renal lymphomas, squamous cell carcinomas, juxtaglomerular tumors (reninomas), transitional cell carcinomas, angiomyolipomas, oncocytomas and Wilm's tumors. The peptidomimetic macrocycles of the invention may be administered in conjunction with a second therapy such as a therapy that is part of the standard of care. Treatment for renal cancer may involve surgery, percutaneous therapies, radiation therapies, chemotherapy, vaccines, or other medication. Surgical techniques useful for treatment of renal cancer in combination with the peptidomimetic macrocycles of the invention include nephrectomy, which may include removal of the adrenal gland, retroperitoneal lymph nodes, and any other surrounding tissues affected by the invasion of the tumor. Percutaneous therapies include, for example, image-guided therapies which may involve imaging of a tumor followed by its targeted destruction by radiofrequency ablation or cryotherapy. In some cases, other chemotherapeutic or other medications useful in treating renal cancer may be alpha-interferon, interleukin-2, bevacizumab, sorafenib, sunitib, temsirolimus or other kinase inhibitors.

Pancreatic Cancer

In other aspects, the invention provides methods of treating pancreatic cancer by administering peptidomimetic macrocycles of the invention, such as a pancreatic cancer selected from the following: an epitheliod carcinoma in the pancreatic duct tissue and an adenocarcinoma in a pancreatic duct. The most common type of pancreatic cancer is an adenocarcinoma, which occurs in the lining of the pancreatic duct. Possible treatments available for pancreatic cancer include surgery, immunotherapy, radiation therapy, and chemotherapy. Possible surgical treatment options include a distal or total pancreatectomy and a pancreaticoduodenectomy (Whipple procedure). Radiation therapy may be an option for pancreatic cancer patients, specifically external beam radiation where radiation is focused on the tumor by a machine outside the body. Another option is intraoperative electron beam radiation administered during an operation. Chemotherapy may also be used to treat pancreatic cancer patients. Suitable anti-cancer drugs include, but are not limited to, 5-fluorouracil (5-FU), mitomycin, ifosfamide, doxorubicin, streptozocin, chlorozotocin, and combinations thereof. The methods provided by the invention can provide a beneficial effect for pancreatic cancer patients, by administration of a polypeptide of the invention or a combination of administration of a peptidomimetic macrocycle and surgery, radiation therapy, or chemotherapy.

Colon Cancer

In one aspect, peptidomimetic macrocycles of the invention may be used for the treatment of colon cancer, including but not limited to non-neoplastic polyps, adenomas, familial syndromes, colorectal carcinogenesis, colorectal carcinoma, and carcinoid tumors. Possible treatments available for colon cancer that may be used in conjunction with the peptidomimetic macrocycles of the invention include surgery, chemotherapy, radiation therapy or targeted drug therapy.

Radiation therapy may include external beam radiation therapy and/or brachytherapy. Chemotherapy may be used to reduce the likelihood of metastasis developing, shrink tumor size, or slow tumor growth. Chemotherapy is often applied after surgery (adjuvant), before surgery (neo-adjuvant), or as the primary therapy if surgery is not indicated (palliative). For example, exemplary regimens for adjuvant chemotherapy involve the combination of infusional 5-fluorouracil, leucovorin, and oxaliplatin (FOLFOX). First line chemotherapy regimens may involve the combination of infusional 5-fluorouracil, leucovorin, and oxaliplatin (FOLFOX) with a targeted drug such as bevacizumab, cetuximab or panitumumab or infusional 5-fluorouracil, leucovorin, and irinotecan (FOL-FIRI) with targeted drug such as bevacizumab, cetuximab or panitumumab. Other chemotherapeutic agents that may be useful in the treatment or prevention of colon cancer in combination with the peptidomimetic macrocycles of the invention are Bortezomib (Velcade®), Oblimersen (Genasense®, G3139), Gefitinib and Erlotinib (Tarceva®) and Topotecan (Hycamtin®).

Lung Cancer

Some embodiments provide methods for the treatment of lung cancer using the peptidomimetic macrocycles of the invention. Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

The most common type of lung cancer is non-small cell lung cancer (NSCLC), which accounts for approximately 80-85% of lung cancers and is divided into squamous cell carcinomas, adenocarcinomas, and large cell undifferentiated carcinomas. Small cell lung cancer, e.g. small cell lung carcinomas, accounts for 15-20% of lung cancers. Treatment options for lung cancer include surgery, immunotherapy, radiation therapy, chemotherapy, photodynamic therapy, or a combination thereof. Some possible surgical options for treatment of lung cancer are a segmental or wedge resection, a lobectomy, or a pneumonectomy. Radiation therapy may be external beam radiation therapy or brachytherapy. Some anticancer drugs that may be used in chemotherapy to treat lung cancer in combination with the peptidomimetic macrocycles of the invention include cisplatin, carboplatin, paclitaxel, docetaxel, gemcitabine, vinorelbine, irinotecan, etoposide, vinblastine, gefitinib, ifosfamide, methotrexate, or a combination thereof. Photodynamic therapy (PDT) may be used to treat lung cancer patients. The methods described herein can provide a beneficial effect for lung cancer patients, by administration of a peptidomimetic macrocycle or a combination of administration of a peptidomimetic macrocycle and surgery, radiation therapy, chemotherapy, photodynamic therapy, or a combination thereof.

Examples of cellular proliferative and/or differentiative disorders of the liver include, but are not limited to, nodular hyperplasias, adenomas, and malignant tumors, including primary carcinoma of the liver and metastatic tumors.

Immunoproliferative Disorders

Immunoproliferative disorders (also known as "immunoproliferative diseases" or "immunoproliferative neoplasms") are disorders of the immune system that are characterized by the abnormal proliferation of the primary cells of the immune system, which includes B cells, T cells and Natural Killer (NK) cells, or by the excessive production of immunoglobulins (also known as antibodies). Such disorders include the general categories of lymphoproliferative disorders, hypergammaglobulinemias, and paraproteinemias. Examples of such disorders include, but are not limited to, X-linked lymphoproliferative disorder, autosomal lymphoproliferative disorder, Hyper-IgM syndrome, heavy chain disease, and cryoglobulinemia. Other immunoproliferative disorders can be graft versus host disease (GVHD); psoriasis; immune disorders associated with graft transplantation rejection; T cell lymphoma; T cell acute lymphoblastic leukemia; testicular angiocentric T cell lymphoma; benign lymphocytic angiitis; and autoimmune diseases such as lupus erythematosus, Hashimoto's thyroiditis, primary myxedema, Graves' disease, pernicious anemia, autoimmune atrophic gastritis, Addison's disease, insulin dependent diabetes mellitus, good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjogren's syndrome, rheumatoid arthritis, polymyositis, scleroderma, and mixed connective tissue disease.

Combination Treatments

In one embodiment, peptidomimetic macrocycles of the invention may be used for the treatment of cancer in conjunction with alkylating and alkylating-like agents. Such agents include, for example, nitrogen mustards such as chlorambucil, chlormethine, cyclophosphamide, ifosfamide, and melphalan; nitrosoureas such as carmustine, fotemustine, lomustine, and streptozocin; platinum therapeutic agents such as carboplatin, cisplatin, oxaliplatin, BBR3464, and satraplatin; or other agents, including but not limited to busulfan, dacarbazine, procarbazine, temozolomide, thiotepa, treosulfan, or uramustine.

In another embodiment, peptidomimetic macrocycles of the invention may be used in conjunction with an antineoplastic agent which is an antimetabolite. For example, such an antineoplastic agent may be a folic acid such as aminopterin, methotrexate, pemetrexed, or raltitrexed. Alternatively, the antineoplastic agent may be a purine, including but not limited to cladribine, clofarabine, fludarabine, mercaptopurine, pentostatin, thioguanine. In further embodiments, the antineoplastic agent may be a pyrimidine such as capecitabine, cytarabine, fluorouracil, floxuridine, and gemcitabine.

In still other embodiments, peptidomimetic macrocycles of the invention may be used in conjunction with an antineoplastic agent which is an spindle poison/mitotic inhibitor. Agents in this category include taxanes, for example docetaxel and paclitaxel; and vinca alkaloids such as vinblastine, vincristine, vindesine, and vinorelbine. In yet other embodiments, peptidomimetic macrocycles of the invention may be used in combination with an antineoplastic agent which is a cytotoxic/antitumor antibiotic from the anthracycline family such as daunorubicin, doxorubicin, epirubicin, idarubicin, mitoxantrone, pixantrone, or valrubicin; an antibiotic from the streptomyces family such as actinomycin, bleomycin, mitomycin, or plicamycin; or hydroxyurea. Alternatively, agents used for combination therapy may be topoisomerase inhibitors including, but not limited to camptothecin, topotecan, irinotecan, etoposide, or teniposide.

Alternatively, the antineoplastic agent may be an antibody or antibody-derived agent. For example, a receptor tyrosine kinase-targeted antibody such as cetuximab, panitumumab, or trastuzumab may be used Alternatively, the antibody may be an anti-CD20 antibody such as rituximab or tositumomab, or any other suitable antibody including but not limited to alemtuzumab, bevacizumab, and gemtuzumab. In other embodiments, the antineoplastic agent is a photosensitizer such as aminolevulinic acid, methyl aminolevulinate, porfimer sodium, or verteporfin. In still other embodiments, the antineoplastic agent is a tyrosine kinase inhibitor such as dediranib, dasatinib, erlotinib, gefitinib, imatinib, lapatinib, nilotinib, sorafenib, sunitinib, or vandetanib. Other neoplastic agents suitable in the use of the invention include, for example, alitretinoin, tretinoin, altretamine, amsacrine, anagrelide, arsenic trioxide, asparaginase (pegaspargase), bexarotene, bortezomib, denileukin diftitox, estramustine, ixabepilone, masoprocol, or mitotane.

In other or further embodiments, the peptidomimetics macrocycles described herein are used to treat, prevent or diagnose conditions characterized by overactive cell death or cellular death due to physiologic insult, etc. Some examples of conditions characterized by premature or unwanted cell death are or alternatively unwanted or excessive cellular proliferation include, but are not limited to hypocellular/hypoplastic, acellular/aplastic, or hypercellular/hyperplastic conditions. Some examples include hematologic disorders including but not limited to fanconi anemia, aplastic anemia, thalaessemia, congenital neutropenia, myelodysplasia In other or further embodiments, the peptidomimetics macrocycles of the invention that act to decrease apoptosis are used to treat disorders associated with an undesirable level of cell death. Thus, in some embodiments, the anti-apoptotic peptidomimetics macrocycles of the invention are used to treat disorders such as those that lead to cell death associated with viral infection, e.g., infection associated with infection with human immunodeficiency virus (HIV). A wide variety of neurological diseases are characterized by the gradual loss of specific sets of neurons, and the anti-apoptotic peptidomimetics macrocycles of the invention are used, in some embodiments, in the treatment of these disorders. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

Other Methods of Use

In other or further embodiments, the anti-apoptotic peptidomimetics macrocycles of the invention are used to treat all such disorders associated with undesirable cell death.

Some examples of immunologic disorders that are treated with the peptidomimetics macrocycles described herein include but are not limited to organ transplant rejection, arthritis, lupus, IBD, Crohn's disease, asthma, multiple sclerosis, diabetes, etc.

Some examples of neurologic disorders that are treated with the peptidomimetics macrocycles described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, Bovine Spongiform Encephalitis, a prion-mediated disease, and Huntington's Disease.

Some examples of endocrinologic disorders that are treated with the peptidomimetics macrocycles described herein include but are not limited to diabetes, hypothyroidism, hypopituitarism, hypoparathyroidism, hypogonadism, etc.

indicated below. The macrocycles used in this study are shown below. The corresponding uncrosslinked polypeptides are indicated as "WT Sequence" and represent the natural counterparts of the peptidomimetic macrocycles of the invention.

| Macro-cycle | WT Sequence | Sequence | SEQ ID NO: | Calculated m/z (M + H) | Calculated m/z (M + 3H) | Found m/z (M + 3H) |
|---|---|---|---|---|---|---|
| SP-1 | BID-BH3 | Ac-DIIRNIARHLA$VGD$NleDRSI-NH2 | 95 | 2438.40 | 813.47 | 813.7 |
| SP-2 | BID-BH3 | Ac-DIIRNIARHLA$VED$NleDRSI-NH2 | 96 | 2510.42 | 837.48 | 837.25 |
| SP-3 | BID-BH3 | Ac-DIIRNIARHLAQVGDSNleDRSI-NH2 | 97 | 2403.32 | 801.78 | 801.89 |
| SP-4 | BIM-BH3 | Ac-IWIAQELR$IGD$FNAYYARR-NH2 | 98 | 2646.43 | 882.82 | 883.15 |
| SP-5 | BIM-BH3 | Ac-IWIAQELR$IED$FNAYYARR-NH2 | 99 | 2718.45 | 906.82 | 906.9 |
| SP-6 | BIM-BH3 | Ac-IWIAQELRRIGDEFNAYYARR-NH2 | 100 | 2681.41 | 894.47 | 894.69 |
| SP-7 | BID-BH3 | Pr-RNIARHLA$VAibD$NleDRSI-NH2 | 101 | 2139.25 | 713.76 | 713.79 |
| SP-8 | BID-BH3 | Pr-RNIARHLAib$VAibD$NleDRSI-NH2 | 102 | 2153.27 | 718.43 | 718.56 |
| SP-9 | BID-BH3 | Pr-RNIARHLA$VAibD$FARSI-NH2 | 103 | 2129.25 | 710.42 | 710.3 |
| SP-10 | BID-BH3 | Pr-RNIARHLA$VGD$NleAibRSI-NH2 | 104 | 2081.25 | 694.42 | 694.42 |
| SP-11 | BIM-BH3 | Ac-IWIAQALR$IGD$FNAYYARR-NH2 | 105 | 2588.43 | 863.48 | 863.85 |
| SP-12 | BIM-BH3 | Ac-RWIAQALR$IGNle$FNAYYARR-NH2 | 106 | 2629.5 | 877.17 | 877.8 |
| SP-13 | BIM-BH3 | Pr-RNChgARHLA$VAibD$FNAYYARR-NH2 | 107 | 2622.45 | 874.82 | 875.22 |
| SP-14 | BIM-BH3 | Ac-IWIAQALR$IGD$FNAibYYARR-NH2 | 108 | 2602.44 | 868.15 | 868.54 |
| SP-15 | BIM-BH3 | Ac-RWIAQALR$IGD$FNAFYARR-NH2 | 109 | 2615.45 | 872.49 | 872.64 |
| SP-16 | BIM-BH3 | Ac-RWIAQALR$IGA$FNAYYARR-NH2 | 110 | 2587.45 | 863.16 | 863.39 |
| SP-17 | BIM-BH3 | Ac-IWIAQAibLR$IGD$FNAibYYARR-NH2 | 111 | 2616.46 | 872.82 | 872.91 |
| SP-18 | BIM-BH3 | Ac-IWIAQQLR$IGD$FNAYYARR-NH2 | 112 | 2645.45 | 882.49 | 882.62 |
| SP-19 | BIM-BH3 | Ac-RWIAQQLR$IGD$FNAYYARR-NH2 | 113 | 2688.46 | 896.83 | 896.84 |
| SP-20 | BIM-BH3 | Ac-IWIAQALR$IGD$FNARRA-NH2 | 114 | 2262.3 | 754.77 | 755.08 |
| SP-21 | BIM-BH3 | Ac-IWIAQALR$IGD$FNAYKA-NH2 | 115 | 2241.26 | 747.76 | 748.12 |
| SP-22 | BIM-BH3 | Ac-IWIAQALR$IGD$FNAYK-NH2 | 116 | 2170.22 | 724.08 | 724.35 |
| SP-23 | BIM-BH3 | Ac-RWIAQALR$IGN$FNAYYARR-NH2 | 117 | 2630.45 | 877.48 | 877.36 |
| SP-24 | BIM-BH3 | Ac-IWIAQAAR$DIG$ANAYYARR-NH2 | 118 | 2470.34 | 824.11 | 824.10 |
| SP-25 | BIM-BH3 | Ac-IWIAQALR$IGN$FNAYYARR-NH2 | 119 | 2587.43 | 863.14 | 863.00 |
| SP-26 | BIM-BH3 | Ac-IWIAQALRRIGDEFNAYYARR-NH2 | 120 | 2623.39 | 875.13 | 874.97 |

Examples of cardiovascular disorders (e.g., inflammatory disorders) that are treated or prevented with the peptidomimetics macrocycles of the invention include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices. Preferred cardiovascular disorders include atherosclerosis, myocardial infarction, aneurism, and stroke.

EXAMPLES

The following section provides illustrative examples of the present invention.

Example 1

Synthesis of Peptidomimetic Macrocycles of the Invention

α-helical BID and BIM peptidomimetic macrocycles were synthesized, purified and analyzed as previously described (Walensky et al (2004) Science 305:1466-70; Walensky et al (2006) Mol Cell 24:199-210) and as Alpha, alpha-disubstituted non-natural amino acids containing olefinic side chains were synthesized according to Williams et al. (1991) J. Am. Chem. Soc. 113:9276; and Schafineister et al. (2000) J. Am. Chem Soc. 122:5891. BID-BH3 and BIM-BH3 peptidomimetic macrocycles were designed by replacing two naturally occurring amino acids with the corresponding synthetic amino acids. Substitutions were made at the i and i+4 positions. BID BH3 and BIM-BH3 macrocycles were generated by solid phase peptide synthesis followed by olefin metathesis-based crosslinking of the synthetic amino acids via their olefin-containing side chains. The control sequences for BID and BIM peptidomimetic macrocycles, as well as specific sequence mutations generated are shown above.

In the sequences shown, "Nle" represents norleucine, "Aib" represents 2-aminoisobutyric acid, "Chg" represents cyclohexylglycine, "Ac" represents acetyl and "Pr" represents propionyl Amino acids represented as $ connect an all-carbon crosslinker comprising one double bond and wherein each α-carbon atom to which the crosslinker is attached is additionally substituted with a methyl group. In all cases, the crosslinker is a linear all-carbon crosslinker comprising eight carbon atoms between the alpha carbons of each amino acid. If a double bond is present, it is positioned between the fourth and fifth carbon atom.

The non-natural amino acids (R and S enantiomers of the 5-carbon olefinic amino acid and the S enantiomer of the 8-carbon olefinic amino acid) were characterized by nuclear magnetic resonance (NMR) spectroscopy (Varian Mercury 400) and mass spectrometry (Micromass LCT). Peptide synthesis was performed either manually or on an automated peptide synthesizer (Applied Biosystems, model 433A), using solid phase conditions, rink amide AM resin (Novabiochem), and Fmoc main-chain protecting group chemistry. For the coupling of natural Fmoc-protected amino acids (Novabiochem), 10 equivalents of amino acid and a 1:1:2 molar ratio of coupling reagents HBTU/HOBt (Novabiochem)/DIEA were employed. Non-natural amino acids (4 equiv) were coupled with a 1:1:2 molar ratio of HATU (Applied Biosystems)/HOBt/DIEA. Olefin metathesis was performed in the solid phase using 10 mM Grubbs catalyst (Blackewell et al. 1994 supra) (Strem Chemicals) dissolved in degassed dichloromethane and reacted for 2 hours at room temperature. Isolation of metathesized compounds was achieved by trifluoroacetic acid-mediated deprotection and cleavage, ether precipitation to yield the crude product, and high performance liquid chromatography (HPLC) (Varian ProStar) on a reverse phase C18 column (Varian) to yield the pure compounds. Chemical composition of the pure products was confirmed by LC/MS mass spectrometry (Micromass LCT interfaced with Agilent 1100 HPLC system) and amino acid analysis (Applied Biosystems, model 420A).

Cell Lines:

Cell lines used in this study are indicated in the table below:

| Cells | Type | Source |
| --- | --- | --- |
| Jurkat | human acute T cell leukemia | ATCC |
| K562 | human chronic myelogeneous leukemia | ATCC |
| Karpas299 | human T cell lymphoma | ATCC |
| MOLT4 | human T cell leukemia | NCI |
| RPMI8226 | human B lymphoblastoma | NCI |
| Ramos | human B cell lymphoma | ATCC |
| Raji | human B cell lymphoma | ATCC |
| HL-60 | Human myeloid leukemia | NCI |
| Malme-3M | lung malignant melanoma | NCI |
| SKMEL2 | human malignant melanoma | NCI |
| SKMEL5 | human malignant melanoma | NCI |
| PC3 | human prostate adenocarcinoma | NCI |
| Caki1 | human kidney clear cell carcinoma | NCI |
| HCT116 | human colorectal carcinoma | NCI |
| HT-29 | Colorectal adenocarcinoma | NCI |
| HEPG2 | human hepatocellular carcinoma | ATCC |
| MDAMB231 | human breast adenocarcinoma | NCI |
| MCF7 | human breast adenocarcinoma | NCI |
| A549 | human non-small cell lung carcinoma | NCI |
| H460 | human non-small cell lung carcinoma | NCI |
| NCI-H220 | human small cell lung carcinoma | NCI |
| NCI-H146 | human small cell lung carcinoma | NCI |
| NCI-H128 | human small cell lung cancer | ATCC |
| SKOV3 | human ovary adenocarcinoma | NCI |
| Panc-1 | human pancreas carcinoma | ATCC |
| U251 | Human glioblastoma | ATCC |
| NCI-H82 | Human small cell lung carcinoma | |
| Supt1 | Human T cell lymphoma | |
| DHL-6 | Human B cell lymphoma | |
| RS4; 11 | Human lymphoblastic leukemia | |
| MM1S | Human multiple myeloma | |
| SEMK2 | Human mixed lineage leukemia | |
| A375 | Human malignant melanoma | |
| OVCAR8 | Human ovarian carcinoma | |

Example 2

Cell Viability Assays

Cell viability assays shown in FIGS. 1-32 were performed according to the following protocol. Tumor cell lines were grown in specific serum-supplemented media (growth media) as necessary. A day prior to the initiation of the study, cells were plated at optimal cell density (15,000 to 25,000 cells/well) in 200 µl growth media in microtiter plates. The next day, cells were washed twice in serum-free/phenol red-free RPMI complete media (assay buffer) and a final volume of 100 µl assay buffer was added to each well. Human peripheral blood lymphocytes (hPBLs) were isolated from Buffy coats (San Diego Blood Bank) using Ficoll-Paque gradient separation and plated on the day of the experiment at 25,000 cells/well.

Peptidomimetic macrocycles were diluted from 1 mM stocks (100% DMSO) in sterile water to prepare 400 µM working solutions. The peptidomimetic macrocycles and controls were then diluted 10 or 40 fold or alternatively serially two-fold diluted in assay buffer in dosing plates to provide concentrations of either 40 and 20 µM or between 1.2 and 40 µM, respectively. 100 µL of each dilution was then added to the appropriate wells of the test plate to achieve final concentrations of the peptidomimetic macrocycles equal to 20 or 5 µM, or between 0.6 to 20 µM, respectively. Controls included wells without peptidomimetic macrocycles containing the same concentration of DMSO as the wells containing the peptidomimetic macrocycles, wells containing 0.1% Triton X-100, wells containing a chemo cocktail comprised of 1 µM Velcade, 100 µM Etoposide and 20 µM Taxol and wells containing no cells. Plates were incubated for 4 hours at 37° C. in humidified 5% $CO_2$ atmosphere.

Towards the end of the 4 hour incubation time, 22 µl FBS was added to each well for a total concentration of 10% FBS. After addition of serum, the plates were incubated for an additional 44 hours at 37° C. in humidified 5% $CO_2$ atmosphere. At the end of the incubation period, MTT assay was performed according to manufacturer's instructions (Sigma, catalog #M2128) and absorbance was measured at 560 nm using Dynex Opsys MR Plate reader.

Figure 2:
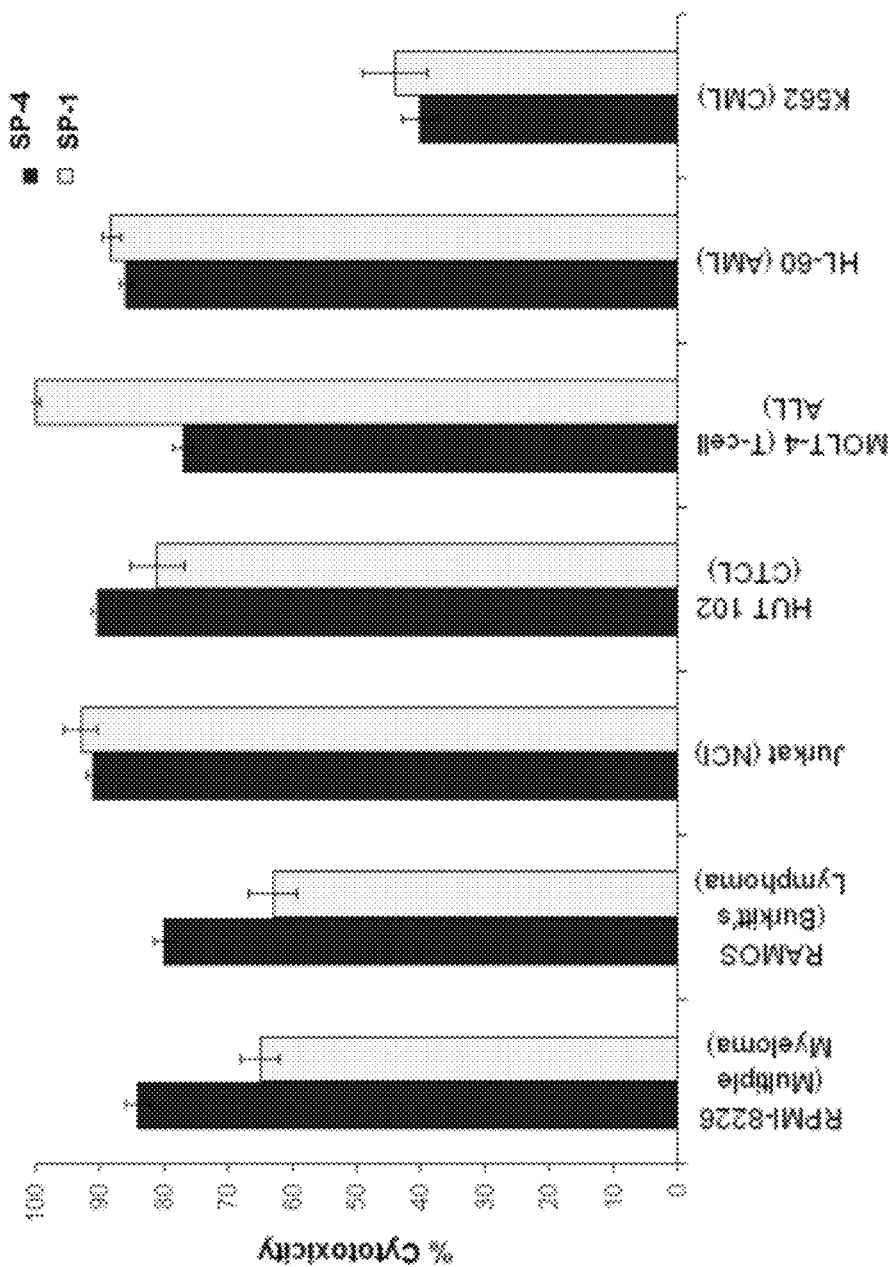
FIG. 2 shows the sensitivity of 7 human leukemia/lymphoma cell lines to treatment with 5 µM of either SP-1 or SP-4.
Figure 3:
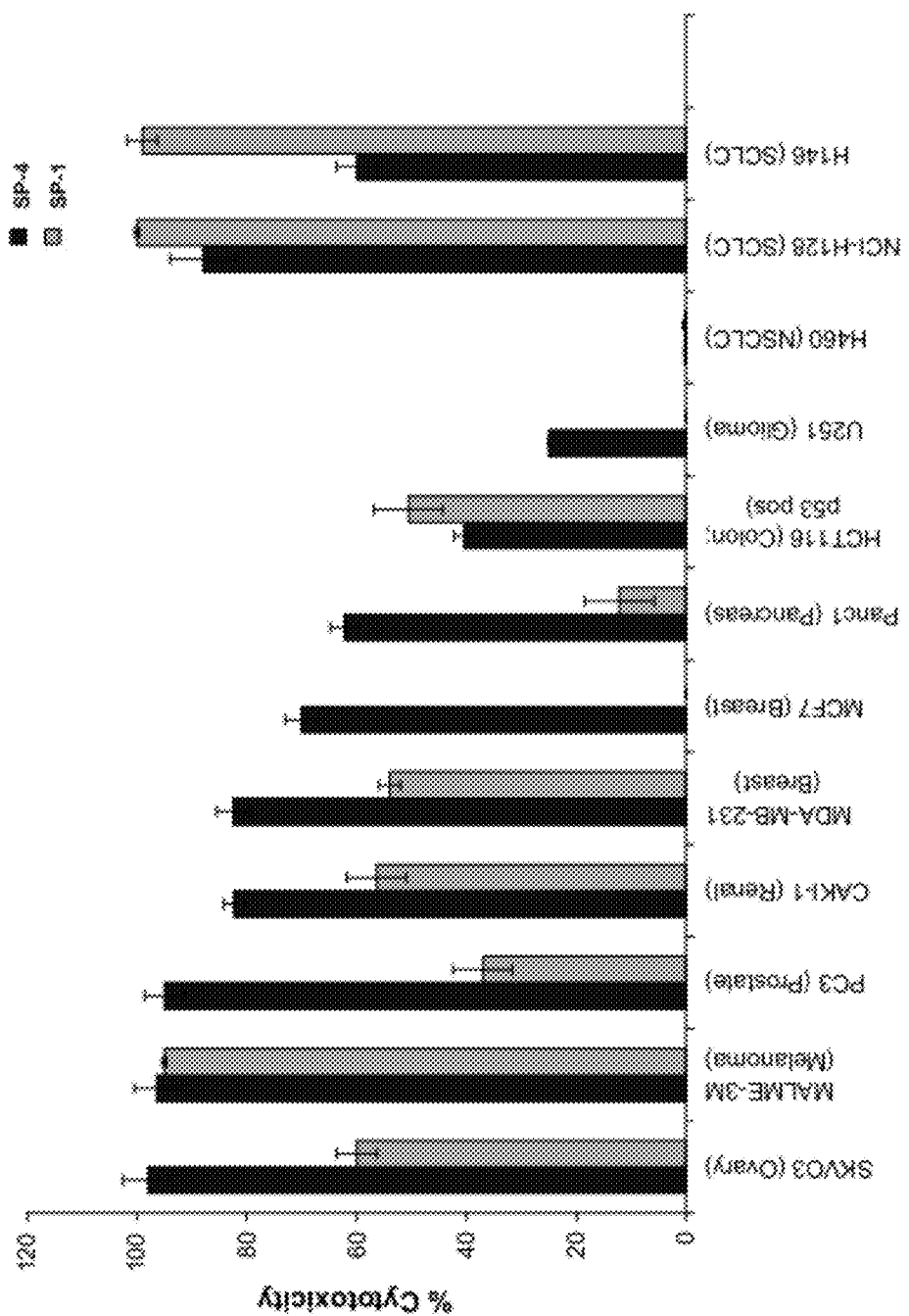
FIG. 3 shows the sensitivity of twelve human solid tumor lines to treatment with 20 µM of either SP-1 or SP-4.
Figure 4:
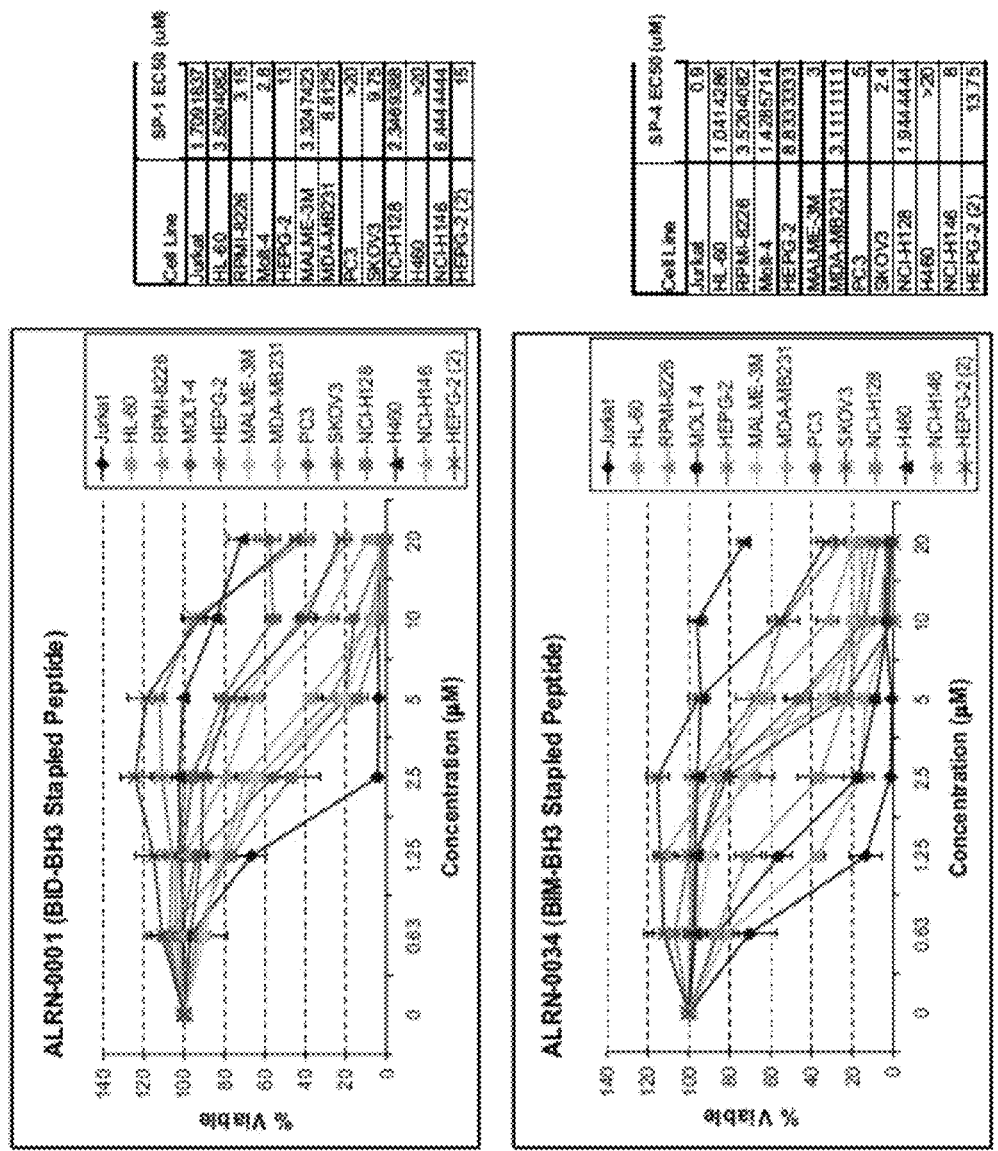
FIG. 4 shows $EC_{50}$ curves for SP-1 or SP-4 tested against a variety of cell lines.
Figure 5:
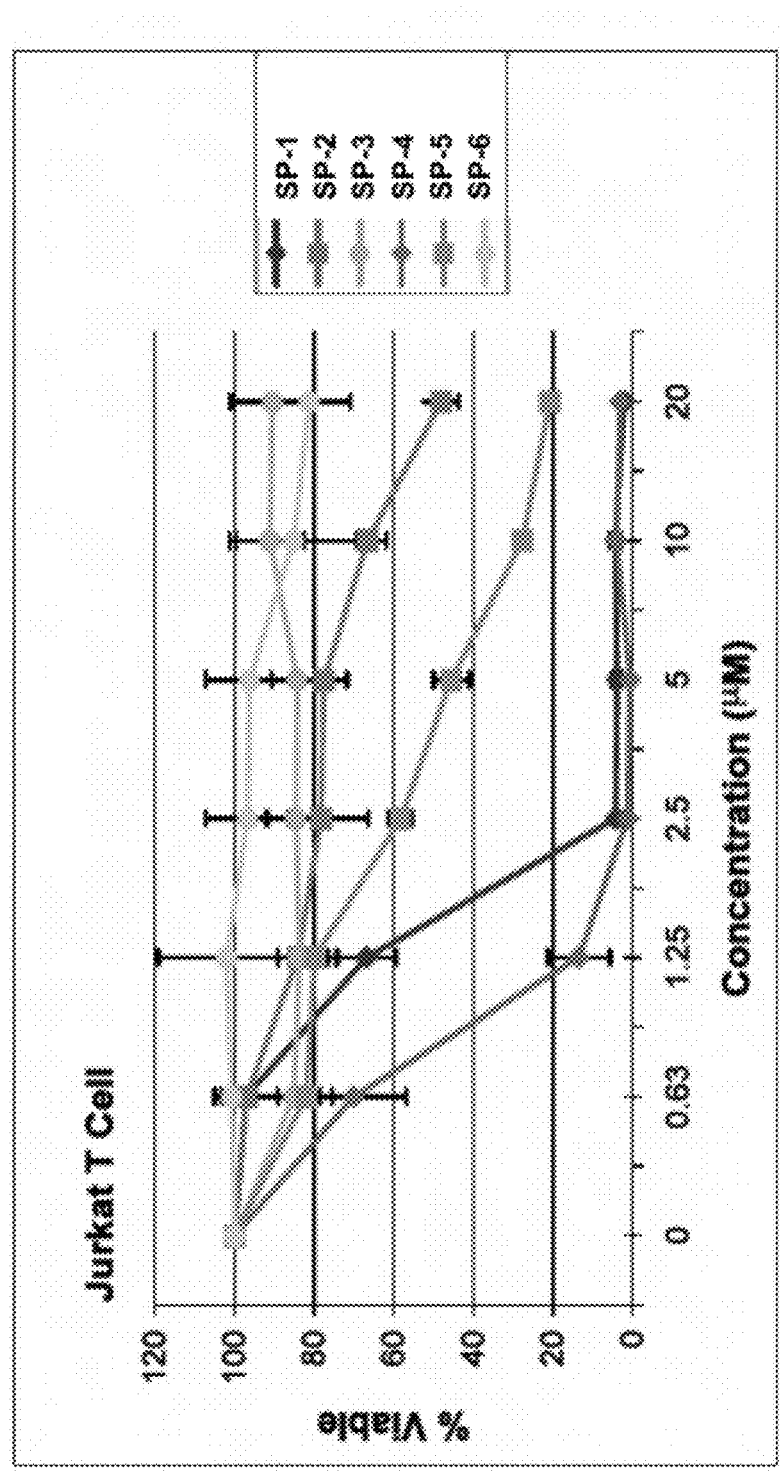
FIGS. 5-15 describe $EC_{50}$ curves for SP-1, SP-2, SP-3, SP-4, SP-5 and SP-6 tested against several individual cell lines.
Figure 6:
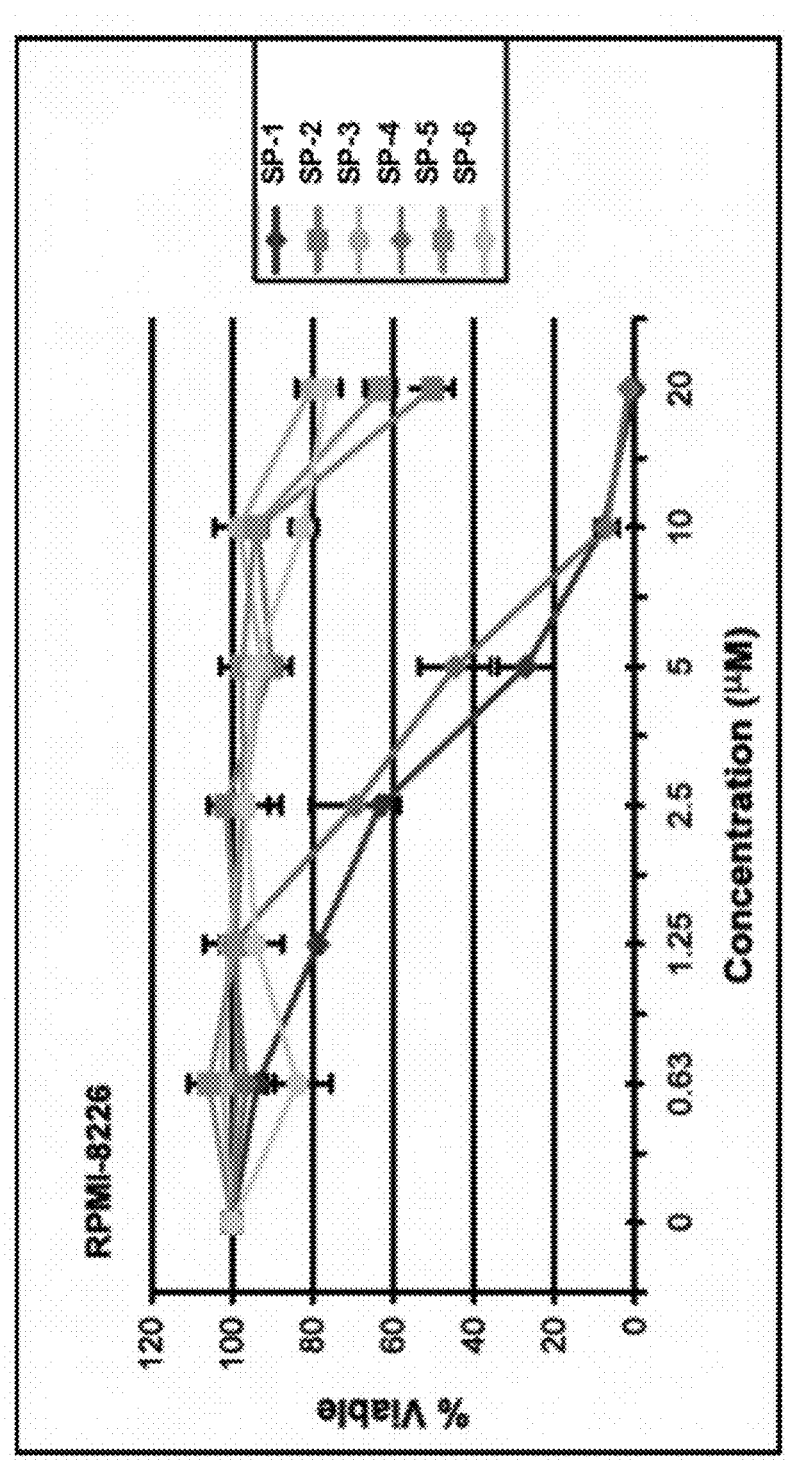

In FIGS. 1-3, the values were plotted as percent cytotoxicity, i.e as a percentage of the positive control corresponding to 100% cell death. In FIGS. 4-15, 25 and 26, values were plotted as percent viable, i.e as percent of negative control corresponding to 100% viable cells. All assays were performed in quadruplicates.

FIG. 1 shows human tumor cell lines treated with SP-1 (20 µM) and assessed for cell viability by an MTT assay 48 hrs post test article addition. All leukemia/lymphoma lines tested were sensitive to SP-1. In addition, SP-1 also induced apoptosis of several solid tumor lines including three small cell lung carcinoma (SCLC) lines, NCI-H220, NCI-H128 and NCI-H146. Conversely, there were several solid tumor lines resistant to SP-1 including non-small cell lung carcinoma (NSCLC) lines A-549 and H-460, MCF7 (breast cancer) and U251 (glioma). FIG. 2 shows seven leukemia/lymphoma human cell lines were treated with 5 µM of either SP-1 or SP-4 for 48 hrs and assessed for cell viability. As shown, all cell lines exhibited similar sensitivity to both macrocycles at this concentration.

FIG. 3 shows twelve human solid tumor lines tested for sensitivity to either SP-1 or SP-4 (20 µM). As shown, there seems to be a cell-specific difference of sensitivity for each macrocycle tested. $EC_{50}$ curves for SP-1, SP-2, SP-3, SP-4, SP-5 and SP-6 for individual cell lines are shown in FIGS. 4-15.

Cell viability assays shown in FIGS. 34-52 were performed according to a similar protocol. Cells were split at optimal cell density a day prior to the initiation of the study. The next day, cells were washed twice in serum-free Opti-MEM media and 4000 cells/well were added to each well in a final volume of 100 µl Opti-MEM. For serum-free experiments, macrocycles were diluted from 2 mM stocks (100% DMSO) in sterile water to prepare 400 µM working solutions. A 40 µM solution was then generated by ten-fold dilution in assay buffer. The macrocycle and controls were then serially diluted two-fold in assay buffer in dosing plates to provide concentrations between 1.2 and 40 µM, respectively. For experiments in 2% human serum, macrocycles were diluted from 10 mM stocks (100% DMSO) in sterile water to prepare 1 mM working solutions. A 100 µM solution was generated by ten-fold dilution in assay buffer. The macrocycles and controls were then serially diluted two-fold in assay buffer in dosing plates to provide concentrations between 3 and 100 µM, respectively. 50 µL of each dilution was then added to the appropriate wells of the test plate to achieve final concentrations of the macrocycle between 0.6 to 20 µM (for serum free experiment) or 1.5 to 50 µM (for 2% serum experiment), respectively. Controls included wells without macrocycles containing the same concentration of DMSO as the macrocycle-containing wells, wells containing 0.1% Triton X-100, and wells containing no cells. Plates were incubated for 24 hours at 37° C. in a humidified 5% $CO_2$ atmosphere. At the end of a 24 hr incubation period, a CellTiter-Glo Luminescent Cell Viability Assay was performed according to manufacturer's instructions (Promega, catalog #G7571) and the luminescence was measured using a BIO-TEK synergy HT Plate reader. Values were plotted as percent viable, i.e. as a percentage of the negative control value (derived from cells exposed to DMSO only). All assays were performed in duplicate.

The following tables summarize the $EC_{50}$ values (µM) observed with peptidomimetic macrocycles of the invention in various cell lines:

| $EC_{50}$ values in serum-free media | | | | | |
|---|---|---|---|---|---|
| Compound | MDA-MB231-Met | A375 | PC3 | OVCAR8 | NCI-H82 (SCLC-MCL1+) |
| SP-1 | 9.8 | 11 | 20 | 20 | 2.5 |
| SP-2 | >20 | >20 | ND | >20 | >20 |
| SP-9 | 2.9 | 4.1 | 5.7 | 7.1 | 4.2 |
| SP-10 | 3.1 | 5.2 | 6 | 8.1 | 5.7 |
| SP-4 | 8.5 | 8 | 5 | 20 | 4.9 |
| SP-11 | 2 | 4.3 | 4.6 | 3.2 | 1.2 |
| SP-15 | 0.9 | 0.8 | 2.1 | 1.8 | ND |
| SP-23 | 0.6 | 1 | 2 | 0.9 | 0.6 |
| SP-12 | 0.5 | 0.7 | 1.9 | 0.7 | 0.9 |
| SP-24 | >20 | >20 | >20 | >20 | >20 |
| SP-25 | 1 | 1 | 0.6 | 1.4 | 0.5 |

| $EC_{50}$ values in 2% human serum | | | | |
|---|---|---|---|---|
| Compound | MDA-MB231-Met | A375 | PC3 | OVCAR8 |
| SP-9 | ND | ND | 25.5 | 18.4 |
| SP-10 | ND | ND | 24.4 | 19.1 |
| SP-4 | 40 | 27 | >50 | >50 |
| SP-11 | ND | ND | 23.4 | 10.7 |
| SP-15 | 2.6 | 2.7 | 9.3 | 6.4 |
| SP-23 | 3.8 | 2.7 | 4.2 | 4 |
| SP-24 | >50 | >50 | >50 | >50 |
| SP-25 | 4.3 | 3.8 | 9.5 | 6.9 |
| SP-26 | >50 | >50 | >50 | >50 |

| $EC_{50}$ values for various liquid tumors | | | | | | | |
|---|---|---|---|---|---|---|---|
| Compound | Jurkat | SEMK2 | Molt-4 | RS4; 11 | Raji | DHL-6 | MM1S |
| SP-1 | 2.5 | 10 | 4.3 | >20 | 13 | 7 | 3.5 |
| SP-2 | >20 | >20 | >20 | >20 | >20 | ND | >20 |
| SP-3 | >20 | >20 | >20 | >20 | >20 | >20 | >20 |
| SP-9 | 1.9 | 8.1 | 1 | 4.3 | 5.7 | 2.7 | 5.5 |
| SP-10 | 1.9 | 8.2 | 1.9 | 3.5 | 5 | 1.9 | 2.5 |
| SP-4 | 1.6 | 4 | 2.2 | 10 | 9 | 3.8 | 4.9 |
| SP-11 | 0.9 | 2.6 | 1.6 | 3.7 | 2.7 | 0.9 | 1.9 |
| SP-15 | 0.4 | 0.8 | 0.7 | 1.7 | 1 | 0.5 | 0.6 |
| SP-23 | 0.9 | 1 | 0.6 | 1 | 1.8 | 0.5 | 0.7 |
| SP-12 | 0.4 | 0.5 | 0.7 | 1.71 | 0.3 | ND | ND |
| SP-24 | >20 | ND | ND | ND | ND | ND | ND |
| SP-25 | 0.5 | 0.9 | 0.9 | 1 | 1.8 | 0.6 | 0.6 |

Example 3

Figure 7:
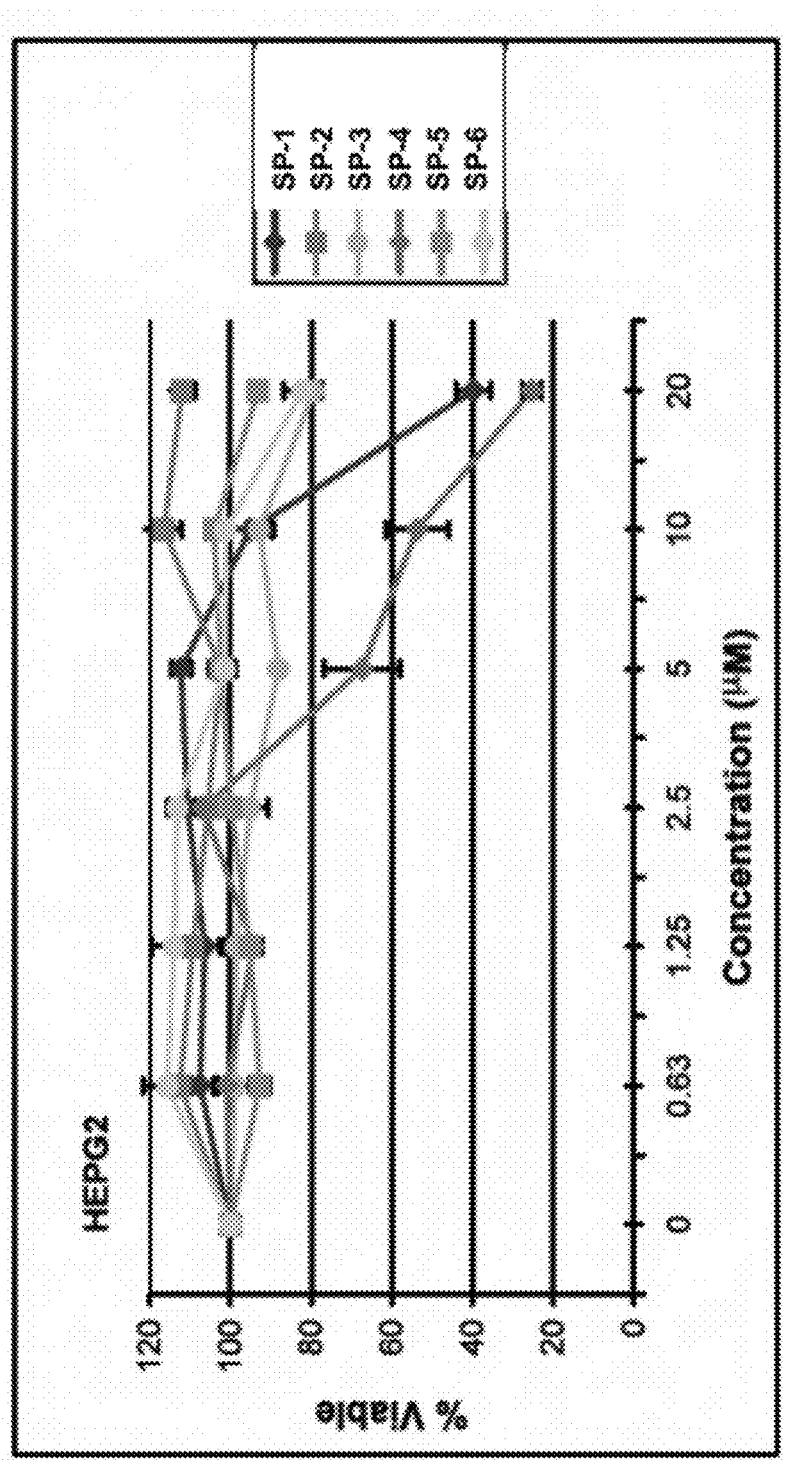
Figure 8:
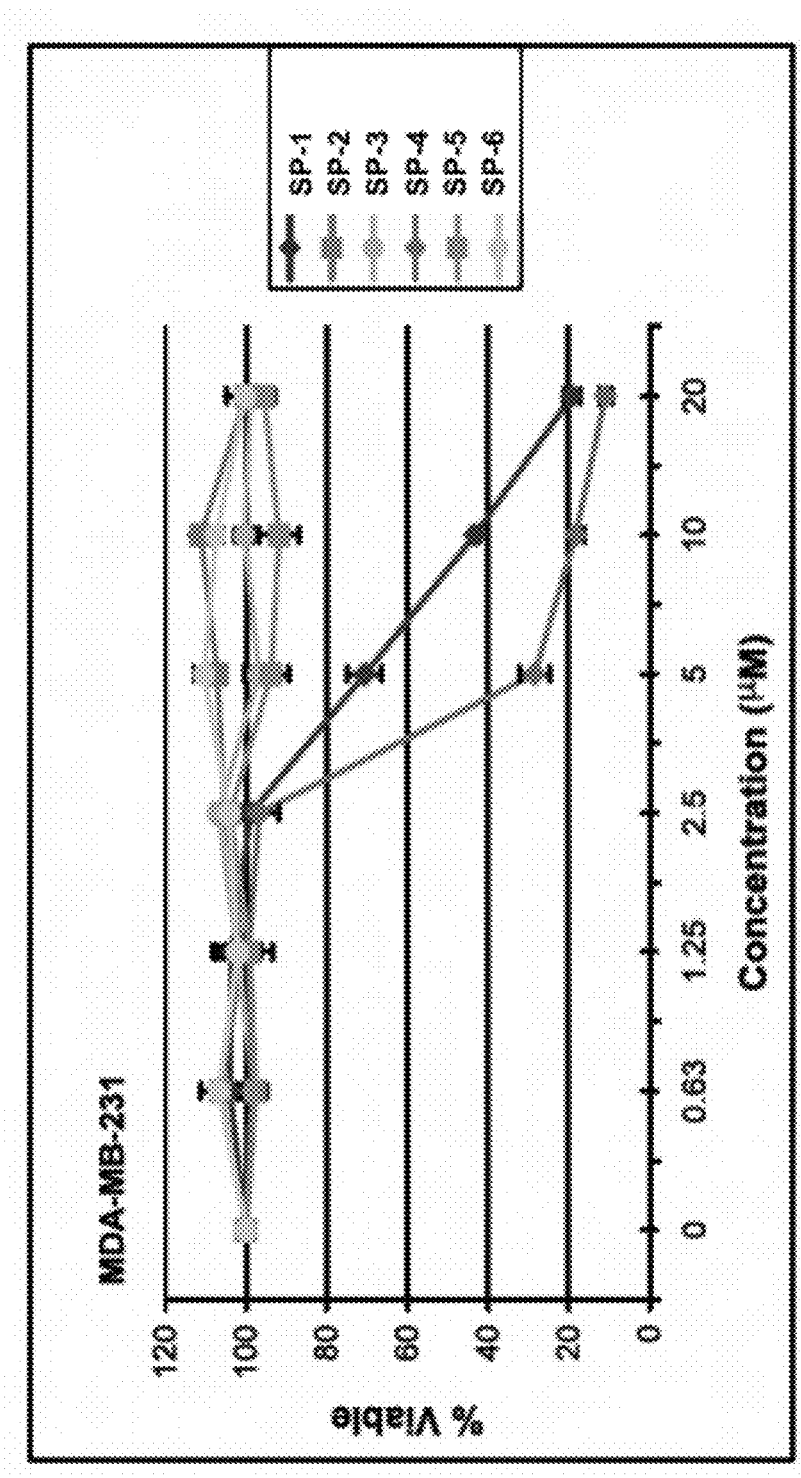
Figure 9:
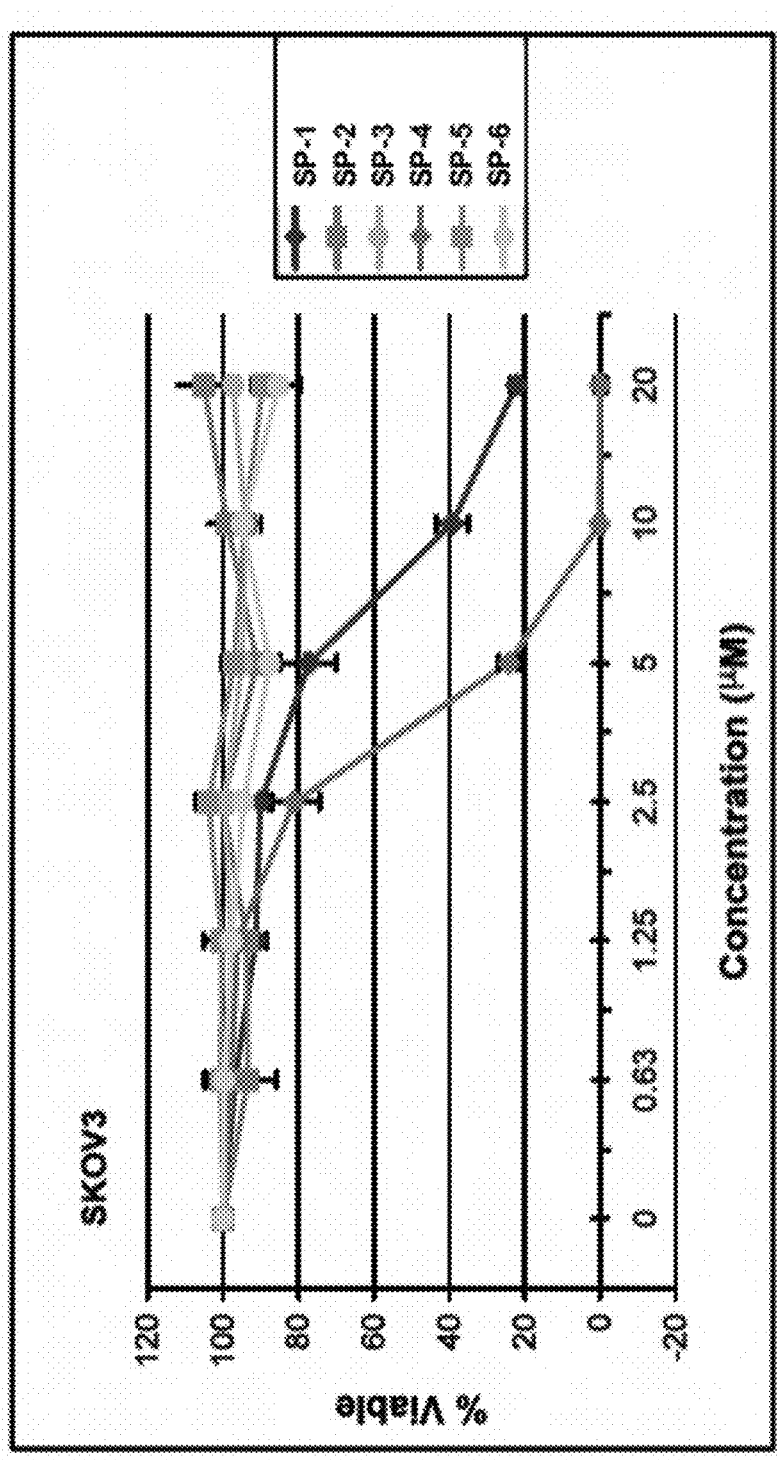
Figure 10:
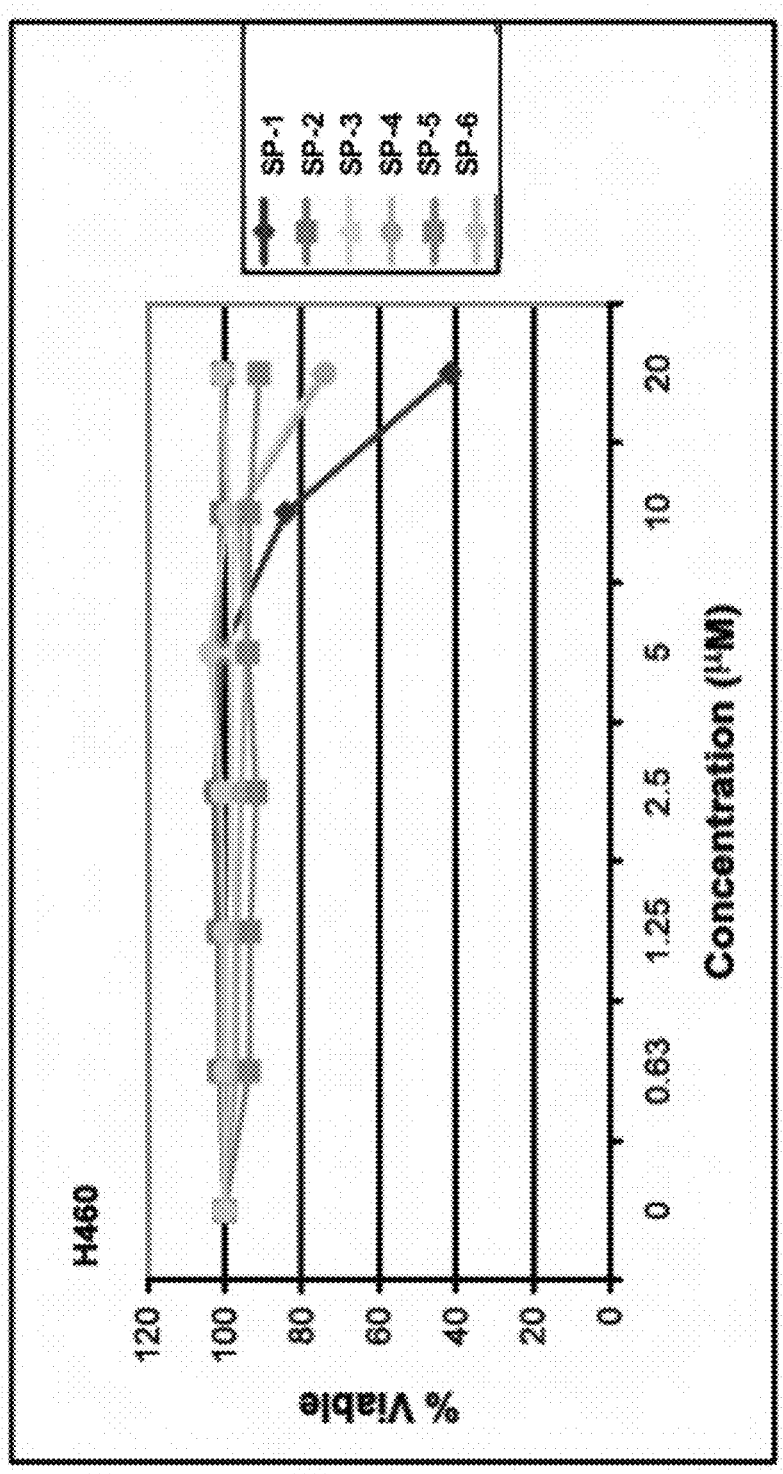
Figure 11:
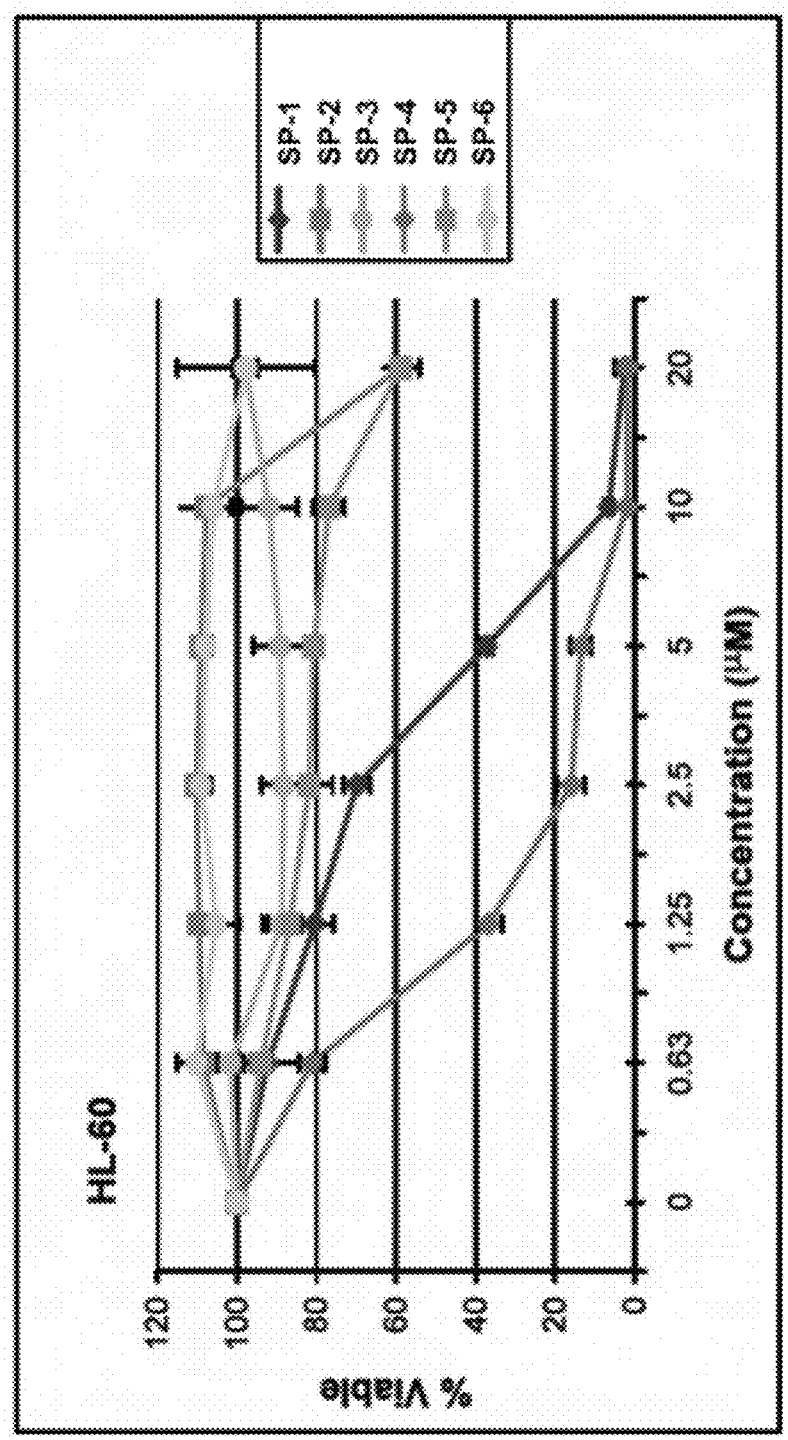
Figure 12:
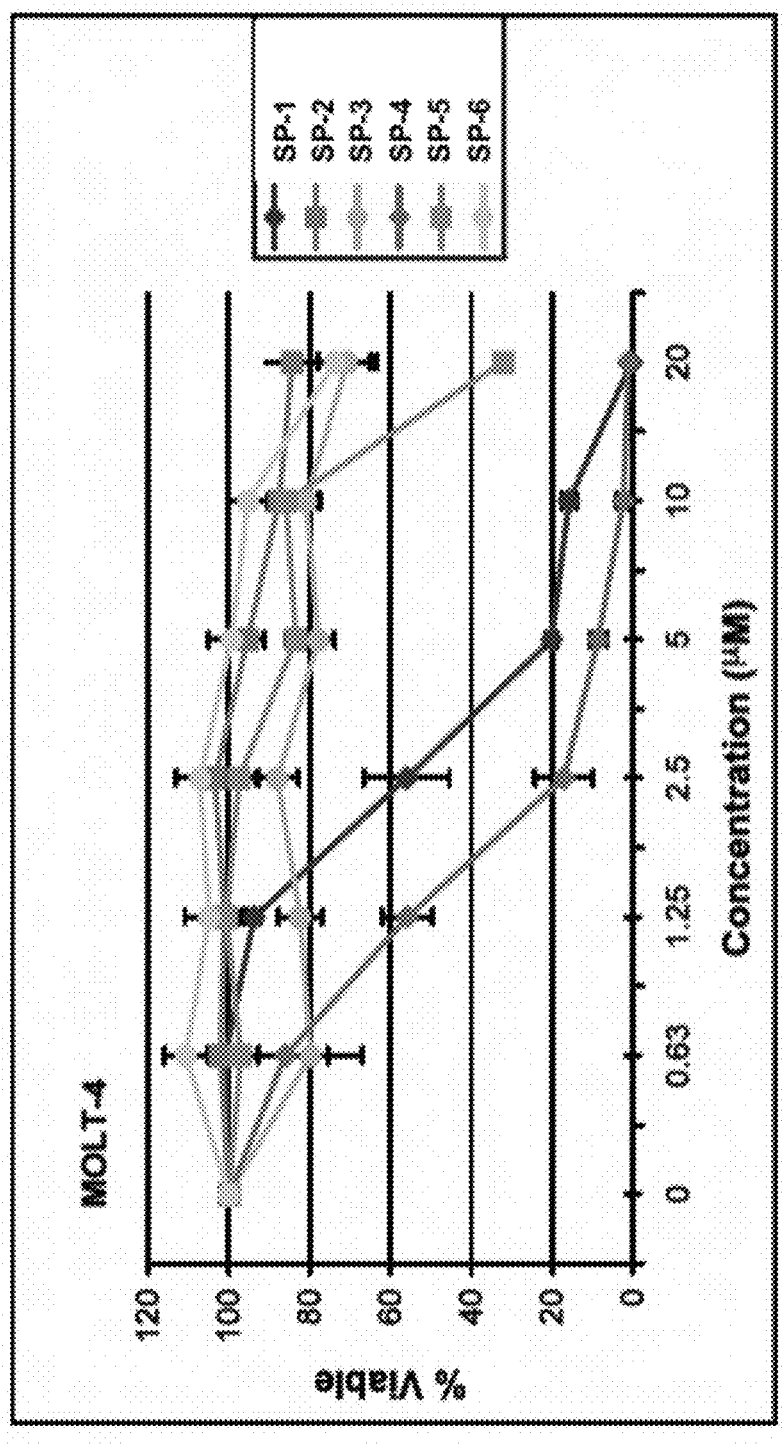
Figure 13:
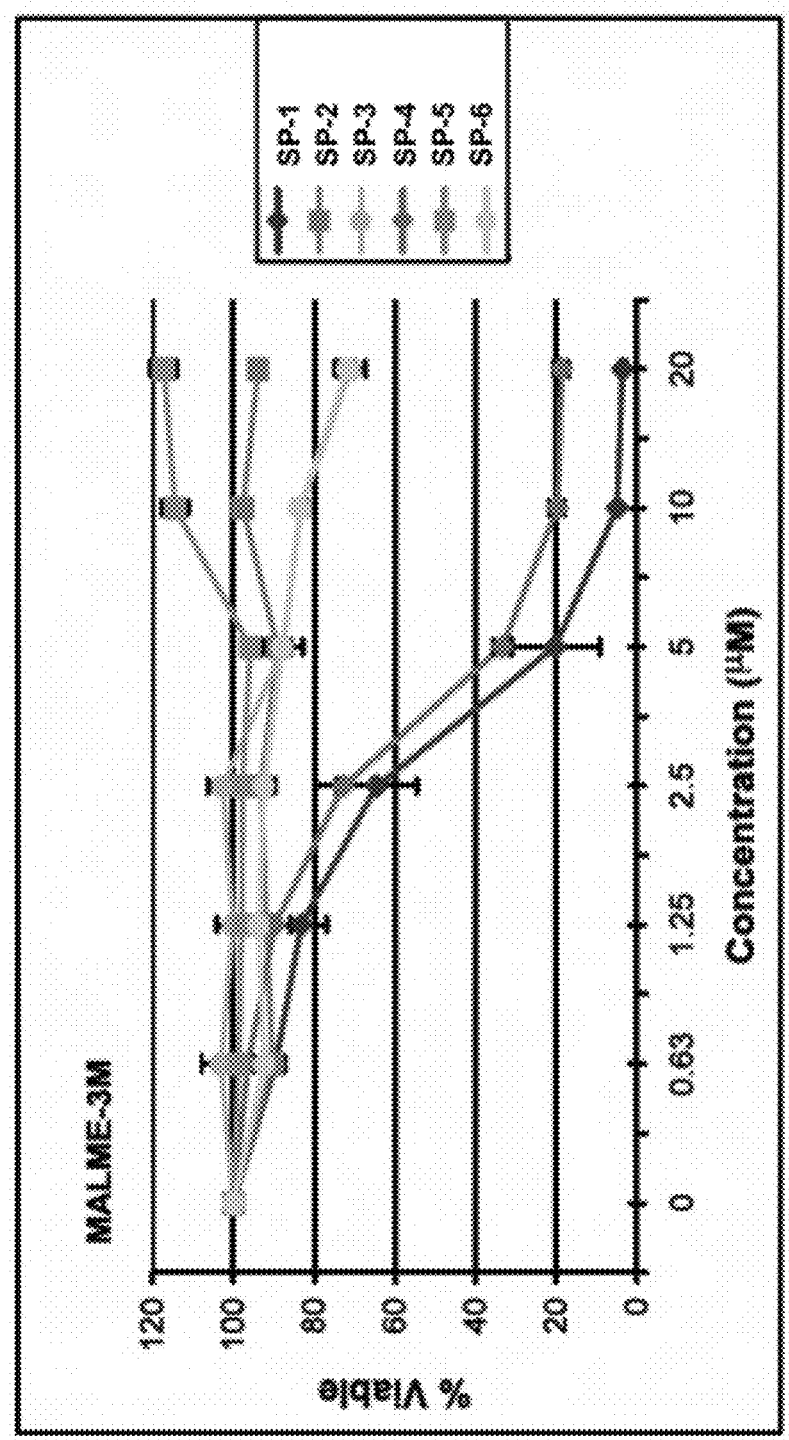
Figure 14:
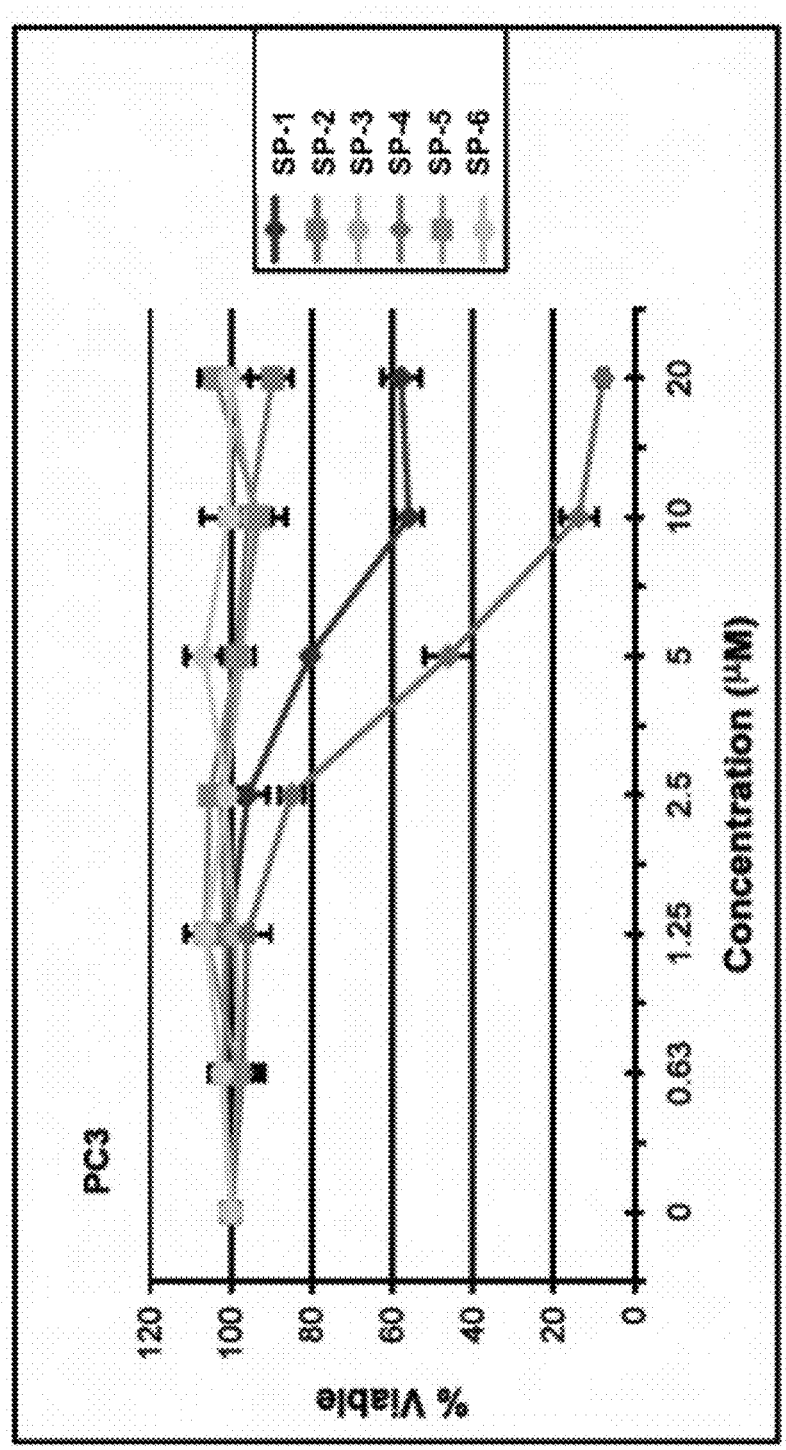
Figure 15:
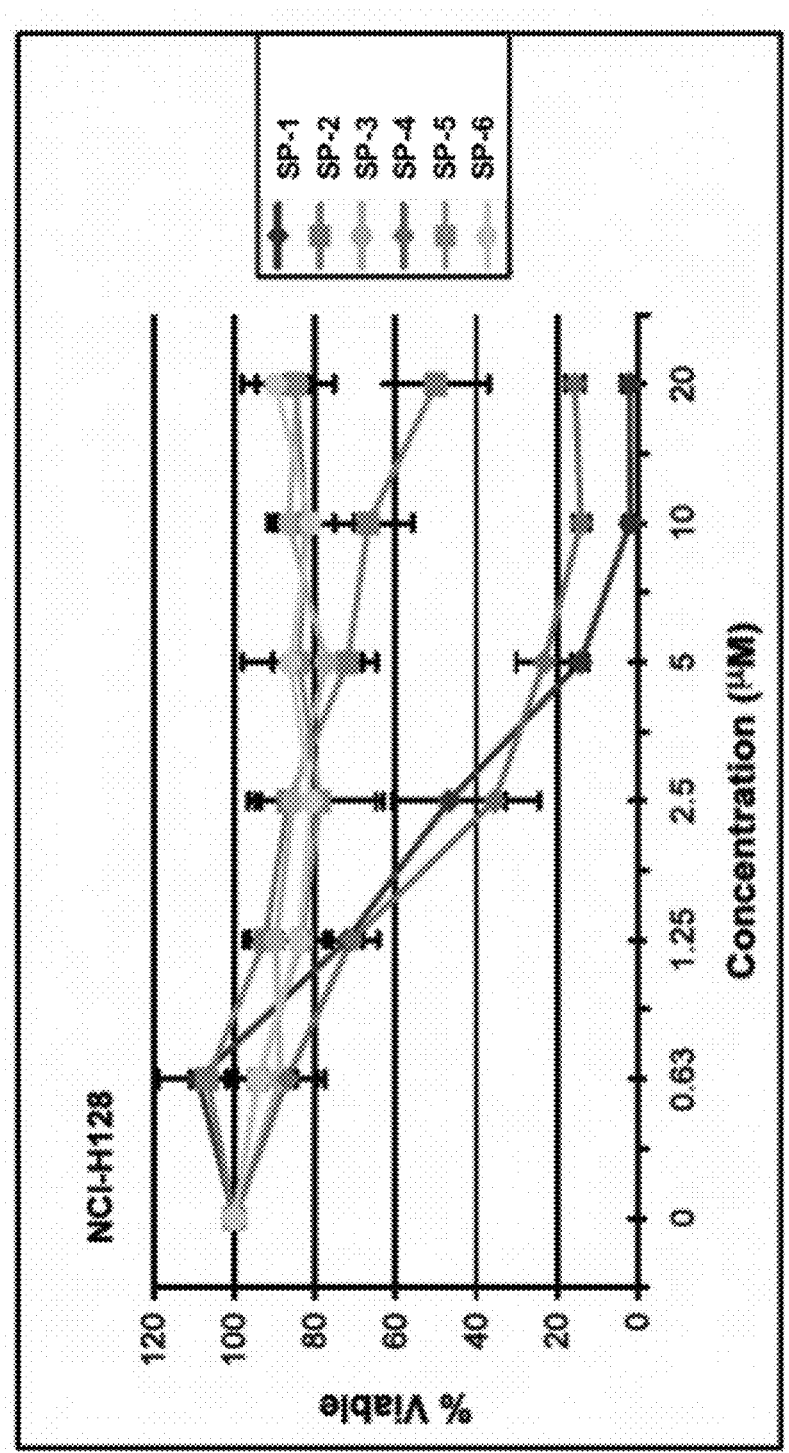
Figure 16:
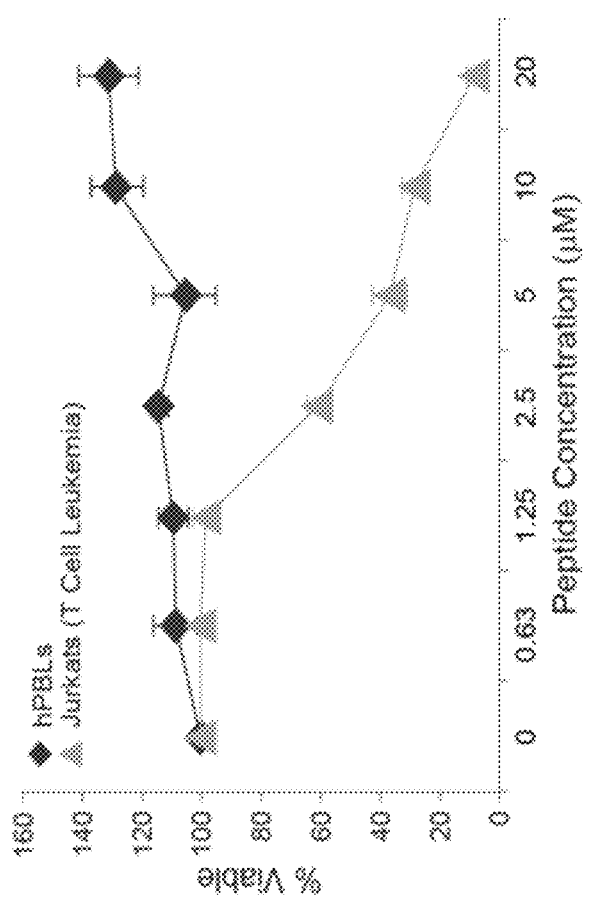
FIG. 16 indicates that SP-1 does not induce programmed cell death of resting human peripheral lymphocytes (hPBLs).
Figure 17:
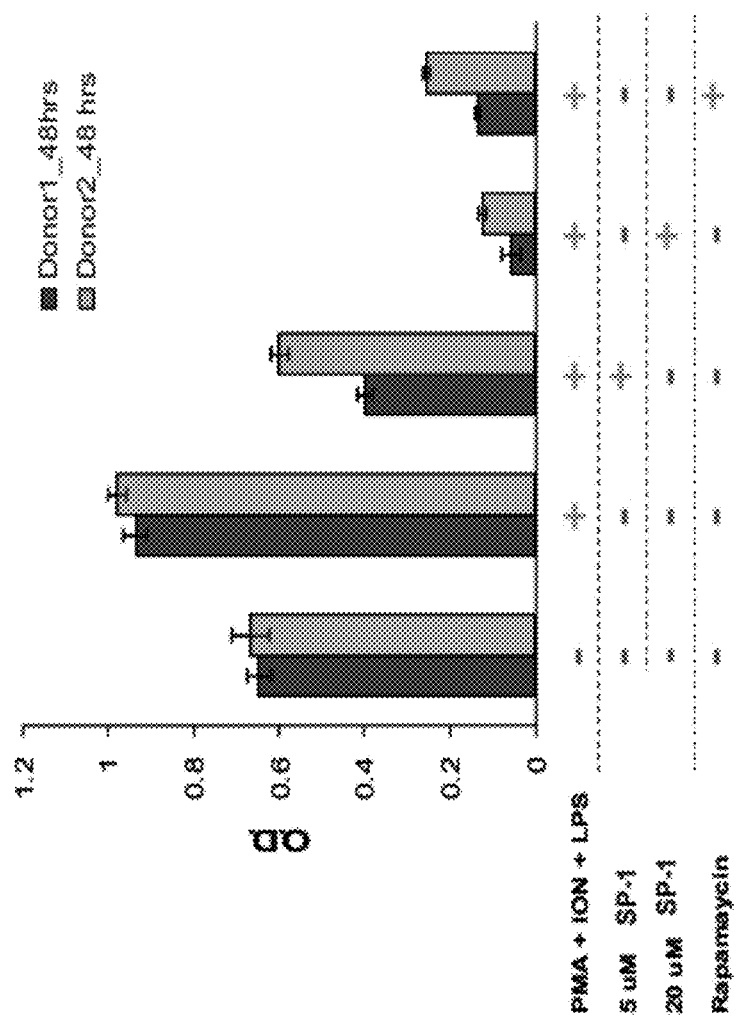
FIG. 17 exemplifies that SP-1 is as effective as rapamycin in blocking the proliferation of hPBLs activated by PMA+ionomycin+LPS treatment.

BrdU Cell Proliferation Assay hPBLs isolated from two different donors were stimulated or not with 5 µg/ml PHA, 1 µM Ionomycin and 1 µg/ml LPS and treated with either 5 or 20 µM of SP-1 in assay buffer. 1 µM Rapamycin was used as a positive control to inhibit BrdU incorporation. The cells were incubated for 48 hrs under the conditions indicated in FIG. 17. BrdU incorporation was assayed by ELISA according to manufacturer's instructions (Roche, catalog number 11444611001). In FIG. 7, the Y axis shows OD=Absorbance ($A_{405}$ nm/$A_{492}$ nm.)

Example 4

Efficacy of Peptidomimetic Macrocycles in a Human Leukemia Xenograft Model

Figure 18:
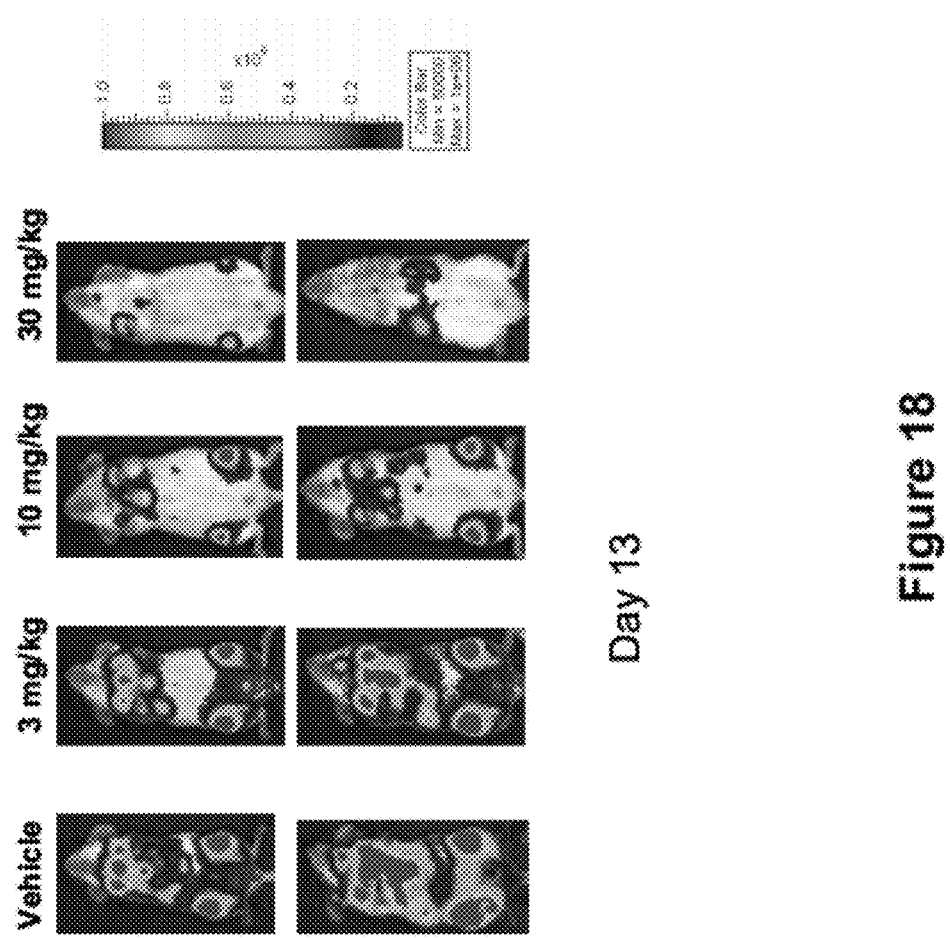
FIGS. 18 and 19 show that SP-1 decreases tumor burden in a SEMK2 human leukemia xenograft model.
Figure 19:
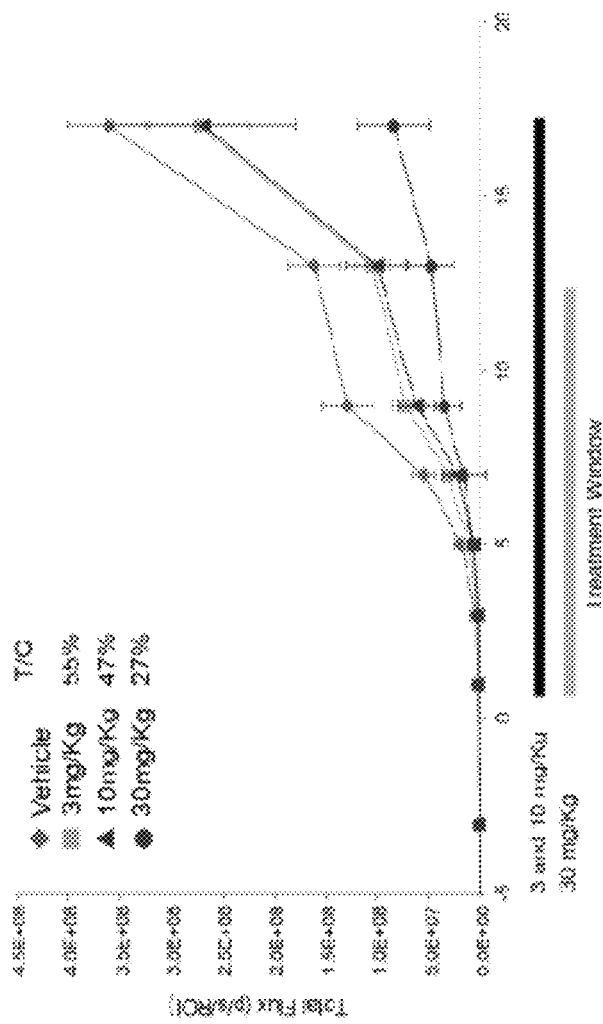

SEMK2-LN cells stably expressing luciferase were generated as previously described (Armstrong et al (2003) Cancer Cell 3:173-83). 6-8 week old female NOD-SCID mice (Jackson Laboratory) were injected with $5 \times 10^6$ SEMK2-LN cells by tail vein. The animals were imaged as described (Walensky et al., Science 305:1466-1470 (2004)) using Xenogen's In Vivo Imaging System (Caliper Life Sciences) and total body bioluminescence quantified by integration of photonic flux (photons/sec) (Living Imaging Software for Xenogen In Vivo Imaging System, Caliper Life Sciences). Animals were imaged on days 8 and 12, post-injection of leukemic cells, to identify animals with established leukemia. On day 12, prior to the initiation of treatment (treatment day 1), animals were divided into cohorts with statistically equivalent bioluminescence. Leukemic mice received a daily tail vein injection of peptidomimetic macrocycle at 3 or 10 mg/Kg/day for 21 days or 30 mg/Kg/day for 12 days. Animals were imaged at days 1, 3, 5, 7, 9, 13 and 17 during treatment, and the resulting tumor reduction is shown in FIG. 18.

Example 5

Figure 20:
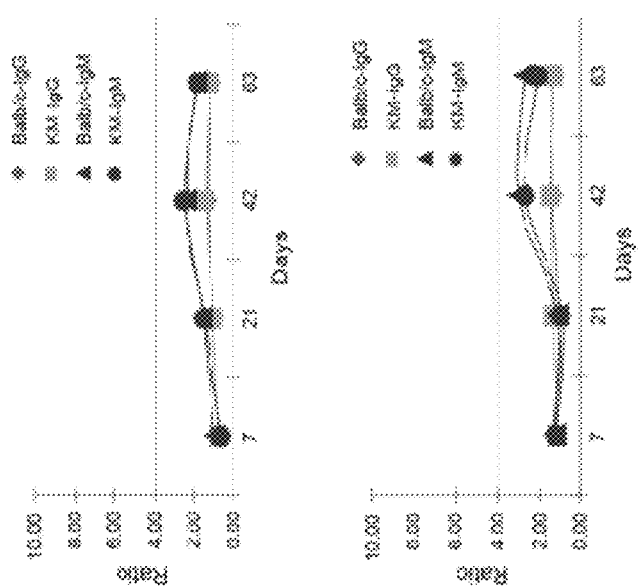
FIG. 20 shows that SP-1 does not elicit an antibody response in rodents.

Immunogenicity Determination 6-8 week old Balb/c or KM female mice were immunized with unconjugated SP-1 or SP-4. Sera were collected pre-immunization and 25 µg of each peptide in D5W were injected by tail vein using the following immunization schedule: sera were collected seven days following the first two immunizations at days 1 and 14 and 14 days following the third and fourth immunizations. Antibody titers were determined by indirect ELISA. In brief, microtiter plates were coated with either SP-1 or SP-3 (5 μg/ml) overnight at 4° C. The next day, the plates were washed 5 times with PBS/0.05% Tween20 (PBST) and blocked with 5% non-fat milk/PBST for one hour at 37° C., followed by additional washing with PBST. The anti-sera was serially diluted and added to the coated plates for 1 hr at 37° C. The plates were then washed extensively with PBST and further incubated with either HRP-conjugated anti-mouse IgG or IgM for 1 hr at 37° C. and washed 5 times with PBST prior to the addition of HRP substrate. Plates were incubated at room temperature for 10 minutes and the reaction stopped with 0.5 M oxalic acid solution. Absorbance was read at 450 nm in an ELISA microplate reader. The OD values were determined for both control- and anti-sera at 1:100 dilution. The graphs in FIG. 20 are plotted as the ratio of OD anti-sera/OD control sera. A ratio below 4 was considered negative.

Example 6

Melting Temperature ($T_m$) Determination

Figure 21:
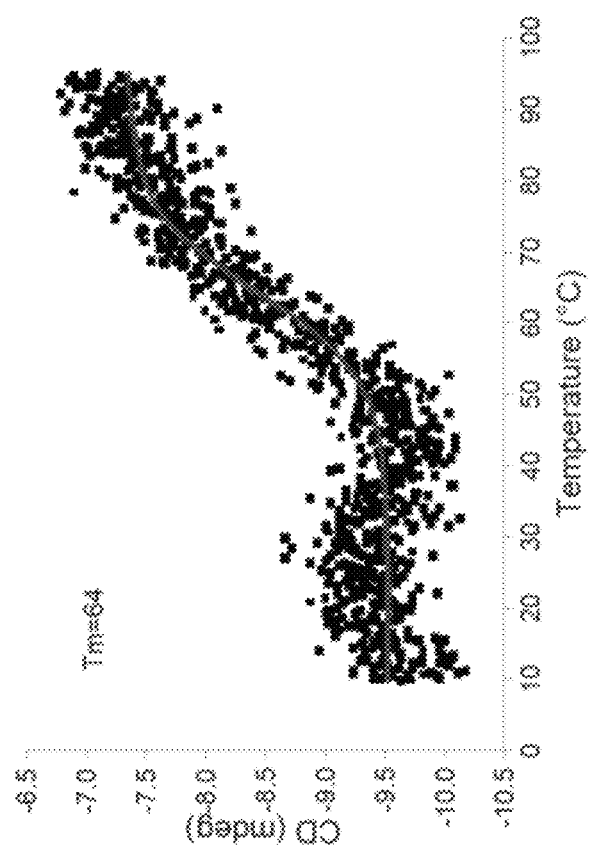
FIG. 21 illustrates that SP-1 is highly stable, and maintains its helical conformation as temperature increases up to 64° C.

Lyophilized SP-1 was dissolved in $ddH_2O$ to a final concentration of 50 μM. Tm was determined by measuring the circular dichroism (CD) spectra in a Jasco-810 spectropolarimeter at a fixed wavelength of 222 nm between the temperatures of 5-95° C. The following parameters were used for the measurement: data pitch, 0.1° C.; bandwidth, 1 nm and path length, 0.1 cm averaging the signal for 16 seconds. The results are shown in FIG. 21.

Example 7

Sample Preparation for Plasma Stability Determination

Figure 22:
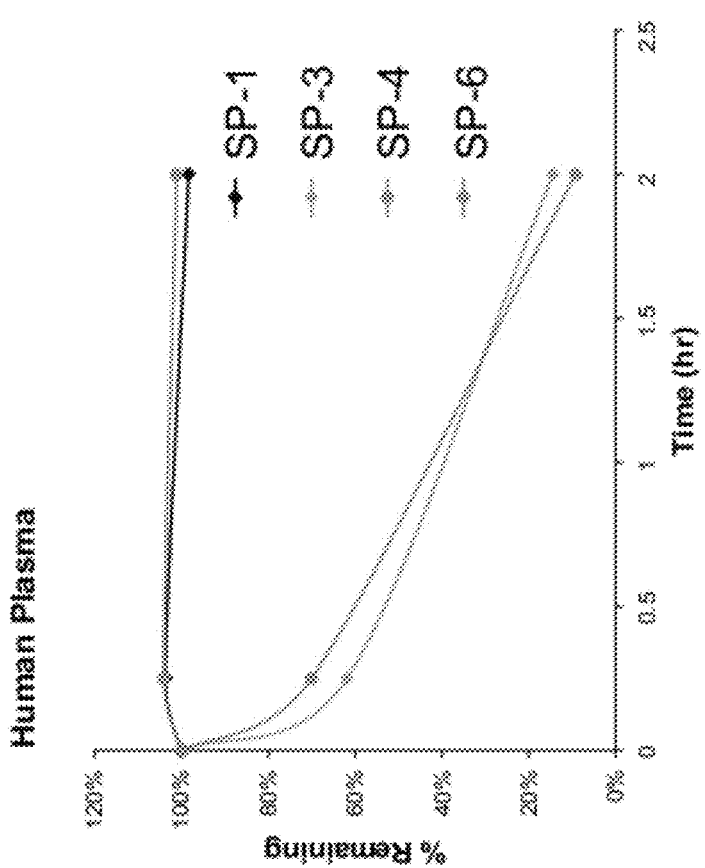
FIG. 22 describes the human plasma stability of a series of peptidomimetic macrocycles of the invention.
Figure 23:
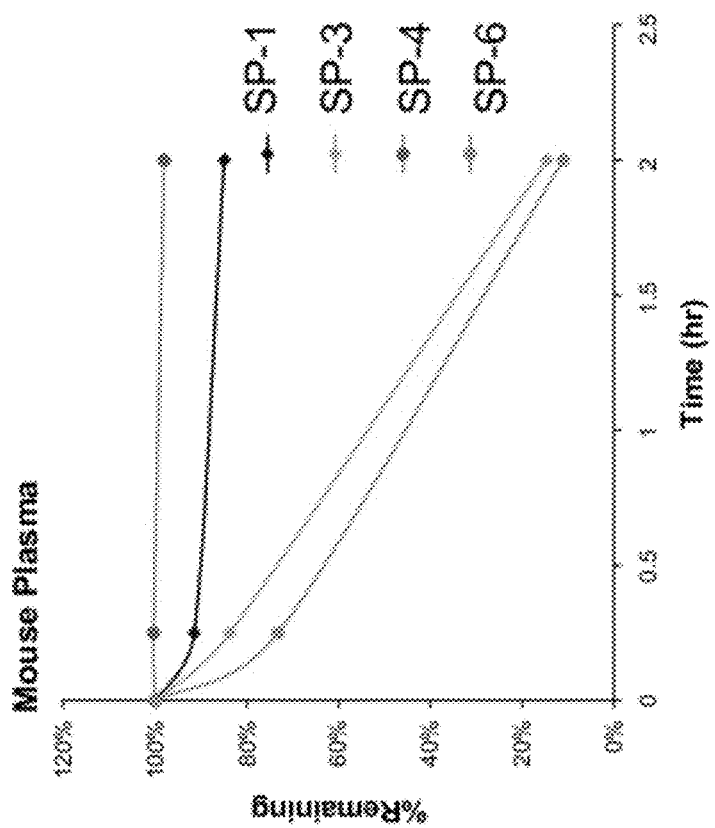
FIG. 23 describes the mouse plasma stability of a series of peptidomimetic macrocycles of the invention.
Figure 25:
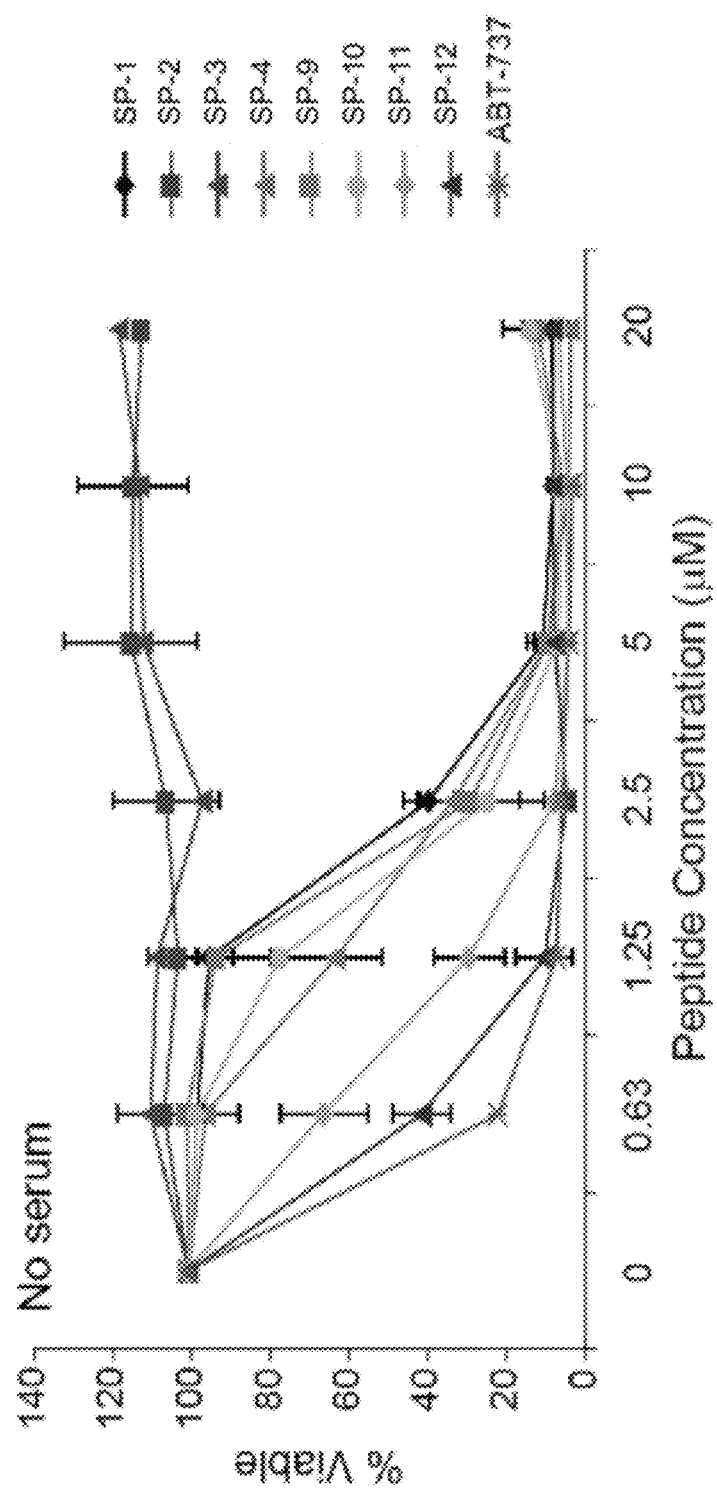
FIG. 25 describes the induction of programmed cell death in Jurkat tumor cells by peptidomimetic macrocycles of the invention in the absence of human serum and compares the potency of BH3 peptidomimetic macrocycles of the invention to BCL-2/BCL-XL-specific antagonists such as ABT-737.
Figure 26:
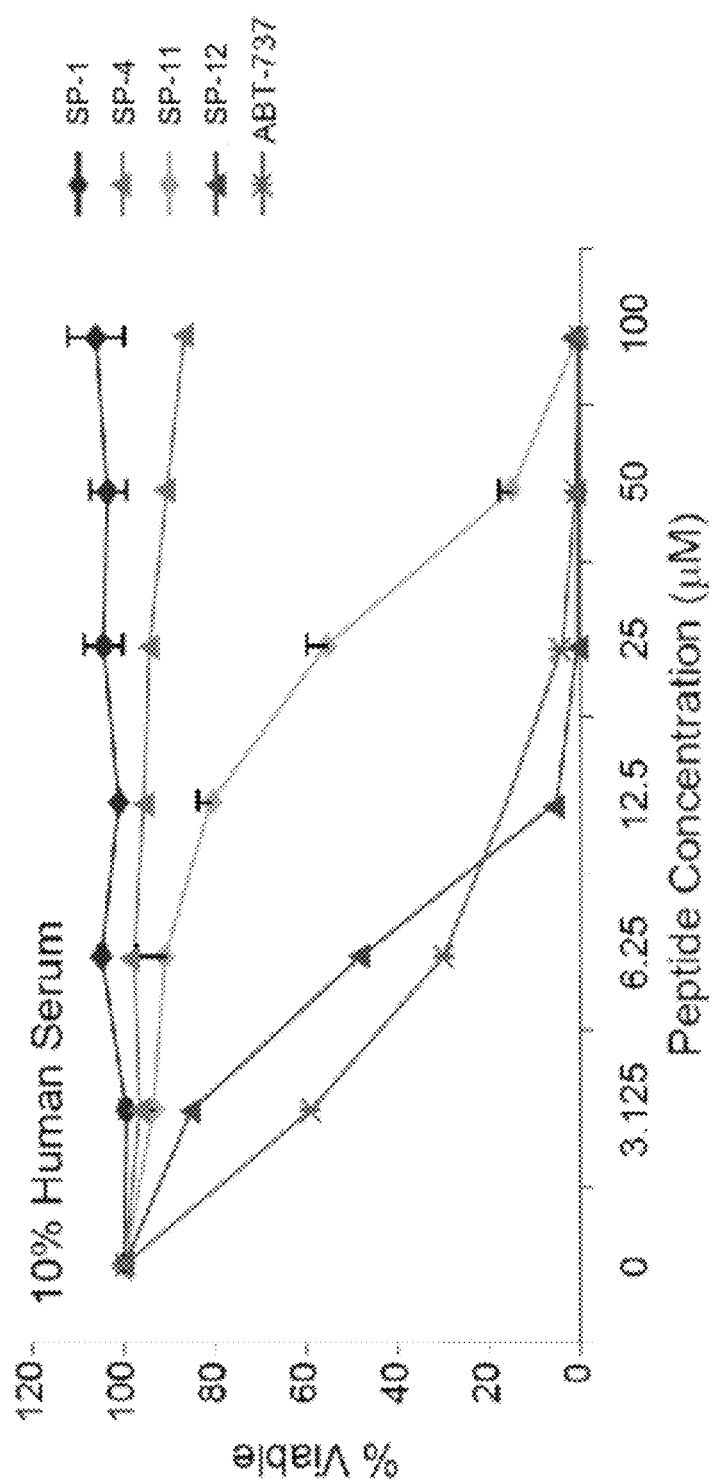
FIG. 26 describes the induction of programmed cell death in Jurkat tumor cell line by peptidomimetic macrocycles of the invention in the presence of 10% human serum and compares the potency of BH3 peptidomimetic macrocycles of the invention to BCL-2/BCL-XL-specific antagonists such as ABT-737.
Figure 27:
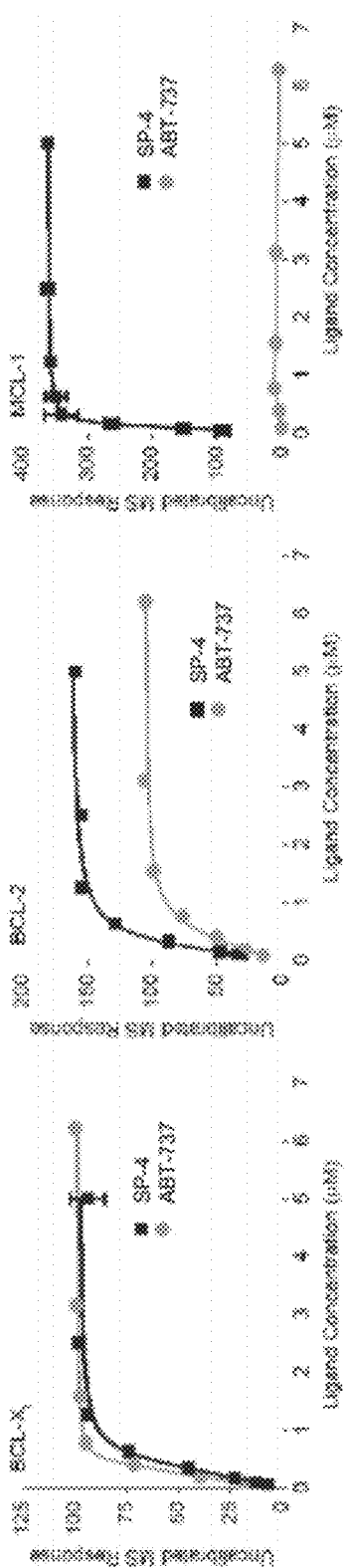
FIG. 27 compares the binding affinity of several BH3 peptidomimetic macrocycles of the invention and ABT-737 to Bcl-$X_L$, Bcl-2, and Mcl-1.
Figure 28:
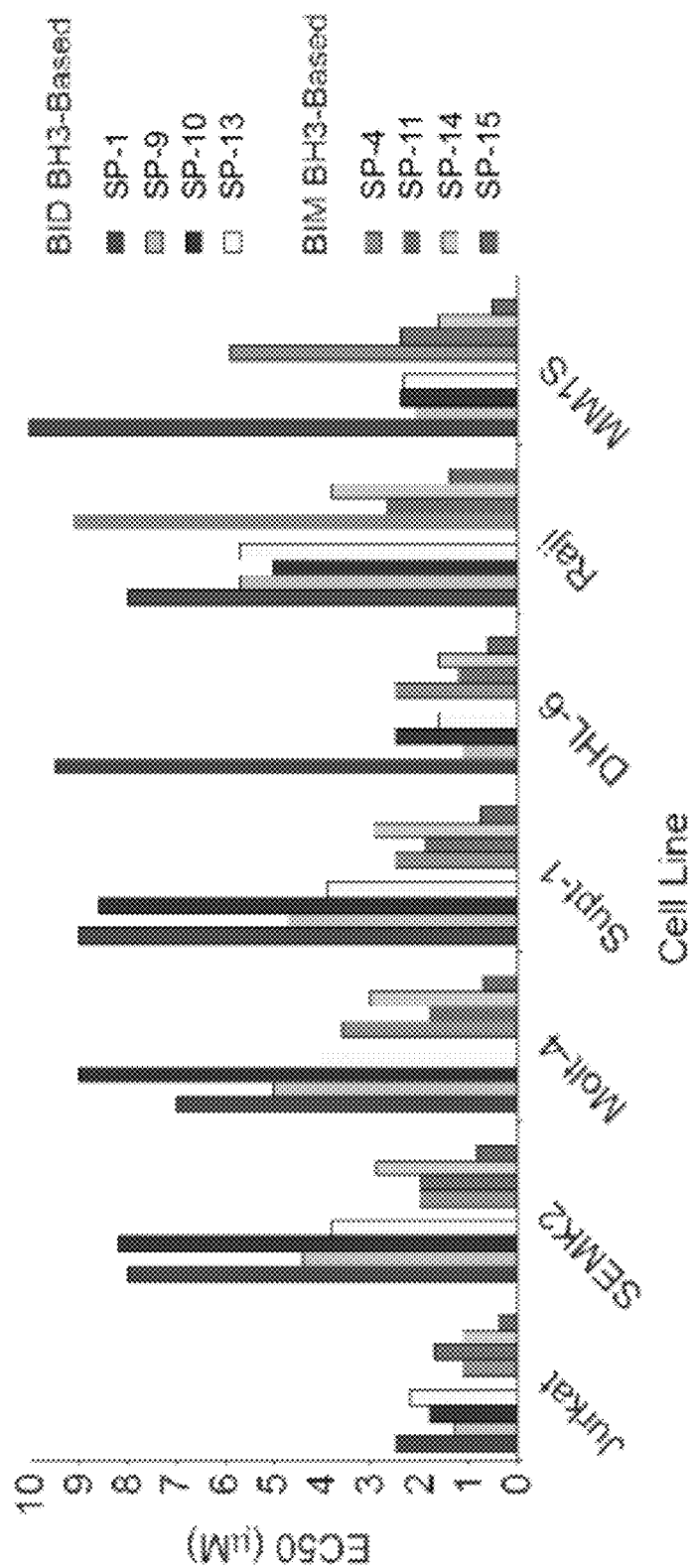
FIG. 28 shows efficacy of peptidomimetic macrocycles to a number of hematological malignancies.
Figure 29:
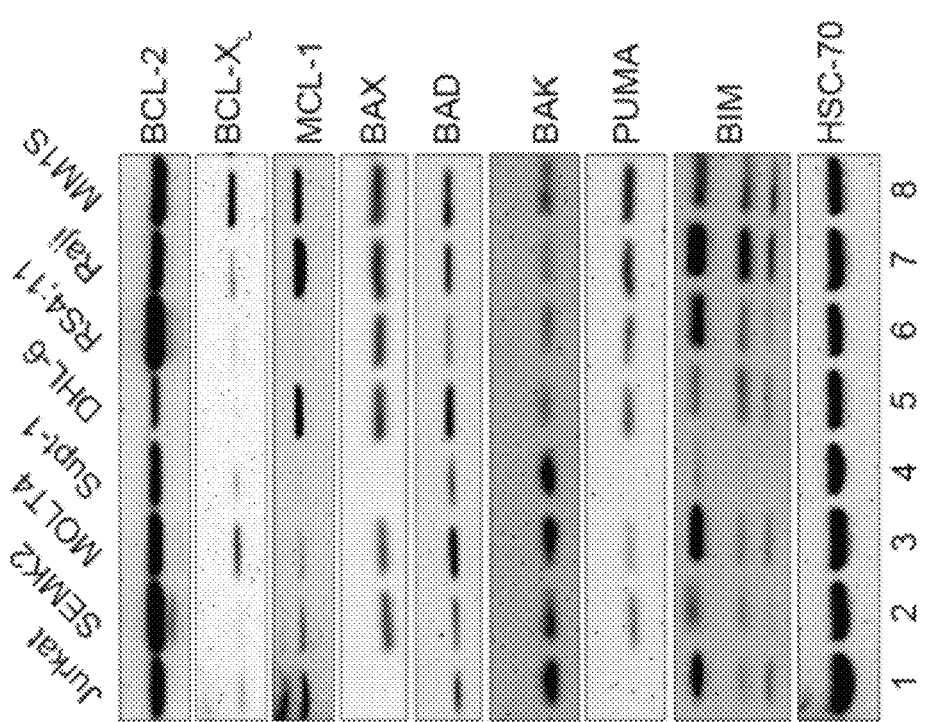
FIG. 29 illustrates the varied Bcl-2 family protein expression profile of cell lines sensitive to treatment by compositions of the invention.
Figure 30:
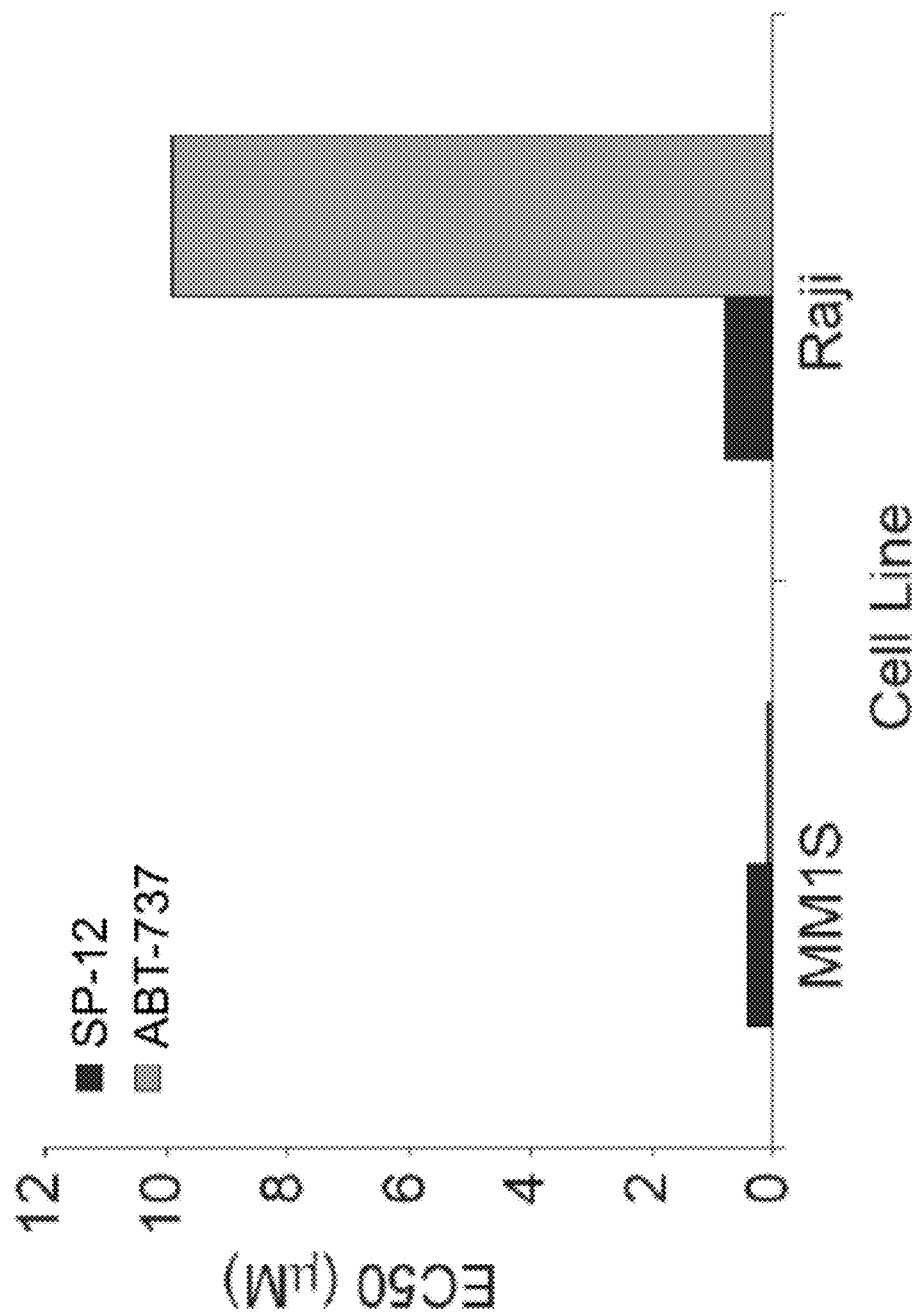
FIG. 30 compares efficacy of peptidomimetic macrocycles with ABT-737 in Raji, an ABT-737 resistant Burkitt's lymphoma cell line.
Figure 31:
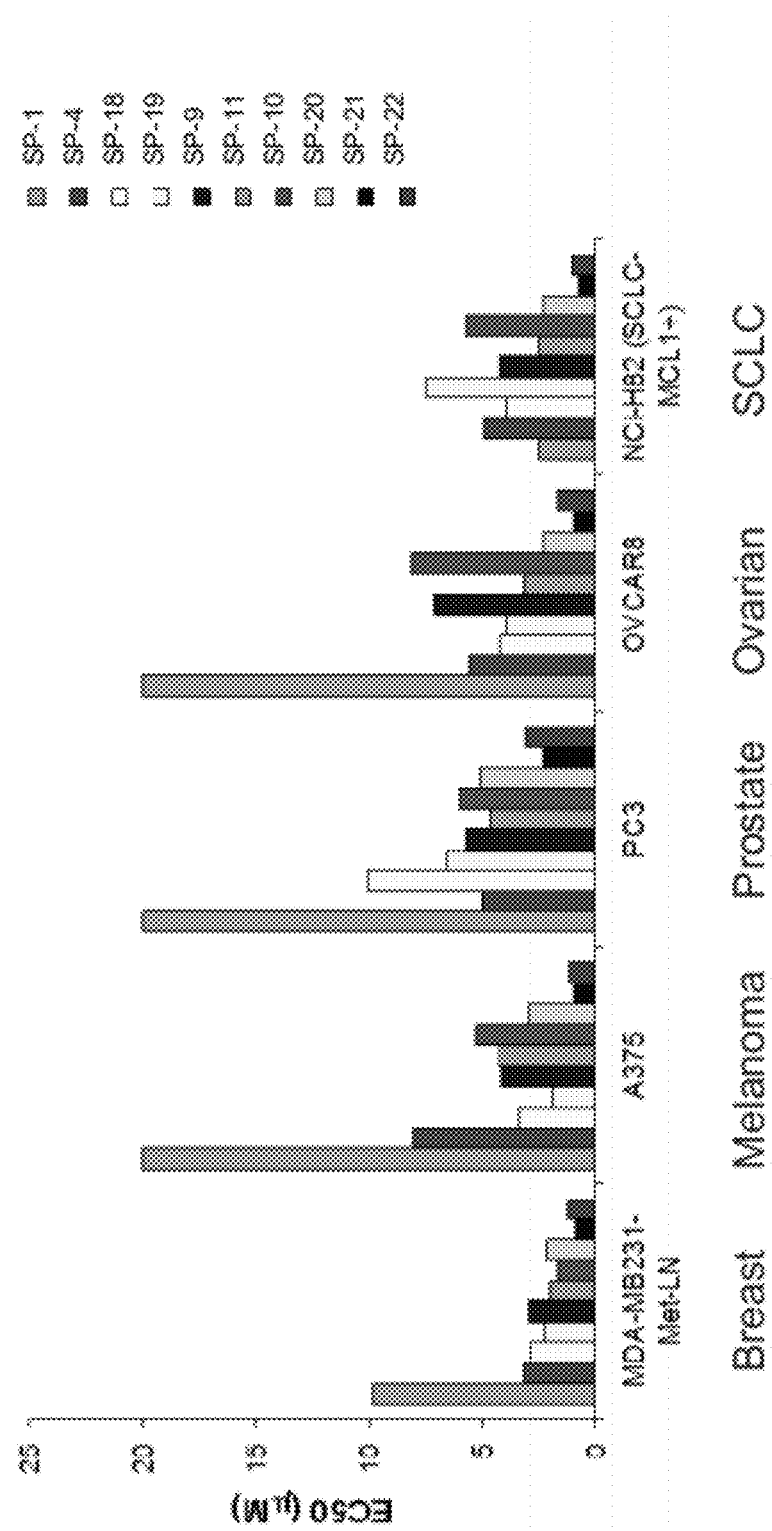
FIG. 31 illustrates efficacy of BH3 peptidomimetic macrocycles against a variety of solid tumor cell lines.
Figure 32:
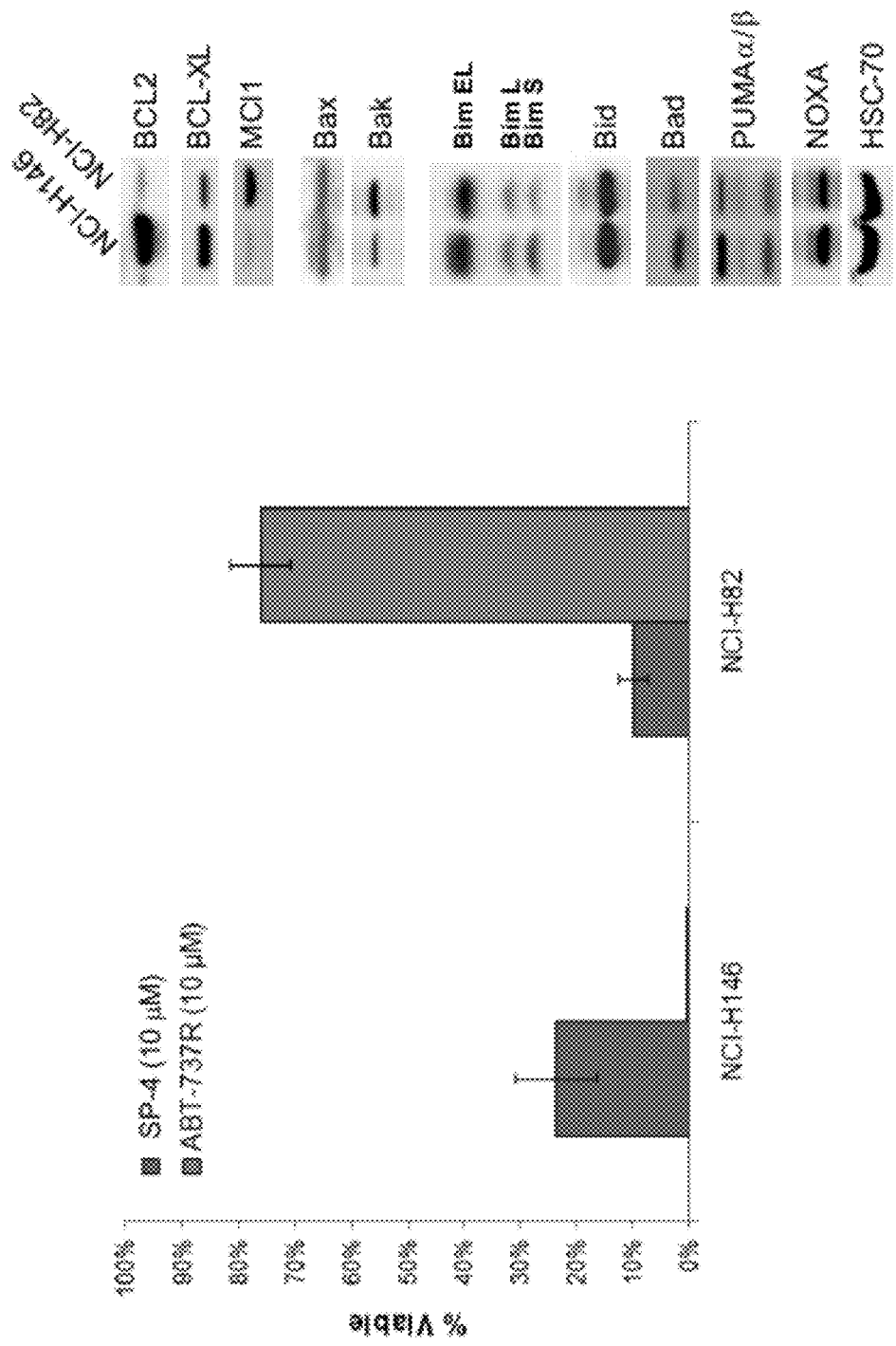
FIG. 32 depicts induction of programmed cell death by a peptidomimetic macrocycle of the invention in an ABT-737 resistant small cell lung cancer line (NCI-H82).
Figure 33:
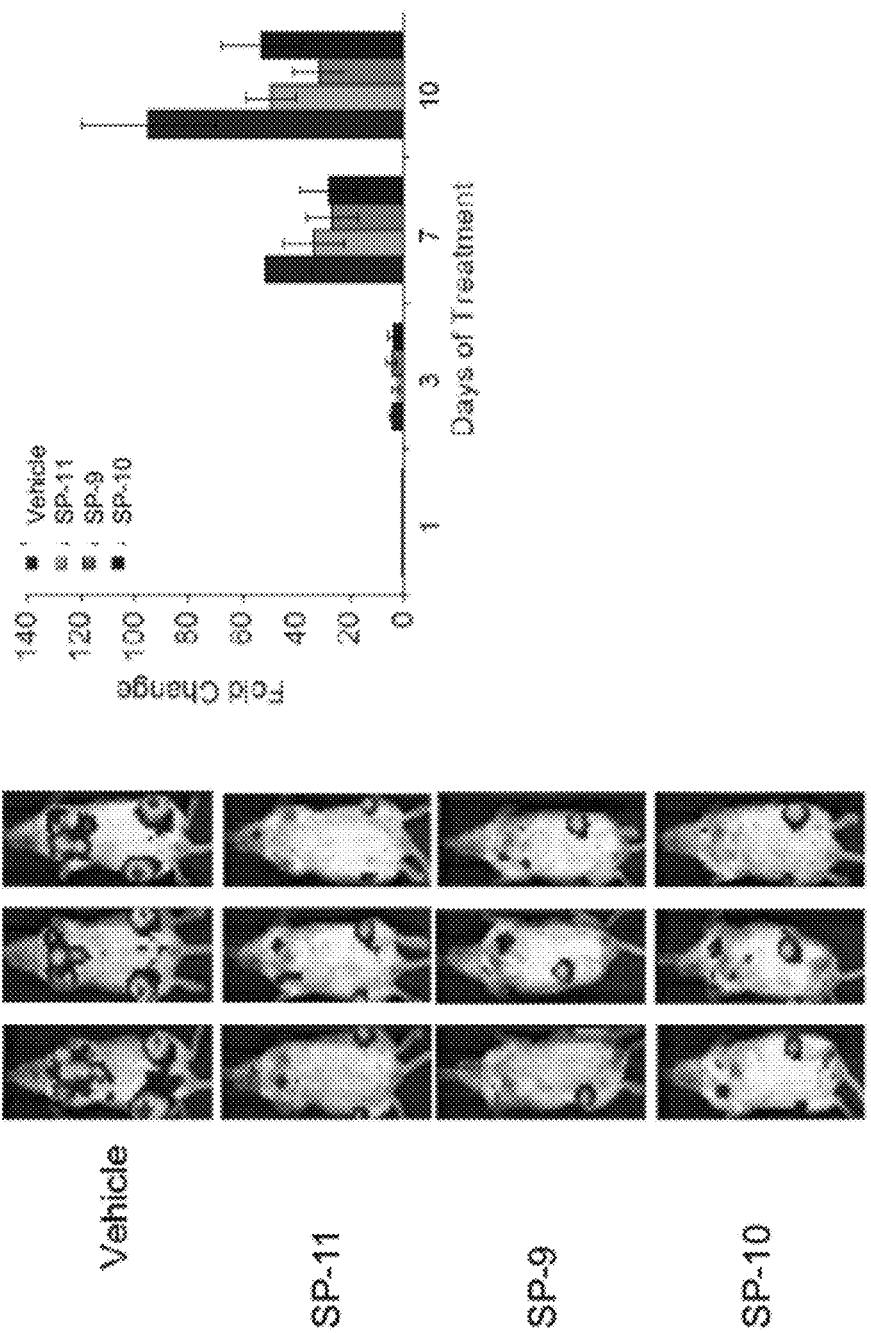
FIG. 33 shows suppression of SEMK-2 tumor progression in NOD-SCID mice by compounds of the invention.
Figure 34:
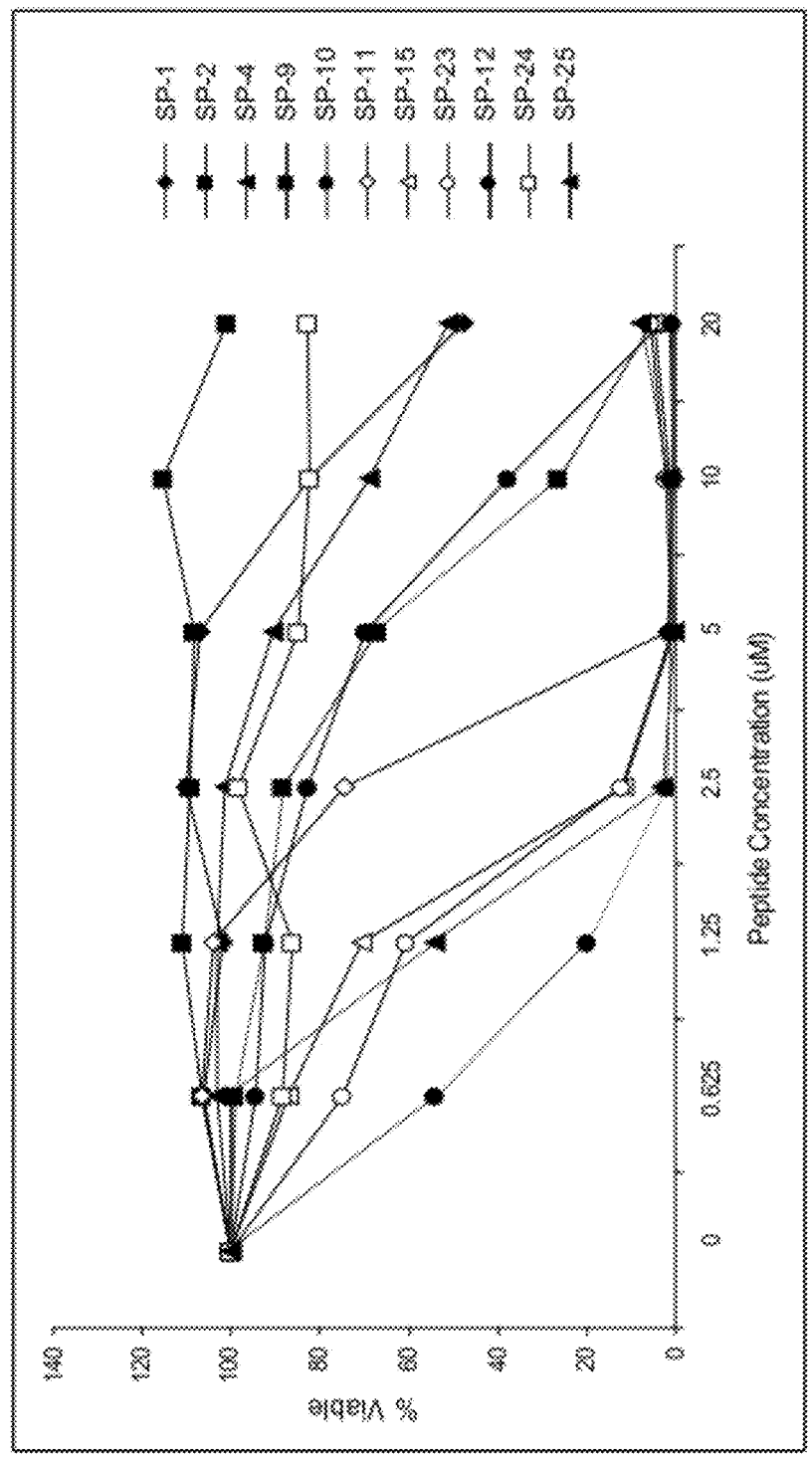
FIG. 34 describes induction of programmed cell death by peptidomimetic macrocycles of the invention in an ovarian tumor cell line (OVCAR8), treated in the absence of serum.
Figure 35:
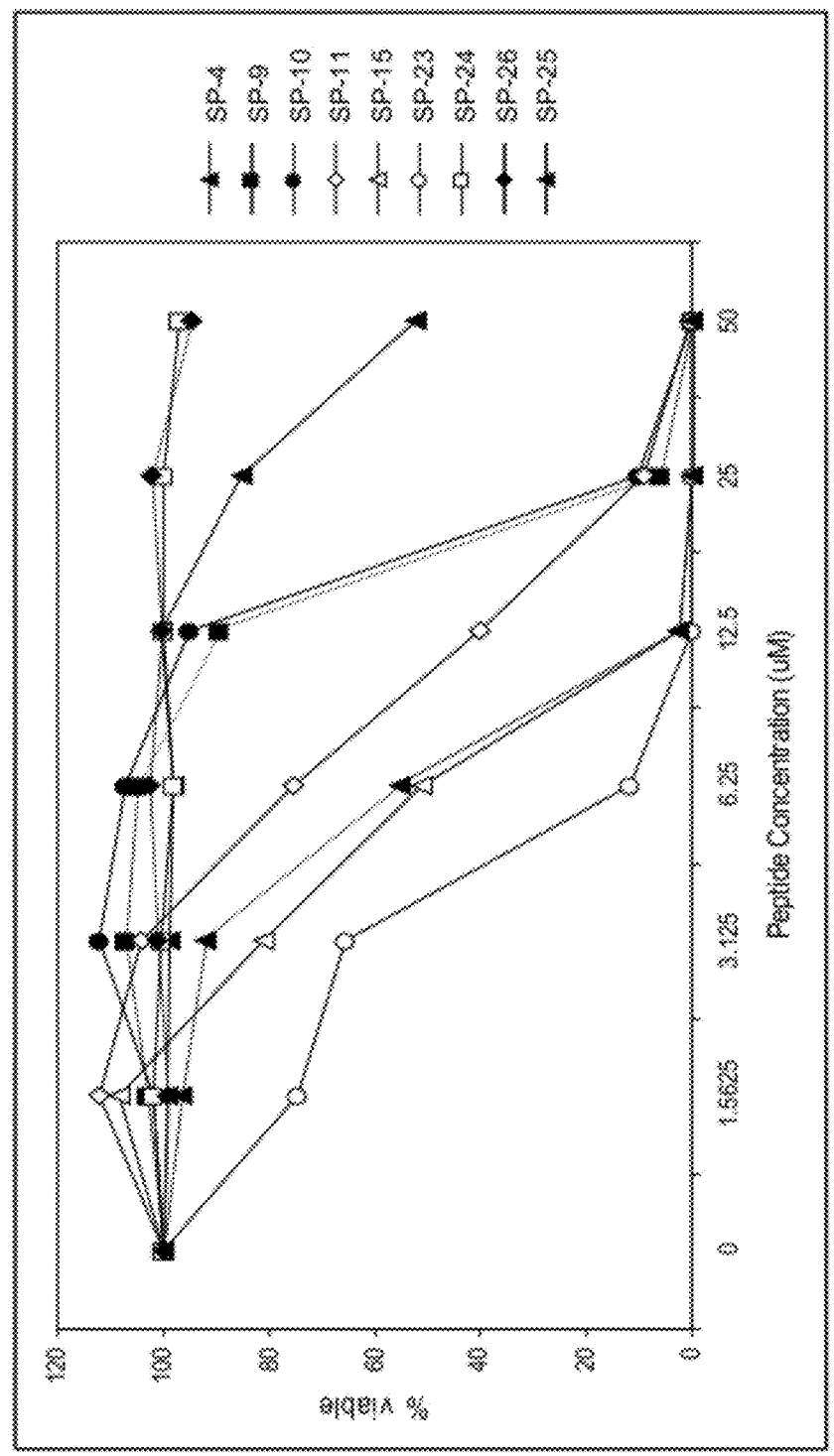
FIG. 35 depicts induction of programmed cell death by peptidomimetic macrocycles of the invention in an ovarian tumor cell line (OVCAR8), treated in the presence of 2% human serum.
Figure 36:
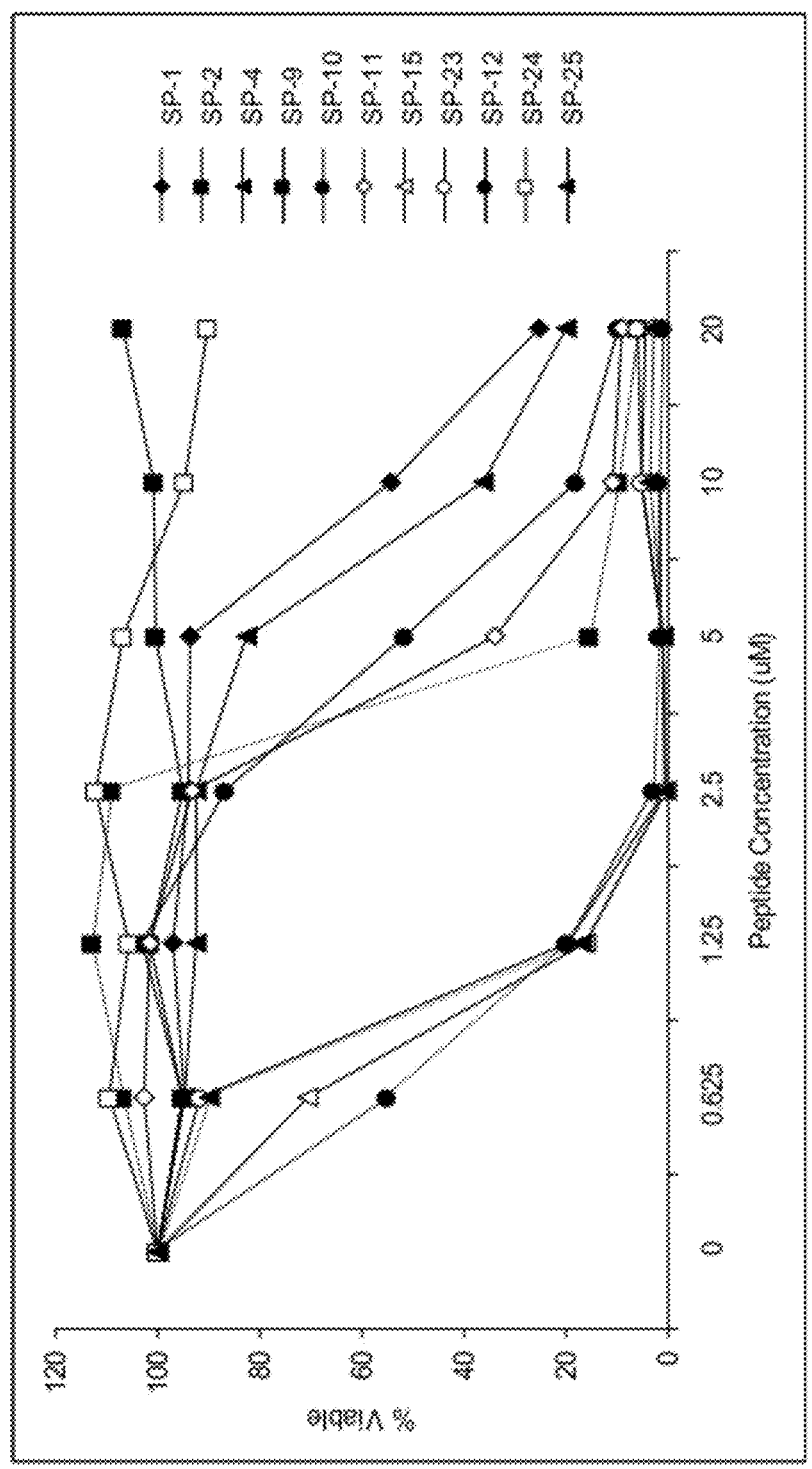
FIG. 36 depicts induction of programmed cell death by peptidomimetic macrocycles of the invention in a melanoma cell line (A375), treated in the absence of serum.
Figure 37:
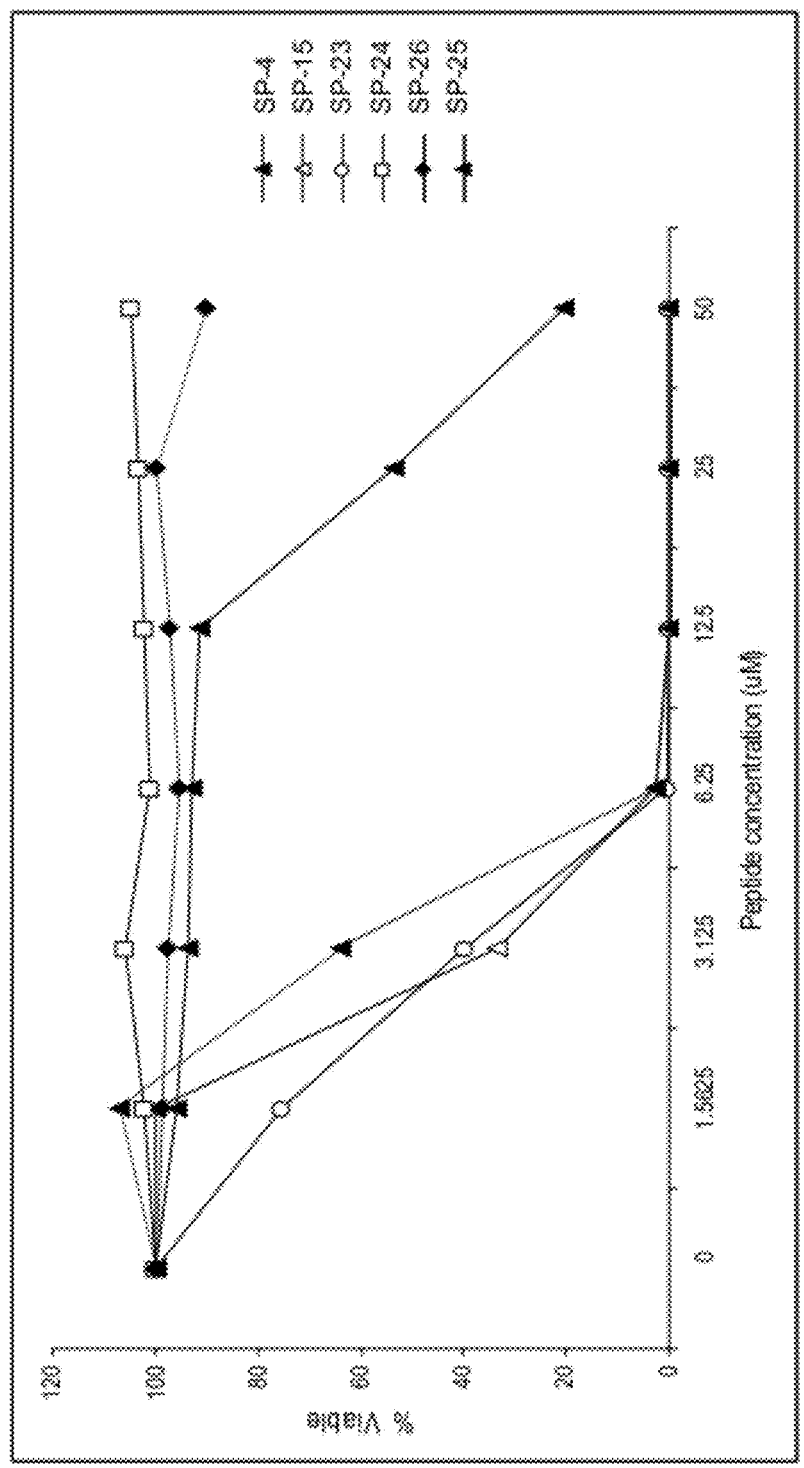
FIG. 37 depicts induction of programmed cell death by peptidomimetic macrocycles of the invention in a melanoma cell line (A375), treated in the presence of 2% human serum.
Figure 38:
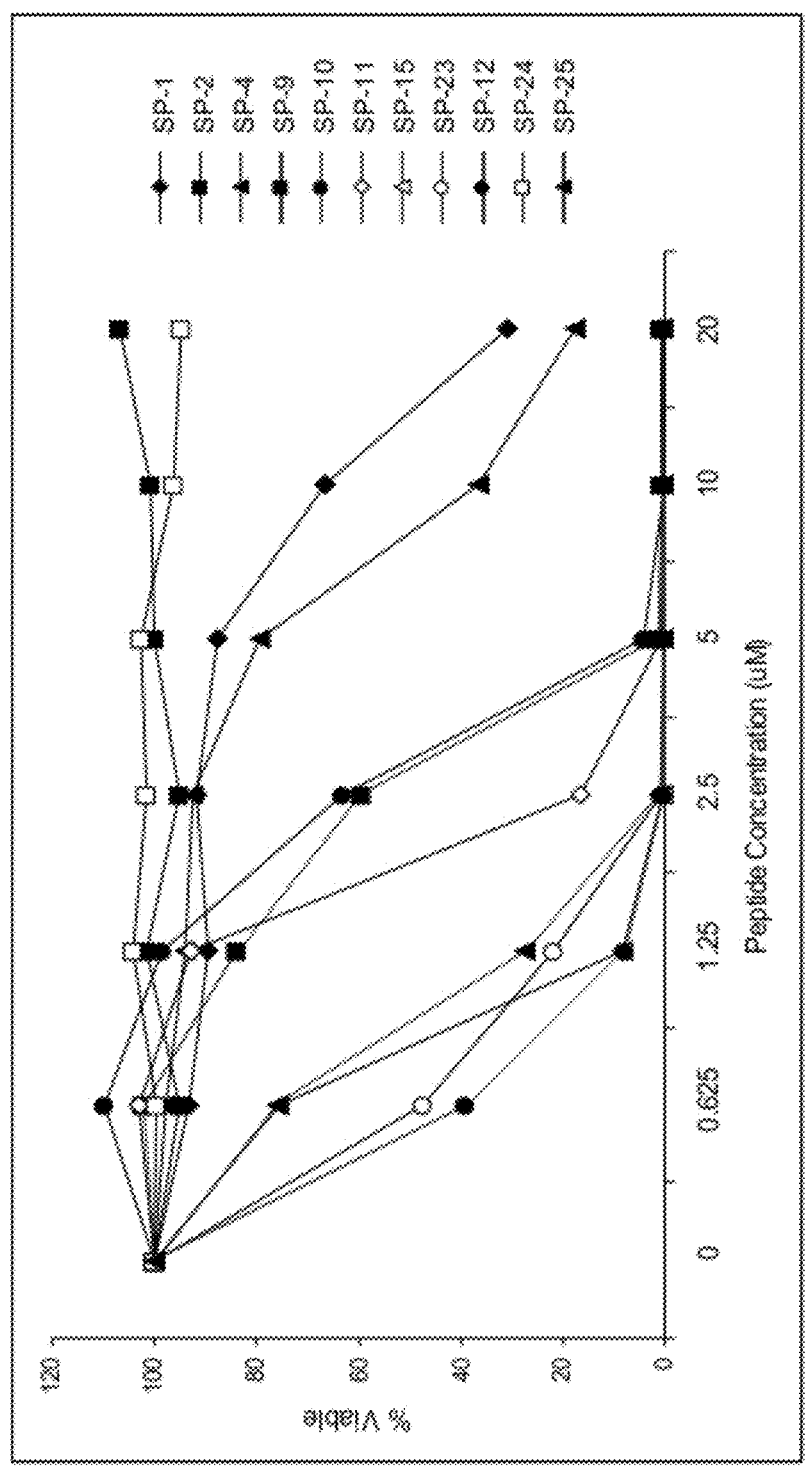
FIG. 38 depicts induction of programmed cell death by peptidomimetic macrocycles of the invention in a breast tumor cell line (MDA-MD-231-Met), treated in the absence of serum.
Figure 39:
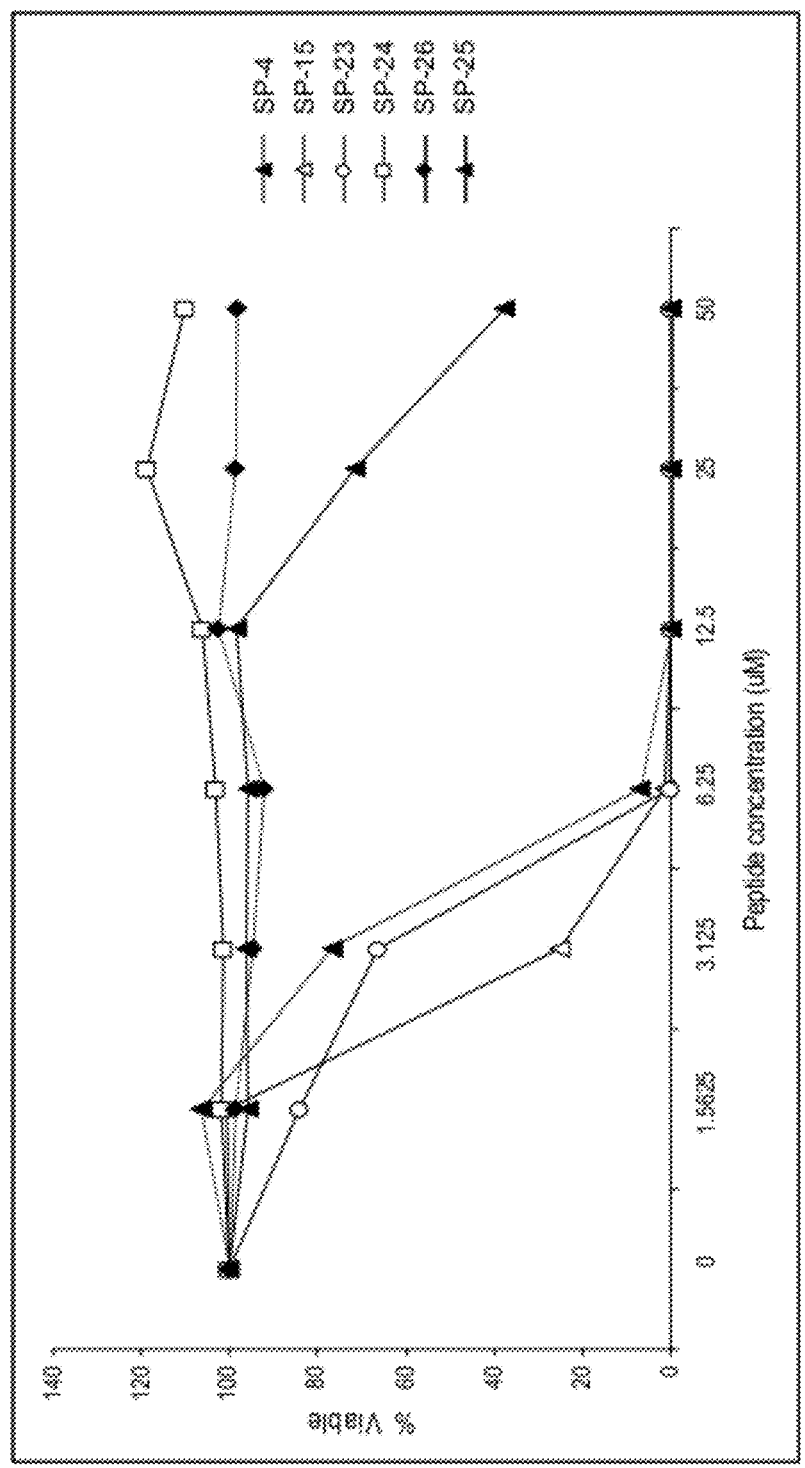
FIG. 39 depicts induction of programmed cell death by peptidomimetic macrocycles of the invention in a breast tumor cell line (MDA-MD-231-Met), treated in 2% human serum.
Figure 40:
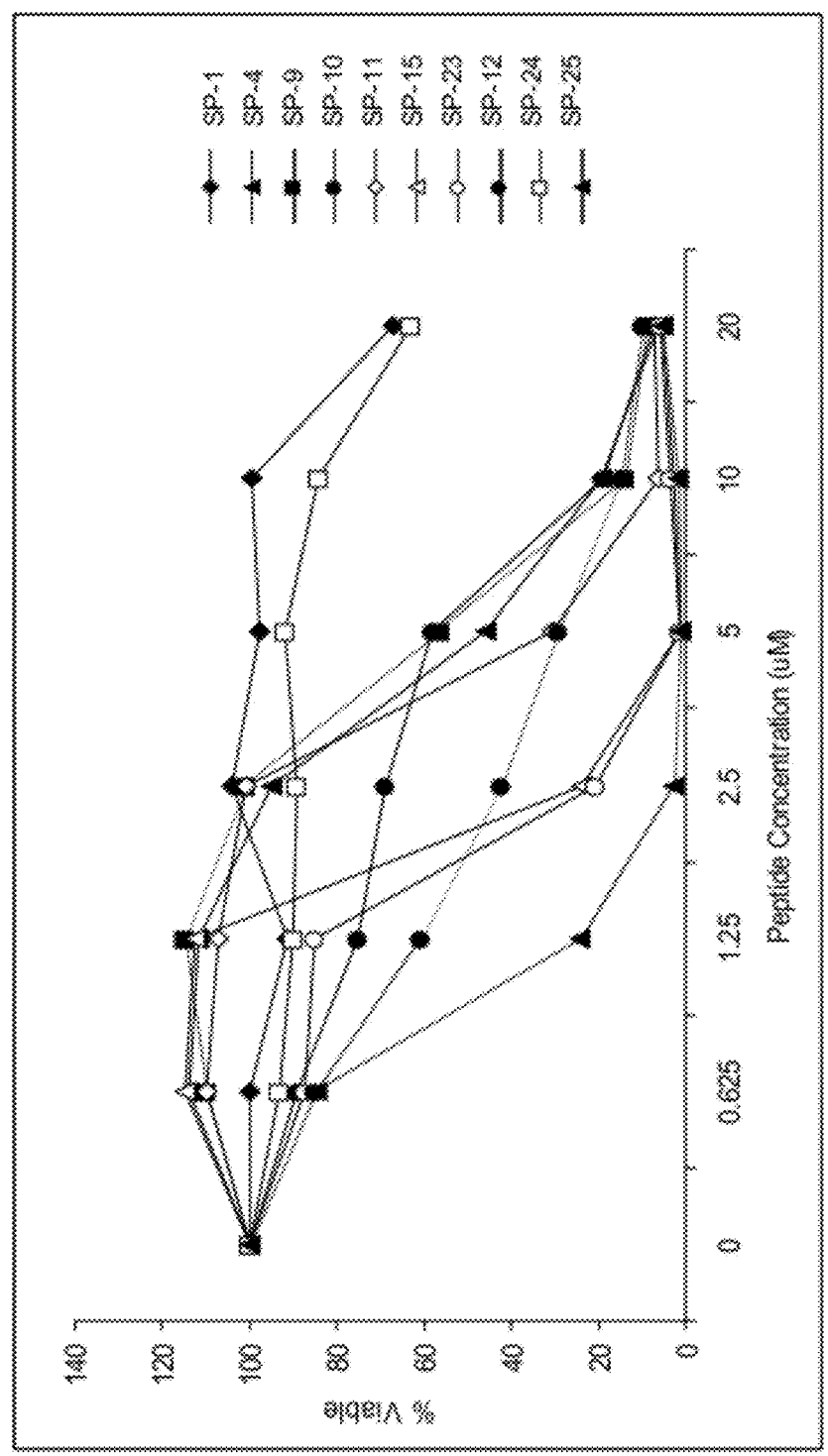
FIG. 40 depicts induction of programmed cell death by peptidomimetic macrocycles of the invention in a prostate tumor cell line (PC3), treated in the absence of serum.
Figure 41:
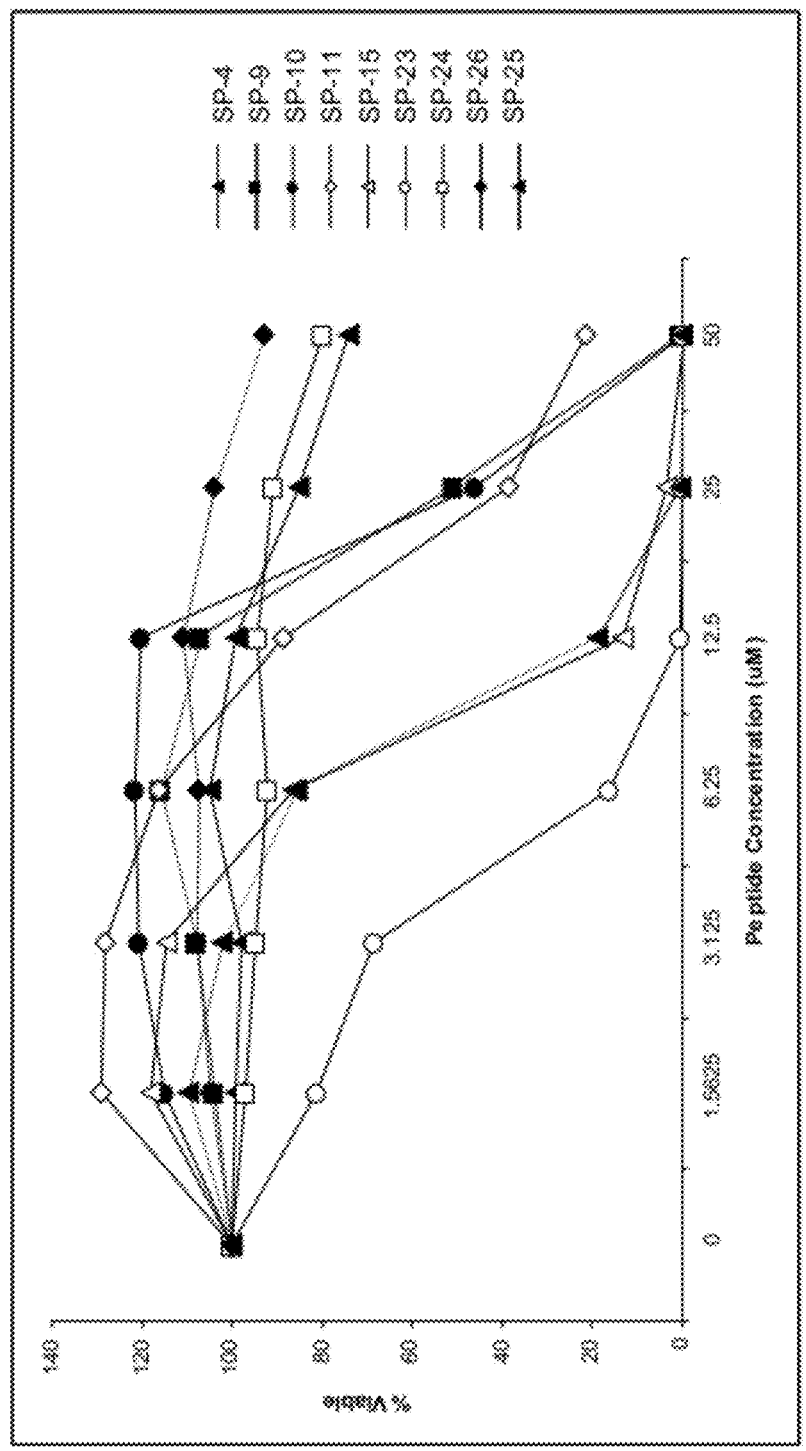
FIG. 41 depicts induction of programmed cell death by peptidomimetic macrocycles of the invention in a prostate tumor cell line (PC3), treated in 2% human serum.
Figure 42:
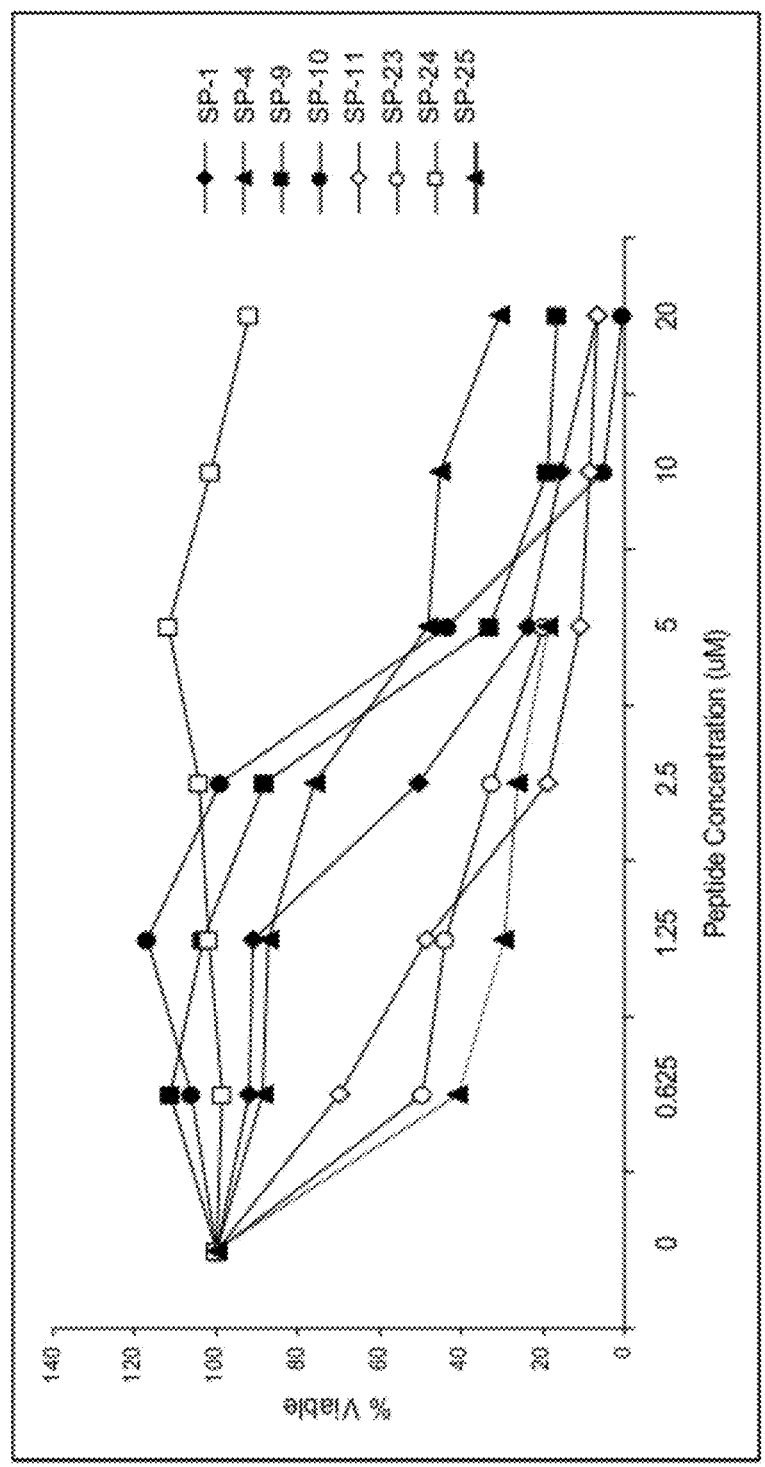
FIG. 42 depicts induction of programmed cell death by peptidomimetic macrocycles of the invention in a small cell lung cancer cell line (NCI-H-82), treated in the absence of serum.

For ex-vivo plasma stability studies 10 μM of SP-1, SP-3, SP-4 and SP-6 were incubated with pre-cleared human and mouse plasma at 37° C. for 0, 15 and 120 minutes. At the end of each incubation time, 100 μL of sample was removed, placed in a fresh low retention eppendorf tube with 300 μl of ice cold MeOH. The samples were centrifuged at 10,000 rpm, the supernatant removed and placed in a fresh low retention eppendorf tube and 200 μl of water was added to each sample. Samples were then analyzed by LC-MS/MS as indicated below. The results are shown in FIGS. 22 and 23.

Example 8

Intravenous Pharmacokinetic Analysis

The IV dose formulation was prepared by dissolving SP-1 or SP-4 in 5% DMSO/D5W to achieve a 10 mg/Kg/dose. Canulated Crl:CD® (SD) male rats (7-8 weeks old, Charles River Laboratories) were used in these studies. Intravenous doses were administered via the femoral cannula and the animals were dosed at 10 mL/kg per single injection. Blood for pharmacokinetic analysis was collected at 10 time points (0.0833, 0.25, 0.5, 1, 2, 4, 6, 8, 12 and 24 hrs post-dose). Animals were terminated (without necropsy) following their final sample collection.

The whole blood samples were centrifuged (~1500×g) for 10 min at ~4° C. Plasma was prepared and transferred within 30 min of blood collection/centrifugation to fresh tubes that were frozen and stored in the dark at ~−70° C. until they were prepared for LC-MS/MS analysis.

Sample extraction was achieved by adding 10 μL of 50% formic acid to 100 μL plasma (samples or standards), following by vortexing for 10 seconds. 500 μL acetonitrile was added to the followed by vortexing for 2 minutes and centrifuged at 14,000 rpm for 10 minutes at ~4° C. Supernatants were transferred to clean tubes and evaporated on turbovap<10 psi at 37° C. Prior to LC-MS/MS analysis samples were reconstituted with 100 μL of 50:50 acetonitrile:water.

The peak plasma concentration ($C_{max}$), the time required to achieve the peak plasma concentration ($t_{max}$), the plasma terminal half-life ($t_{1/2}$), the area under the plasma concentration time curve (AUC), the clearance and volume of distribution were calculated from the plasma concentration data. All pharmacokinetic calculations were done using WinNonlin version 4.1 (Pharsight Corp) by non-compartmental analysis. FIG. 24 summarizes the observed results.

The following LC-MS/MS method was used. In brief, the LC-MS/MS instruments used was an API 365 (Applied Biosystems). The analytical column was a Phenomenex Synergi (4μ, Polar-RP, 50 mm×2 mm) and mobile phases A (0.1% formic acid in water) and B (0.1% formic acid in methanol) were pumped at a flow rate of 0.4 ml/min to achieve the following gradient:

| Time (min) | % B |
|---|---|
| 0 | 15 |
| 0.5 | 15 |
| 1.5 | 95 |
| 4.5 | 95 |
| 4.6 | 15 |
| 8.0 | Stop |

MRM: 814.0 to 374.2 (positive ionization)

Example 9

FACS Analysis of Detection of FITC-Labeled Peptidomimetic Macrocycles in Treated Cells Cells (e.g. Jurkat cells) were cultured in suspension in RPMI1640 medium with 2 mM L-Glutamine (Invitrogen) and supplemented with 10% FBS and 1% penicillin-Streptomycin. Cells were subcultured a day prior to the day of experiment to keep them in an exponential growing phase. To analyze the uptake of FITC-labeled peptidomimetic macrocycles by FACS, exponentially growing Jurkat cells were seeded in 0.9 ml of serum-free medium at density of 1×10$^6$ cells. Cells were allowed to settle down until compounds were diluted. Test compounds were diluted to 2 mM stock in DMSO, followed by dilution to 400 μM in sterile water; further dilution to 100 μM was done using OptiMEM. Thus 100 μl of 100 uM FITC-labeled peptidomimetic macrocycle was then added to appropriate wells to achieve a final concentration of 10 μM in 1 ml volume. Plates were returned to 37° C., 5% $CO_2$ incubators for designated time points. At the end of each time point, the cell suspension was diluted with media, washed twice and subjected to trypsin (0.25%) for 15 min at 37° C. Cells were then washed with OptiMem and finally resuspended in 500 μl of PBS. Cellular fluorescence was measured using Beckman Coulter FACS instrument counting at least 20000 events per sample. Analysis was done using Summit version 4, Dako Colorado, Inc.

Example 10

Protein-Ligand Binding Experiments

Protein-ligand binding experiments were conducted according to the following representative procedure outlined for a system-wide control experiment using 1 µM SP-4 plus 5 µM Bcl-$X_L$. A 1 µL DMSO aliquot of a 40 µM stock solution of peptidomimetic macrocycle was dissolved in 19 µL of PBS (Phosphate-buffered saline: 50 mM, pH 7.5 Phosphate buffer containing 150 mM NaCl). The resulting solution was mixed by repeated pipetting and clarified by centrifugation at 10 000 g for 10 min. To a 4 µL aliquot of the resulting supernatant was added 4 µL of 10 µM BCL-$X_L$ in PBS. Each 8.0 µL experimental sample thus contained 40 µmol (1.5 µg) of protein at 5.0 µM concentration in PBS plus 1 µM peptidomimetic macrocycle and 2.5% DMSO. Duplicate samples thus prepared for each concentration point were incubated for 60 min at room temperature, and then chilled to 4° C. prior to size-exclusion chromatography-LC-MS analysis of 5.0 µL injections. Samples containing a target protein, protein-ligand complexes, and unbound compounds were injected onto an SEC column, where the complexes were separated from non-binding component by a rapid SEC step. The SEC column eluate was monitored using UV detectors to confirm that the early-eluting protein fraction, which elutes in the void volume of the SEC column, was well resolved from unbound components that are retained on the column. After the peak containing the protein and protein-ligand complexes elutes from the primary UV detector, it entered a sample loop where it was excised from the flow stream of the SEC stage and transferred directly to the LC-MS via a valving mechanism. The $(M+3H)^{3+}$ ion of ALRN-0034 is observed by ESI-MS at m/z 883.8, confirming the detection of the protein-ligand complex.

Example 11

Competitive Binding Experiments

A mixture of ligands at 40 µM per component was prepared by combining 2 µL aliquots of 400 µM stocks of each of the three compounds with 14 µL of DMSO. Then, 1 µL aliquots of this 40 µM per component mixture were combined with 1 µL DMSO aliquots of a serially diluted stock solution of titrant peptidomimetic macrocycle (10, 5, 2.5, . . . , 0.078 mM). These 2 µL samples were dissolved in 38 µL of PBS. The resulting solutions were mixed by repeated pipetting and clarified by centrifugation at 10 000 g for 10 min. To 4.0 µL aliquots of the resulting supernatants was added 4.0 µL of 10 µM BCL-$X_L$ in PBS. Each 8.0 µL experimental sample thus contained 40 µmol (1.5 µg) of protein at 5.0 µM concentration in PBS plus 0.5 µM ligand, 2.5% DMSO, and varying concentrations (125, 62.5, . . . , 0.98 µM) of the titrant peptidomimetic macrocycle. Duplicate samples thus prepared for each concentration point were incubated at room temperature for 60 min, then chilled to 4° C. prior to SEC-LC-MS analysis of 2.0 µL injections. Additional details on these and other methods are provided in "*A General Technique to Rank Protein-Ligand Binding Affinities and Determine Allosteric vs. Direct Binding Site Competition in Compound Mixtures.*" Annis, D. A.; Nazef, N.; Chuang, C. C.; Scott, M. P.; Nash, H. M. *J. Am. Chem. Soc.* 2004, 126, 15495-15503; also in "*ALIS: An Affinity Selection-Mass Spectrometry System for the Discovery and Characterization of Protein-Ligand Interactions*" D. A. Annis, C.-C. Chuang, and N. Nazef. In Mass Spectrometry in Medicinal Chemistry. Edited by Wanner K, Höfner G: Wiley-VCH; 2007:121-184. Mannhold R, Kubinyi H, Folkers G (Series Editors): Methods and Principles in Medicinal Chemistry.

Example 12

Quantitative Analysis of FITC-Labeled Peptidomimetic Macrocycle Uptake Using Fluorimetry Cells (e.g. INA-6 or Jurkat cells) were cultured in suspension in RPMI1640 medium with 2 mM L-Glutamine and (Invitrogen) supplemented with 10% FBS and 1% penicillin-Streptomycin as well as 1 ng/ml of recombinant human IL-6 supplements in the case of INA-6 cells. Cells were subcultured a day prior to the day of experiment to keep them in an exponential growing phase. To analyze the uptake of FITC-labeled peptidomimetic macrocycles in cells, exponentially growing cells were seeded in 0.9 ml of serum-free medium at density of $0.5 \times 10^6$ cells. Cells were allowed to settle down until compounds were diluted. Test compounds were diluted to 2 mM stock in DMSO, followed by dilution to 400 µM in sterile water; further dilution to 100 µM was done using OptiMEM. Thus $100_1 11$ of 100 uM FITC-labeled peptidomimetic macrocycle was then added to appropriate wells to achieve a final concentration of 10 µM in 1 ml volume. Plates were returned to 37° C., 5% $CO_2$ incubators for designated time points. If needed, further dilutions of test compounds were also prepared in OptiMEM. At the end of each time point, cells were harvested, washed twice with RPMI supplemented with FBS, and washed once with PBS+0.5% BSA. Pelleted cells were resuspended and incubated with 0.25% Trypsin-EDTA for 15 min at 37° C., 5% $CO_2$. Post-incubation, cells were washed with media containing serum once and twice with PBS with 0.5% BSA. At the end of washes, cells were lysed with Triton X-100-containing cell lysis buffer from Cell Signaling Technologies. Fluorescence intensity was measured on a BioTek Synergy 4 instrument. Dilutions of FITC-labeled peptidomimetic macrocycles for the standard curves made in cell lysis buffer and were used for quantitation of the amount of peptidomimetic macrocycles in cells. Analysis was done using Gen 5 software provided by Biotek Inc.

Example 13

Efficacy of Peptidomimetic Macrocycles in an Orthotopic Prostate Tumor Model

Figure 43:
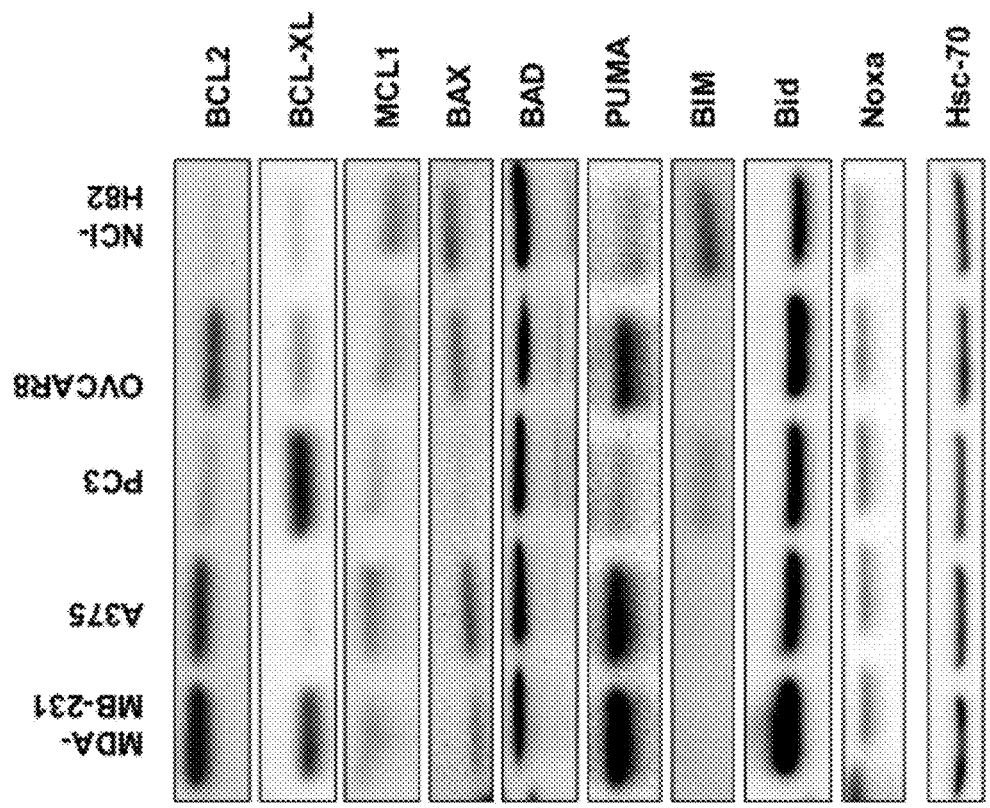
FIG. 43 depicts a Western Blot showing variable expression of various BCL-family proteins in cancers that are sensitive to peptidomimetic macrocycles of the invention.
Figure 44:
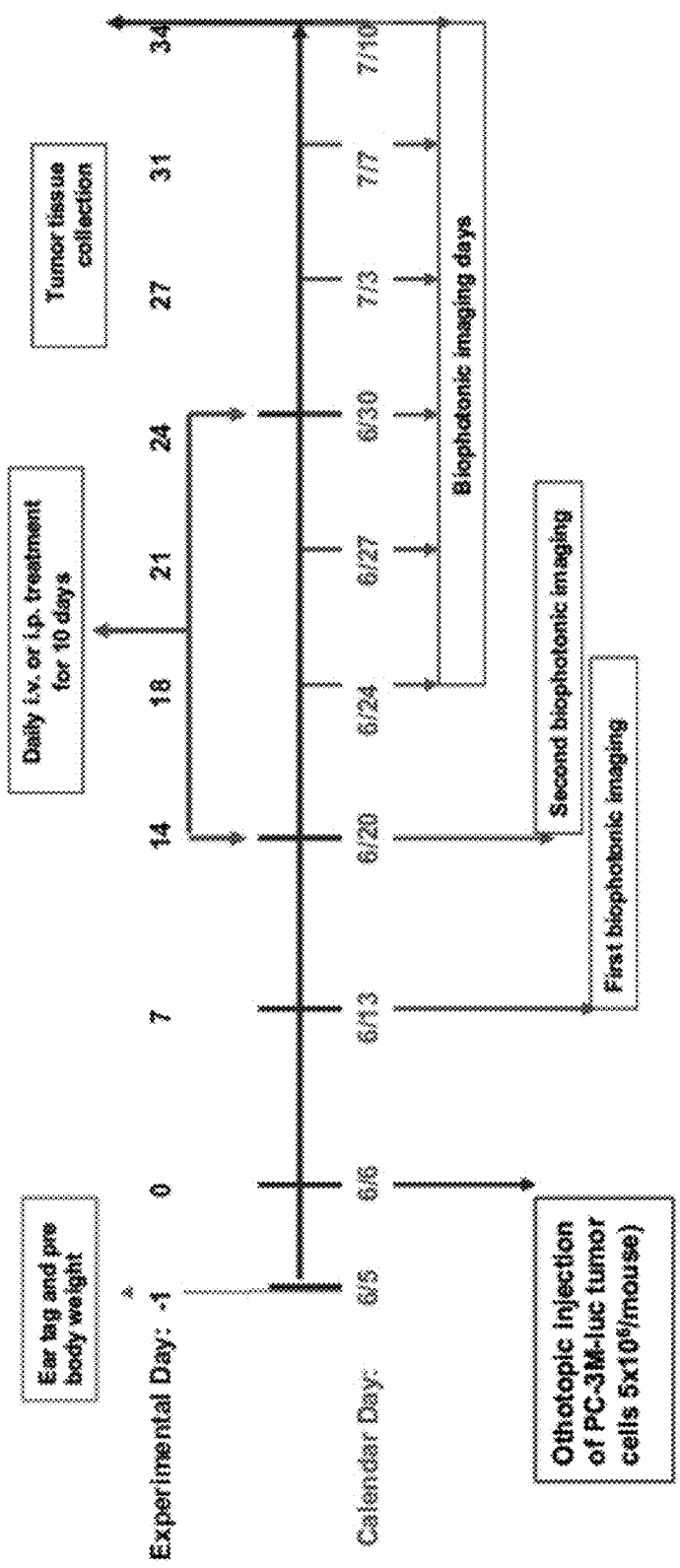
FIG. 44 depicts a timeline for mouse treatment in a prostate cancer orthotopic xenograft model.
Figure 45:
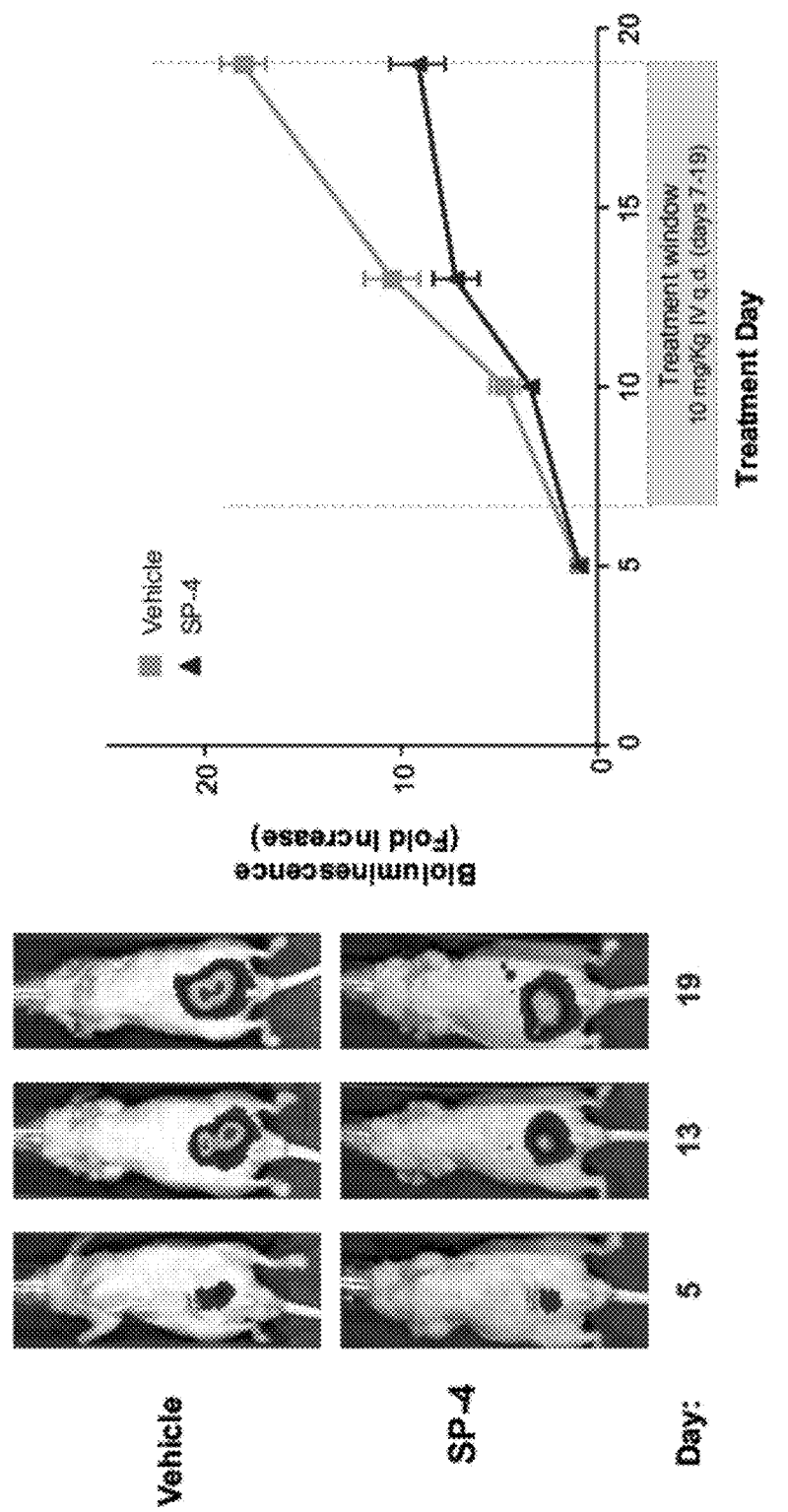
FIG. 45 depicts efficacy of a peptidomimetic macrocycle of the invention in a prostate cancer orthotopic xenograft model.
Figure 46:
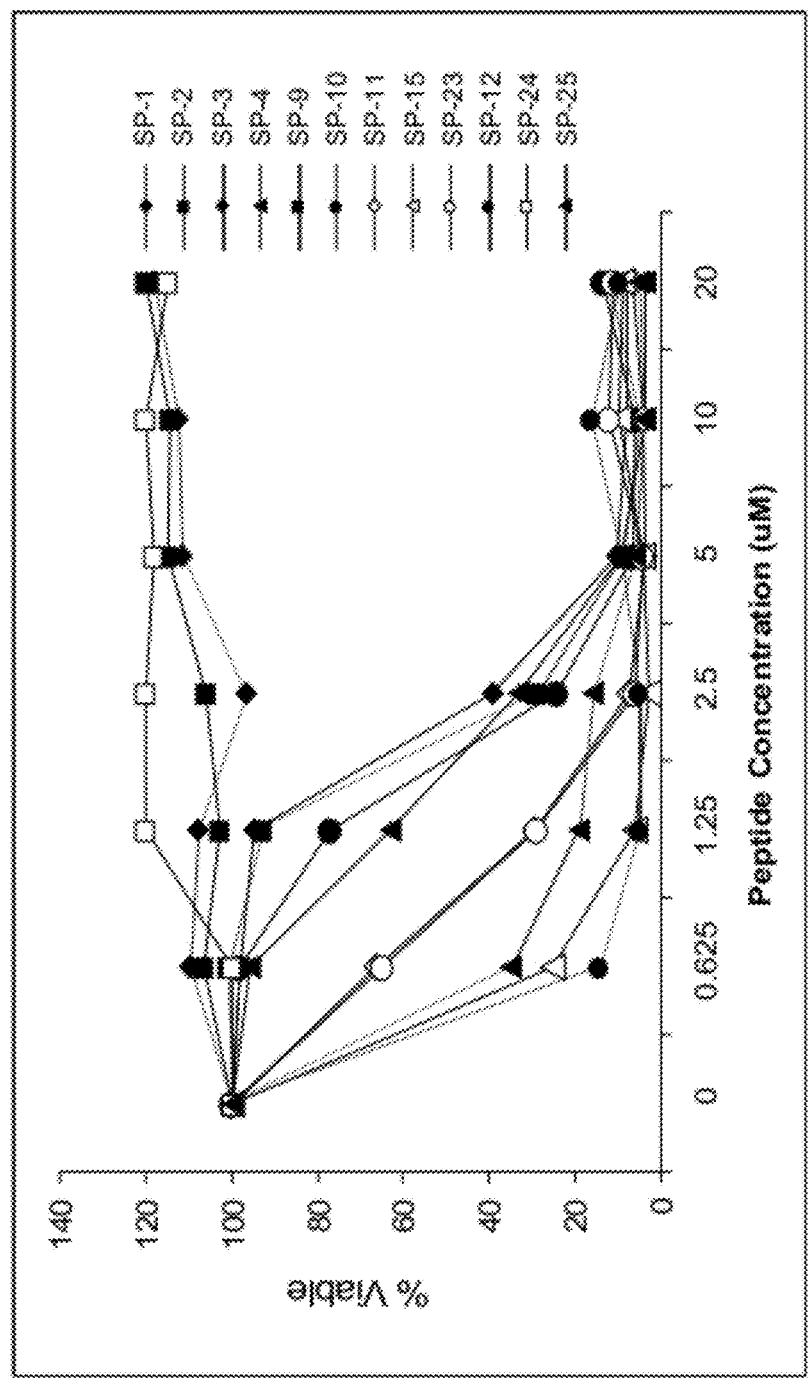
FIG. 46 describes induction of programmed cell death by peptidomimetic macrocycles of the invention in a T-cell leukemia cell line (Jurkat), treated in the absence of serum.
Figure 47:
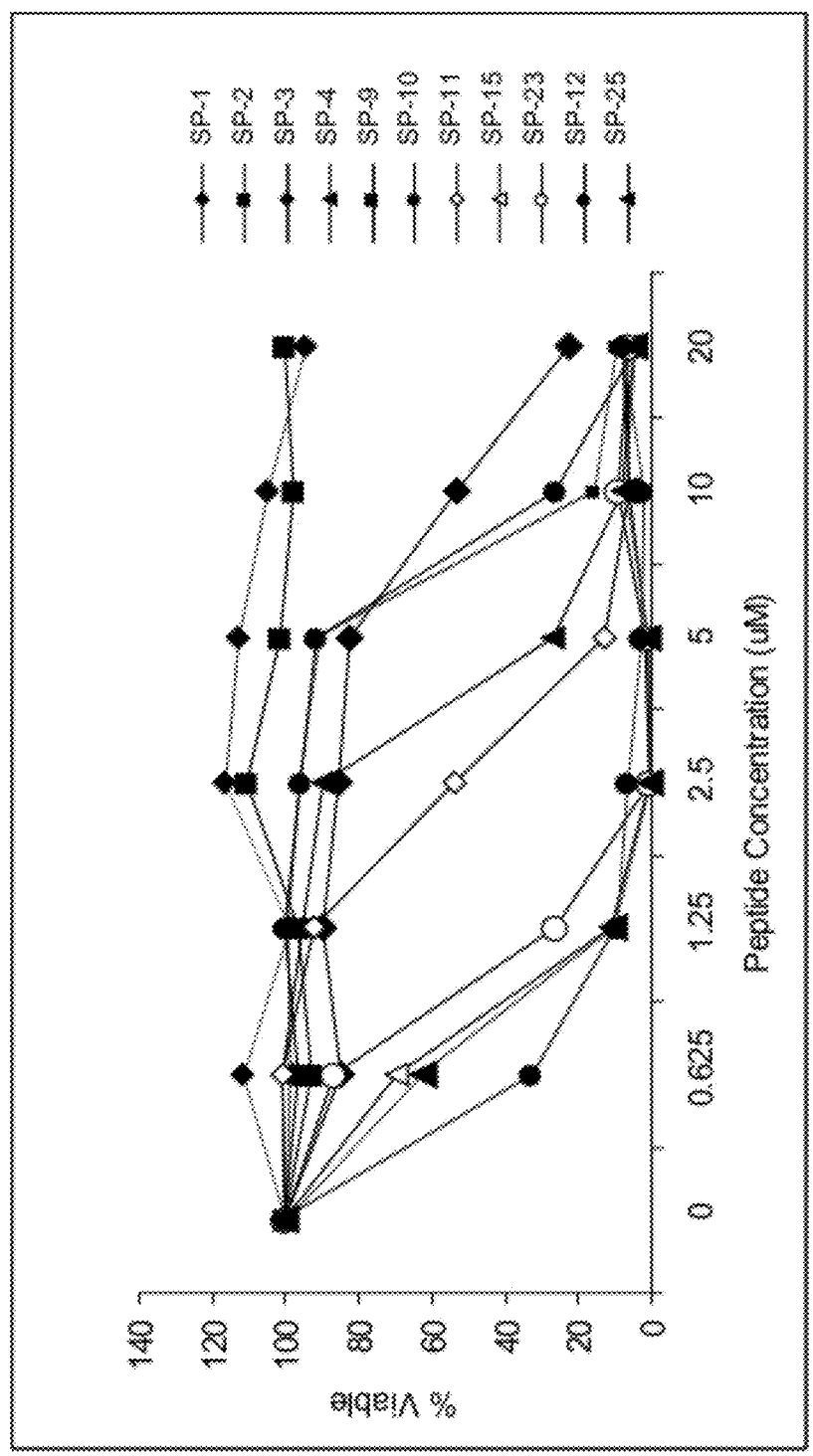
FIG. 47 describes induction of programmed cell death by peptidomimetic macrocycles of the invention in a mixed-lineage T/B-cell leukemia cell line (SEMK2), treated in the absence of serum.
Figure 48:
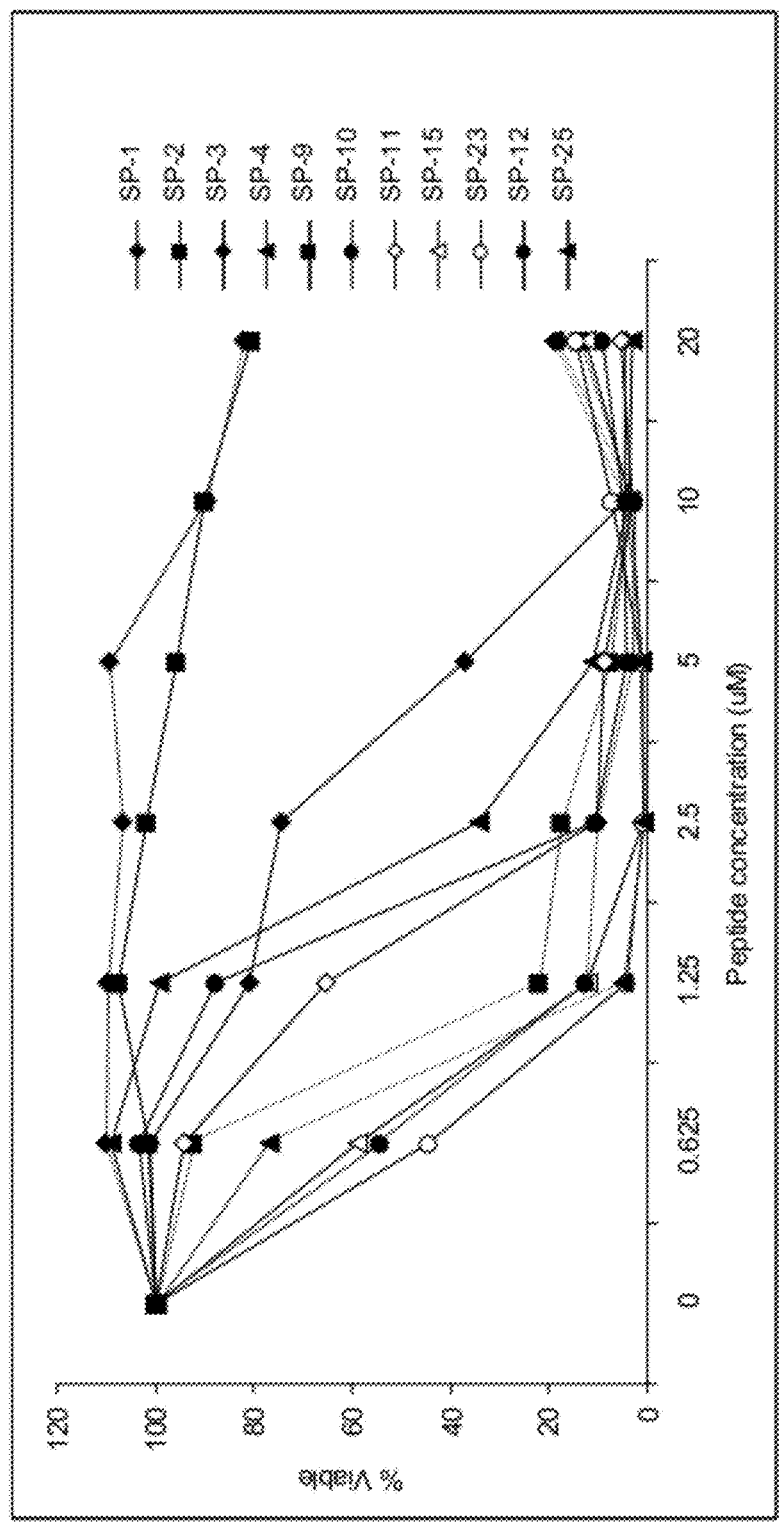
FIG. 48 describes induction of programmed cell death by peptidomimetic macrocycles of the invention in a T-cell leukemia cell line (MOLT-4), treated in the absence of serum.
Figure 49:
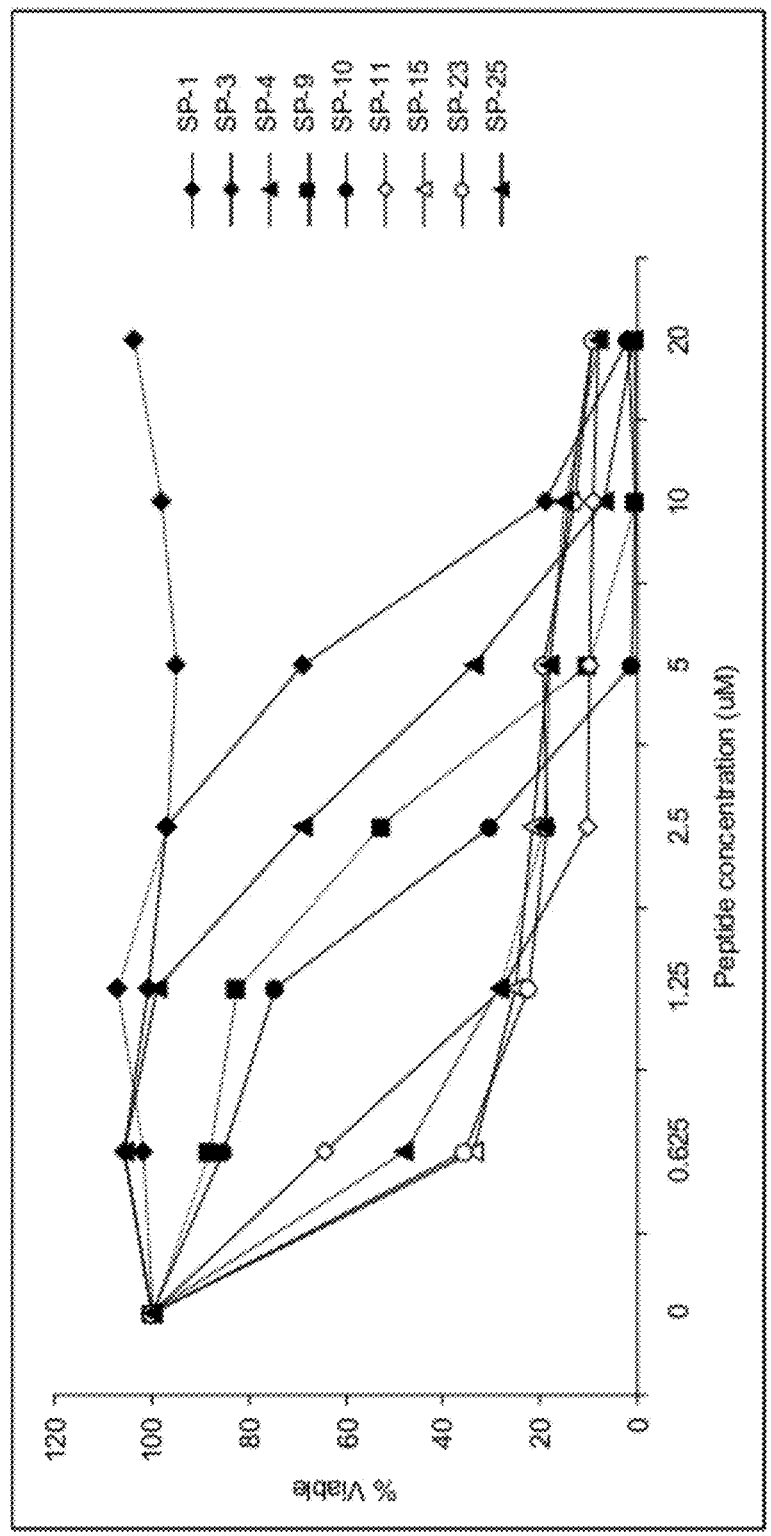
FIG. 49 describes induction of programmed cell death by peptidomimetic macrocycles of the invention in a diffuse large B-cell lymphoma cell line (DHL-6), treated in the absence of serum.
Figure 50:
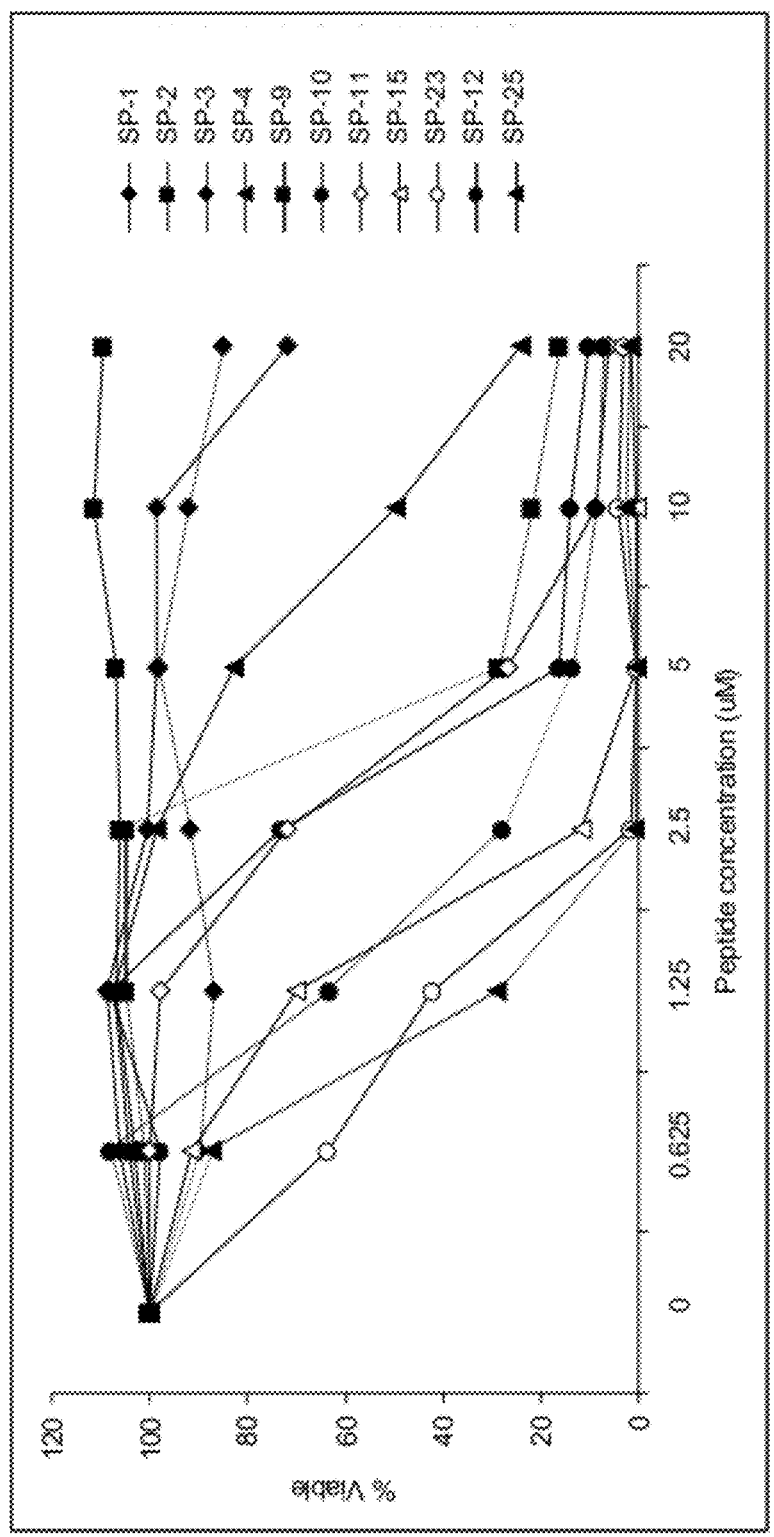
FIG. 50 describes induction of programmed cell death by peptidomimetic macrocycles of the invention in a mixed-lineage T/B-cell leukemia cell line (RS4;11), treated in the absence of serum.
Figure 51:
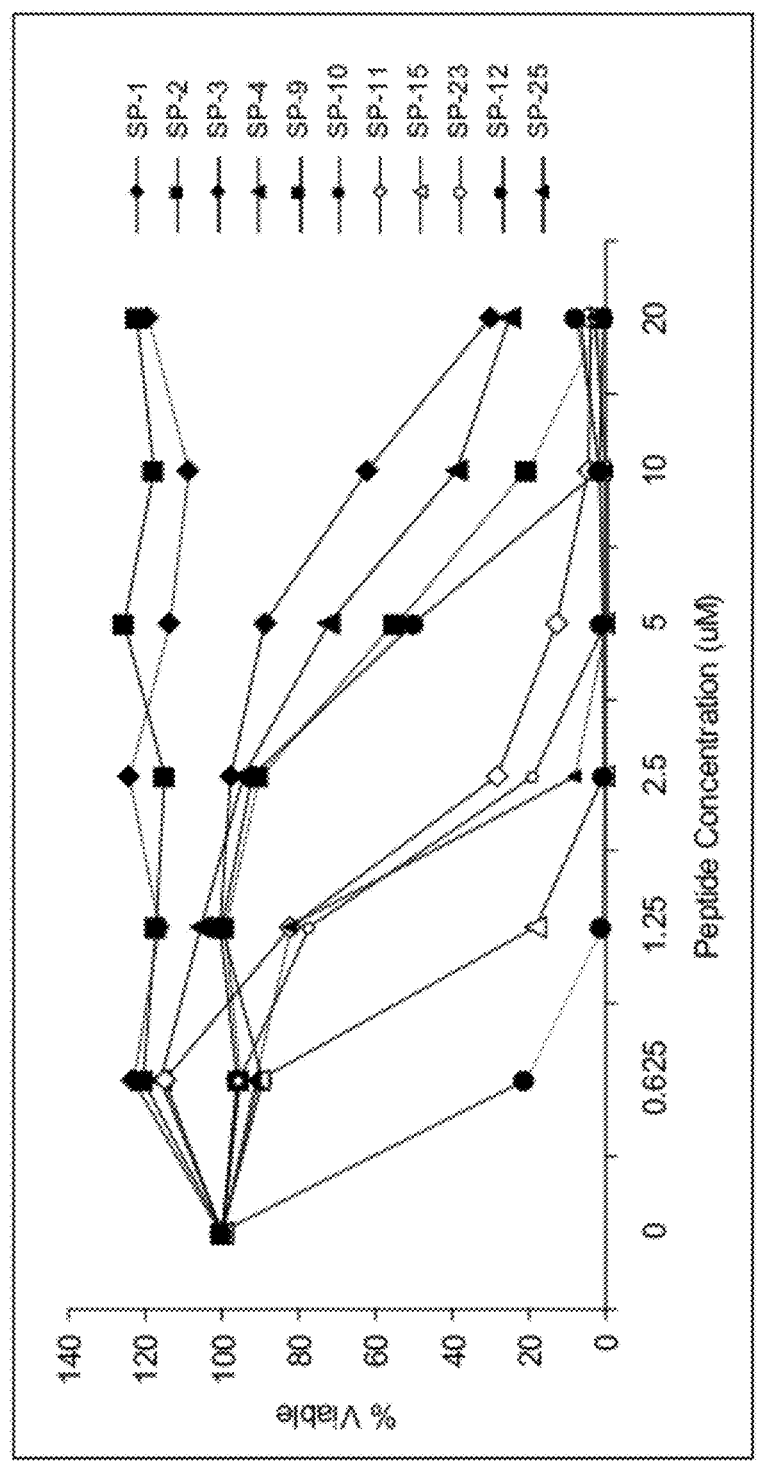
FIG. 51 describes induction of programmed cell death by peptidomimetic macrocycles of the invention in a Burkitt's lymphoma cell line (Raji), treated in the absence of serum.
Figure 52:
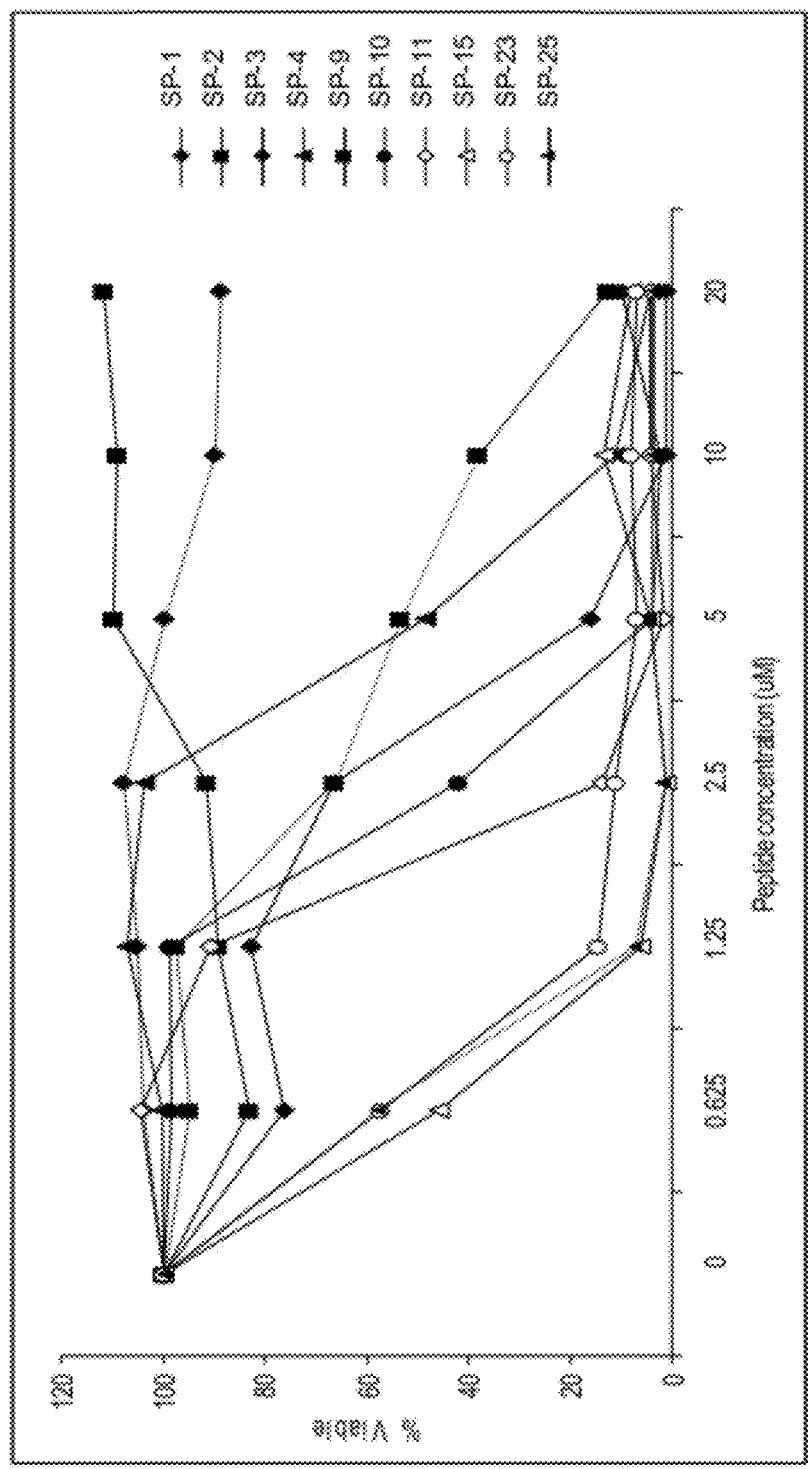
FIG. 52 describes induction of programmed cell death by peptidomimetic macrocycles of the invention in a multiple myeloma cell line (MM1S), treated in the absence of serum.
Figure 53:
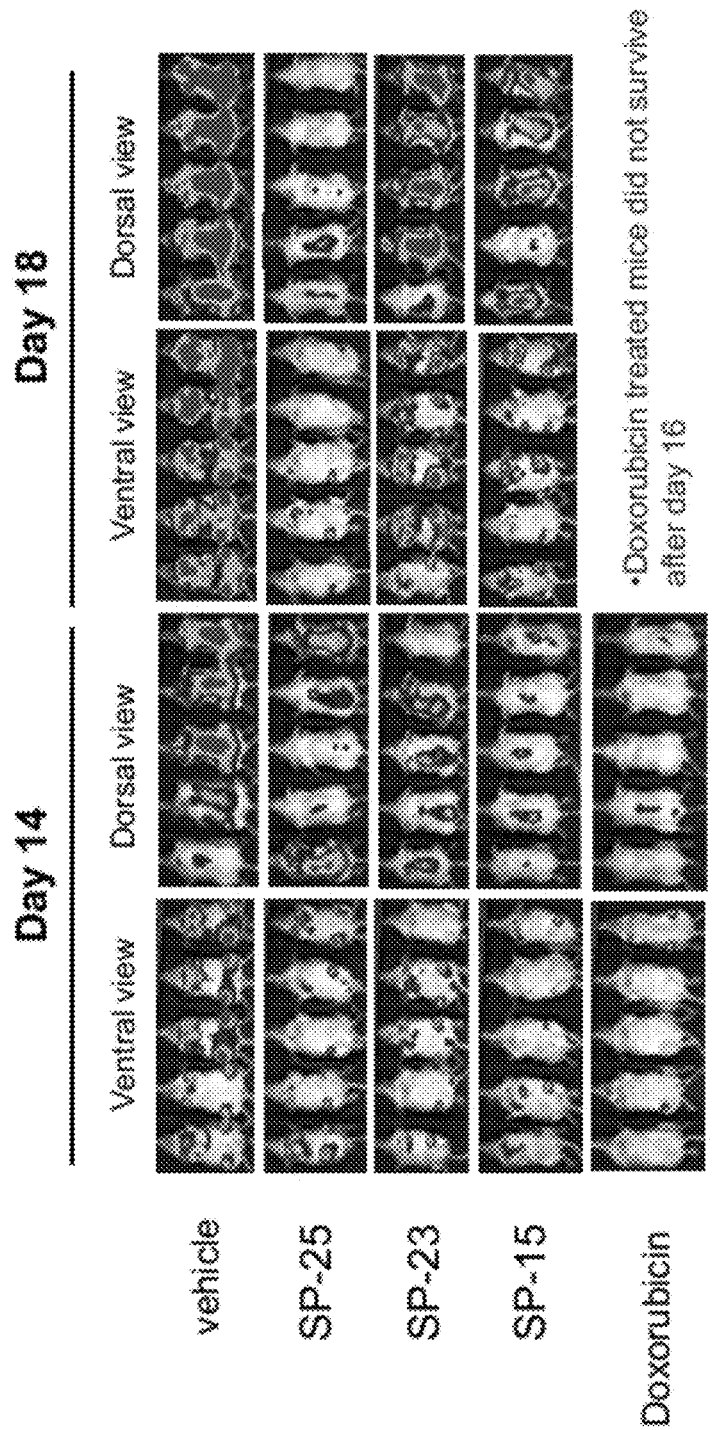
FIG. 53 depicts efficacy of a peptidomimetic macrocycle of the invention in a SEMK2 leukemia orthotopic xenograft model, as measured by reduced tumor burden in treated animals.
Figure 54:
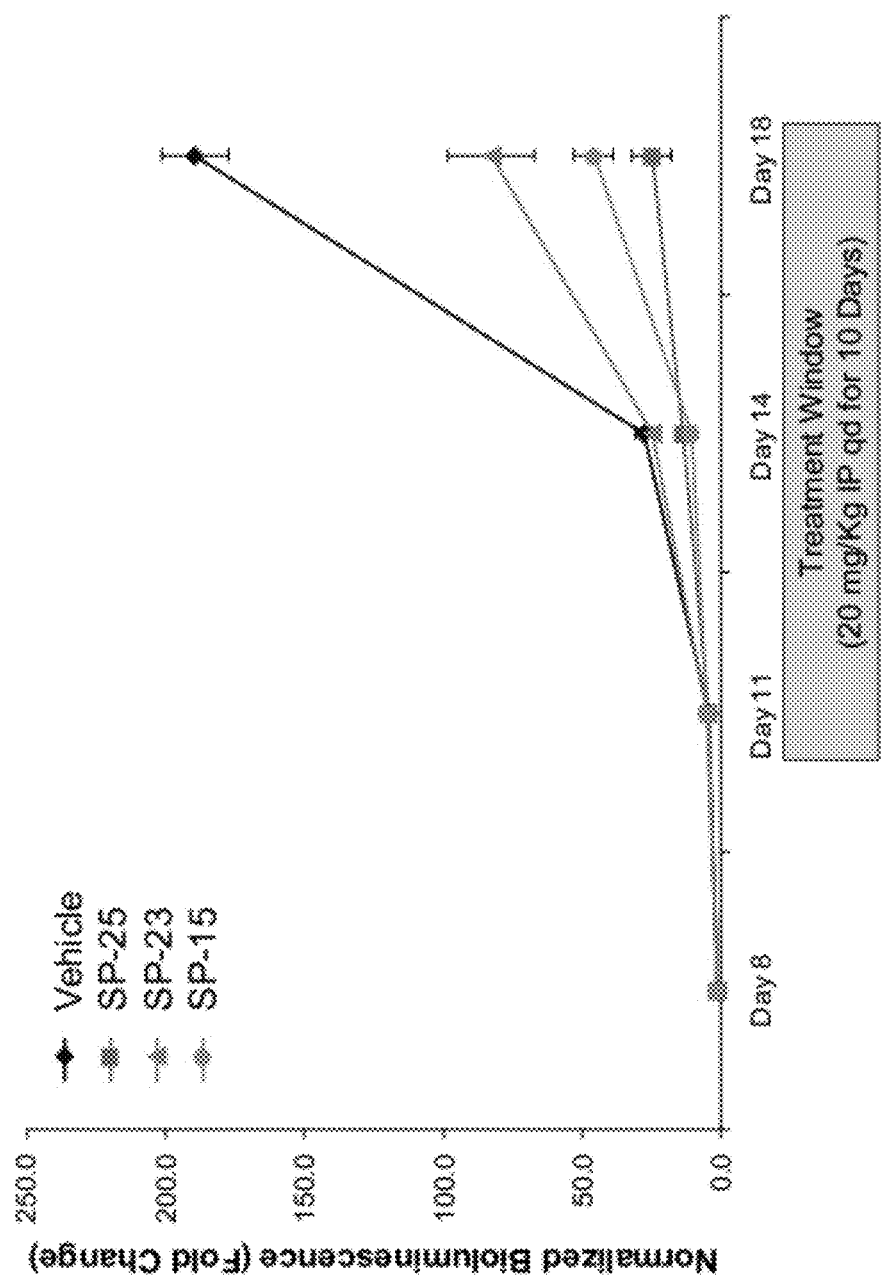
FIG. 54 depicts efficacy of a peptidomimetic macrocycle of the invention in a SEMK2 leukemia orthotopic xenograft model, as measured by reduced tumor burden in treated animals.
Figure 55:
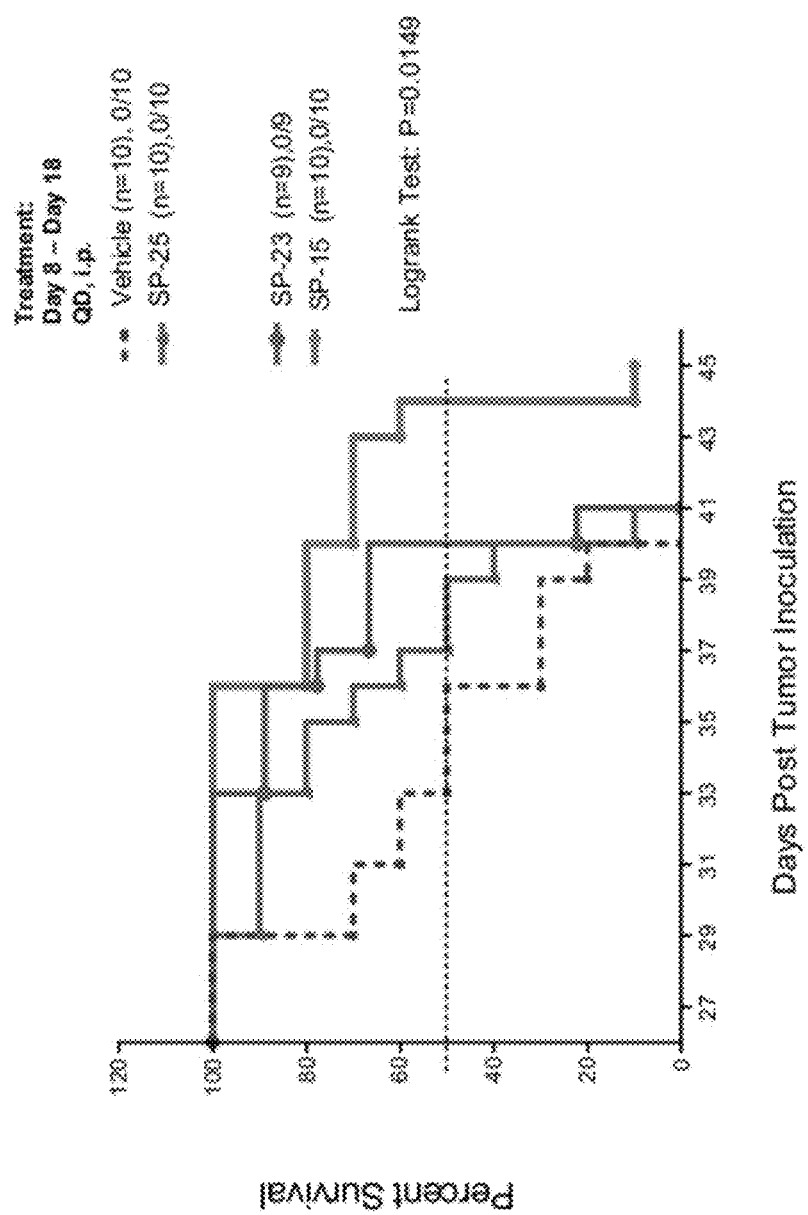
FIG. 55 depicts efficacy of a peptidomimetic macrocycle of the invention in a SEMK2 leukemia orthotopic xenograft model, as measured by increased survival of treated animals.
Figure 56:
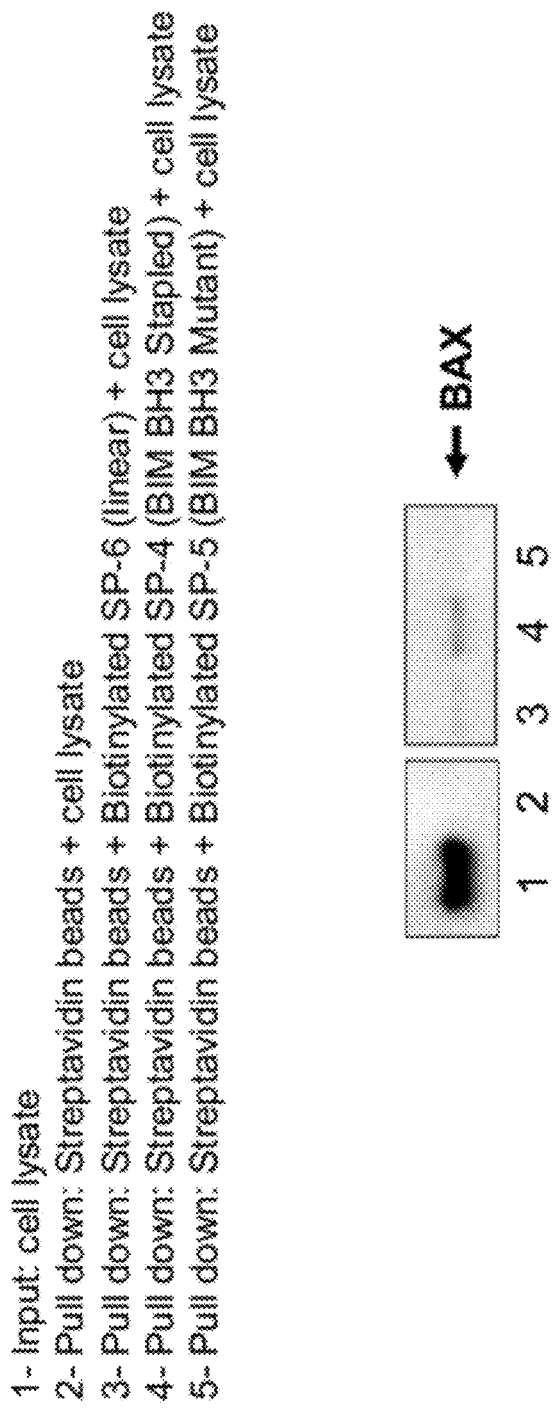
FIG. 56 shows sequence-specific and structure-specific binding of peptidomimetic macrocycles of the invention to the pro-apoptotic target protein BAX in multiple myeloma (MM1S) cell lysates, as demonstrated by immunoprecipitation with the stapled SP-4 peptide.

Experiments were conducted using a Bioware® Cell Line (PC-3M-Luc-C6) and using $5 \times 10^6$ cells/mouse/100 µl. A total of 70 nu/nu male mice were used (7-10 weeks old). Male nu/nu mice were anesthetized and incisions along the posterior midline of their abdomens, right above the prostate, were created. The bladder was retracted and pressed lightly to expose the prostate. PC-3M-luc-C6 cells ($5 \times 10^5$) were slowly injected into either dorsal prostatic lobe. The peritoneal incision was sutured and the skin was closed. The mice were given buprenorphine (0.1 mg/kg in 50 µl) subcutaneously after the surgical procedure. Animals were first imaged on day 7 after wound healing. The final 50 mice were grouped into 5 groups (10 mice per group) based on BLI before the start of the treatment. The experimental mice were imaged twice weekly starting from day 14 for 2.5 weeks. At the end of the experiment, the tumors were dissected and weighed. The tumors were then cut into two pieces for snap freeze and fixed in 10% formalin. Test compound treatment was initiated after two stable or increasing bioluminescent signals were registered from the tumor cell inoculation site. Several test groups were used: Group 1 (Vehicle, IV daily dosing), Group 2 (test compound, IV daily dosing at 10 mg/kg), Group 3 (Vehicle, i.p. daily dosing), Group 4 (test compound, i.p. daily dosing at 10 mg/kg), and Group 5 (Taxotere, IV weekly dosing for two doses at 30 mg/kg). The test peptidomimetic macrocycles were formulated as follows. Only low retention/siliconized plastic tubes and tips were used. A 60 mg/mL stock solution of each peptidomimetic macrocycle was prepared by dissolving 140 mg of each macrocycle into 2.3 mL of 100% DMSO. The stock solution was divided into 10 aliquots of 0.23 mL for daily dosing (14 mg per vial) and kep frozen at −20 C. One vial was thawed on each day of dosing. Workin concentrations (2 mg/mL) of each macrocycle wer prepared by diluting one aliquot of the stock solution into 6.5 mL of filter sterilized 5% dextrose. The DMSO stock was added dropwise into the D5W with constant stirring. The solution was adjusted to a final volume of 7 mL with 5% dextrose, without filter sterilizing the final dose formation. The dosing volume was 5 µL/g (125 µL for a 25 g mouse). The dose is delivered to the mouse by slow bolus (over 30 seconds). FIG. 45 shows a time treatment for the prostate cancer orthotopic xenograft model. The bioluminescence of the prostate region of each experimental animal was measured and expressed as photons/second. The in vivo tumor growth kinetics were graphed and two-way ANOVA for repeated measure (using time and treatment as two main factors) were used. The kinetic mouse images from representative mice from each group were obtained and are shown in FIG. 43.

Example 14

Orthotopic Xenograft Tumor Model Using Ovarian Cancer (SKOV3-Luc) Tumors $1 \times 10^6$ SKOV3-Luc cells stably expressing firefly luciferase are injected into the ovarian bursa of anesthetized SCID-beige mice (9 weeks old, female). The animals are monitored weekly by bioluminescent imaging (BLI). Test compound treatment is initiated after two stable or increasing bioluminescent signals are registered from the tumor cell inoculation site (up to 9 weeks in this model). Prior to the initiation of the treatment animals are randomized into control and treatment groups (10 mice/group). Animals are treated by daily injection (IP, IV or SC) of test compound (low, med, high doses) and vehicle control for 10, 14 and/or 21 days, as needed. Efficacy is determined by comparison of the tumor burden between peptidomimetic macrocycle and vehicle control treated animals. Tumor growth/volume is monitored by BLI after IP injection of 150 mg/kg D-luciferin and imaged by IVIS Imaging System both dorsally and ventrally. Metastatic lesions can be imaged by shielding the primary tumor bioluminescence. At the conclusion of the experiment, the animals are humanely euthanized and the ovarian tumor is excised, weighed and prepared for subsequent analysis.

Example 15

Orthotopic Xenograft Tumor Model Using Breast Cancer (MDA-MB-231-Luc) Tumors $1 \times 10^6$ MDA-MB-231-Luc cells stably expressing firefly luciferase are injected into the breast tissue of anesthetized SCID-beige mice (9 weeks old, female). The animals are monitored weekly by bioluminescent imaging. Test compound treatment is initiated after two stable or increasing bioluminescent signals are registered from the tumor cell inoculation site. Prior to the initiation of the treatment animals are randomized into control and treatment groups (10 mice/group). Animals are treated by daily injection (IP, IV or SC) of test compound (low, med, high doses) and vehicle control for 10, 14 and/or 21 days, as needed. Efficacy is determined by comparison of the tumor burden between test compound and vehicle control treated animals. Tumor growth/volume is monitored by bioluminescent imaging (BLI) after IP injection of 150 mg/kg D-luciferin and imaged by IVIS Imaging System both dorsally and ventrally. Metastatic lesions can be imaged by shielding the primary tumor bioluminescence. At the conclusion of the experiment, the animals are humanely euthanized and the ovarian tumor is excised, weighed and prepared for subsequent analysis.

Example 16

Subcutaneous Xenograft Tumor Model Using Melanoma (A375) or Small Cell Lung Cancer (NCI-H-82) Tumors An optimized amount of tumor cells is injected into the flank of anesthetized NOD/SCID or nu/nu mice, as required, by subcutaneous injection. When the tumors reach an average volume of 20-50 mm$^3$, the animals are sorted into control and treatment groups (10 mice/group). Animals are treated by daily injection (IP, IV or SC) of test compound (low, medium, and high doses) and vehicle control for 10, 14 and/or 21 days, as needed. Efficacy is determined by comparison of the tumor volume between test compound and vehicle control treated animals. Tumor growth/volume is monitored by external caliper measurement (L×W×D). At the conclusion of the experiment, the animals are humanely euthanized and the tumor is excised, weighed and prepared for subsequent analysis.

Example 17

Metastatic Tumor Model Using Metastatic Breast Cancer (MDA-MB-231-Met-Luc) Tumors Anesthetized NOD/SCID mice (9 weeks old, female) are injected with the optimized amount of MDA-MB-213-MET-Luc cells stably expressing firefly luciferase into the left ventricle of the heart (hence directly into arterial system). A successful intracardiac injection is indicated by day zero images showing a systemic bioluminescence distributed throughout the animals and only mice with evidence of a satisfactory injection will remain in the experiment. The animals are sorted into control and treatment groups (10 mice/group). Animals are treated by daily injection (IP, IV or SC) of test compound (low, medium, and high doses) and vehicle control for 10, 14 and/or 21 days, as needed. The development of subsequent metastasis is monitored twice a week in vivo by BLI after IP injection of 150 mg/kg D-luciferin and imaged by IVIS Imaging System both dorsally and ventrally. Lung and bone metastases in particular are monitored. At the conclusion of the experiment, the animals are humanely euthanized and tissues of interest are excised and prepared for ex vivo imaging and subsequent analysis.

The above tumor models are described in more detail in Jenkins, D. E. et al., Clin. & Exp. Metastasis. 2003, 20, 745-756.; Scatena C. D. et al., Prostate 2004, 59, 292-303; Greenaway J. Et al., Mol. Cancer Ther. 2009, 8, 64-74; Guan, J. et al., Cancer Chemo Pharma. 2008, Online Pub December 24; and Lelekakis, M. et al., Clin & Exp Metastasis. 1999, 163-170.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of selecting a peptidomimetic macrocycle that generates a reduced antibody response capable of being used in therapy to treat a cell proliferative disorder, comprising:

a) preparing a peptidomimetic macrocycle by forming a cross-linker connecting two amino acid residues of a polypeptide to stabilize a secondary structure of the peptidomimetic macrocycle;

b) testing the peptidomimetic macrocycle for a reduced antibody response in an in vivo assay as compared to a corresponding uncross-linked polypeptide; and c) selecting the tested peptidomimetic macrocycle as the peptidomimetic macrocycle that generates the reduced antibody response capable of being used in therapy to treat a cell proliferative disorder if the tested peptidomimetic macrocycle has the reduced antibody response; and wherein the peptidomimetic macrocycle that generates the reduced antibody response is of Formula (I):

Formula (I)

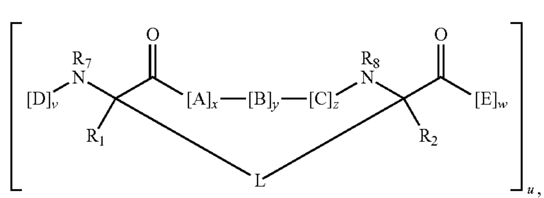

wherein:
each A, C, D, and E, is independently a natural or non-natural amino acid;
B is a natural or non-natural amino acid, amino acid analog,

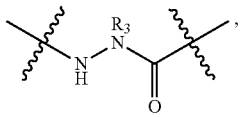

[—NH-$L_3$-CO—], [—NH-$L_3$-$SO_2$—], or [—NH-$L_3$-];

$R_1$ and $R_2$ are independently —H, alkyl, alkenyl, alkynyl, arylalkyl, cycloalkyl, cycloalkylalkyl, heteroalkyl, or heterocycloalkyl, each of which except —H is unsubstituted or substituted with halo-;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, each of which except hydrogen is optionally substituted with $R_5$;

L is a macrocycle-forming linker of the formula -$L_1$-$L_2$-;

$L_1$ and $L_2$ and $L_3$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each $R_4$ is independently alkylene, alkenylene, alkynylene, heteroalkylene, cycloalkylene, heterocycloalkylene, arylene, or heteroarylene;

each K is independently O, S, SO, $SO_2$, CO, $CO_2$, or $CONR_3$;

each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope, or a therapeutic agent;

each $R_6$ is independently —H, alkyl, alkenyl, alkynyl, arylalkyl, cycloalkylalkyl, heterocycloalkyl, a fluorescent moiety, a radioisotope, or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, each of which except —H is optionally substituted with $R_5$, or part of a cyclic structure with a D residue;

$R_8$ is —H, alkyl, alkenyl, alkynyl, arylalkyl, cycloalkyl, heteroalkyl, cycloalkylalkyl, heterocycloalkyl, cycloaryl, or heterocycloaryl, each of which except —H is optionally substituted with $R_5$, or part of a cyclic structure with an E residue;

each of v and w is independently an integer from 1-1000;

each of x, y, and z, is independently an integer from 0-10;

u is an integer from 1-10; and n is an integer from 1-5.

2. The method of claim 1, wherein the peptidomimetic macrocycle that generates the reduced antibody response comprises a helix.

3. The method of claim 1, wherein the peptidomimetic macrocycle that generates the reduced antibody response comprises an α-helix.

4. The method of claim 1, wherein the polypeptide comprises a BH3 domain.

5. The method of claim 1, wherein an α-carbon atom in the peptidomimetic macrocycle that generates the reduced antibody response is additionally substituted with independent substituents of formula R—, wherein R— is alkyl, alkenyl, alkynyl, arylalkyl, cycloalkylalkyl, heteroalkyl, or heterocycloalkyl, each of which is unsubstituted or substituted with halo-.

6. The method of claim 5, wherein an α-carbon atom to which the cross-linker is not attached is additionally substituted with a substituent of formula R—, wherein R— is alkyl, alkenyl, alkynyl, arylalkyl, cycloalkylalkyl, heteroalkyl, or heterocycloalkyl, each of which is unsubstituted or substituted with halo-.

7. The method of claim 1, wherein in the peptidomimetic macrocycle that generates the reduced antibody response of Formula (I), $R_1$ and $R_2$ are each, independently, alkyl, alkenyl, alkynyl, arylalkyl, cycloalkyl, cycloalkylalkyl, heteroalkyl, or heterocycloalkyl, each of which is unsubstituted or substituted with halo-.

8. The method of claim 5, wherein R— is alkyl.

9. The method of claim 1, wherein the cross-linker is formed of consecutive carbon-carbon bonds.

10. The method of claim 1, wherein the cross-linker contains about 9 consecutive bonds.

11. The method of claim 1, wherein the cross-linker contains about 12 consecutive bonds.

12. The method of claim 1, wherein the cross-linker comprises about 6 carbon atoms.

13. The method of claim 1, wherein the cross-linker comprises about 9 carbon atoms.

14. The method of claim 1, wherein the peptidomimetic macrocycle that generates the reduced antibody response is cell permeable.

15. The method of claim 3, wherein the length of the cross-linker is about 5 Å to about 9 Å per turn of the alpha-helix.

16. The method of claim 1, wherein the secondary structure is an α-helical structure.

* * * * *